US012492171B2

(12) United States Patent
Parnell et al.

(10) Patent No.: US 12,492,171 B2
(45) Date of Patent: Dec. 9, 2025

(54) HETEROCYCLIC INHIBITORS OF MCT4

(71) Applicant: Vettore, LLC, San Francisco, CA (US)

(72) Inventors: Kenneth Mark Parnell, Kaysville, UT (US); John McCall, Boca Grande, FL (US); Donna Romero, Chesterfield, MO (US)

(73) Assignee: Vettore, LLC, San Francisco, CA (US)

( * ) Notice: Subject to any disclaimer, the term of this patent is extended or adjusted under 35 U.S.C. 154(b) by 951 days.

(21) Appl. No.: 17/652,022

(22) Filed: Feb. 22, 2022

(65) Prior Publication Data

US 2022/0251047 A1 Aug. 11, 2022

Related U.S. Application Data

(63) Continuation of application No. 16/222,949, filed on Dec. 17, 2018, now Pat. No. 11,292,767, which is a continuation of application No. 15/839,539, filed on Dec. 12, 2017, now Pat. No. 10,214,492.

(60) Provisional application No. 62/433,113, filed on Dec. 12, 2016.

(51) Int. Cl.

| | |
|---|---|
| ***C07D 231/56*** | (2006.01) |
| ***A61K 31/415*** | (2006.01) |
| ***A61K 45/06*** | (2006.01) |
| ***A61P 35/00*** | (2006.01) |
| ***C07C 59/01*** | (2006.01) |
| ***C07D 205/02*** | (2006.01) |
| ***C07D 207/24*** | (2006.01) |
| ***C07D 213/12*** | (2006.01) |
| ***C07D 231/14*** | (2006.01) |
| ***C07D 401/04*** | (2006.01) |
| ***C07D 403/04*** | (2006.01) |
| ***C07D 403/06*** | (2006.01) |
| ***C07D 403/10*** | (2006.01) |
| ***C07D 403/14*** | (2006.01) |
| ***C07D 405/04*** | (2006.01) |
| ***C07D 405/06*** | (2006.01) |
| ***C07D 405/12*** | (2006.01) |
| ***C07D 405/14*** | (2006.01) |
| ***C07D 409/04*** | (2006.01) |
| ***C07D 413/04*** | (2006.01) |
| ***C07D 417/04*** | (2006.01) |

(52) U.S. Cl.

CPC .......... *C07D 231/14* (2013.01); *A61K 31/415* (2013.01); *A61K 45/06* (2013.01); *A61P 35/00* (2018.01); *C07C 59/01* (2013.01); *C07D 205/02* (2013.01); *C07D 207/24* (2013.01); *C07D 213/12* (2013.01); *C07D 231/56* (2013.01); *C07D 401/04* (2013.01); *C07D 403/04* (2013.01); *C07D 403/06* (2013.01); *C07D 403/10* (2013.01); *C07D 403/14* (2013.01); *C07D 405/04* (2013.01); *C07D 405/06* (2013.01); *C07D 405/12* (2013.01); *C07D 405/14* (2013.01); *C07D 409/04* (2013.01); *C07D 413/04* (2013.01); *C07D 417/04* (2013.01)

(58) Field of Classification Search

None

See application file for complete search history.

(56) References Cited

U.S. PATENT DOCUMENTS

| | | | | |
|---|---|---|---|---|
| 3,895,026 | A | 7/1975 | Palazzo | |
| 5,078,780 | A | 1/1992 | Moser | |
| 5,925,768 | A | 7/1999 | Barth | |
| 8,901,314 | B2 | 12/2014 | Wall | |
| 9,296,728 | B2 | 3/2016 | Mereddy | |
| 10,202,350 | B2 * | 2/2019 | Parnell | C07D 409/04 |
| 10,214,492 | B2 * | 2/2019 | Parnell | C07D 405/14 |
| 11,155,522 | B2 * | 10/2021 | Parnell | C07D 409/04 |
| 11,292,767 | B2 * | 4/2022 | Parnell | A61K 45/06 |

(Continued)

FOREIGN PATENT DOCUMENTS

| | | |
|---|---|---|
| WO | 2008060771 | 5/2008 |
| WO | 2009109613 | 9/2009 |

(Continued)

OTHER PUBLICATIONS

Tuder, et. al. "Lactate, a Novel Trigger of Transforming Growth Factor-↑[2] Activation in Idiopathic Pulmonary Fibrosis" American Journal of Respiratory and Critical Care Medicine 2012, 186, 8, 701-703. DOI: 10.1164/rccm.201208-1491ED (Year: 2012).*

Self et. al. "Romazarit. A potential disease-modifying antirheumatic drug" J. Med. Chem. 1991, 34, 772-777. DOI: 10.1021/jm00106a044 (Year: 1991).*

(Continued)

*Primary Examiner* — Kortney L. Klinkel

*Assistant Examiner* — Sophia Reilly

(74) *Attorney, Agent, or Firm* — Global Patent Group Inc.; Cynthia Hathaway; Michael Sertic

(57) ABSTRACT

Disclosed herein are compounds and compositions useful in the treatment of MCT4 mediated diseases, such as proliferative and inflammatory diseases, having the structure of Formula I:

(I)

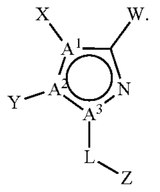

Methods of inhibition MCT4 activity in a human or animal subject are also provided.

9 Claims, No Drawings

(56) References Cited

U.S. PATENT DOCUMENTS

| | | | |
|---|---|---|---|
| 11,724,989 | B2 | 8/2023 | Parnell |
| 12,187,682 | B2 | 1/2025 | Parnell |
| 2009/0042864 | A2 | 2/2009 | Shia |
| 2011/0003874 | A1 | 1/2011 | Guglielmotti |
| 2011/0160248 | A1 | 6/2011 | Zhou |
| 2013/0190324 | A1 | 7/2013 | Kompella |
| 2014/0378477 | A1 | 12/2014 | Lisanti |
| 2016/0115146 | A1 | 4/2016 | Draoui |
| 2016/0362378 | A1 | 12/2016 | Parnell |
| 2018/0162822 | A1 | 6/2018 | Parnell |
| 2019/0112274 | A1 | 4/2019 | Parnell |
| 2019/0112275 | A1 | 4/2019 | Parnell |
| 2021/0009524 | A1 | 1/2021 | Parnell |

FOREIGN PATENT DOCUMENTS

| | | |
|---|---|---|
| WO | 2015188934 | 12/2015 |
| WO | 2016192982 | 12/2016 |
| WO | 2016201416 | 12/2016 |

OTHER PUBLICATIONS

Raiford et. al. "Formation of Pyrazolines From Unsymmetrically Substituted Dibenzalacetones" J. Org. Chem. Soc. 1940, 5, 6, 561-673. DOI: 10.1021/jo01212a004 (Year: 1940).*

Dyson, et al., "Mir", Chemistry of Synthetic Drugs, Moscow: Publishing House, pp. 12-19, (1964).

Pokrovskii, V. (1997), Popular Medical Encyclopedia, Ulianovsk: Knogochei Publishing House, 1997, p. 317.

Naim, M. et al., "Current status of pyrazole and its biological activities" J Pharm Bioallied Sci., 8(1):2-17, (2016).

U.S. Appl. No. 16/222,949; Examiner-Initiated Interview Summary, dated Nov. 9, 2021; 1 page.

U.S. Appl. No. 17/481,660; Non-Final Office Action, dated Oct. 14, 2022; 28 pages.

U.S. Appl. No. 17/481,660; Notice of Allowance, dated Mar. 22, 2023; 12 pages.

U.S. Appl. No. 18/337,313; Notice of Allowance, dated Aug. 28, 2024; 7 pages.

U.S. Appl. No. 18/958,610; Application as filed, dated Nov. 25, 2024; 106 pages.

* cited by examiner

HETEROCYCLIC INHIBITORS OF MCT4

This application is a continuation of U.S. patent application Ser. No. 16/222,949, filed Dec. 17, 2018, which is a continuation of U.S. patent application Ser. No. 15/839,539, filed Dec. 12, 2017, which claims the benefit of priority of U.S. Provisional Application No. 62/433,113, filed Dec. 12, 2016, the contents of which are incorporated by reference as if written herein in their entireties for all purposes.

Disclosed herein are new heterocyclic compounds and compositions and their application as pharmaceuticals for the treatment of disease. Methods of inhibition of MCT4 activity in a human or animal subject are also provided for the treatment diseases such as cancer.

Lactic acid export from glycolytic cells is typically mediated by the monocarboxylate transporter MCT4. MCT4 exhibits weak affinity for lactate ($K_m$=28 mM) coupled with a high turnover rate, allowing rapid export of large amounts of lactic acid. MCT4 expression is normally limited to highly glycolytic tissues such as white muscle fibers, lymphocytes, astrocytes, and Sertoli cells. Though MCT4 is absent from most normal tissues, MCT4 expression is highly upregulated, and correlates with poor survival, in many cancer indications, including colorectal cancer, glioma, head and neck cancer, triple-negative breast cancer, prostate cancer, KRAS mutant lung cancer, liver cancer, and kidney cancer.

The correlation of MCT4 expression and poor cancer outcome appears to be of significant functional consequence in multiple cancer models. Stable expression of MCT4 is highly tumorigenic in a respiration-impaired, Ras-transformed fibroblast xenograft model. Conversely, MCT4 silencing slows or ablates tumor growth in xenograft models of breast cancer, colorectal cancer, and glioma. MCT4 expression is required for inflammatory cytokine IL-8-mediated angiogenesis in breast and colon cancer xenograft models. MCT4 has also been shown to play important roles in cancer cell migration, invasion, and various aspects of the Warburg effect (e.g., proliferation on glucose, extracellular acidification, and lactate secretion).

Inhibition of MCT4-mediated lactic acid export may be an effective strategy to impair the Warburg effect in cancer. Unfortunately, no potent and selective MCT4 inhibitors have been described. Moderate to weak MCT4 inhibitors are known (e.g., phloretin and D-CN-4-OH-cinnamate); however, these compounds promiscuously inhibit a number of other transporters, including MCT1.

Thus, there is a need for potent and selective MCT4 inhibitors for use in the treatment or prevention of cancer.

DETAILED DESCRIPTION

Novel compounds and pharmaceutical compositions, certain of which have been found to inhibit MCT4 have been discovered, together with methods of synthesizing and using the compounds including methods for the treatment of MCT4-mediated diseases in a patient by administering the compounds.

Provided is a compound of structural Formula I

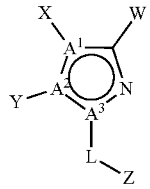

(I)

or a salt thereof, wherein:

$A^1$, $A^2$, and $A^3$ are independently chosen from N and C, wherein at least one of $A^1$, $A^2$, and $A^3$ is N;

L is chosen from a bond, methylene, and ethylene;

W is chosen from

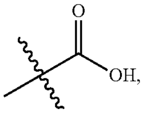

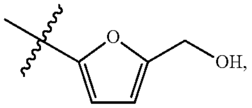

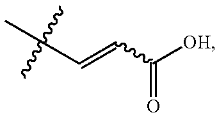

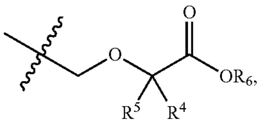

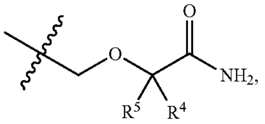

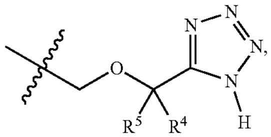

and

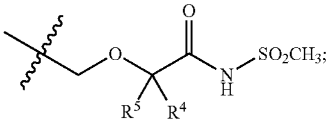

X is H or null, or is chosen from alkenylamino, alkyl, aminoalkenyl, and aminoalkyl, any of which is optionally substituted with one to three $R^1$ groups;

Y is chosen from alkenyl, alkenylamino, alkyl, aminoalkenyl, aminoalkyl, aryl, arylmethyl, arylamino, aryloxy, cycloalkyl, heterocycloalkyl, and heteroaryl, any of which is optionally substituted with one to three $R^2$ groups, or X and Y together with the atoms to which they are attached may form an aryl, cycloalkyl, heteroaryl, or heterocycloalkyl ring, any of which is optionally substituted with one to three $R^7$ groups; and Z is chosen from alkyl, cycloalkyl, heterocycloalkyl, aryl and heteroaryl, any of which is optionally substituted with one to three $R^3$ groups;

each $R^1$ is independently chosen from alkyl, alkenyl, alkoxy, haloalkyl, haloalkoxy, amino, carboxamido, sulfonamido, halo, cyano, hydroxy, cycloalkyl, aryl, heteroaryl;

each $R^2$ is independently chosen from alkyl, alkenyl, alkoxy, alkoxyalkyl, alkylthio, haloalkyl, haloalkoxy, cycloalkoxy, cycloalkylmethoxy, heterocycloalkylmethoxy, amino, aminoalkyl, carboxamido, sulfonamido, halo, cyano, hydroxy, cycloalkyl, heterocycloalkyl, aryl, and heteroaryl, or two $R^2$, together with the intervening atoms, form a 5-7 membered cycloalkyl or heterocycloalkyl ring;

each $R^3$ is independently chosen from alkyl, alkenyl, alkoxy, haloalkyl, haloalkoxy, cycloalkoxy, amino, aminoalkyl, carboxamido, sulfonamido, halo, cyano, hydroxy, cycloalkyl, heterocycloalkyl, aryl, and heteroaryl, and is optionally substituted with one to three $R^8$ groups, or two $R^3$, together with the intervening atoms, form a 5-7 membered cycloalkyl or heterocycloalkyl ring;

$R^4$ and $R^5$ are independently chosen from H and $C_1$-$C_6$alkyl, wherein $R^4$ and $R^5$ together comprise no more than 6 carbons, or $R^4$ and $R^5$, together with the atoms to which they are attached, form a 3-7 membered cycloalkyl or heterocycloalkyl ring;

$R^6$ is chosen from H and $C_1$-$C_4$alkyl;

each $R^7$ is independently chosen from alkyl, alkenyl, alkoxy, haloalkyl, haloalkoxy, amino, carboxamido, sulfonamido, halo, cyano, hydroxy, cycloalkyl, aryl, and heteroaryl; and each $R^8$ is independently chosen from cyano, halo, hydroxy, and oxo.

Certain compounds disclosed herein may possess useful MCT4 inhibiting activity, and may be used in the treatment or prophylaxis of a disease or condition in which MCT4 plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for inhibiting MCT4. Other embodiments provide methods for treating a MCT4-mediated disorder in a patient in need of such treatment, comprising administering to said patient a therapeutically effective amount of a compound or composition according to the present invention. Also provided is the use of certain compounds disclosed herein for use in the manufacture of a medicament for the treatment of a disease or condition ameliorated by the inhibition of MCT4.

In certain embodiments, X is chosen from alkenylamino, alkyl, aminoalkenyl, aminoalkyl, and H; and Y is chosen from alkenyl, alkenylamino, alkyl, aminoalkenyl, aminoalkyl, aryl, cycloalkyl, and heteroaryl.

In certain embodiments, X and Y together with the atoms to which they are attached may form an aryl, cycloalkyl, heteroaryl, or heterocycloalkyl ring.

In certain embodiments, exactly two of $A^1$, $A^2$, and $A^3$ is N.

In certain embodiments, exactly one of $A^1$, $A^2$, and $A^3$ is N.

In certain embodiments, $A^1$ and $A^2$ are C; and $A^3$ is N.

In certain embodiments, X is hydrogen.

In certain embodiments, W is chosen from

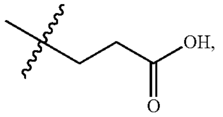

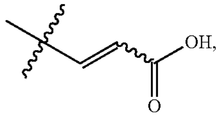

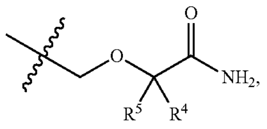

-continued

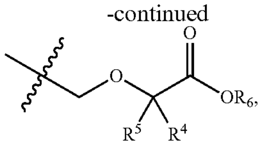

and

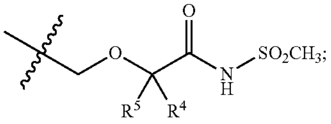

In certain embodiments, W is chosen from

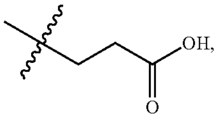

and

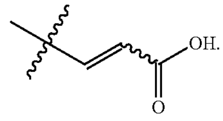

In certain embodiments, W is

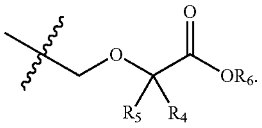

In certain embodiments, Y is chosen from aryl and heteroaryl, any of which is optionally substituted with one to three $R^2$ groups.

In certain embodiments, Y is chosen from phenyl, thienyl, thiazolyl, quinolinyl, isoquinolinyl, cinnolinyl, indazolyl, and indolyl.

In certain embodiments, Y is chosen from quinolinyl, isoquinolinyl, cinnolinyl, indazolyl, and indolyl.

In certain embodiments, Y is chosen from phenyl, thienyl, and thiazolyl.

In certain embodiments, Z is chosen from phenyl, pyridinyl, quinolinyl, isoquinolinyl, cinnolinyl, indazolyl, and indolyl.

In certain embodiments, Z is chosen from phenyl and pyridinyl.

In certain embodiments, each $R^2$ is independently chosen from alkenyl, alkoxy, alkoxyalkyl, cycloalkoxy, cycloalkylmethoxy, haloalkoxy, alkyl, aryl, halo, heteroaryl, and haloalkyl.

In certain embodiments, each $R^2$ is independently chosen from alkoxy, alkoxyalkyl, cycloalkoxy, cycloalkylmethoxy, haloalkoxy, alkyl, halo, and haloalkyl.

In certain embodiments, two $R^2$, together with the intervening atoms, form a 5-7 membered cycloalkyl or heterocycloalkyl ring.

In certain embodiments, each $R^3$ is independently chosen from alkenyl, alkoxy, alkyl, aryl, halo, heteroaryl, and haloalkyl.

In certain embodiments, each $R^3$ is independently chosen from alkoxy, alkyl, aryl, and heteroaryl.

In certain embodiments, two $R^3$, together with the intervening atoms, form a 5-7 membered cycloalkyl or heterocycloalkyl ring.

In certain embodiments, each $R^3$ is alkoxy.

In certain embodiments, each $R^3$ is methoxy.

In certain embodiments, each $R^3$ is halo.

In certain embodiments, each $R^3$ is independently selected from F, Br, and I.

In certain embodiments, each $R^3$ is F.

In certain embodiments, $R^4$ and $R^5$ are independently chosen from H and $C_1$-$C_2$alkyl.

In certain embodiments, $R^4$ and $R^5$ are independently chosen from H and methyl.

In certain embodiments, $R^4$ and $R^5$, together with the atoms to which they are attached, form a 3-7 membered cycloalkyl or heterocycloalkyl ring.

In certain embodiments, $R^6$ is chosen from H and $C_1$-$C_2$alkyl.

In certain embodiments, $R^6$ is chosen from H and methyl.

In certain embodiments, each $R^7$ is independently chosen from alkyl, alkoxy, haloalkyl, haloalkoxy, amino, carboxamido, halo, cyano, hydroxy, cycloalkyl, aryl, and heteroaryl.

In certain embodiments, each $R^7$ is independently chosen from alkyl and alkoxy.

In certain embodiments, the compounds have structural formula Ia:

(Ia)

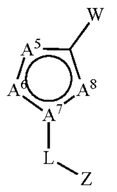

or a salt or tautomer thereof, wherein:

$A^5$ is chosen from C—X and N;

$A^6$ is chosen from C—Y and N;

and $A^7$ are and $A^8$ are chosen from the following combinations:

$A^7$ is C and $A^8$ is NH, or $A^7$ is N and $A^8$ is N;

wherein at least one of $A^5$, $A^6$, and $A^7$ is N;

L is chosen from a bond and methylene;

W is chosen from

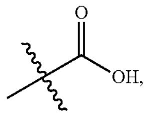

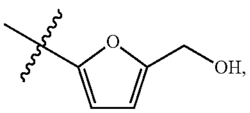

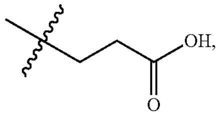

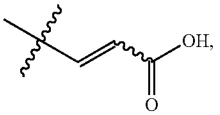

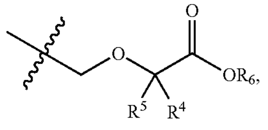

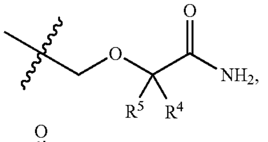

and

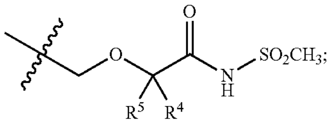

X is H, or is chosen from alkenylamino, alkyl, aminoalkenyl, and aminoalkyl, any of which is optionally substituted with one to three $R^1$ groups;

Y is chosen from alkenyl, alkenylamino, alkyl, aminoalkenyl, aminoalkyl, aryl, cycloalkyl, and heteroaryl, any of which is optionally substituted with one to three $R^2$ groups, or X and Y together with the atoms to which they are attached may form an aryl, cycloalkyl, heteroaryl, or heterocycloalkyl ring, any of which is optionally substituted with one to three $R^7$ groups; and Z is chosen from alkyl, cycloalkyl, heterocycloalkyl, aryl and heteroaryl, any of which is optionally substituted with one to three $R^3$ groups;

each $R^1$ is independently chosen from alkyl, alkenyl, alkoxy, haloalkyl, haloalkoxy, amino, carboxamido, sulfonamido, halo, cyano, hydroxy, cycloalkyl, aryl, heteroaryl;

each $R^2$ is independently chosen from alkyl, alkenyl, alkoxy, alkoxyalkyl, haloalkyl, haloalkoxy, cycloalkoxy, cycloalkylmethoxy, amino, carboxamido, sulfonamido, halo, cyano, hydroxy, cycloalkyl, aryl, and heteroaryl;

each $R^3$ is independently chosen from alkyl, alkenyl, alkoxy, haloalkyl, haloalkoxy, amino, carboxamido, sulfonamido, halo, cyano, hydroxy, cycloalkyl, aryl, and heteroaryl;

$R^4$ and $R^5$ are independently chosen from H and $C_1$-$C_6$alkyl, wherein $R^4$ and $R^5$ together comprise no more than 6 carbons;

$R^6$ is chosen from H and $C_1$-$C_4$alkyl; and each $R^7$ is independently chosen from alkyl, alkenyl, alkoxy, haloalkyl, haloalkoxy, amino, carboxamido, sulfonamido, halo, cyano, hydroxy, cycloalkyl, aryl, and heteroaryl.

In certain embodiments, the compounds have structural Formula II:

(II)

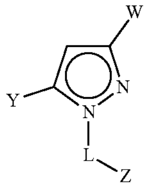

or a salt thereof, wherein:

L is chosen from a bond and methylene;

W is chosen from

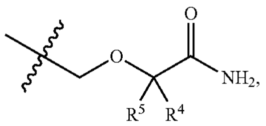

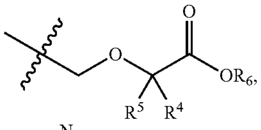

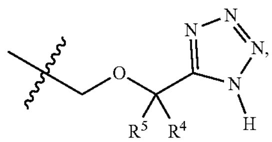

and

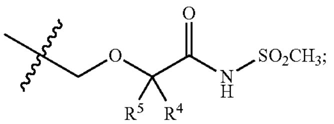

Y is chosen from aryl, arylmethyl, arylamino, aryloxy, cycloalkyl, heterocycloalkyl, and heteroaryl, any of which is optionally substituted with one to three $R^2$ groups;

Z is chosen from aryl and heteroaryl, either of which is optionally substituted with one to three $R^3$ groups;

each $R^2$ is independently chosen from alkyl, alkoxy, alkoxyalkyl, alkylthio, haloalkyl, haloalkoxy, cycloalkoxy, cycloalkylmethoxy, heterocycloalkylmethoxy, amino, aminoalkyl, carboxamido, sulfonamido, halo, cyano, hydroxy, cycloalkyl, heterocycloalkyl, aryl, and heteroaryl, or two $R^2$, together with the intervening atoms, form a 5-7 membered cycloalkyl or heterocycloalkyl ring;

each $R^3$ is independently chosen from alkyl, alkoxy, haloalkyl, haloalkoxy, cycloalkoxy, amino, aminoalkyl, carboxamido, sulfonamido, halo, cyano, hydroxy, cycloalkyl, heterocycloalkyl, aryl, and heteroaryl, and is optionally substituted with one to three $R^8$ groups, or two $R^3$, together with the intervening atoms, form a 5-7 membered cycloalkyl or heterocycloalkyl ring;

$R^4$ and $R^5$ are independently chosen from H and $C_1$-$C_6$alkyl, wherein $R^4$ and $R^5$ together comprise no more than 6 carbons and wherein at least one of $R^4$ and $R^5$ is $C_1$-$C_6$alkyl, or $R^4$ and $R^5$, together with the atoms to which they are attached, form a 3-7 membered cycloalkyl or heterocycloalkyl ring;

$R^6$ is chosen from H and $C_1$-$C_4$alkyl; and each $R^8$ is independently chosen from cyano, halo, hydroxy, and oxo.

In certain embodiments of structural formula II,

L is a bond; and each $R^2$ is chosen from alkenyl, $C_2$-$C_6$alkoxy, cycloalkoxy, cycloalkylmethoxy, haloalkoxy, alkyl, aryl, halo, heteroaryl, and haloalkyl.

In certain embodiments of structural formula II,

Z is chosen from aryl and heteroaryl, either of which is substituted with one to three $R^3$ groups;

each $R^2$ is chosen from alkenyl, $C_2$-$C_6$alkoxy, cycloalkoxy, cycloalkylmethoxy, haloalkoxy, alkyl, aryl, heteroaryl, and haloalkyl; and each $R^3$ is independently chosen from alkyl, alkenyl, alkoxy, haloalkyl, haloalkoxy, amino, carboxamido, sulfonamido, cycloalkyl, aryl, and heteroaryl.

In certain embodiments of structural formula II,

Y is heteroaryl, and is substituted with one to three $R^2$ groups; and each $R^2$ is chosen from alkenyl, $C_2$-$C_6$alkoxy, cycloalkoxy, cycloalkylmethoxy, haloalkoxy, alkyl, aryl, halo, heteroaryl, and haloalkyl.

In certain embodiments of structural formula II,

Y is selected from the group consisting of furyl, thienyl, pyrrolyl, imidazolyl, and oxazolyl, any of which is substituted with one to three $R^2$ groups; and each $R^2$ is chosen from alkenyl, $C_2$-$C_6$alkoxy, cycloalkoxy, cycloalkylmethoxy, haloalkoxy, alkyl, aryl, halo, heteroaryl, and haloalkyl.

In certain embodiments of structural formula II, at least one of $R^4$ and $R^5$ is H.

In certain embodiments of structural formula II, exactly one of $R^4$ and $R^5$ is H.

In certain embodiments, the compounds have structural Formula III:

(III)

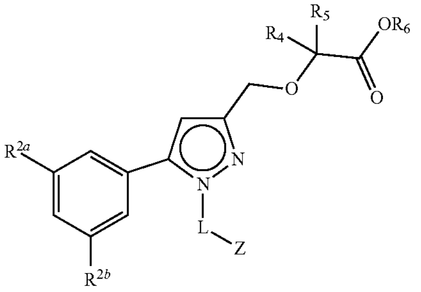

or a salt thereof, wherein:

L is chosen from a bond and methylene;

Z is chosen from aryl and heteroaryl, either of which is optionally substituted with one or two $R^3$ groups;

$R^{2a}$ and $R^{2b}$ are independently chosen from H, alkyl, alkoxy, haloalkyl, haloalkoxy, cycloalkoxy, cycloalkylmethoxy, halo, cycloalkyl, and heterocycloalkyl;

each $R^3$ is independently chosen from alkyl, alkoxy, haloalkyl, haloalkoxy, amino, aminoalkyl, carboxamido, halo, cyano, hydroxy, and cycloalkyl, and is optionally substituted with one or two $R^8$ groups;

$R^4$ and $R^5$ are independently chosen from H and $C_1$-$C_6$alkyl, wherein $R^4$ and $R^5$ together comprise no more than 6 carbons and wherein at least one of $R^4$ and $R^5$ is $C_1$-$C_6$alkyl, or $R^4$ and $R^5$, together with the atoms to which they are attached, form a 3-7 membered cycloalkyl or heterocycloalkyl ring;

$R^6$ is chosen from H and methyl; and each $R^8$ is independently chosen from cyano, halo, hydroxy, and oxo.

In certain embodiments of structural formula III,

Z is chosen from quinolinyl, isoquinolinyl, cinnolinyl, indazolyl, and indolyl, any of which is optionally substituted with one to three $R^3$ groups; and each $R^3$ is independently chosen from alkyl, alkenyl, alkoxy, haloalkyl, haloalkoxy, amino, carboxamido, sulfonamido, halo, cyano, hydroxy, cycloalkyl, aryl, and heteroaryl.

In certain embodiments of structural formula III, Z is chosen from alkyl, cycloalkyl, and heterocycloalkyl, any of which is optionally substituted with one to three $R^3$ groups;

In certain embodiments of structural formula III, $R^2$ is chosen from alkenyl, $C_2$-$C_6$alkoxy, cycloalkoxy, cycloalkylmethoxy, haloalkoxy, alkyl, aryl, halo, heteroaryl, and haloalkyl.

In certain embodiments of structural formula III, $R^2$ is selected from alkoxy, alkyl, halo, haloalkyl, and haloalkoxy.

In certain embodiments of structural formula III, each $R^3$ is independently chosen from alkenyl, alkoxy, alkyl, amino, aryl, halo, heteroaryl, and haloalkyl; and In certain embodiments of structural formula III, Z is chosen from alkyl, cycloalkyl, and heterocycloalkyl, any of which is optionally substituted with one to three $R^3$ groups;

In certain embodiments of structural formula III,

L is a bond;

Z is chosen from aryl and heteroaryl, either of which is substituted with one to three $R^3$ groups; and each $R^3$ is independently chosen from alkenyl, alkoxy, alkyl, amino, fluoro, bromo, and iodo.

In certain embodiments of structural formula III,

L is methylene;

Z is chosen from aryl and heteroaryl, either of which is substituted with one to three $R^3$ groups; and each $R^3$ is independently chosen from alkenyl, $C_2$-$C_6$alkoxy, $C_4$-$C_8$alkyl, aryl, and iodo.

In certain embodiments of structural formula III,

L is a bond; and

Z is chosen from pyridin-3-yl and pyridin-4-yl, and is optionally substituted with one to three $R^3$ groups.

In certain embodiments of structural formula III,

L is methylene; and

Z is pyridyl, and is optionally substituted with one to three $R^3$ groups.

In certain embodiments of structural formula III,

L is methylene; and

Z is pyridyl, and is optionally substituted with two or three $R^3$ groups.

In certain embodiments, the compounds have structural Formula IV:

(IV)

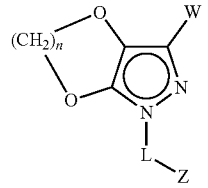

or a salt thereof, wherein:

L is chosen from a bond and methylene;

W is chosen from

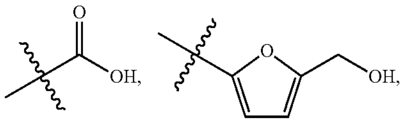

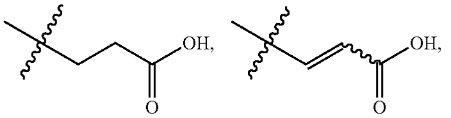

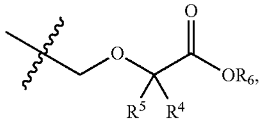

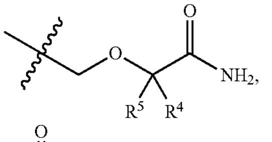

and

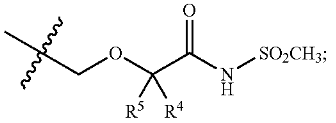

Z is chosen from alkyl, cycloalkyl, heterocycloalkyl, aryl and heteroaryl, any of which is optionally substituted with one to three $R^3$ groups;

each $R^3$ is independently chosen from alkyl, alkenyl, alkoxy, haloalkyl, haloalkoxy, amino, carboxamido, sulfonamido, halo, cyano, hydroxy, cycloalkyl, aryl, and heteroaryl;

$R^4$ and $R^5$ are independently chosen from H and $C_1$-$C_6$alkyl, wherein $R^4$ and $R^5$ together comprise no more than 6 carbons;

$R^6$ is chosen from H and $C_1$-$C_4$alkyl; and n is selected from 1, 2, and 3.

In certain embodiments, the compounds have structural Formula V:

(V)

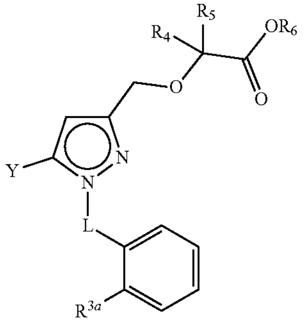

or a salt thereof, wherein:

L is chosen from a bond and methylene;

Y is chosen from phenyl, thienyl, furyl, thiazolyl, and oxazolyl, any of which is optionally substituted with one or two $R^2$ groups, or each $R^2$ is independently chosen from alkoxy, alkylthio, haloalkoxy, cycloalkoxy, cycloalkylmethoxy, heterocycloalkylmethoxy, and halo;

$R^{3a}$ is chosen from H, alkoxy, haloalkoxy, cycloalkoxy, amino, and halo;

$R^4$ and $R^5$ are independently chosen from $C_1$-$C_3$alkyl, or $R^4$ and $R^5$, together with the atoms to which they are attached, form a 3-7 membered cycloalkyl or heterocycloalkyl ring; and $R^6$ is chosen from H and $C_1$-$C_4$alkyl.

In certain embodiments, the compounds have structural Formula VI:

(VI)

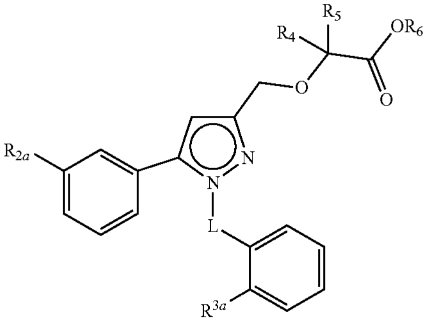

or a salt thereof, wherein:

L is chosen from a bond and methylene;

$R^{2a}$ is chosen from alkoxy, alkylthio, haloalkoxy, cycloalkoxy, cycloalkylmethoxy, heterocycloalkylmethoxy, and halo;

$R^{3a}$ is chosen from H, alkoxy, haloalkoxy, cycloalkoxy, amino, and halo;

$R^4$ and $R^5$ are independently chosen from $C_1$-$C_3$alkyl, or $R^4$ and $R^5$, together with the atoms to which they are attached, form a 3-7 membered cycloalkyl or heterocycloalkyl ring; and $R^6$ is chosen from H and $C_1$-$C_4$alkyl.

In certain embodiments, the compounds have structural Formula VII:

(VII)

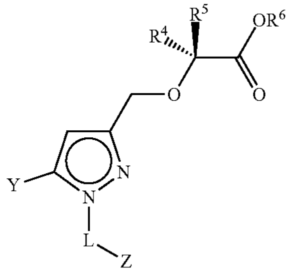

or a salt thereof, wherein:

Y is chosen from aryl, arylmethyl, arylamino, aryloxy, cycloalkyl, heterocycloalkyl, and heteroaryl, any of which is optionally substituted with one to three $R^2$ groups, or Z is chosen from aryl and heteroaryl, either of which is optionally substituted with one to three $R^3$ groups;

each $R^2$ is independently chosen from alkyl, alkenyl, alkoxy, alkoxyalkyl, alkylthio, haloalkyl, haloalkoxy, cycloalkoxy, cycloalkylmethoxy, heterocycloalkylmethoxy, amino, aminoalkyl, carboxamido, sulfonamido, halo, cyano, hydroxy, cycloalkyl, heterocycloalkyl, aryl, and heteroaryl, or two $R^2$, together with the intervening atoms, form a 5-7 membered cycloalkyl or heterocycloalkyl ring;

each $R^3$ is independently chosen from alkyl, alkenyl, alkoxy, haloalkyl, haloalkoxy, cycloalkoxy, amino, aminoalkyl, carboxamido, sulfonamido, halo, cyano, hydroxy, cycloalkyl, heterocycloalkyl, aryl, and heteroaryl, and is optionally substituted with one to three $R^8$ groups, or two $R^3$, together with the intervening atoms, form a 5-7 membered cycloalkyl or heterocycloalkyl ring;

$R^4$ and $R^5$ are independently chosen from $C_1$-$C_6$alkyl, wherein exactly one of $R^4$ and $R^5$ is methyl;

$R^6$ is chosen from H and $C_1$-$C_4$alkyl; and each $R^8$ is independently chosen from cyano, halo, hydroxy, and oxo.

In certain embodiments, the compounds have structural Formula VII:

(VII)

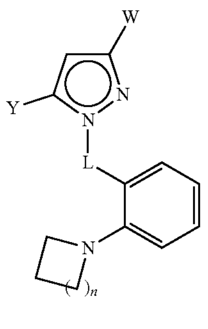

or a salt thereof, wherein:

L is chosen from a bond and methylene;

W is chosen from

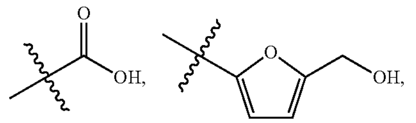

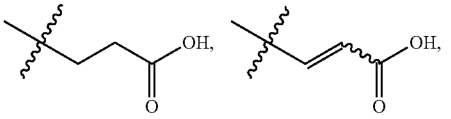

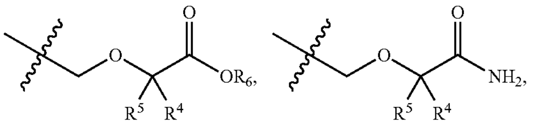

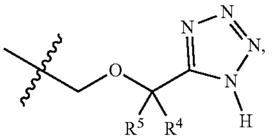

and

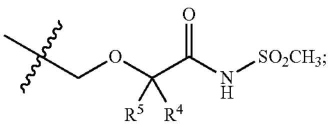

Y is chosen from alkenyl, alkenylamino, alkyl, aminoalkenyl, aminoalkyl, aryl, arylmethyl, arylamino, aryloxy, cycloalkyl, heterocycloalkyl, and heteroaryl, any of which is optionally substituted with one to three $R^2$ groups;

each $R^2$ is independently chosen from alkyl, alkenyl, alkoxy, alkoxyalkyl, alkylthio, haloalkyl, haloalkoxy, cycloalkoxy, cycloalkylmethoxy, heterocycloalkylmethoxy, amino, aminoalkyl, carboxamido, sulfonamido, halo, cyano, hydroxy, cycloalkyl, heterocycloalkyl, aryl, and heteroaryl;

n is 1 or 2 (forming an azetidin-1-yl or pyrrolidin-1-yl);

$R^4$ and $R^5$ are independently chosen from $C_1$-$C_3$alkyl; and $R^6$ is chosen from H and $C_1$-$C_4$alkyl.

In certain embodiments of structural formula VII, Y is chosen from aryl and heteroaryl, either of which is optionally substituted with one to three $R^2$ groups.

In certain embodiments of structural formula VII, each $R^2$ is independently chosen from alkoxy, cycloalkoxy, haloalkoxy, alkyl, halo, and haloalkyl.

In certain embodiments of structural formula VII W is

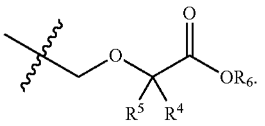

In certain embodiments of structural formula VII, n is 1, forming azetidin-1-yl.

In certain embodiments of structural formula VII, L is a bond.

In certain embodiments, the compounds have structural Formula VIII:

(VIII)

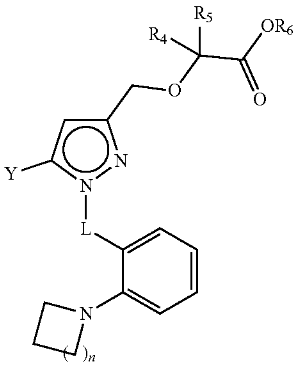

or a salt thereof, wherein:

L is chosen from a bond and methylene;

Y is chosen from phenyl, indazolyl, thienyl, indazolyl, and indolyl, any of which is optionally substituted with one or two $R^2$ groups;

n is 1 or 2 (forming an azetidin-1-yl or pyrrolidin-1-yl);

each $R^2$ is independently chosen from alkyl, alkoxy, alkylthio, haloalkoxy, cycloalkoxy, cycloalkylmethoxy, heterocycloalkylmethoxy, and halo;

$R^4$ and $R^5$ are independently chosen from $C_1$-$C_3$alkyl; and $R^6$ is chosen from H and $C_1$-$C_4$alkyl.

In certain embodiments of structural formula VIII, Y is chosen from phenyl and indazolyl, either of which is optionally substituted with one or two $R^2$ groups.

In certain embodiments of structural formula VIII, each $R^2$ is independently chosen from alkoxy, cycloalkoxy, haloalkoxy, alkyl, halo, and haloalkyl.

In certain embodiments of structural formula VIII, n is 1, forming azetidin-1-yl.

In certain embodiments of structural formula VIII, L is a bond.

In certain embodiments of structural formula VIII, Y is phenyl substituted with one or two $R^2$ groups independently chosen from alkoxy, cycloalkoxy, haloalkoxy, alkyl, halo, and haloalkyl.

In certain embodiments of structural formula VIII, each $R^2$ is independently chosen from $C_1$-$C_4$alkoxy, cyclopropoxy, cyclobutoxy, and $C_1$-$C_3$alkyl.

In certain embodiments of structural formula VIII, Y is indazolyl substituted with an $R^2$ groups chosen from methyl, ethyl, and propyl.

In certain embodiments of structural formula VIII, Y is chosen from:

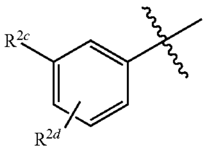

and

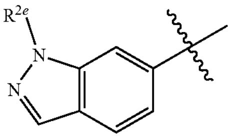

;

$R^{2c}$ is chosen from $C_1$-$C_4$alkoxy and $C_1$-$C_4$cycloalkoxy;

$R^{2d}$ is chosen from null and $C_1$-$C_4$alkoxy; and $R^{2e}$ is $C_1$-$C_4$alkyl.

In certain embodiments, the compounds have structural Formula IX:

(IX)

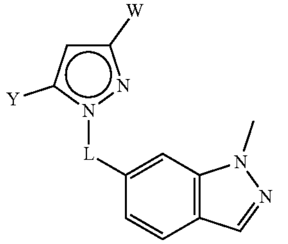

or a salt thereof, wherein:

L is chosen from a bond and methylene;

W is chosen from

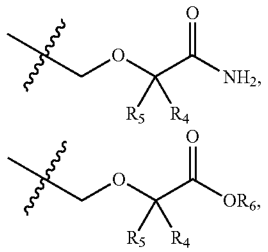

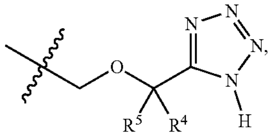

and

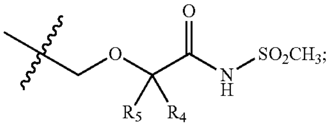

Y is chosen from aryl, arylmethyl, arylamino, aryloxy, cycloalkyl, heterocycloalkyl, and heteroaryl, any of which is optionally substituted with one to three $R^2$ groups;

Z is chosen from aryl and heteroaryl, either of which is optionally substituted with one to three $R^3$ groups;

each $R^2$ is independently chosen from alkyl, alkoxy, alkoxyalkyl, alkylthio, haloalkyl, haloalkoxy, cycloalkoxy, cycloalkylmethoxy, heterocycloalkylmethoxy, amino, aminoalkyl, carboxamido, sulfonamido, halo, cyano, hydroxy, cycloalkyl, heterocycloalkyl, aryl, and heteroaryl;

$R^4$ and $R^5$ are independently chosen from $C_1$-$C_3$alkyl; and $R^6$ is chosen from H and $C_1$-$C_4$alkyl.

In certain embodiments of structural formula IX, Y is chosen from aryl and heteroaryl, either of which is optionally substituted with one to three $R^2$ groups.

In certain embodiments of structural formula IX, each $R^2$ is independently chosen from alkoxy, cycloalkoxy, haloalkoxy, alkyl, halo, and haloalkyl.

In certain embodiments of structural formula IX, W is

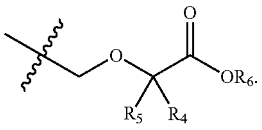

In certain embodiments of structural formula IX, L is a bond.

In certain embodiments of structural formula IX, Y is phenyl substituted with one or two $R^2$ groups independently chosen from alkoxy, cycloalkoxy, haloalkoxy, alkyl, halo, and haloalkyl.

In certain embodiments of structural formula IX, each $R^2$ is independently chosen from $C_1$-$C_4$alkoxy, cyclopropoxy, cyclobutoxy, and $C_1$-$C_3$alkyl.

In certain embodiments, the compounds have structural Formula X:

(X)

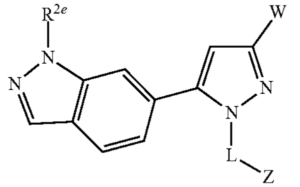

or a salt thereof, wherein:

W is chosen from

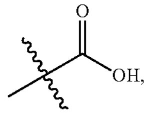

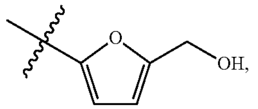

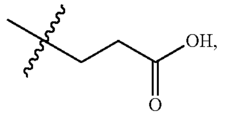

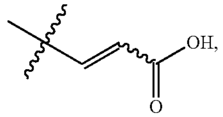

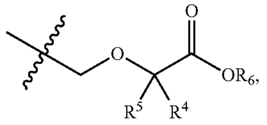

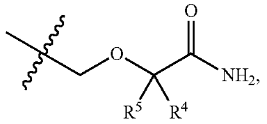

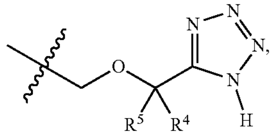

and

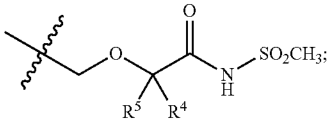

$R^{2e}$ is $C_1$-$C_4$alkyl;

L is chosen from a bond and methylene;

Z is chosen from aryl and heteroaryl, either of which is optionally substituted with one to three $R^3$ groups;

each $R^3$ is independently chosen from alkyl, alkoxy, haloalkyl, haloalkoxy, cycloalkoxy, amino, aminoalkyl, carboxamido, sulfonamido, halo, cyano, hydroxy, cycloalkyl, heterocycloalkyl, aryl, and heteroaryl, and is optionally substituted with one to three $R^8$ groups, or two $R^3$, together with the intervening atoms, form a 5-7 membered cycloalkyl or heterocycloalkyl ring;

$R^4$ and $R^5$ are independently chosen from $C_1$-$C_3$alkyl;

$R^6$ is chosen from H and $C_1$-$C_4$alkyl; and each $R^8$ is independently chosen from cyano, halo, hydroxy, and oxo.

In certain embodiments of structural formula X, W is

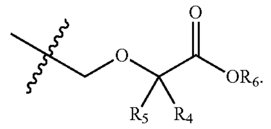

In certain embodiments of structural formula X, L is a bond.

In certain embodiments of structural formula X, Z is chosen from phenyl and indazolyl, either of which is optionally substituted with one to three $R^3$ groups.

In certain embodiments of structural formula X, Z is chosen from:

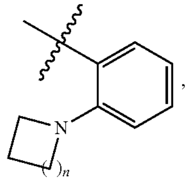

,

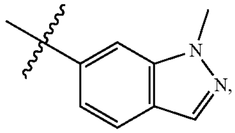

and

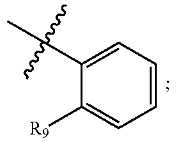

n is 1 or 2 (forming an azetidin-1-yl or pyrrolidin-1-yl);

$R^4$ and $R^5$ are independently chosen from $C_1$-$C_3$alkyl;

$R^6$ is chosen from H and $C_1$-$C_4$alkyl; and $R^9$ is chosen from halo, amino, and $C_1$-$C_4$alkoxy.

In certain embodiments of structural formula X, $R^9$ is chosen from chloro, dimethylamino, and ethoxy.

In certain embodiments of structural formula X, $R^9$ is chosen from chloro and ethoxy.

In certain embodiments of structural formula X, n is 1, forming azetidin-1-yl.

In certain embodiments, the compounds have structural Formula XI:

(XI)

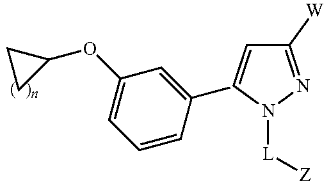

or a salt thereof, wherein:

W is chosen from

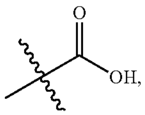
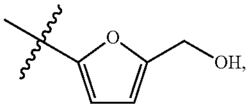
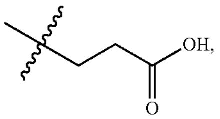
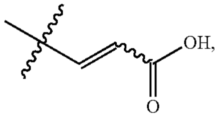
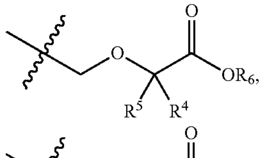
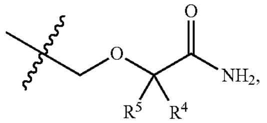
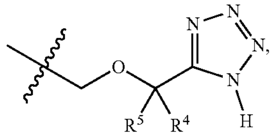
and
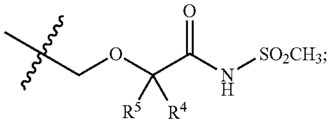

n is 1, 2, or 3 (forming a cyclopropyl, cyclobutyl, or cyclopentyl);

L is chosen from a bond and methylene;

Z is chosen from aryl and heteroaryl, either of which is optionally substituted with one to three $R^3$ groups;

each $R^3$ is independently chosen from alkyl, alkoxy, haloalkyl, haloalkoxy, cycloalkoxy, amino, aminoalkyl, carboxamido, sulfonamido, halo, cyano, hydroxy, cycloalkyl, heterocycloalkyl, aryl, and heteroaryl, and is optionally substituted with one to three $R^8$ groups, or two $R^3$, together with the intervening atoms, form a 5-7 membered cycloalkyl or heterocycloalkyl ring;

$R^4$ and $R^5$ are independently chosen from $C_1$-$C_3$alkyl;

$R^6$ is chosen from H and $C_1$-$C_4$alkyl; and each $R^8$ is independently chosen from cyano, halo, hydroxy, and oxo.

In certain embodiments of structural formula XI, W is

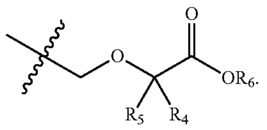

In certain embodiments of structural formula XI, L is a bond.

In certain embodiments of structural formula XI, Z is chosen from phenyl and indazolyl, either of which is optionally substituted with one to three $R^3$ groups.

In certain embodiments of structural formula XI, Z is chosen from:

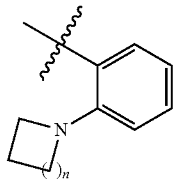
,
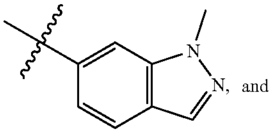
and
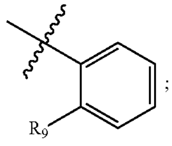
;

n is 1 or 2 (forming an azetidin-1-yl or pyrrolidin-1-yl);

$R^4$ and $R^5$ are independently chosen from $C_1$-$C_3$alkyl;

$R^6$ is chosen from H and $C_1$-$C_4$alkyl; and $R^9$ is chosen from halo, amino, and $C_1$-$C_4$alkoxy.

In certain embodiments of structural formula XI, $R^9$ is chosen from chloro, dimethylamino, and ethoxy.

In certain embodiments of structural formula XI, $R^9$ is chosen from chloro and ethoxy.

In certain embodiments of structural formula XI, n is 1, forming azetidin-1-yl.

In certain embodiments, the compounds have structural Formula II:

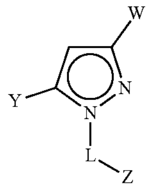
(II)

or a salt thereof, wherein:

L is chosen from a bond and methylene;

W is chosen from

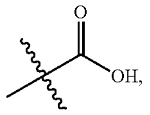
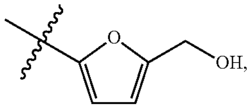
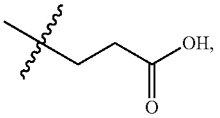
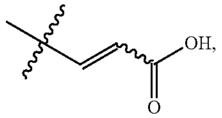
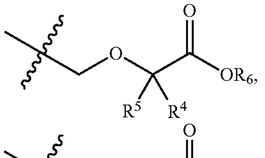
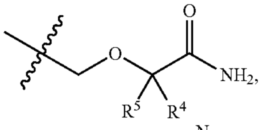
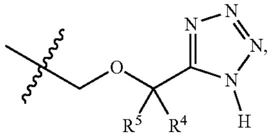
and -continued

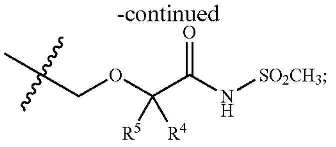

Y is chosen from:

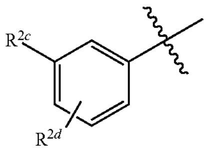

and

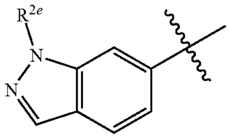

;

$R^{2e}$ is $C_1$-$C_4$alkyl;

Z is chosen from:

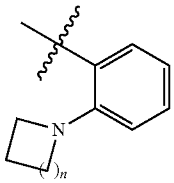

,

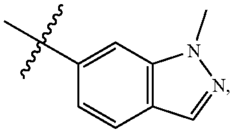

, and

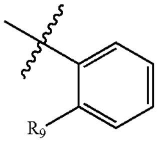

;

n is 1 or 2 (forming an azetidin-1-yl or pyrrolidin-1-yl);

$R^4$ and $R^5$ are independently chosen from $C_1$-$C_3$alkyl;

$R^6$ is chosen from H and $C_1$-$C_4$alkyl; and $R^9$ is chosen from halo and $C_1$-$C_4$alkoxy.

In certain embodiments of structural formula II, W is

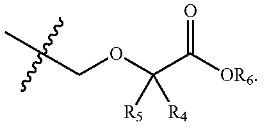

In certain embodiments of structural formula II, $R^9$ is chosen from chloro and ethoxy.

In certain embodiments of structural formula II, L is a bond.

In certain embodiments of structural formula II:

Y is

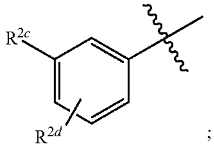

;

$R^{2c}$ is chosen from $C_1$-$C_4$alkoxy and $C_1$-$C_4$cycloalkoxy; and $R^{2d}$ is chosen from null and $C_1$-$C_4$alkoxy.

In certain embodiments of structural formula II:

$R^{2e}$ is chosen from methoxy, methylpropoxy, cyclopropoxy, and cyclobutoxy; and $R^{2d}$ is chosen from null and methoxy.

In certain embodiments of structural formula II:

Y is

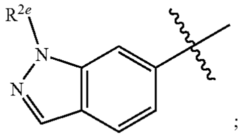

;

and $R^{2e}$ is $C_1$-$C_4$alkyl.

In certain embodiments of structural formula II, $R^{2e}$ is chosen from ethyl and propyl.

In certain embodiments of structural formula II, Z is

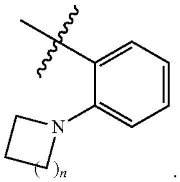

.

In certain embodiments of structural formula II, n is 1, forming azetidin-1-yl.

In certain embodiments of structural formula II, Z is

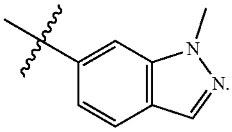 [SMILES: *c1ccc2cnn(C)c2c1]

In certain embodiments of structural formula II, Z is

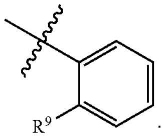

.

In certain embodiments of structural formula II, $R^9$ is chosen from chloro and ethoxy.

Also provided are embodiments wherein any embodiment above may be combined with any one or more of these embodiments, provided the combination is not mutually exclusive.

As used herein, two embodiments are "mutually exclusive" when one is defined to be something which is different than the other. For example, an embodiment wherein two groups combine to form a cycloalkyl is mutually exclusive with an embodiment in which one group is ethyl the other group is hydrogen. Similarly, an embodiment wherein one group is CH2 is mutually exclusive with an embodiment wherein the same group is NH.

Also provided is a compound chosen from the Examples disclosed herein.

The present invention also relates to a method of inhibiting at least one MCT4 function comprising the step of contacting MCT4 with a compound as described herein. The cell phenotype, cell proliferation, activity of MCT4, change in biochemical output produced by active MCT4, expression of MCT4, or binding of MCT4 with a natural binding partner may be monitored. Such methods may be modes of treatment of disease, biological assays, cellular assays, biochemical assays, or the like.

Also provided herein is a method of treatment of a MCT4-mediated disease comprising the administration of a therapeutically effective amount of a compound as disclosed herein, or a salt thereof, to a patient in need thereof.

In certain embodiments, the disease is chosen from proliferative inflammatory diseases.

In certain embodiments, the disease is a metabolic disease.

In certain embodiments, said metabolic disease is chosen from metabolic syndrome, diabetes, dyslipidemia, fatty liver disease, non-alcoholic steatohepatitis, obesity, and insulin resistance.

In certain embodiments, said diabetes is Type II diabetes.

In certain embodiments, said dyslipidemia is hyperlipidemia.

Further provided is a method for achieving an effect in a patient comprising the administration of a therapeutically effective amount of a compound as disclosed above to a patient, wherein the effect is selected from the group consisting of reduction of triglycerides, reduction of cholesterol, and reduction of hemoglobin Alc.

Further provided is the method as disclosed above wherein said cholesterol is chosen from LDL and VLDL cholesterol.

Further provided is the method as disclosed above wherein said triglycerides are chosen from plasma triglycerides and liver triglycerides.

Also provided herein is a compound as disclosed herein for use as a medicament.

Also provided herein is a compound as disclosed herein for use as a medicament for the treatment of a MCT4-mediated disease.

Also provided is the use of a compound as disclosed herein as a medicament.

Also provided is the use of a compound as disclosed herein as a medicament for the treatment of a MCT4-mediated disease.

Also provided is a compound as disclosed herein for use in the manufacture of a medicament for the treatment of a MCT4-mediated disease.

Also provided is the use of a compound as disclosed herein for the treatment of a MCT4-mediated disease.

Also provided herein is a method of inhibition of MCT4 comprising contacting MCT4 with a compound as disclosed herein, or a salt thereof.

Also provided herein is a method for achieving an effect in a patient comprising the administration of a therapeutically effective amount of a compound as disclosed herein, or a salt thereof, to a patient, wherein the effect is chosen from cognition enhancement.

In certain embodiments, the MCT4-mediated disease is chosen from proliferative inflammatory diseases.

Also provided is a method of modulation of a MCT4-mediated function in a subject comprising the administration of a therapeutically effective amount of a compound as disclosed herein.

Also provided is a pharmaceutical composition comprising a compound as disclosed herein, together with a pharmaceutically acceptable carrier.

In certain embodiments, the pharmaceutical composition is formulated for oral administration.

In certain embodiments, the oral pharmaceutical composition is chosen from a tablet and a capsule.

Abbreviations and Definitions

To facilitate understanding of the disclosure, a number of terms and abbreviations as used herein are defined below as follows:

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

When ranges of values are disclosed, and the notation "from $n_1$ . . . to $n_2$" or "between $n_1$ . . . and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a $-C(O)CH_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH═CH—),(—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 8 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene ($—CH_2—$) and ethylene ($—CH_2CH_2—$). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido", "carboxamido", and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino ($CH_3C(O)NH—$).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical C6H4=derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF2-), chloromethylene (—CHCl—) and the like.

The term "heteroalkyl," as used herein, alone or in combination, refers to a stable straight or branched chain, or combinations thereof, fully saturated or containing from 1 to 3 degrees of unsaturation, consisting of the stated number of carbon atoms and from one to three heteroatoms chosen from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, —CH2-NH—OCH3.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from N, O, and S. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member, wherein each said heteroatom may be independently chosen from nitrogen, oxygen, and sulfur. In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms (i.e., C1-C6 alkyl).

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four said members may be heteroatoms chosen from N, O, and S, or 2) bicyclic heteroaryl, wherein each of the fused rings comprises five or six ring members, comprising between them one to four heteroatoms chosen from N, O, and S.

The term "lower cycloalkyl," as used herein, alone or in combination, means a monocyclic cycloalkyl having between three and six ring members (i.e., C3-C6 cycloalkyl). Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from N, O, and S (i.e., C3-C6 heterocycloalkyl). Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen and lower alkyl, either of which may be optionally substituted.

The term "mercaptyl" as used herein, alone or in combination, refers to an RS— group, where R is as defined herein.

The term "nitro," as used herein, alone or in combination, refers to —NO2.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —SO3H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)2-.

The term "N-sulfonamido" refers to a RS(O)2NR'— group with R and R' as defined herein.

The term "S-sulfonamido" refers to a —S(O)2NRR', group, with R and R' as defined herein.

The term "sulfonamido" encompasses both N-sulfonamido and S-sulfonamido groups.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a X3CS(O)2NR— group with X is a halogen and R as defined herein.

The term "trihalomethanesulfonyl" refers to a X3CS(O)2- group where X is a halogen.

The term "trihalomethoxy" refers to a X3CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N3, SH, SCH3, C(O)CH3, CO2CH3, CO2H, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH2CH3), fully substituted (e.g., —CF2CF3), monosubstituted (e.g., —CH2CH2F) or substituted at a level anywhere in-between fully substituted and monosubstituted (e.g., —CH2CF3). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and Rn where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "MCT4 inhibitor" is used herein to refer to a compound that exhibits an IC50 with respect to MCT4 activity of no more than about 100 μM and more typically not more than about 50 μM, as measured in the MCT4 enzyme assay described generally herein below. IC50 is that concentration of inhibitor that reduces the activity of an enzyme (e.g., MCT4) to half-maximal level. Certain compounds disclosed herein have been discovered to exhibit inhibition against MCT4. In certain embodiments, compounds will exhibit an IC50 with respect to MCT4 of no more than about 10 μM; in further embodiments, compounds will exhibit an IC50 with respect to MCT4 of no more than about 5 μM; in yet further embodiments, compounds will exhibit an IC50 with respect to MCT4 of not more than about 1 μM; in yet further embodiments, compounds will exhibit an IC50 with respect to MCT4 of not more than about 200 nM, as measured in the MCT4 binding assay described herein.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in Hydrolysis in Drug and Prodrug Metabolism: Chemistry, Biochemistry, and Enzymology (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Pharmaceutical Salts: Properties, Selection, and Use (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragée-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragée cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragée coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Thus, in another aspect, certain embodiments provide methods for treating MCT4-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of MCT4-mediated disorders.

Also provided herein is a method of treating a monocarboxylate transporter MCT4-mediated disorder in a subject in need thereof, comprising the sequential or co-administration of a compound as disclosed herein or a pharmaceutically acceptable salt thereof, and another therapeutic agent.

In certain embodiments, the therapeutic agent is a protein kinase inhibitor.

In certain embodiments, the protein kinase inhibitor is chosen from Aurora B, EGFR, PLK-1, CDKs inhibitors.

In certain embodiments, the therapeutic agent is chosen from an antimetabolite, bcr-abl inhibitor, DNA damaging agent, EGFR inhibitor, microtubule stabilizing inhibitor, mitotic arrest inhibitor, S-phase inhibitor, and a taxane.

In certain embodiments, the therapeutic agent is a DNA damaging agent chosen from an alkylating agent, anthracycline, antimetabolite agent, crosslinking agent, DNA replication inhibitor, intercalator, microtubule disruptor, PARP inhibitor, radiomimetic agent, radiosensitizer, strand break agent, and topoisomerase II inhibitor.

In certain embodiments, the therapeutic agent is chosen from aminoglutethimide, amsacrine, anastrozole, asparaginase, barasertib, bcg, bicalutamide, bleomycin, buserelin, busulfan, campothecin, capecitabine, carboplatin, carmustine, chlorambucil, chloroquine, cisplatin, cladribine, clodronate, colchicine, cyclophosphamide, cyproterone, cytarabine, dacarbazine, dactinomycin, daunorubicin, demethoxyviridin, dichloroacetate, dienestrol, diethylstilbestrol, docetaxel, doxorubicin, epirubicin, estradiol, estramustine, etoposide, everolimus, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, lonidamine, mechlorethamine, medroxyprogesterone, megestrol, melphalan, mercaptopurine, mesna, metformin, methotrexate, mitomycin, mitotane, mitoxantrone, nilutamide, nocodazole, olaparib, octreotide, oxaliplatin, paclitaxel, pamidronate, pentostatin, perifosine, plicamycin, porfimer, procarbazine, raltitrexed, rituximab, sorafenib, streptozocin, sunitinib, suramin, tamoxifen, temozolomide, temsirolimus, teniposide, testosterone, thioguanine, thiotepa, titanocene dichloride, topotecan, trastuzumab, tretinoin, vinblastine, vincristine, vindesine, and vinorelbine.

For use in cancer and neoplastic diseases a MCT4 inhibitor may be optimally used together with one or more of the following non-limiting examples of anti-cancer agents: (1) alkylating agents, including but not limited to cisplatin (PLATIN), carboplatin (PARAPLATIN), oxaliplatin (ELOXATIN), streptozocin (ZANOSAR), busulfan (MYLERAN) and cyclophosphamide (ENDOXAN); (2) antimetabolites, including but not limited to mercaptopurine (PURINETHOL), thioguanine, pentostatin (NIPENT), cytosine arabinoside (ARA-C), gemcitabine (GEMZAR), fluorouracil (CARAC), leucovorin (FUSILEV) and methotrexate (RHEUMATREX); (3) plant alkaloids and terpenoids, including but not limited to vincristine (ONCOVIN), vinblastine and paclitaxel (TAXOL); (4) topoisomerase inhibitors, including but not limited to irinotecan (CAMPTOSAR), topotecan (HYCAMTIN) and etoposide (EPOSIN); (5) cytotoxic antibiotics, including but not limited to actinomycin D (COSMEGEN), doxorubicin (ADRIAMYCIN), bleomycin (BLENOXANE) and mitomycin (MITOSOL); (6) angiogenesis inhibitors, including but not limited to sunitinib (SUTENT) and bevacizumab (AVASTIN); and (7) tyrosine kinase inhibitors, including but not limited to imatinib (GLEEVEC), erlotinib (TARCEVA), lapatininb (TYKERB) and axitinib (INLYTA).

Where a subject is suffering from or at risk of suffering from an inflammatory condition, a MCT4 inhibitor compound described herein is optionally used together with one or more agents or methods for treating an inflammatory condition in any combination. Therapeutic agents/treatments for treating an autoimmune and/or inflammatory condition include, but are not limited to any of the following examples: (1) corticosteroids, including but not limited to cortisone, dexamethasone, and methylprednisolone; (2) nonsteroidal anti-inflammatory drugs (NSAIDs), including but not limited to ibuprofen, naproxen, acetaminophen, aspirin, fenoprofen (NALFON), flurbiprofen (ANSAID), ketoprofen, oxaprozin (DAYPRO), diclofenac sodium (VOLTAREN), diclofenac potassium (CATAFLAM), etodolac (LODINE), indomethacin (INDOCIN), ketorolac (TORADOL), sulindac (CLINORIL), tolmetin (TOLECTIN), meclofenamate (MECLOMEN), mefenamic acid (PONSTEL), nabumetone (RELAFEN) and piroxicam (FELDENE); (3) immunosuppressants, including but not limited to methotrexate (RHEUMATREX), leflunomide (ARAVA), azathioprine (IMURAN), cyclosporine (NEORAL, SANDIMMUNE), tacrolimus and cyclophosphamide (CYTOXAN); (4) CD20 blockers, including but not limited to rituximab (RITUXAN); (5) Tumor Necrosis Factor (TNF) blockers, including but not limited to etanercept (ENBREL), infliximab (REMICADE) and adalimumab (HUMIRA); (6) interleukin-1 receptor antagonists, including but not limited to anakinra (KINERET); (7) interleukin-6 inhibitors, including but not limited to tocilizumab (ACTEMRA); (8) interleukin-17 inhibitors, including but not limited to AIN457; (9) Janus kinase inhibitors, including but not limited to tasocitinib; and (10) syk inhibitors, including but not limited to fostamatinib.

In certain embodiments, the method further comprises administering non-chemical methods of cancer treatment.

In certain embodiments, the method further comprises administering radiation therapy.

In certain embodiments, the method further comprises administering surgery, thermoablation, focused ultrasound therapy, cryotherapy, or any combination thereof.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating MCT4-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of MCT4-mediated disorders.

The present disclosure provides compounds and pharmaceutical compositions that inhibit glutaminase activity, particularly MCT4 activity and are thus useful in the treatment or prevention of disorders associated with MCT4. Compounds and pharmaceutical compositions of the present disclosure selectively modulate MCT4 and are thus useful in the treatment or prevention of a range of disorders associated with MCT4 and include, but are not limited to, proliferative and inflammatory diseases.

Accordingly, provided herein is a method for inhibiting activity of the monocarboxylate transporter MCT4, or a mutant thereof, in a biological sample comprising the step of contacting said biological sample with a compound as disclosed herein, or a salt thereof.

Also provided herein is a method for inhibiting activity of the monocarboxylate transporter MCT4, or a mutant thereof, in a patient comprising the step of administering to the patient a compound as disclosed herein, or a salt thereof.

Also provided herein is a method for selectively inhibiting activity of the monocarboxylate transporter MCT4, or a mutant thereof, over the monocarboxylate transporter MCT1, or a mutant thereof, in a patient comprising the step of administering to the patient a compound as disclosed herein, or a salt thereof.

In certain embodiments, the inhibition is at least 100-fold selective for MCT4 over MCT1.

In certain embodiments, the compounds and pharmaceutical compositions of the present disclosure may be useful in the treatment or prevention of cancer.

In certain embodiments, the compounds of the present disclosure may be used to prevent or treat cancer, wherein the cancer is one or a variant of Acute Lymphoblastic Leukemia (ALL), Acute Myeloid Leukemia (AML), Adrenocortical Carcinoma, AIDS-Related Cancers (Kaposi Sarcoma and Lymphoma), Anal Cancer, Appendix Cancer, Atypical Teratoid/Rhabdoid Tumor, Basal Cell Carcinoma, Bile Duct Cancer (including Extrahepatic), Bladder Cancer, Bone Cancer (including Osteosarcoma and Malignant Fibrous Histiocytoma), Brain Tumor (such as Astrocytomas, Brain and Spinal Cord Tumors, Brain Stem Glioma, Central Nervous System Atypical Teratoid/Rhabdoid Tumor, Central Nervous System Embryonal Tumors, Craniopharyngioma, Ependymoblastoma, Ependymoma, Medulloblastoma, Medulloepithelioma, Pineal Parenchymal Tumors of Intermediate Differentiation, Supratentorial Primitive Neuroectodermal Tumors and Pineoblastoma), Breast Cancer, Bronchial Tumors, Burkitt Lymphoma, Carcinoid Tumor, Carcinoma of Unknown Primary, Central Nervous System (such as Atypical Teratoid/Rhabdoid Tumor, Embryonal Tumors and Lymphoma), Cervical Cancer, Childhood Cancers, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma (Mycosis Fungoides and Sézary Syndrome), Duct, Bile (Extrahepatic), Ductal Carcinoma In Situ (DCIS), Embryonal Tumors (Central Nervous System), Endometrial Cancer, Ependymoblastoma, Ependymoma, Esophageal Cancer, Esthesioneuroblastoma, Ewing Sarcoma Family of Tumors, Extracranial Germ Cell Tumor, Extragonadal Germ Cell Tumor, Extrahepatic Bile Duct Cancer, Eye Cancer (like Intraocular Melanoma, Retinoblastoma), Fibrous Histiocytoma of Bone (including Malignant and Osteosarcoma) Gallbladder Cancer, Gastric (Stomach) Cancer, Gastrointestinal Carcinoid Tumor, Gastrointestinal Stromal Tumors (GIST), Germ Cell Tumor (Extracranial, Extragonadal, Ovarian), Gestational Trophoblastic Tumor, Glioma, Hairy Cell Leukemia, Head and Neck Cancer, Heart Cancer, Hepatocellular (Liver) Cancer, Histiocytosis, Langerhans Cell, Hodgkin Lymphoma, Hypopharyngeal Cancer, Intraocular Melanoma, Islet Cell Tumors (Endocrine, Pancreas), Kaposi Sarcoma, Kidney (including Renal Cell), Langerhans Cell Histiocytosis, Laryngeal Cancer, Leukemia (including Acute Lymphoblastic (ALL), Acute Myeloid (AML), Chronic Lymphocytic (CLL), Chronic Myelogenous (CML), Hairy Cell), Lip and Oral Cavity Cancer, Liver Cancer (Primary), Lobular Carcinoma In Situ (LCIS), Lung Cancer (Non-Small Cell and Small Cell), Lymphoma (AIDS-Related, Burkitt, Cutaneous T-Cell (Mycosis Fungoides and Sézary Syndrome), Hodgkin, Non-Hodgkin, Primary Central Nervous System (CNS), Macroglobulinemia, Waldenström, Male Breast Cancer, Malignant Fibrous Histiocytoma of Bone and Osteosarcoma, Medulloblastoma, Medulloepithelioma, Melanoma (including Intraocular (Eye)), Merkel Cell Carcinoma, Mesothelioma (Malignant), Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic (CML), Myeloid Leukemia, Acute (AML), Myeloma and Multiple Myeloma, Myeloproliferative Disorders (Chronic), Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip and, Oropharyngeal Cancer, Osteosarcoma and Malignant Fibrous Histiocytoma of Bone, Ovarian Cancer (such as Epithelial, Germ Cell Tumor, and Low Malignant Potential Tumor), Pancreatic Cancer (including Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pineal Parenchymal Tumors of Intermediate Differentiation, Pineoblastoma and Supratentorial Primitive Neuroectodermal Tumors, Pituitary Tumor, Plasma Cell Neoplasm/Multiple Myeloma, Pleuropulmonary Blastoma, Pregnancy and Breast Cancer, Primary Central Nervous System (CNS) Lymphoma, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma (like Ewing Sarcoma Family of Tumors, Kaposi, Soft Tissue, Uterine), Sézary Syndrome, Skin Cancer (such as Melanoma, Merkel Cell Carcinoma, Nonmelanoma), Small Cell Lung Cancer, Small Intestine Cancer, Soft Tissue Sarcoma, Squamous Cell Carcinoma, Squamous Neck Cancer with Occult Primary, Metastatic, Stomach (Gastric) Cancer, Supratentorial Primitive Neuroectodermal Tumors, T-Cell Lymphoma (Cutaneous, Mycosis Fungoides and Sézary Syndrome), Testicular Cancer, Throat Cancer, Thymoma and Thymic Carcinoma, Thyroid Cancer, Transitional Cell Cancer of the Renal Pelvis and Ureter, Trophoblastic Tumor (Gestational), Unknown Primary, Unusual Cancers of Childhood, Ureter and Renal Pelvis, Transitional Cell Cancer, Urethral Cancer, Uterine Cancer, Endometrial, Uterine Sarcoma, Waldenström Macroglobulinemia or Wilms Tumor.

In certain embodiments, the cancer to be treated is one specific to T-cells such as T-cell lymphoma and lymphoblastic T-cell leukemia.

In certain embodiments, methods described herein are used to treat a disease condition comprising administering to a subject in need thereof a therapeutically effective amount of a compound of Formula I or pharmaceutically acceptable salt thereof, wherein the condition is cancer which has developed resistance to chemotherapeutic drugs and/or ionizing radiation.

In certain embodiments, the compounds and pharmaceutical compositions of the present disclosure may be useful in the treatment or prevention of an inflammatory disease.

In certain embodiments, the compounds of the present disclosure may be used to prevent or treat inflammatory disease, wherein the inflammatory disease is one or a variant of acid-induced lung injury, acne (PAPA), acute respiratory distress syndrome, Addison's disease, adrenal hyperplasia, adrenocortical insufficiency, ageing, AIDS, alcoholic hepatitis, alcoholic liver disease, allergen induced asthma, allergic bronchopulmonary aspergillosis, allergic conjunctivitis, alopecia, Alzheimer's disease, amyloidosis, amyotrophic lateral sclerosis, angina pectoris, angioedema, anhidrotic ectodermal dysplasia (e.g. with immune deficiency), ankylosing spondylitis, anterior segment inflammation, antiphospholipid syndrome, aphthous stomatitis, appendicitis, asthma, atherosclerosis, atopic dermatitis, autoimmune diseases, autoimmune hepatitis, bee sting-induced inflammation, Behcet's disease, Bell's Palsy, berylliosis, Blau syndrome, bone pain, bronchiolitis, burns, bursitis, cardiac hypertrophy, carpal tunnel syndrome, catabolic disorders, cataracts, cerebral aneurysm, chemical irritant-induced inflammation, chorioretinitis, chronic heart failure, chronic lung disease of prematurity, chronic obstructive pulmonary disease, colitis, complex regional pain syndrome, connective tissue disease, corneal ulcer, Crohn's disease, cryopyrin-associated periodic syndromes, cryptococcosis, cystic fibrosis, deficiency of the interleukin-1-receptor antagonist, dermatitis, dermatitis endotoxemia, dermatomyositis, endometriosis, endotoxemia, epicondylitis, erythroblastopenia, familial amyloidotic polyneuropathy, familial cold urticaria, familial Mediterranean fever, fetal growth retardation, glaucoma, glomerular disease, glomerular nephritis, gout, gouty arthritis, graft-versus-host disease, gut diseases, head injury, headache, hearing loss, heart disease, hemolytic anemia, Henoch-Scholein purpura, hepatitis, hereditary periodic fever syndrome, herpes zoster and simplex, HIV-1, Huntington's disease, hyaline membrane disease, hyperammonemia, hypercalcemia, hypercholesterolemia, hyperimmunoglobulinemia D with recurrent fever, hypoplastic and other anemias, idiopathic pulmonary fibrosis, idiopathic thrombocytopenic purpura, incontinentia pigmenti, infectious mononucleosis, inflammatory bowel disease, inflammatory lung disease, inflammatory neuropathy, inflammatory pain, insect bite-induced inflammation, iritis, ischemia/reperfusion, juvenile rheumatoid arthritis, keratitis, kidney disease, kidney injury caused by parasitic infections, kidney transplant rejection prophylaxis, leptospirosis, Loeffler's syndrome, lung injury, lupus, lupus nephritis, meningitis, mesothelioma, mixed connective tissue disease, Muckle-Wells syndrome (urticaria deafness amyloidosis), multiple sclerosis, muscle wasting, muscular dystrophy, myasthenia gravis, myocarditis, mycosis fungoides, myelodysplastic syndrome, myositis, nasal sinusitis, necrotizing enterocolitis, neonatal onset multisystem inflammatory disease (NOMID), nephrotic syndrome, neuritis, neuropathological diseases, non-allergen induced asthma, obesity, ocular allergy, optic neuritis, organ transplant, osteoarthritis, otitis media, Paget's disease, pain, pancreatitis, Parkinson's disease, pemphigus, pericarditis, periodic fever, periodontitis, pertussis, perineal or peritoneal endometriosis, pharyngitis and adenitis (PFAPA syndrome), plant irritant-induced inflammation, pneumocystis infection, pneumonia, pneumonitis, poison ivy/urushiol oil-induced inflammation, polyarteritis nodosa, polychondritis, polycystic kidney disease, polymyositis, psoriasis, psychosocial stress disease, pulmonary disease, pulmonary fibrosis, pulmonary hypertension, pyoderma gangrenosum, pyogenic sterile arthritis, renal disease, retinal disease, rheumatic disease, rheumatoid arthritis, rheumatic carditis, sarcoidosis, sebborrhea, sepsis, severe pain, sickle cell, sickle cell anemia, silica-induced diseases, Sjögren's syndrome, skin diseases, sleep apnea, spinal cord injury, Stevens-Johnson syndrome, stroke, subarachnoid hemorrhage, sunburn, systemic sclerosis (scleroderma), temporal arteritis, tenosynovitis, thrombocytopenia, thyroiditis, tissue transplant, TNF receptor associated periodic syndrome (TRAPS), Toxoplasmosis, transplant, traumatic brain injury, tuberculosis, type 1 diabetes, type 2 diabetes, ulcerative colitis, urticaria, uveitis, Wegener's granulomatosis, and weight loss.

Thus, in another aspect, certain embodiments provide methods for treating a monocarboxylate transporter MCT4-mediated disorder in a subject in need thereof, comprising the step of administering to said patient a compound as disclosed herein, or a pharmaceutically acceptable salt thereof.

In certain embodiments, the subject is a human.

In certain embodiments, the monocarboxylate transporter MCT4-mediated disorder is chosen from an inflammatory disorder and a proliferative disorder.

In certain embodiments, the monocarboxylate transporter MCT4-mediated disorder is a proliferative disorder.

In certain embodiments, the proliferative disorder is cancer.

In certain embodiments, the cancer is chosen from adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, and Wilms' tumor.

In certain embodiments, the monocarboxylate transporter MCT4-mediated disorder is an inflammatory disorder.

In certain embodiments, the inflammatory disorder is chosen from Crohn's disease, ulcerative colitis, idiopathic pulmonary fibrosis, muscular dystrophy, rheumatoid arthritis, and systemic sclerosis (scleroderma).

Also provided herein is a compound as disclosed herein, or a pharmaceutically acceptable salt thereof, for use in human therapy.

Also provided herein is a compound as disclosed herein, or a pharmaceutically acceptable salt thereof, for use in treating a monocarboxylate transporter MCT4-mediated disorder, for example as disclosed in any of the embodiments and paragraphs above pertaining to methods of treatment.

Also provided herein is the use of a compound as disclosed herein, or a pharmaceutically acceptable salt thereof, for the manufacture of a medicament to treat a monocarboxylate transporter MCT4-mediated disorder, for example as disclosed in any of the embodiments and paragraphs above pertaining to methods of treatment.

Metabolic syndrome (also known as metabolic syndrome X) is characterized by having at least three of the following symptoms: insulin resistance; abdominal fat—in men this is defined as a 40 inch waist or larger, in women 35 inches or larger; high blood sugar levels—at least 110 milligrams per deciliter (mg/dL) after fasting; high triglycerides—at least 150 mg/dL in the blood stream; low HDL—less than 40 mg/dL; pro-thrombotic state (e.g. high fibrinogen or plasminogen activator inhibitor in the blood); or blood pressure of 130/85 mmHg or higher. A connection has been found between metabolic syndrome and other conditions such as obesity, high blood pressure and high levels of LDL cholesterol, all of which are risk factors for cardiovascular diseases. For example, an increased link between metabolic syndrome and atherosclerosis has been shown. People with metabolic syndrome are also more prone to developing type 2 diabetes, as well as PCOS (polycystic ovarian syndrome) in women and prostate cancer in men.

As described above, insulin resistance can be manifested in several ways, including type 2 diabetes. Type 2 diabetes is the condition most obviously linked to insulin resistance. Compensatory hyperinsulinemia helps maintain normal glucose levels—often for decades, before overt diabetes develops. Eventually the beta cells of the pancreas are unable to overcome insulin resistance through hypersecretion. Glucose levels rise, and a diagnosis of diabetes can be made. Patients with type 2 diabetes remain hyperinsulinemic until they are in an advanced stage of disease. As described above, insulin resistance can also correlate with hypertension. One half of patients with essential hypertension are insulin resistant and hyperinsulinemic, and there is evidence that blood pressure is linked to the degree of insulin resistance. Hyperlipidemia, too, is associated with insulin resistance. The lipid profile of patients with type 2 diabetes includes increased serum very-low-density lipoprotein cholesterol and triglyceride levels and, sometimes, a decreased low-density lipoprotein cholesterol level. Insulin resistance has been found in persons with low levels of high-density lipoprotein. Insulin levels have also been linked to very-low-density lipoprotein synthesis and plasma triglyceride levels.

Accordingly, also disclosed are methods of treating insulin resistance in a subject comprising selecting a subject in need of treatment for insulin resistance; and administering to the subject an effective amount of a compound that inhibits MCT4.

Specific diseases to be treated by the compounds, compositions, and methods disclosed herein are those mediated at least in part by MCT4. Accordingly, disclosed herein are methods: for reducing glycogen accumulation in a subject; for raising HDL or HDLc, lowering LDL or LDLc, shifting LDL particle size from small dense to normal LDL, lowering VLDL, lowering triglycerides, or inhibiting cholesterol absorption in a subject; for reducing insulin resistance, enhancing glucose utilization or lowering blood pressure in a subject; for reducing visceral fat in a subject; for reducing serum transaminases in a subject; or for treating disease; all comprising the administration of a therapeutic amount of a compound as described herein, to a patient in need thereof. In further embodiments, the disease to be treated may be a metabolic disease. In further embodiment, the metabolic disease may be selected from the group consisting of: obesity, diabetes melitus, especially Type 2 diabetes, hyperinsulinemia, glucose intolerance, metabolic syndrome X, dyslipidemia, hypertriglyceridemia, hypercholesterolemia, and hepatic steatosis. In other embodiments, the disease to be treated may be selected from the group consisting of: cardiovascular diseases including vascular disease, atherosclerosis, coronary heart disease, cerebrovascular disease, heart failure and peripheral vessel disease. In preferred embodiments, the methods above do not result in the induction or maintenance of a hypoglycemic state.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

List of Abbreviations $Ac_2O$=acetic anhydride; AcCl=acetyl chloride; AcOH=acetic acid; AIBN=azobisisobutyronitrile;

aq.=aqueous; BAST=bis(2-methoxyethyl)aminosulfur trifluoride; BCECF=2',7'-bis-(carboxyethyl)-5(6)-carboxyfluorescein; Bu=butyl; Bu3SnH=tributyltin hydride; $CD_3OD$=deuterated MeOH; $CDCl_3$=deuterated chloroform; CDI=1,1'-carbonyldiimidazole; DAST=(diethylamino)sulfur trifluoride; dba=dibenzylideneacetone; DBU=1,8-diazabicyclo[5.4.0]undec-7-ene; DCM=dichloromethane; DEAD=diethyl azodicarboxylate; DIAD=diisopropyl azodicarboxylate; DIBAL-H=di-iso-butyl aluminium hydride; DIEA=DIPEA=N,N-diisopropylethylamine; DMAP=4-dimethylaminopyridine; DMF=N,N-dimethylformamide; DMSO-$d_6$=deuterated dimethyl sulfoxide; DMSO=dimethyl sulfoxide; DPPA=diphenylphosphoryl azide; dppf=1,1'-bis(diphenylphosphino)ferrocene; EDC.HCl=EDCI.HCl=1-ethyl-3-(3-dimethylaminopropyl)carbodiimide hydrochloride; Et=ethyl; $Et_2O$=diethyl ether; EtOAc=ethyl acetate; EtOH=ethanol; h=hour; HATU=2-(1H-7-azabenzotriazol-1-yl)-1,1,3,3-tetramethyl uronium hexafluorophosphate methanaminium; HMDS=hexamethyldisilazane; HOBT=1-hydroxybenzotriazole; i-Pr=isopropyl=2-propyl; i-PrOH=isopropanol; LAH=lithium aluminium hydride; LDA=lithium diisopropyl amide; LiHMDS=Lithium bis(trimethylsilyl)amide; MeCN=acetonitrile; MeI=methyl iodide; MeOH=MeOH; MP-carbonate resin=macroporous triethylammonium methylpolystyrene carbonate resin; MsCl=mesyl chloride; MTBE=methyl tertiary butyl ether; n-BuLi=n-butyllithium; NaHMDS=sodium bis(trimethylsilyl)amide; NaOEt=sodium ethoxide; NaOMe=sodium methoxide; NaOtBu=sodium t-butoxide; NBS=N-bromosuccinimide; NCS=N-chlorosuccinimide; NIS=N-iodosuccinimide; NMP=N-Methyl-2-pyrrolidone; $Pd(PPh_3)_4$=tetrakis(triphenylphosphine)-palladium(0); $Pd_2(dba)_3$=tris(dibenzylideneacetone)dipalladium(0); $PdCl_2(PPh_3)2$=bis(triphenylphosphine)palladium(II) dichloride; PG=protecting group; Ph=phenyl; prep-HPLC=preparative high-performance liquid chromatography; PMB=para-methoxybenzyl; PMBCl=para-methoxybenzyl chloride; PMBOH=para-methoxybenzyl alcohol; PyBop=(benzotriazol-1-yloxy)tripyrrolidinophosphonium hexafluorophosphate; Pyr=pyridine; RT=room temperature; RuPhos=2-dicyclohexylphosphino-2',6'-diisopropoxybiphenyl; sat.=saturated; ss=saturated solution; tBu=t-Bu=tert-butyl=1,1-dimethylethyl; TBAF=tetrabutylammonium fluoride; TBDPS=t-butyldiphenylsilyl; t-BuOH=tert-butanol; T3P=Propylphosphonic Anhydride; TEA=$Et_3N$=triethylamine; TFA=trifluoroacetic acid; TFAA=trifluoroacetic anhydride; THF=tetrahydrofuran; TIPS=triisopropylsilyl; Tol=toluene; TsCl=tosyl chloride; Trt=trityl=(triphenyl)methyl; Xantphos=4,5-Bis(diphenylphosphino)-9,9-dimethylxanthene; XPhos=2-dicyclohexylphosphino-2',4',6'-triisopropylbiphenyl.

General Synthetic Methods for Preparing Compounds

The following schemes can be used to practice the present invention.

Scheme I

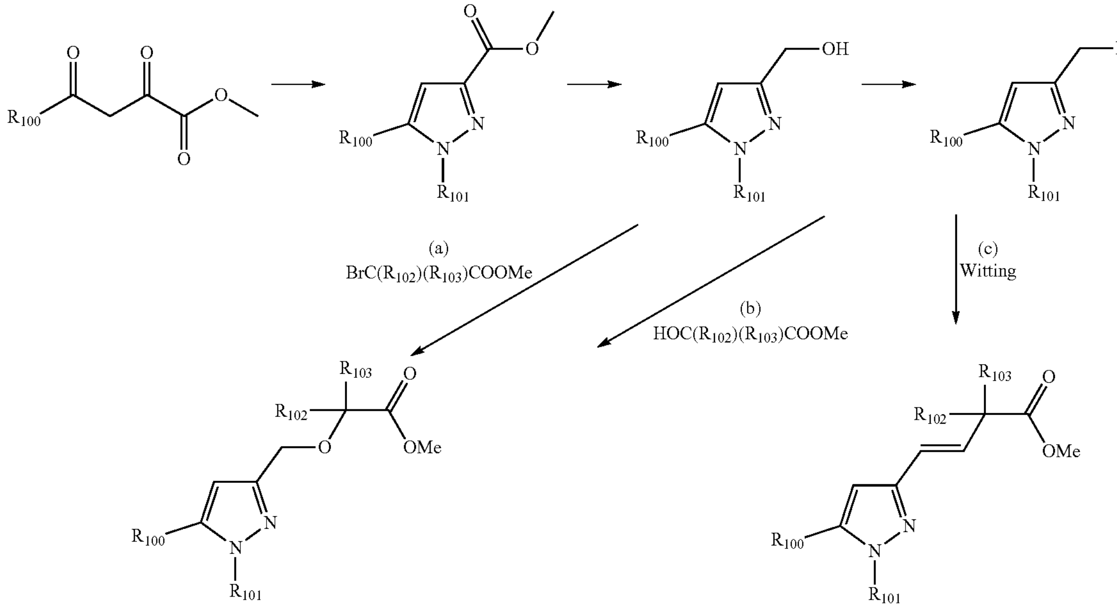

A general, but not intended to be limiting, synthetic scheme for the examples in this disclosure is depicted in Scheme I. An appropriately substituted 2,4-diketobutanoic ester is reacted with a substituted hydrazine to form the pyrazole core. Reduction of the ester gives a hydroxymethyl compound. The side chain can be completed by direct alkylation with a 2-haloester, as shown in pathway (a). Alternatively, the hydroxymethyl functionality is converted to a halomethyl group, which can undergo displacement with a 2-hydroxyester, as shown in pathway (b), or be transformed via Wittig chemistry, as shown in pathway (c) to given an alkene.

Scheme II (a)
$R_{100}X$ i) BuLi
ii) MeCON(Me)(OMe)
201

-continued

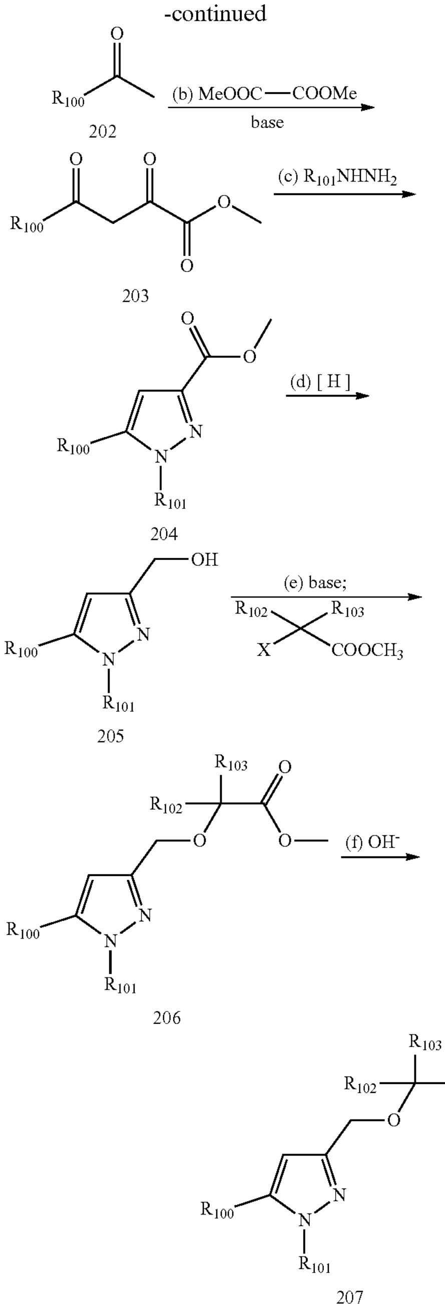

Scheme II, depicted above, may be use to prepare certain examples disclosed herein. In step (a), organohalide 201 is converted to an organolithium, followed by condensation with the substituted acetamide to give acetyl functionalized compound 202. This compound is reacted in step (b) under Claisen conditions with an oxalate ester to give 2,4-diketoester 203, which is then reacted with a substituted hydrazine in step (c) to construct the pyrazole core of 204. The ester functionality is reduced in step (d), and in step (e) the resulting alcohol 205 is alkylated with an appropriate haloacetate ester, affording ether 206. Finally, the ester is hydrolyzed in step (f) under basic conditions to give carboxylic acid 207. In the scheme as depicted, $R_{100}$-$R_{103}$ will be understood by one of skill in the art to be any appropriate group. For example, in certain embodiments, $R_{100}$ and $R_{101}$ may be independently chosen from aryl, cycloalkyl, heterocycloalkyl, and heteroaryl, any of which is optionally substituted. Likewise, in certain embodiments, $R_{102}$ and $R_{103}$ may be independently chosen from hydrogen, alkyl, and halogen. $R_{100}$-$R_{103}$ may also correspond to the groups defined in Formula I, II, or any other formula disclosed herein. Finally, this scheme may be joined at any point by employing a suitable intermediate shown herein that is available either from commercial sources or alternate synthetic methods.

Scheme III

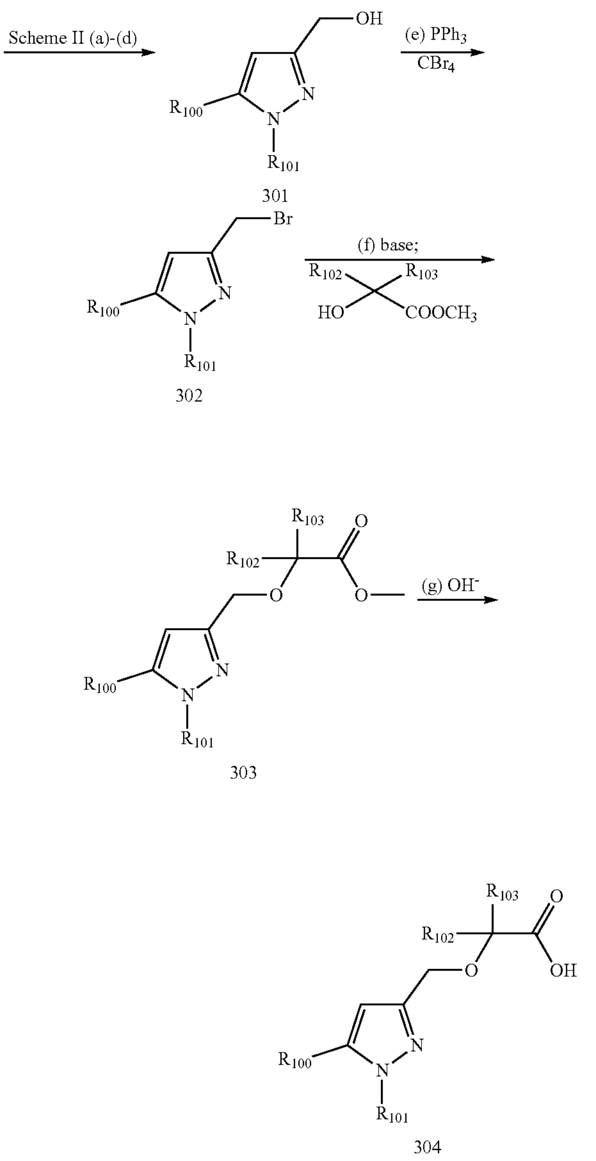

Scheme III, depicted above, can be used to prepare certain example compounds disclosed herein. Steps (a)-(d) from Scheme I are used to obtain pyrazolemethanol 301, which is then converted to bromomethyl compound 302 in step (e), using one of various techniques available for this transformation. Alkyl halide 302 is then reacted under Williamson ether conditions with a hydroxyester in step (f), to give 303. Synthesis is then completed in step (g) by ester hydrolysis to 304.

Scheme IV

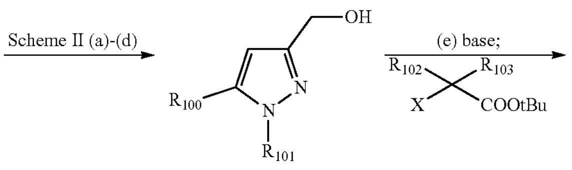

401

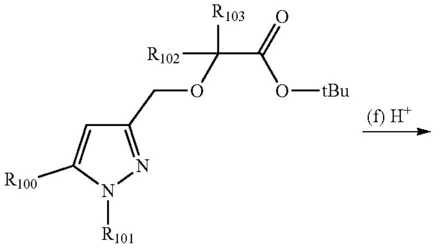

402

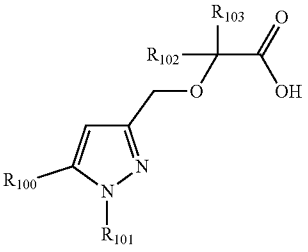

403

Scheme IV, depicted above, can be utilized for certain example compounds disclosed herein. Steps (a)-(d) from Scheme I are used to obtain pyrazolemethanol 401, which is alkylated to give tBu ester 402. Cleavage of the ester is accomplished under acidic conditions, to give acid 403.

Scheme V

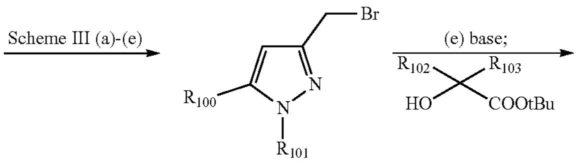

501

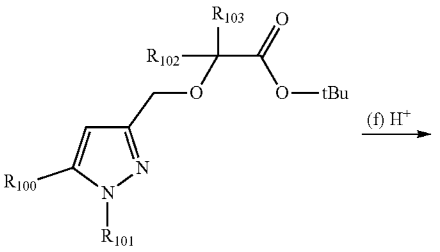

502

-continued

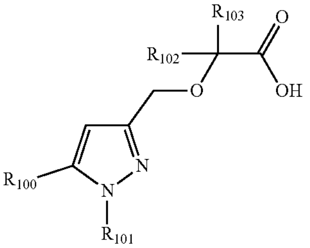

503

Scheme V, depicted above, can be utilized for certain example compounds disclosed herein. Steps (a)-(e) from Scheme III are used to obtain (bromomethyl)pyrazole 501. Reaction with a hydroxyester under basic conditions gives tBu ester 502. Cleavage of the ester is accomplished under acidic conditions, to give acid 503.

Scheme VI

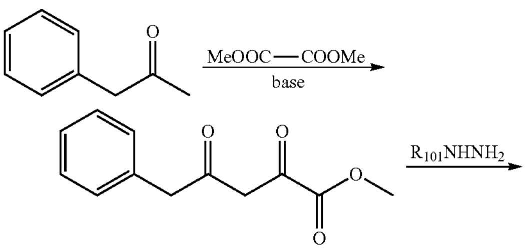

601

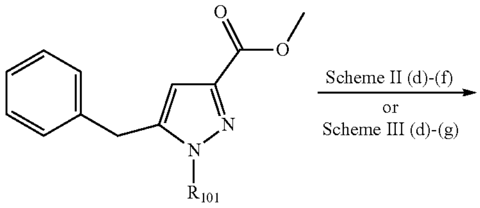

602

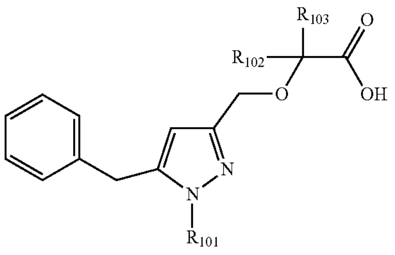

603

Scheme VI, depicted above, may be use to prepare certain example compounds disclosed herein. Phenylacetone is condensed with oxalate ester to give the 5-phenylpentanoate ester 601. Condensation with substituted hydrazine forms the pyrazole core of 602. Ester reduction, alcohol alkylation, and ester hydrolysis proceeds as before. Synthesis of acid 603 is completed by either using steps (d)-(f) from Scheme II, or steps (d)-(g) from Scheme III.

Scheme VII

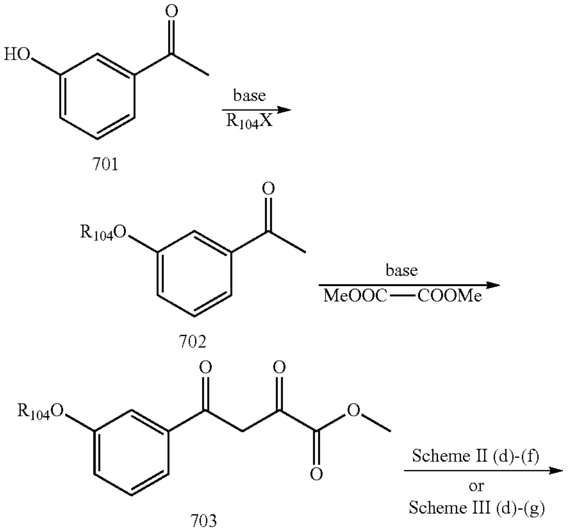

701

702

703

-continued

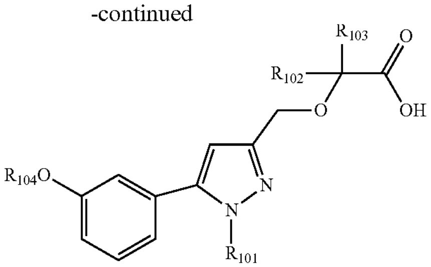

704

Scheme VII, depicted above, can be used to prepare certain example compounds disclosed herein. Acetylated hydroxyaryl compound 701 reacts under Williamson ether conditions with an alkyl halide or similar compound, giving alkoxyaryl compound 702. Condensation with oxalate ester gives a 2,4-diketoester 703, as in Scheme II. Synthesis is completed by either using steps (d)-(f) from Scheme II, or steps (d)-(g) from Scheme III.

Scheme VIII

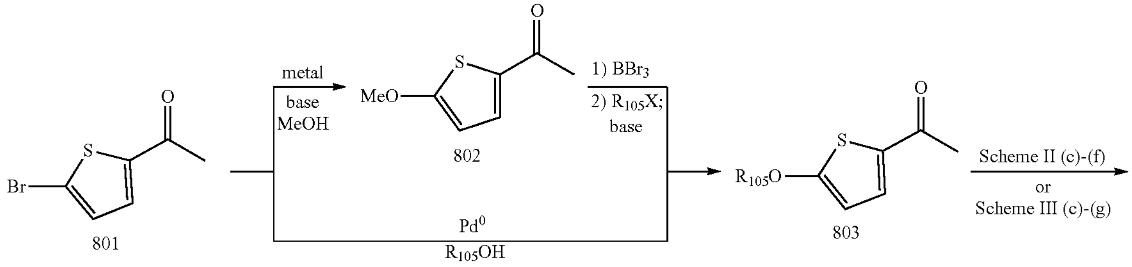

801

802

803

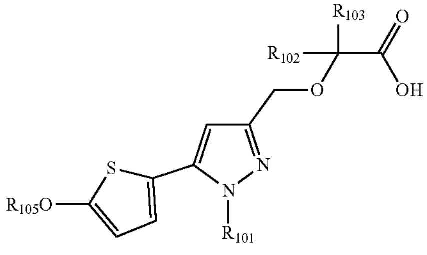

804

Scheme VIII, depicted above, can be used to synthesize certain example compounds disclosed herein. Bromoaryl compound 801 is converted to methoxyaryl compound 802 in the presence of a suitable metal catalyst in the presence of base. The methyl ether is cleaved with a Lewis acid. The resulting hydroxyl compound is reacted under Williamson ether conditions to give alkoxyaryl compound 803. Alternatively, the bromoaryl compound is reacted directly with an alcohol of interest to afford the desired ether 803 directly. In the scheme as depicted, $R_{100}$-$R_{106}$ will be understood by one of skill in the art to be any appropriate group. Synthesis of 804 is completed by either using steps (c)-(f) from Scheme II, or steps (c)-(g) from Scheme III.

Scheme IX

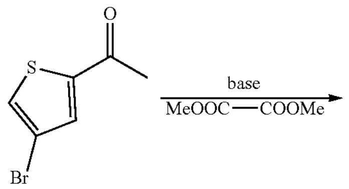

901

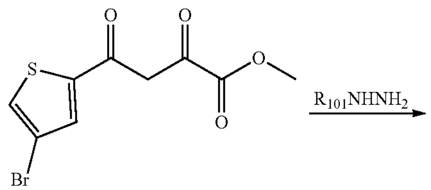

902

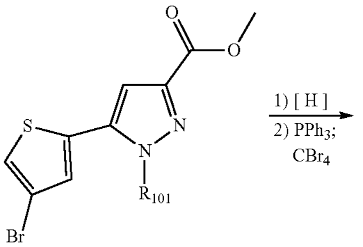

903

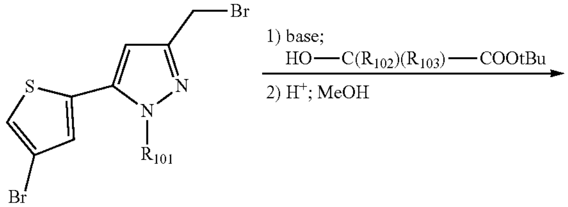

904

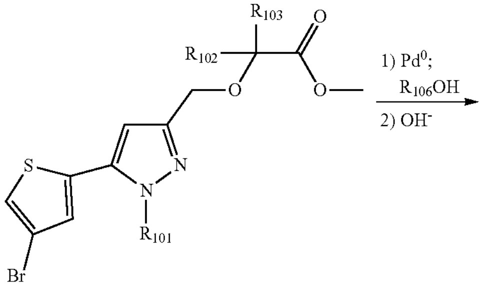

905

-continued

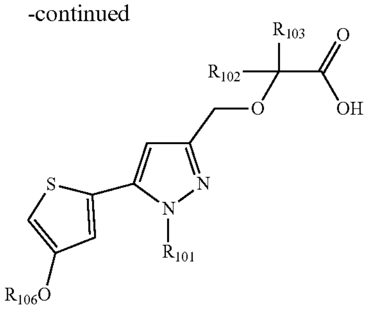

906

Scheme IX, depicted above, can be used to synthesize certain example compounds disclosed herein. Bromoaryl compound 901 is converted to the (bromomethyl) pyrazole 904. The compound is reacted under Williamson ether conditions with a suitable glycolic ester to give ether 905. Transesterification to the methyl ester 905 is followed by displacement of the aryl bromide using an appropriate $Pd^0$ catalyst. Synthesis is completed by basic hydrolysis of the methyl ester, affording acid 906.

Scheme X

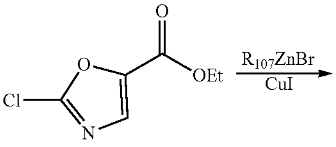

1001

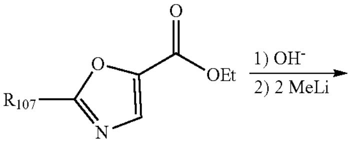

1002

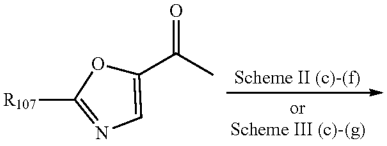

1003

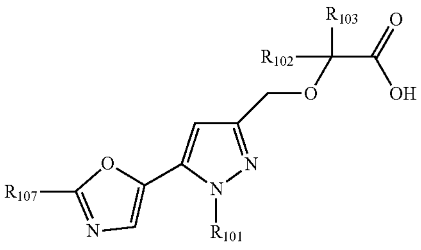

1004

Scheme X, depicted above, can be used to synthesize certain example compounds disclosed herein. Chloroaryl carboxylic ester 1001 is coupled with an organozinc reagent in the presence of copper(I) iodide to give 1002. The ester functionality is converted to methyl ketone 1003. Condensation with diethyl oxalate gives the Q-diketone compound. Synthesis of 1004 is completed by either using steps (c)-(f) from Scheme II, or steps (c)-(g) from Scheme III.

Scheme XI

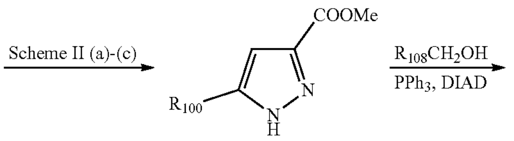

1101

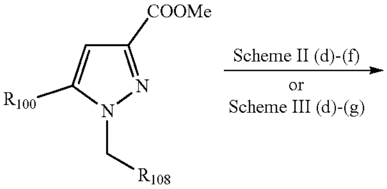

1102

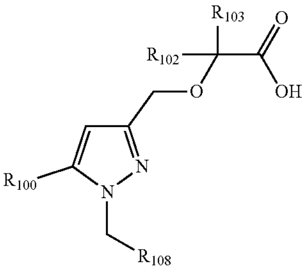

1103

Scheme XI, depicted above, can be used to synthesize certain example compounds disclosed herein. Pyrazole ester 1101 is obtained via steps (a)-(c) of Scheme II. The compound is coupled under Mitsunobu conditions with an appropriate alcohol to give alkylated product 1102. Synthesis of acid 1103 is completed by either using steps (d)-(f) from Scheme II, or steps (d)-(g) from Scheme III.

Scheme XII

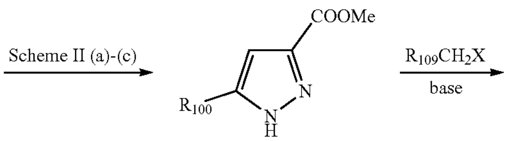

1201

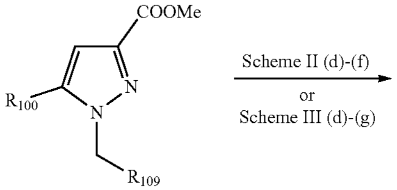

1202

-continued

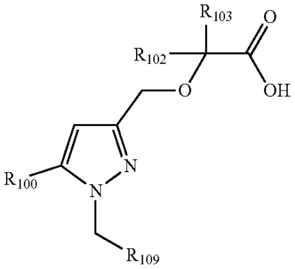

1203

Scheme XII, depicted above, can be used to synthesize certain example compounds disclosed herein. Pyrazole ester 1201 is obtained via steps (a)-(c) of Scheme II. The compound is coupled with an alkyl halide in the presence of base to give 1202. Synthesis of acid 1203 is completed by either using steps (d)-(f) from Scheme II, or steps (d)-(g) from Scheme III.

Scheme XIII

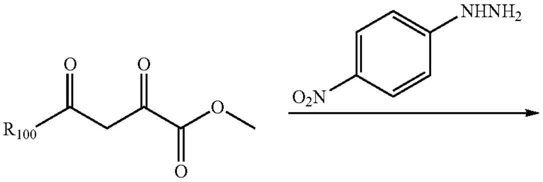

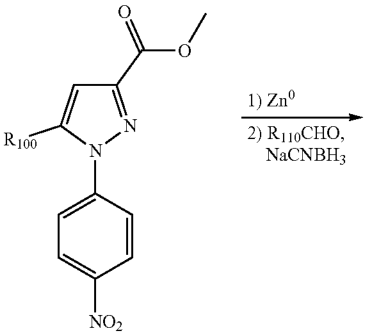

1301

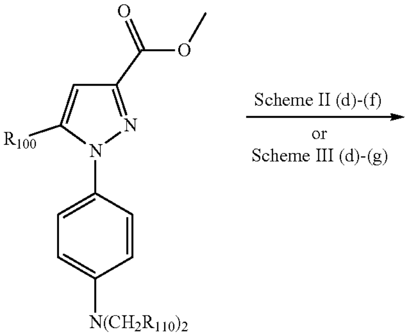

1302

-continued

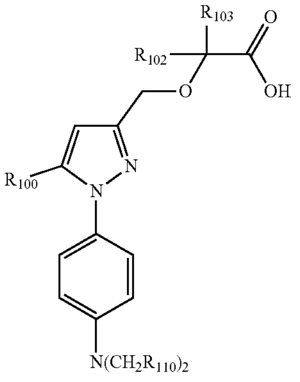

1303

Scheme XIII, depicted above, may be used to prepared certain example compounds disclosed herein. A 2,4-diketoester is condensed with a nitroaromatic compound, such as 4-nitroaniline, to give pyrazole moiety 1301. Reduction of the nitro group is followed by reductive amination to give a (dialkyl)amino compound 1302. Synthesis of acid 1303 is completed by either using steps (d)-(f) from Scheme II, or steps (d)-(g) from Scheme III.

Scheme XIV

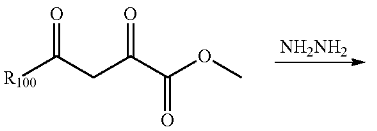

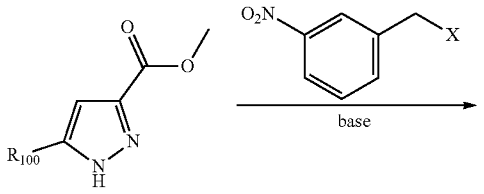

1401

-continued

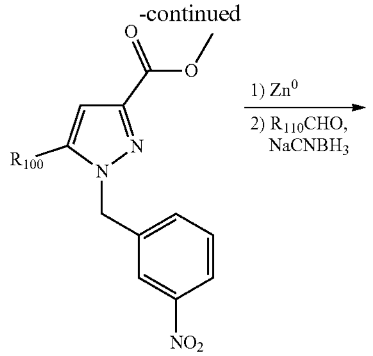

1402

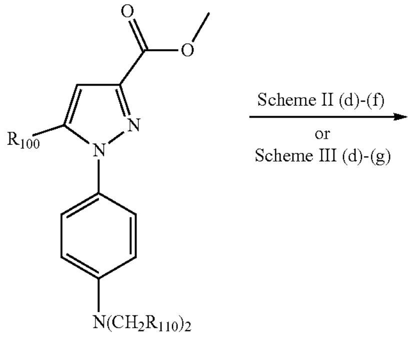

1403

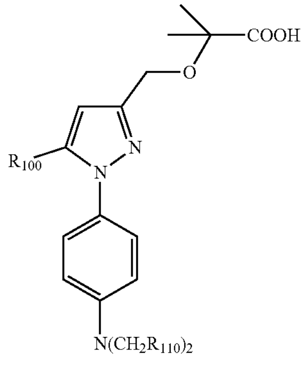

1404

Scheme XIV, depicted above, can be used to synthesize certain example compounds disclosed herein. A 2,4-diketoester is condensed with hydrazine to form pyrazole 1401, which is then alkylated with a substituted benzyl bromide to afford 1402. Reduction to the amine is followed by reductive alkylation to give substituted amine 1403. Synthesis of acid 1404 is completed by either using steps (d)-(f) from Scheme II, or steps (d)-(g) from Scheme III.

Scheme XV

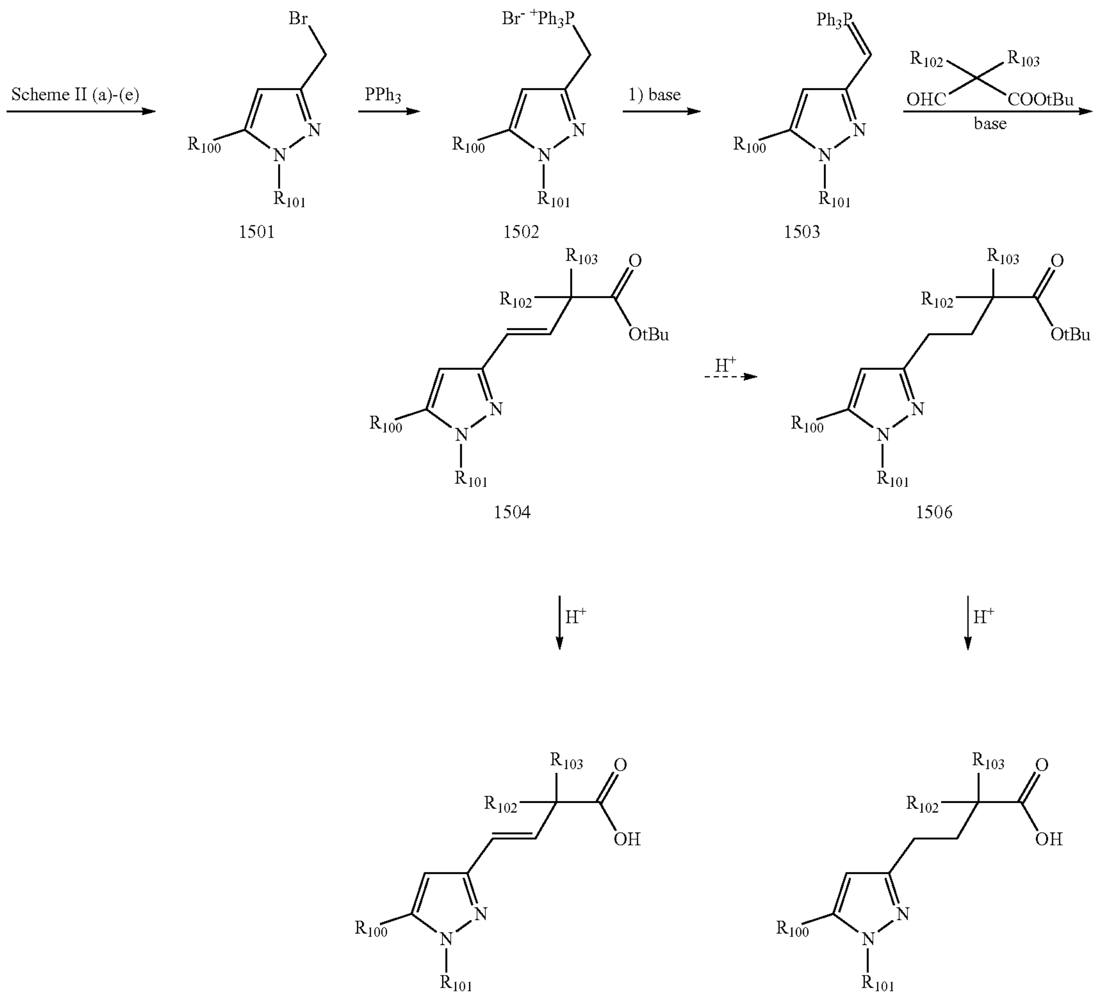

Scheme XV, depicted above, can be used to synthesize certain example compounds disclosed herein. (Bromomethyl) pyrazole 1501, obtained via steps (a)-(e) of Scheme II, is converted to phosphonium salt 1502. Treatment with base forms phosphorane ylid 1503; Wittig reaction with an appropriate aldehyde gives alkene 1504. The alkene can be optionally hydrogenated to give alkane 1506. Synthesis is completed by ester hydrolysis give alkene 1505 or alkane 1507, respectively.

Scheme XVI

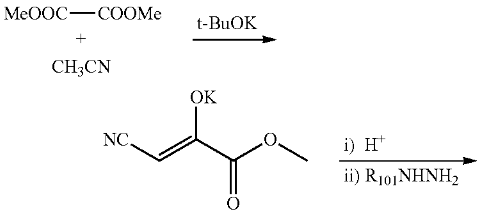

1601

-continued

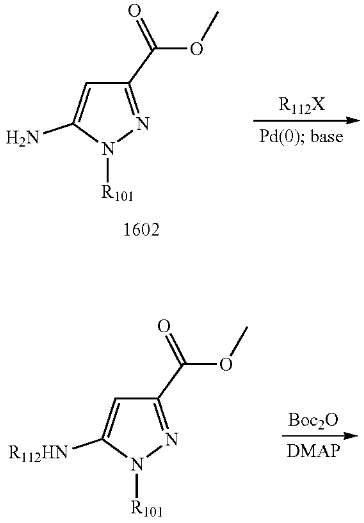

1603

-continued

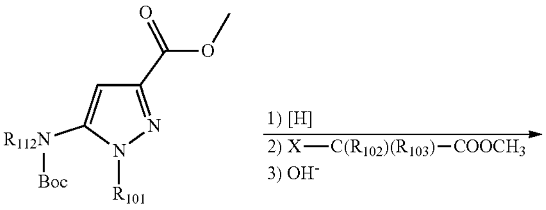

1604

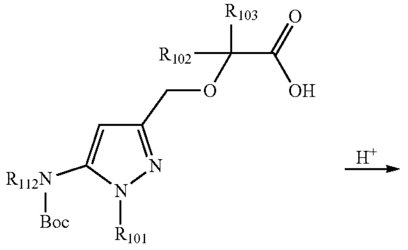

1605

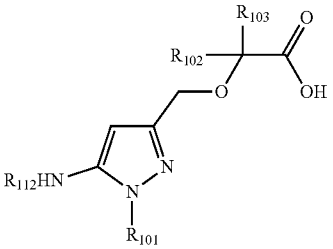

1606

Scheme XVI, depicted above, may be use to prepare certain example compounds disclosed herein. Acetonitrile is condensed with an oxalate ester to give a ketoester product, which can be isolated as its salt 1601. Neutralization of the salt is followed by condensation with a substituted hydrazine to give a 5-aminopyrazole compound 1602. The amino functionality is then substituted by reaction with an organohalide in a palladium (0) mediated reaction, affording 1603, and then protected as its Boc carbamate 1604. Ester reduction, alcohol alkylation, and ester hydrolysis proceeds as before to give acid 1605. The Boc protecting group is removed under acidic conditions, affording 1606.

Scheme XVII

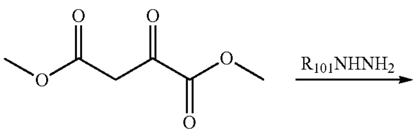

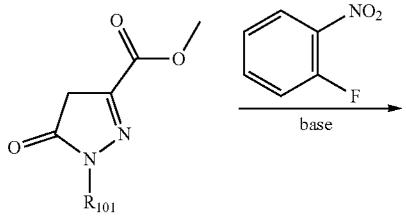

1701

-continued

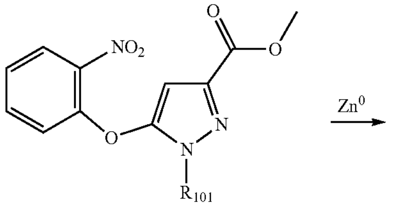

1702

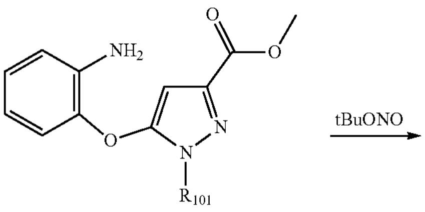

1703

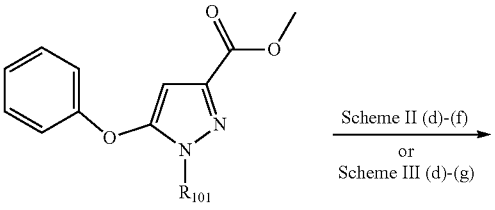

1704

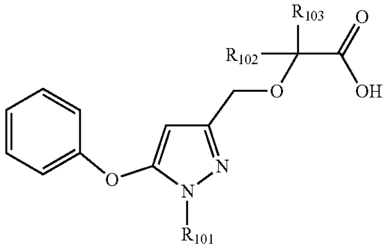

1705

Scheme XVII, depicted above, may be use to prepare certain example compounds disclosed herein. 2-Ketosuccinate ester is condensed with a substituted hydrazine to give 5-hydroxypyrazole compound 1701, shown here as its keto tautomer. The hydroxy group is alkylated with an electrophilic arene, such as 2-fluoronitrobenzene, giving ether 1702. The nitro functionality is removed by stepwise reduction with zinc(0) to amine 1703, followed by deamination with alkyl nitrite, yielding 1704. Synthesis of acid 1705 is completed by either using steps (d)-(f) from Scheme II, or steps (d)-(g) from Scheme III.

Scheme XVIII

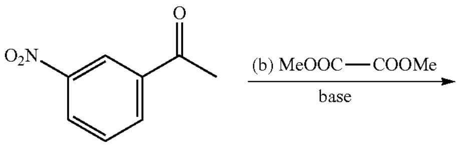

1801

-continued

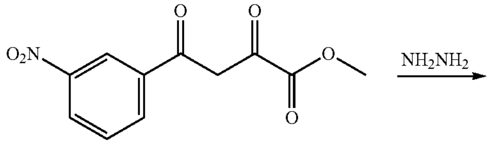

1802

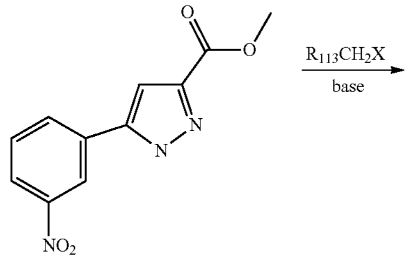

1803

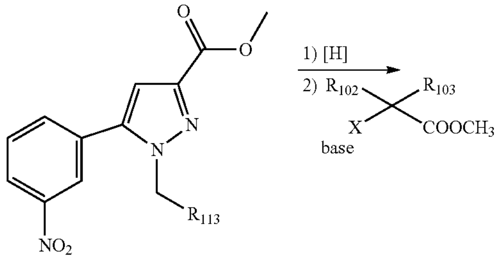

1804

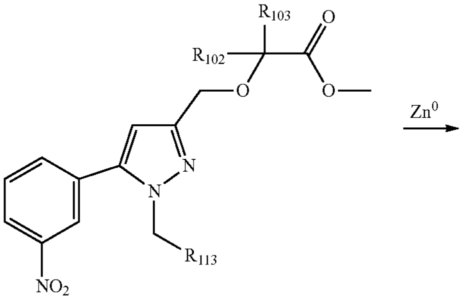

1805

-continued

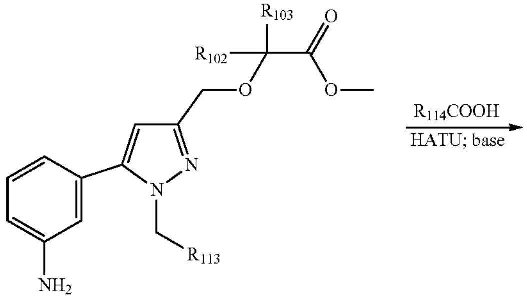

1806

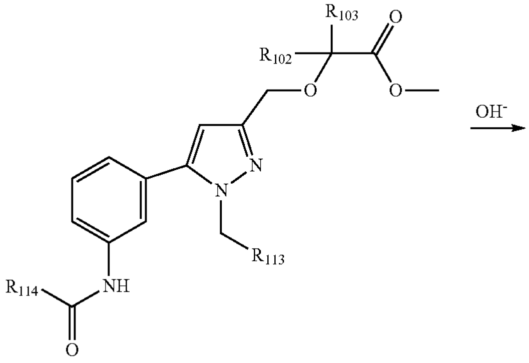

1807

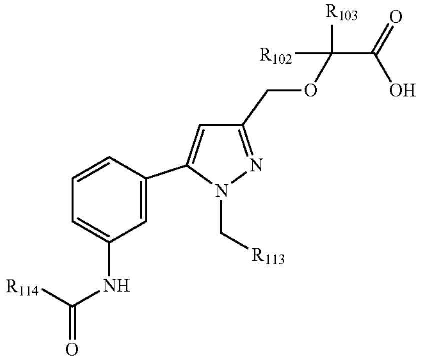

1808

Scheme XVIII, depicted above, may be use to prepare certain example compounds disclosed herein. Nitro acetophenone 1801 is reacted under Claisen conditions with an oxalate ester to give 2,4-diketoester 1802, which is then reacted with a substituted hydrazine in step (c) to construct the pyrazole core of 1803, which is alkylated to provide 1804. The ester functionality is reduced to the alcohol (not shown) and alkylated to give ester 1805. At this point, the nitro group is reduced with zinc to give amine 1806, and acylated using standard coupling reagents to give amide 1807. Synthesis is completed with basic hydrolysis of the ester, affording carboxylic acid 1808.

Scheme XIX

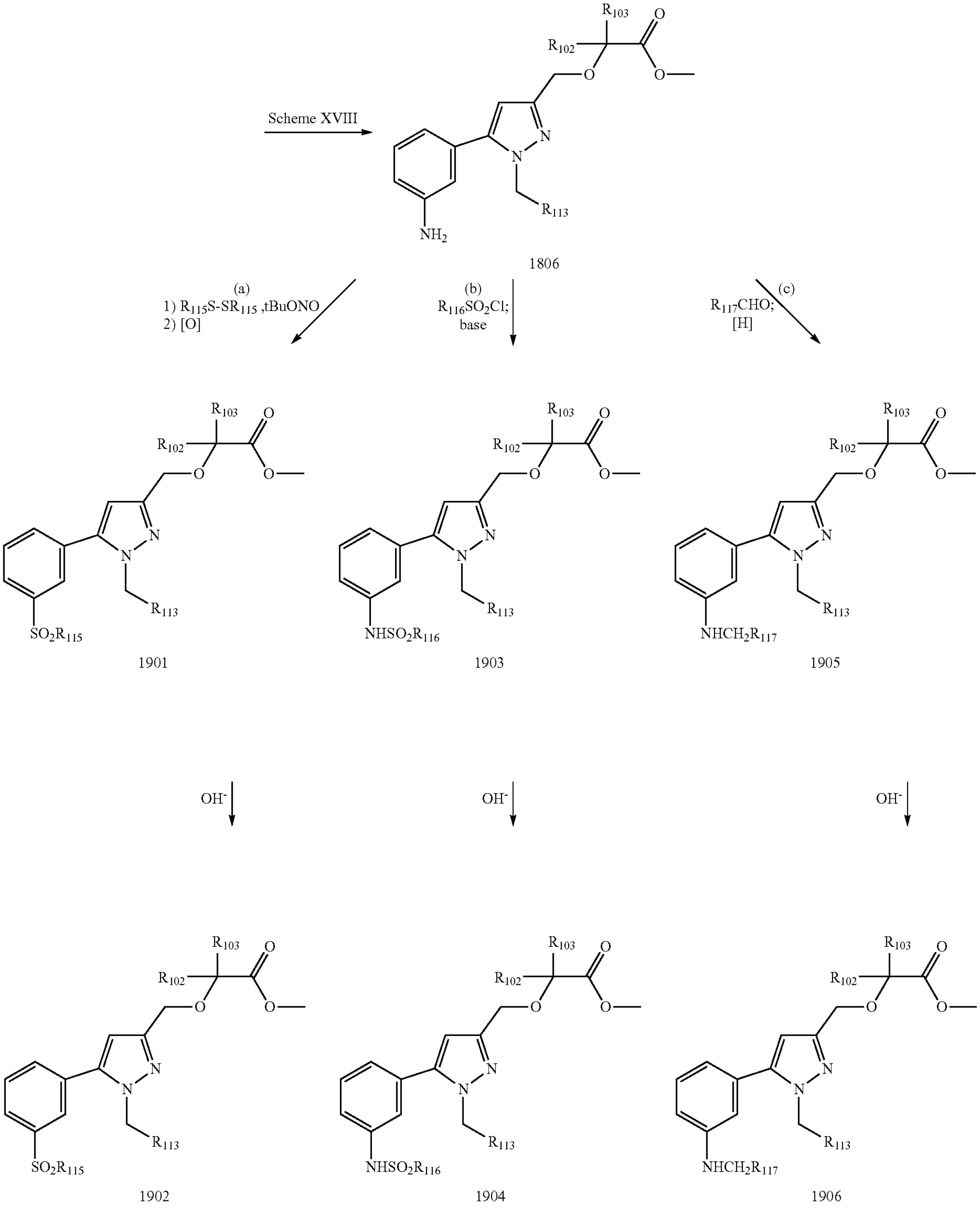

Scheme XIX, depicted above, may be use to prepare certain example compounds disclosed herein. In pathway (a), amine 1806, prepared using the method of Scheme XVIII, is treated with an organonitrite in the presence of a disulfide to afford a thioether, which is oxidized to sulfone 1901. In pathway (b), amine 1806 is reacted with a sulfonyl chloride to give sulfonamide 1903. In pathway (c), amine 1806 is treated with an aldehyde under reductive amination conditions to give amine 1905. In pathways (a), (b), and (c), synthesis is completed with basic hydrolysis of the ester, affording carboxylic acid 1902, 1904, and 1906, respectively.

Scheme XX

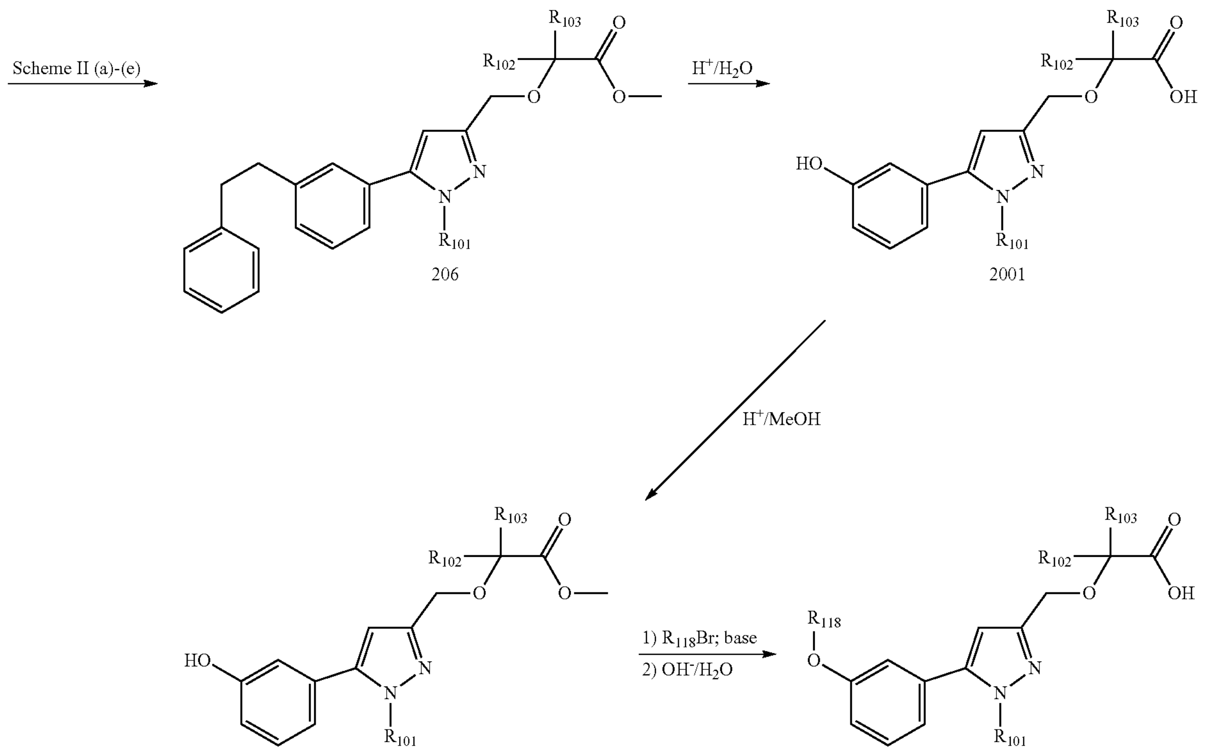

206 2001 2002 2003

Scheme XX, depicted above, may be use to prepare certain example compounds disclosed herein. Benzyl ether 206 is prepared by using steps (a)-(e) of Scheme II. Treatment with acid cleaves both the ether group and the methyl ester to give acid 2001. If desired, synthesis can be continued by Fischer esterification to 2002, alkylation of the phenol under basic conditions, and hydrolysis of the methyl ester to give acid 2003.

Scheme XXI

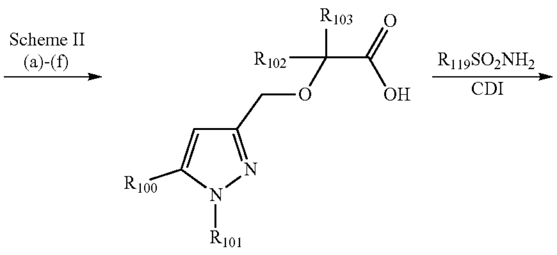

207

-continued

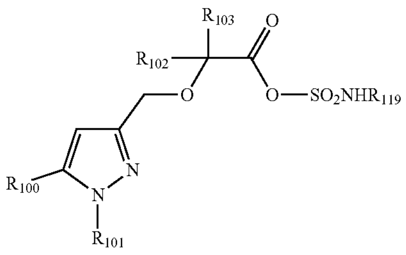

2101

Scheme XXI, depicted above, may be use to prepare certain example compounds disclosed herein. Carboxylic acid 207 is prepared by using steps (a)-(f) of Scheme II. Treatment of the acid with an alkylsulfonamide give ester 2101.

Scheme XXII

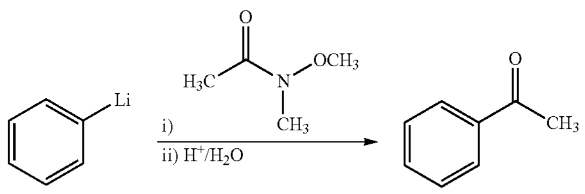

2201 2202

Scheme XXII, depicted above, may be used to prepare certain example compounds disclosed herein. Aryllithium 2201, prepared by lithiation, halogen-metal exchange, or other methods that are available in the art, is reacted with N-methyl-N-methoxyacetamide, which affords acetyl compound 2202, which can be transformed to the desired product through any of the previous schemes.

Scheme XXIII

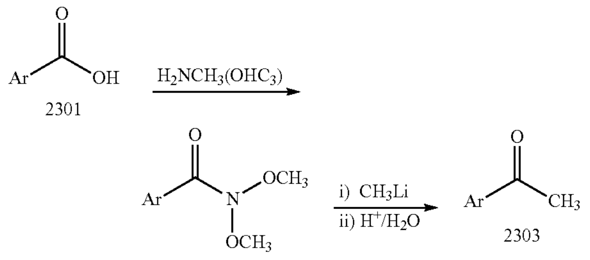

2301

2303

2302

Scheme XXIII, depicted above, may be used to prepare certain example compounds disclosed herein. Carboxylic acid 2301 is converted to the corresponding alkoxy amide 2302 using standard amide formation procedures. The alkoxy amide is then reacted with an appropriate organolithium reagent, which affords ketone compound 2303, which can be transformed to the desired product through any of the previous schemes.

Scheme XXIV

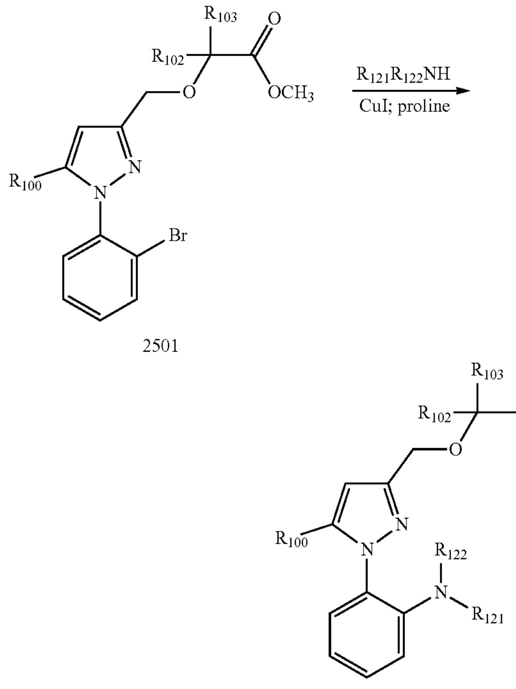

2501

2502

Scheme XXIV, depicted above, may be used to prepare certain example compounds disclosed herein. Aryl halide 2401, prepared using any of the methods disclosed herein, is converted to the corresponding arylamine 2402. This transformation can be accomplished with a copper-based catalyst, or other techniques known in the art. Synthesis can then be completed using methods disclosed herein.

Scheme XXV

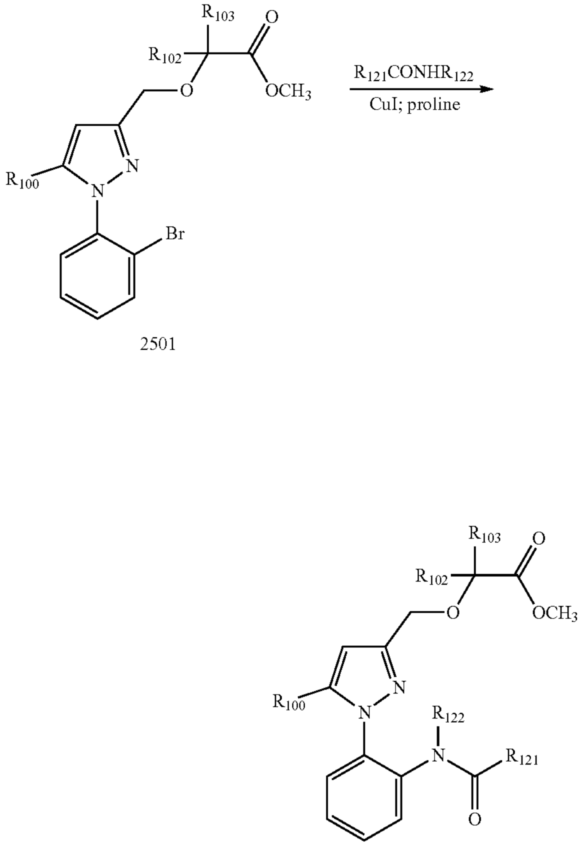

2501

2502

Scheme XXV, depicted above, may be used to prepare certain example compounds disclosed herein. Aryl halide 2501, prepared using any of the methods disclosed herein, is converted to the corresponding arylamide 2502. This transformation can be accomplished with a copper-based catalyst, or other techniques known in the art. Synthesis can then be completed using methods disclosed herein.

Scheme XXVI

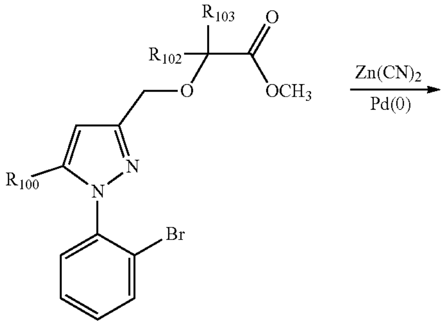

2501

-continued

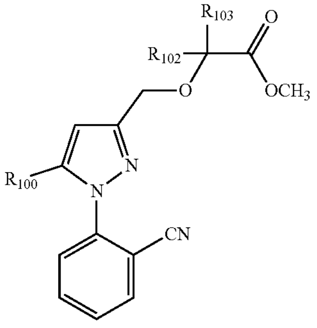

2502

Scheme XXVI, depicted above, may be used to prepare certain example compounds disclosed herein. Aryl halide 2601, prepared using any of the methods disclosed herein, is converted to the corresponding aryl nitrile 2602. This transformation can be accomplished with a Pd-based catalyst, or other techniques known in the art. Synthesis can then be completed using methods disclosed herein.

Scheme XXVII

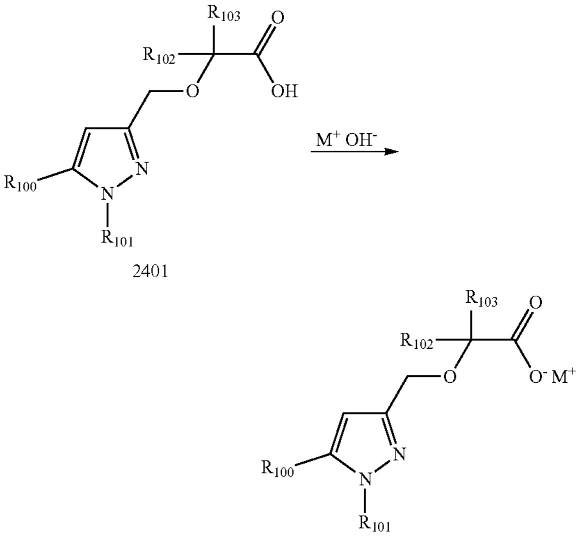

Scheme XXVII, depicted above, may be used to prepare certain example compounds disclosed herein. Carboxylic acid 2701, prepared using any of the methods disclosed herein, is converted to the corresponding carboxylate salt 2702. This transformation can be accomplished with a metal hydroxide or metal oxide. The metal can be chosen from the alkali metals, alkaline earth metals, or other metals.

Scheme XXVIII

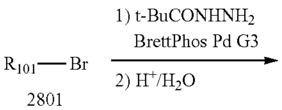

2801

-continued

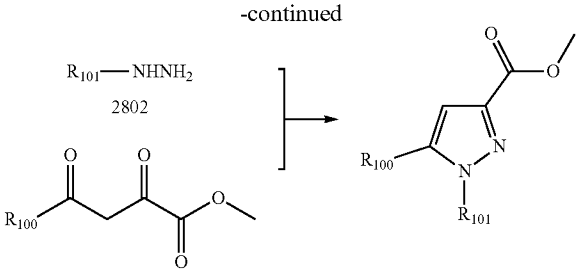

Scheme XXVIII, depicted above, may be used to prepare certain example compounds disclosed herein. An aryl or heteroaryl halide 2801 is converted to the corresponding hydrazine 2802. Synthesis of the pyrazole core is accomplished via condensation with an appropriate carbonyl compound, as disclosed herein. Amine functionality in the aryl or heteroaryl moiety of 2801 can be protected by attachment of a suitable protecting group, such as the SEM protecting group. The protecting group can be removed at a convenient point in synthesis by using methods known in the art.

Intermediates

The following intermediates were synthesized for use in preparing the compounds of this disclosure.

Intermediate A-1: 1-(1-Methyl-1H-indol-6-yl)ethan-1-one

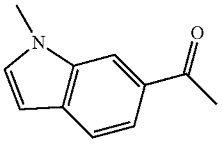

6-Bromo-1-methyl-1H-indole A mixture of 6-bromo-1H-indole (5 g, 25.50 mmol, 1.00 equiv), $K_2CO_3$ (7 g, 50.65 mmol, 2.00 equiv), and $CH_3I$ (7.3 g, 51.43 mmol, 2.00 equiv) in acetone (100 mL) was stirred for 16 h at 55° C., then cooled to rt, diluted with 100 mL $H_2O$, and extracted with 2×200 mL of EtOAc. The combined organic layers were washed with 100 mL of brine, dried over $Na_2SO_4$, concentrated under vacuum, and purified with silica gel chromatography using EtOAc/petroleum ether (1:10) to afford 3.4 g (63%) of the title compound as a yellow oil. LC-MS: (ES, m/z): 208. $^1H$ NMR (300 MHz, DMSO-$d_6$) δ 7.69 (dt, J=1.6, 0.7 Hz, 1H), 7.49 (dd, J=8.4, 0.6 Hz, 1H), 7.34 (d, J=3.1 Hz, 1H), 7.13 (dd, J=8.4, 1.8 Hz, 1H), 6.43 (dd, J=3.1, 0.9 Hz, 1H), 3.77 (s, 3H).

1-(1-Methyl-1H-indol-6-yl)ethan-1-one To a solution of 6-bromo-1-methyl-1H-indole (3.4 g, 16.19 mmol, 1.00 equiv) in THF (100 mL) was added BuLi (12 mL, 2.00 equiv, 2.5 M) dropwise with stirring at −78° C. The solution was stirred for 1 h, then N-methoxy-N-methylacetamide (4.1 g, 39.76 mmol, 2.50 equiv) was added dropwise with stirring at −78° C. The solution was stirred for 30 min, then warmed to rt and stirred an additional 2 h. The reaction mixture was cooled to 0° C., then quenched by the addition of 1 M HCl and extracted with 2×200 mL of EtOAc. The combined organic layers were washed with 100 mL of brine, dried over $Na_2SO_4$, concentrated under vacuum, and purified with silica gel chromatography using EtOAc/petroleum ether (1:5) to afford 1.9 g (68%) of the title compound as a yellow solid. LC-MS: (ES, m/z): 173. $^1$H NMR: (300 MHz, DMSO-$d_6$) δ 8.12 (dt, J=1.5, 0.8 Hz, 1H), 7.70-7.59 (m, 2H), 7.57 (d, J=3.0 Hz, 1H), 6.51 (dd, J=3.0, 0.9 Hz, 1H), 3.88 (s, 3H), 2.63 (s, 3H).

Intermediate A-2: 1-(1-Methyl-1H-indazol-6-yl) ethan-1-one

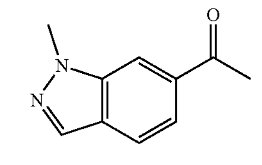

1-(1-methyl-1H-indazol-6-yl)ethan-1-one To a solution of 6-bromo-1-methyl-1H-indazole (2.5 g, 11.85 mmol, 1.00 equiv) in THF (50 mL) under $N_2$ at −78° C. was added n-BuLi (10 mL, 2.00 equiv) dropwise with stirring. The solution was stirred for 60 min at this temperature, then N-methoxy-N-methylacetamide (3 g, 29.09 mmol, 2.50 equiv) was added, and the solution was stirred for an additional 60 min at this temperature. The resulting solution was stirred for 1 h at rt, cooled to 0° C., quenched by the addition of HCl (1M), and extracted with 2×100 mL of EtOAc. The combined organic layers were washed with 50 mL of brine, dried over $Na_2SO_4$, concentrated under vacuum, and purified with silica gel chromatography using EtOAc/petroleum ether (1:10) to afford 1.5 g (73%) of the title compound as a yellow oil. LC-MS: (ES, m/z): 174. $^1$H NMR: (400 MHz, DMSO-$d_6$) δ 8.36 (q, J=1.1 Hz, 1H), 8.16 (d, J=1.0 Hz, 1H), 7.86 (dd, J=8.5, 0.8 Hz, 1H), 7.69 (dd, J=8.5, 1.4 Hz, 1H), 4.16 (s, 3H), 2.70 (s, 3H).

The following acetyl arenes were obtained from similar routes.

TABLE 1

Synthesis of acetyl arenes from aryl bromides.

| Aryl bromide | Product | | Spectral |
|---|---|---|---|
| 1-bromo-3-(propan-2-yl)benzene | 1-[3-(Propan-2-yl)phenyl]-ethan-1-one | A-3 | |
| 6-bromo-1-ethyl-1H-indazole | 1-(1-Ethyl-1H-indazol-6-yl)ethan-1-one | A-4 | LC-MS: (ES, m/z): 189. |
| 1-bromo-3-chloro-5-methoxybenzene | 1-(3-chloro-5-methoxy-phenyl)ethan-1-one | A-5 | LC-MS: (ES, m/z): 182. |
| 5-bromo-1-methyl-1H-indazole | 1-(1-methyl-1H-indazol-5-yl)ethan-1-one | A-6 | LC-MS: (ES, m/z): 174. |
| 4-bromo-1-methyl-1H-indazole | 1-(1-methyl-1H-indazol-4-yl)ethan-1-one | A-7 | LC-MS: (ES, m/z): 174. |
| 6-bromo-1-ethyl-1H-1,2,3-benzotriazole | 1-(1-ethyl-1H-1,2,3-benzotriazol-6-yl)ethan-1-one | A-8 | LC-MS: (ES, m/z) 189. |

The following acetyl arene intermediates were prepared via Scheme XXII.

Intermediate A-9: 1-(3-Cyclobutoxyphenyl)ethan-1-one

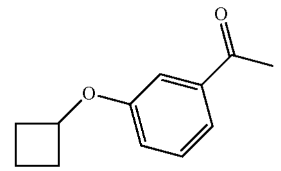

To a mixture of 1-(3-hydroxyphenyl)ethan-1-one (4.5 g, 33.05 mmol, 1.00 equiv) and $Cs_2CO_3$ (10.78 g, 33.09 mmol, 1.00 equiv) in DMA (50 mL) was added dropwise bromocyclobutane (9.0 g, 66.67 mmol, 2.00 equiv) with stirring at rt. The resulting mixture was stirred for 16 h at 130° C., then cooled and diluted with 200 mL of EtOAc. The combined organic layers were washed with 2×200 mL of $H_2O$ and 2×200 mL of brine, then dried over $Na_2SO_4$, concentrated under vacuum, and purified with silica gel chromatography using EtOAc/petroleum ether (1:10) to afford 5.0 g (80%) of the title compound as colorless oil. $^1$H NMR: (300 MHz, DMSO-$d_6$) δ 7.53 (ddd, J=7.6, 1.7, 1.1 Hz, 1H), 7.41 (t, J=7.9 Hz, 1H), 7.32 (dd, J=2.6, 1.6 Hz, 1H), 7.10 (ddd, J=8.1, 2.7, 1.0 Hz, 1H), 4.83-4.67 (m, 1H), 2.55 (s, 3H), 2.47-2.31 (m, 2H), 2.14-1.94 (m, 2H), 1.88-1.72 (m, 1H), 1.72-1.56 (m, 1H).

Intermediate A-10: 1-[3-(Oxetan-3-ylmethoxy)phenyl]ethan-1-one

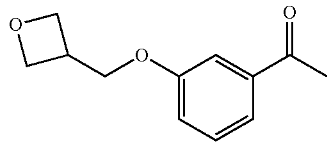

Into a flask under $N_2$ were combined a solution of oxetan-3-ylmethanol (3.24 g, 36.77 mmol, 1.00 equiv) in THF (100 mL), 1-(3-hydroxyphenyl)ethan-1-one (5 g, 36.72 mmol, 1.00 equiv), and $PPh_3$ (14.5 g, 1.50 equiv), followed by the addition of DEAD (8.3 g, 47.66 mmol, 1.30 equiv) dropwise with stirring at 0° C. The resulting solution was stirred for 12 h at rt, then extracted with EtOAc. The combined organic layers were dried over $Na_2SO_4$, concentrated under vacuum, and purified by silica gel chromatography with EtOAc/petroleum ether (0-20%) to afford 4.4 g (58%) of the title compound as light yellow oil. LC-MS: (ES, m/z): 206.90. H-NMR: $\delta_H$ (300 MHz, DMSO-$d_6$) 7.56 (1H, ddd, J=7.6, 1.6, 1.0 Hz), 7.45 (2H, m), 7.23 (1H, ddd, J=8.2, 2.7, 1.1 Hz), 4.71 (2H, dd, J=7.9, 6.0 Hz), 4.44 (2H, t, J=6.0, 6.0 Hz), 4.26 (2H, d, J=6.7 Hz), 3.39 (1H, m), 2.57 (3H, s).

The following alkylated compounds were obtained from Williamson synthesis of 3-hydroxyacetophenone.

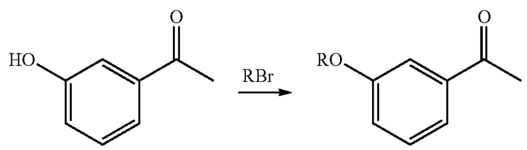

TABLE 2

| Williamson synthesis of alkoxy acetophenones. | | | | | |
|---|---|---|---|---|---|
| Alkyl halide | Base/ solvent | Temp | Product | | Spectral |
| 3-bromo-oxetane | $Cs_2CO_3$/ DMA | 130° C. | 1-[3-(Oxetan-3-yl-oxy)phenyl]ethan-1-one | A-11 | LC-MS: (ES, m/z): 193. |
| Bromocyclo-propane | $Cs_2CO_3$/ DMA | 150° C. | 1-(3-cyclopropoxy-phenyl)ethan-1-one | A-12 | |
| 1-Bromo-2,2-dimethyl-propane | $K_2CO_3$/ DMF | 110° C. | 1-[3-(2,2-Dimeth-ylpropoxy)phenyl]-ethan-1-one | A-13 | LC-MS: (ES, m/z): 206.9. |
| (Bromo-methyl)-cyclobutane | $K_2CO_3$/ DMF | 110° C. | 1-[3-(Cyclobutyl-methoxy)phenyl]ethan-1-one | A-14 | LC-MS: (ES, m/z): 291.25. |
| (Bromo-methyl)-cyclopropane | $K_2CO_3$/ DMF | 80° C. | 1-[3-(Cyclopropyl-methoxy)phenyl]-ethan-1-one | A-15 | LC-MS: (ES, m/z): 191. |
| Iodoethane | $K_2CO_3$/ DMF | 90° C. | 1-(3-Ethoxy-phenyl)ethan-1-one | A-16 | LC-MS: (ES, m/z): 165. |
| Benzyl bromide | $K_2CO_3$/ DMF | 80° C. | 1-[3-(benzyloxy)-phenyl]ethan-1-one | A-17 | LC-MS: (ES, m/z): 226.95. |
| 1-Bromo-2-methylpropane | $K_3PO_4$/ DMSO | 60° C. | 1-[3-(2-Methyl-propoxy)phenyl]-ethan-1-one | A-18 | |

Intermediate A-19: 1-(3,5-Dimethoxyphenyl)ethan-1-one

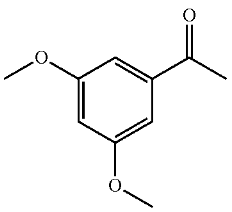

In a flask were combined 1-(3,5-dihydroxyphenyl)ethan-1-one (2 g, 13.15 mmol, 1.00 equiv) iodomethane (6.5 g, 45.79 mmol, 4.00 equiv), $K_2CO_3$ (3.6 g, 25.86 mmol, 2.00 equiv) and acetone (40 mL). The resulting mixture was stirred for 16 h at 56° C., then cooled to rt, diluted with 100 mL of water, and extracted with 2×50 mL of EtOAc. The combined organic layers were washed with 20 mL of brine, dried over $Na_2SO_4$, concentrated under vacuum, and purified with silica gel chromatography using EtOAc/petroleum ether (1:10), to afford 2 g (84%) of the title product as colorless oil. LC-MS: (ES, m/z): 181. $^1$H NMR: (300 MHz, DMSO-d) δ 7.07 (d, J=2.3 Hz, 2H), 6.77 (t, J=2.3 Hz, 1H), 3.89-3.71 (m, 6H), 2.56 (s, 3H).

Intermediate A-20: 1-(3,5-Diethoxyphenyl)ethan-1-one

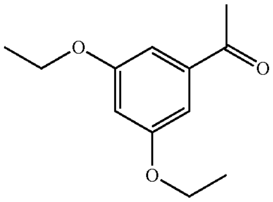

In a flask were combined 1-(3,5-dihydroxyphenyl)ethan-1-one (5 g, 32.86 mmol, 1.00 equiv), iodoethane (20 g, 128.23 mmol, 4.00 equiv), $K_2CO_3$ (18 g, 130.43 mmol, 4.00 equiv), and acetone (100 mL). The resulting mixture was heated to reflux overnight, then cooled to rt and extracted with 3×100 mL of EtOAc. The combined organic layers were dried over $Na_2SO_4$ and concentrated under vacuum to afford 6 g (88%) of the title compound as a brown solid. LC-MS: (ES, m/z): 208.95.

Intermediate A-21: 1-(3-Ethoxy-5-methoxyphenyl)ethan-1-one

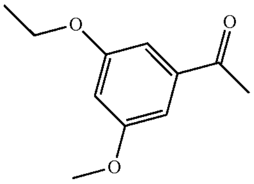

1-(3-Hydroxy-5-methoxyphenyl)ethan-1-one To a mixture of 1-(3,5-dihydroxy-phenyl)ethan-1-one (5.0 g, 32.86 mmol, 1.00 equiv), $K_2CO_3$ (6.85 g, 49.56 mmol, 1.50 equiv), and acetone (100 mL) was added MeI (4.67 g, 32.89 mmol, 1.00 equiv) dropwise with stirring at rt. The resulting solution was heated to reflux for 2 h, concentrated under vacuum, and purified with silica gel chromatography using EtOAc/petroleum ether (1:3) to afford 2 g (37%) of the title compound as a white solid. LC-MS: (ES, m/z): 167.

1-(3-Ethoxy-5-methoxyphenyl)ethan-1-one To a mixture of 1-(3-hydroxy-5-methoxyphenyl)ethan-1-one (2 g, 12.04 mmol, 1.00 equiv), $K_2CO_3$ (2.5 g, 18.09 mmol, 1.50 equiv), and DMF (50 mL) was added EtI (2.8 g, 17.95 mmol, 1.00 equiv) dropwise with stirring at rt. The resulting solution was stirred for 16 h at 90° C., diluted with 100 mL of EtOAc, washed with 1×100 mL of water and 1×100 mL of brine, dried over $Na_2SO_4$, concentrated under vacuum, and purified with silica gel chromatography using EtOAc/petroleum ether (1:5) to afford 950 mg (41%) of the title compound as a colorless oil. LC-MS: (ES, m/z): 195. $^1$H-NMR: (DMSO, ppm): δ: 7.06 (dq, J=2.9, 1.4 Hz, 2H), 6.75 (t, J=2.3 Hz, 1H), 4.07 (q, J=7.0 Hz, 2H), 2.56 (s, 3H), 1.34 (t, J=6.9 Hz, 3H).

Intermediate A-22: 1-[2-(Propan-2-yloxy)-1,3-oxazol-5-yl]ethan-1-one

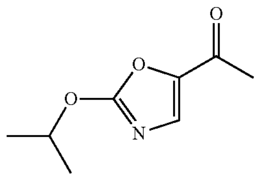

2-Hydroxy-1,3-oxazole-5-carboxylic acid A solution of ethyl 2-chloro-1,3-oxazole-5-carboxylate (3 g, 17.09 mmol, 1.00 equiv) and LiOH (1.7 g, 70.98 mmol, 4.00 equiv) in THF/$H_2O$ (60/15 mL) was stirred for 16 h at 30° C. The pH was then adjusted to 4 with 1 M HCl, and the resulting solution was extracted with 4×50 mL of EtOAc. The combined organic layers were dried over anhydrous $Na_2SO_4$ and concentrated under vacuum to afford 2 g (91%) of the title compound as a yellow solid. LC-MS: (ES, m/z): 129.

2-Hydroxy-N-methoxy-N-methyl-1,3-oxazole-5-carboxamide A solution of N-methoxy-N-methylamine hydrochloride (1.8 g, 18.45 mmol, 1.20 equiv), HATU (7.6 g, 20.54 mmol, 1.30 equiv), DIEA (6 g, 46.43 mmol, 3.00 equiv), and 2-hydroxy-1,3-oxazole-5-carboxylic acid (2 g, 15.50 mmol, 1.00 equiv) in DMF (60 mL) was stirred for 5 h at room temperature. The resulting mixture was concentrated under vacuum and purified with silica gel chromatography using $CH_2Cl_2$/MeOH (50:1) to afford 1.3 g (49%) of the title compound as a yellow solid. LC-MS: (ES, m/z): 173.

N-methoxy-N-methyl-2-(propan-2-yloxy)-1,3-oxazole-5-carboxamide A mixture of 2-hydroxy-N-methoxy-N-methyl-1,3-oxazole-5-carboxamide (1.8 g, 10.46 mmol, 1.00 equiv), 2-iodopropane (3.6 g, 2.00 equiv), $K_2CO_3$ (2.9 g, 2.00 equiv) and DMF (15 mL) in a 20-mL sealed tube was stirred for 16 h at 90° C. The reaction mixture was cooled to rt, diluted with 20 mL of $H_2O$, and extracted with 4×20 mL of EtOAc. The combined organic layers were dried over $Na_2SO_4$, concentrated under vacuum, and purified with silica gel chromatography using $CH_2Cl_2$/MeOH (100:1) to afford 1.5 g (67%) of the title compound as a yellow solid. LC-MS: (ES, m/z): 214.

1-[2-(Propan-2-yloxy)-1,3-oxazol-5-yl]ethan-1-one To a solution of N-methoxy-N-methyl-2-(propan-2-yloxy)-1,3-oxazole-5-carboxamide (1.5 g, 7.00 mmol, 1.00 equiv) in THF (40 mL) under $N_2$ at −78° C. was added in portions MeMgBr (21 mL, 3.00 equiv). The resulting solution was stirred for 2 h at rt, cooled to 0° C., quenched by the addition of HCl (1M), and extracted with 2×50 mL of EtOAc. The combined organic layers were washed with 30 mL of brine, dried over $Na_2SO_4$, concentrated under vacuum, and purified with silica gel chromatography using EtOAc/petroleum ether (1:10) to afford 670 mg (57%) of the title compound as a yellow solid. LC-MS: (ES, m/z): 169.

Intermediate A-23: 1-[1,3-dimethyl-1H-thieno[2,3-c]pyrazol-5-yl]ethan-1-one

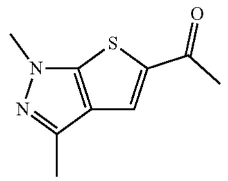

N-methoxy-N,1,3-trimethyl-1H-thieno[2,3-c]pyrazole-5-carboxamide A solution of 1,3-dimethyl-1H-thieno[2,3-c]pyrazole-5-carboxylic acid (2 g, 10.19 mmol, 1.00 equiv) methoxy(methyl)amine hydrochloride (1.06 g, 10.87 mmol, 1.10 equiv), DIEA (4 g, 30.95 mmol, 3.00 equiv), and HATU (5.8 g, 15.26 mmol, 1.50 equiv) in DMF (30 mL) was stirred for 2 h at rt, diluted with 100 mL of water, and extracted with 2×100 mL of EtOAc. The combined organic layers were washed with 100 mL brine, dried over $Na_2SO_4$, concentrated under vacuum, and purified with silica gel chromatography using EtOAc/petroleum ether (1:3) to afford 2.2 g (90%) of the title compound as a yellow solid. LC-MS: (ES, m/z): 240.

1-[1,3-dimethyl-1H-thieno[2,3-c]pyrazol-5-yl]ethan-1-one To a solution of the product from the previous step (2.2 g, 9.19 mmol, 1.00 equiv) in THF (50 mL) at −78° C. under $N_2$ was added methylmagnesium bromide (1.0 M in THF, 29 mL, 3.00 equiv) dropwise with stirring. The resulting solution was stirred for 2 h at room temperature, then cooled to 0° C. and then quenched by the addition of aq HCl. The resulting solution was diluted with 100 mL $H_2O$ and extracted with 2×200 mL of EtOAc. The combined organic layers were washed with 50 mL of brine, dried over $Na_2SO_4$, concentrated under vacuum, and purified with silica gel column chromatography using EtOAc/petroleum ether (1:3) to afford 1.4 g (78%) of the title compound as a white solid.

LC-MS: (ES, m/z): 195. $^1$H NMR (300 MHz, DMSO-$d_6$) δ 8.04 (s, 1H), 3.86 (s, 3H), 2.52 (s, 4H), 2.39 (s, 3H).

Intermediate A-24: 1-(5-Methoxythien-2-yl)ethan-1-one

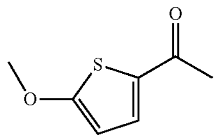

A mixture of 1-(5-chlorothien-2-yl)-1-ethanone (11 g, 96.35 mmol, 1.00 equiv), $Cs_2CO_3$ (22 g, 1.20 equiv), and Brettphos Pd G3 (550 mg) in MeOH (60 mL) was heated in a sealed tube for 1 hr at 100° C. with microwave radiation. The resulting mixture was concentrated under vacuum, then extracted with 3×100 mL of EtOAc. The combined organic layers were dried over anhydrous $MgSO_4$, concentrated under vacuum, and purified with silica gel chromatography using EtOAc/petroleum ether (1/50) to afford 5 g (33%) of the title product as a yellow solid.

Intermediate A-25: 1-[2-(2-Methylpropoxy)-1,3-thiazol-5-yl]ethan-1-one

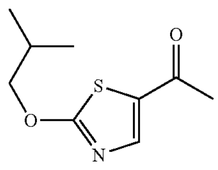

To a solution of 1-(2-bromo-1,3-thiazol-5-yl)ethan-1-one (2 g, 9.71 mmol, 1.00 equiv) in 2-methylpropan-1-ol (15 mL) in a 40 mL sealed tube under $N_2$ was added sequentially $Cs_2CO_3$ (6.4 g, 19.64 mmol, 2.00 equiv) and Brettphos Pd G3 (440 mg, 0.49 mmol, 0.05 equiv). The resulting solution was stirred for 1 h at 90° C. The solution was the cooled, diluted with 50 mL $H_2O$, and extracted with 2×100 mL of EtOAc. The combined organic layers were washed with 50 mL of aq NaCl, dried over anhydrous $Na_2SO_4$, concentrated under vacuum, and purified with silica gel column using EtOAc/petroleum ether (1:10) to afford 550 mg (28%) of the title compound as a yellow oil.

Intermediate A-26: 1-[5-(2-Methylpropoxy)thien-2-yl]ethan-1-one

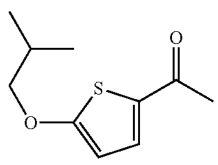

1-(5-Hydroxythien-2-yl)ethan-1-one To a solution of 1-(5-Methoxy-thien-2-yl)ethan-1-one was added $BBr_3$ (180 mL) dropwise with stirring at rt. The resulting solution was stirred for 2 days at 35° C. The reaction mixture was cooled with a water/ice bath. The reaction was then quenched by the addition of 500 mL of water/ice. The resulting solution was diluted with 500 mL of $CH_2Cl_2$. The pH value of the solution was adjusted to 7-8 with (sat) $NaHCO_3$(aq) (500 mol/L). The mixture was dried over anhydrous $Na_2SO_4$ and concentrated under vacuum. The residue was applied onto a silica gel column with EtOAc/petroleum ether (1:10). This resulted in the title compound as a red oil (5.0 g, 61%).

1-[5-(2-Methylpropoxy)thien-2-yl]ethan-1-one To a solution of the product from the previous step (800 mg, 5.63 mmol, 1.00 equiv) in DMF (20 mL) was added $Cs_2CO_3$ (3.67 g, 11.26 mmol, 2.00 equiv), followed by the addition of 1-iodo-2-methylpropane (2.07 g, 11.25 mmol, 2.00 equiv) dropwise with stirring at rt. The resulting solution was stirred for 16 h at 90° C. The resulting solution was diluted with 100 mL of EtOAc then washed with 2×100 mL of water and 2×100 mL of brine. The mixture was dried over anhydrous $Na_2SO_4$ and concentrated under vacuum. The residue was applied onto a silica gel column with EtOAc/petroleum ether (1:10). This resulted in the title compound as a yellow oil (600 mg, 54%).

Intermediate A-27: 1-(4-Methoxythien-2-yl)ethan-1-one

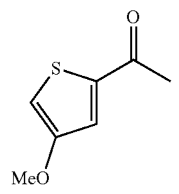

To a solution of 1-(4-bromothien-2-yl)ethan-1-one (3.0 g, 14.63 mmol, 1.00 equiv) in MeOH (25 mL) was added NaOMe (5.4 mL, 2.00 equiv, 5.4M) at room temperature, followed by CuBr (627 mg, 4.38 mmol, 0.30 equiv) at room temperature. The resulting solution was stirred for 16 h at 100° C., then diluted with 100 mL of EtOAc, washed with 2×100 mL of brine, dried over anhydrous $Na_2SO_4$ and concentrated under vacuum. The residue was purified with silica gel chromatography using EtOAc/petroleum ether (1:20) to afford 700 mg (31%) of the title product as a yellow oil.

Intermediate A-28: 1-[2-(2-Methylpropyl)-1,3-oxazol-5-yl]ethan-1-one

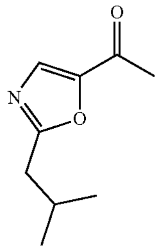

Ethyl 2-(2-methylpropyl)-1,3-oxazole-5-carboxylate To a solution of ethyl 2-chloro-1,3-oxazole-5-carboxylate (3 g, 17.09 mmol, 1.00 equiv) in THF (45 mL), under $N_2$, was added copper(I) iodide (1.5 g, 7.88 mmol, 0.50 equiv). This was followed by the addition of bromo(2-methylpropyl)zinc (15 mL, 2.00 equiv) at −5° C. The resulting solution was stirred for 3 h at room temperature. The reaction was then quenched by the addition of aq 1 M HCl. The resulting solution was extracted with 2×100 mL of EtOAc, and the organic layers were combined and dried over anhydrous $Na_2SO_4$ and concentrated under vacuum. The residue was applied onto a silica gel column with EtOAc/petroleum ether (1:5). This resulted in the title compound as a red oil (1.3 g, 39%).

2-(2-Methylpropyl)-1,3-oxazole-5-carboxylic acid To a solution of the product from the previous step (1.3 g, 6.59 mmol, 1.00 equiv) in THF/$H_2O$ (20/5 mL) was added LiOH (600 mg, 25.05 mmol, 4.00 equiv). The resulting solution was stirred for 3 h at room temperature. The reaction mixture was cooled with a water/ice bath. The pH value of the solution was adjusted to 1 with aq 1 M HCl. The resulting solution was extracted with 2×50 mL of EtOAc, and the organic layers were combined and dried over anhydrous $Na_2SO_4$ and concentrated under vacuum. This resulted in the title compound as a red solid (1 g, 90%).

1-[2-(2-Methylpropyl)-1,3-oxazol-5-yl]ethan-1-one To a solution of the product from the previous step (1 g, 5.91 mmol, 1.00 equiv) in $Et_2O$ (30 mL), under $N_2$, was added MeLi (7.4 mL, 2.00 equiv). The resulting solution was stirred for 3 h at 0° C. in a water/ice bath. The reaction was then quenched by the addition of aq HCl (1M). The resulting solution was extracted with 2×50 mL of EtOAc, and the organic layers were combined and dried over anhydrous $Na_2SO_4$ and concentrated under vacuum. The residue was applied onto a silica gel column with EtOAc/petroleum ether (1:5). This resulted in the title compound as a red oil (800 mg, 81%).

Intermediate A-29: 1-(1-methyl-1H-1,3-benzodiazol-6-yl)ethan-1-one

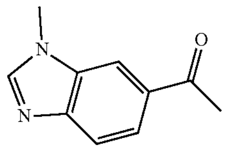

N-methoxy-N,1-dimethyl-1H-1,3-benzodiazole-6-carboxamide To a solution of 1-methyl-1H-1,3-benzodiazole-6-carboxylic acid (5.0 g, 28.38 mmol, 1.00 equiv) in $CH_2Cl_2$ (100 mL) was added methoxy(methyl)amine hydrochloride (2.78 g, 28.50 mmol, 1.00 equiv), EDC (6.54 g, 42.13 mmol, 1.20 equiv), followed by the addition of DMAP (3.46 g, 28.32 mmol, 1.00 equiv), in portions at rt. The resulting solution was stirred for 16 h, concentrated under vacuum, and purified with silica gel chromatography using $CH_2Cl_2$/MeOH (100:1) to afford 4.0 g (64%) of the title compound as a yellow solid. LC-MS: (ES, m/z): [M+1]=220.

1-(1-methyl-1H-1,3-benzodiazol-6-yl)ethan-1-one To a solution of the product from the previous step (2.0 g, 9.12 mmol, 1.00 equiv) in THF (60 mL) under $N_2$ was added MeMgBr (9.1 mL, 3.00 equiv) dropwise with stirring at −60° C. The resulting mixture was stirred at this temperature for 30 min, allowed to warm to rt, then stirred for 2 h at rt. The reaction was then quenched by the addition of water/ice. The resulting solution was extracted with 100 mL of EtOAc, dried over $Na_2SO_4$, concentrated under vacuum, and purified with silica gel chromatography using with $CH_2Cl_2$/MeOH (50:1) to afford 1.3 g (82%) of the title compound as a yellow solid.

Intermediate A-30: 3-Acetyl-N-(propan-2-yl)benzamide

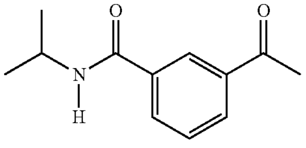

To a suspension of 3-acetylbenzoic acid (10 g, 60.92 mmol), HATU (20 g, 52.60 mmol,) and propan-2-amine (4 g, 67.67 mmol) in DMF (180 mL) at −5° C. was added dropwise DIEA. The resulting mixture was stirred at room temperature for 2 h under $N_2$, then poured into 100 mL $H_2O$, and extracted with EtOAc (3×100 mL). The combined organic layers were washed with 300 mL brine, dried over anhydrous $Na_2SO_4$, filtered and concentrated under vacuum. This resulted in 11 g (88%) of the title product as a yellow solid.

The following 2,4-dioxobutanoate esters were synthesized for use in preparing the compounds of this disclosure, including, but not limited to, use in Scheme I.

Intermediate B-1: Methyl 4-(2-methoxyphenyl)-2,4-dioxobutanoate

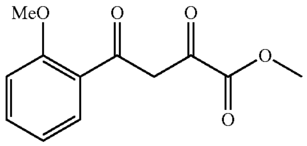 [SMILES: COC(=O)C(=O)CC(=O)c1ccccc1OC]

To a solution of 1-(2-methoxyphenyl)ethan-1-one (1 g, 6.66 mmol, 1.00 equiv) in MeOH (20 mL) was added sequentially dimethyl oxalate (2.36 g, 19.99 mmol, 3.00 equiv), then MeONa (3.7 mL, 3.00 equiv, 5.4 M). The resulting solution was stirred overnight at 30° C. then quenched by the addition of water/ice. The pH value of the solution was adjusted to 5 with aq 1 M HCl. The resulting solution was extracted with 3×50 mL of EtOAc, and the organic layers were combined and dried over anhydrous $Na_2SO_4$ and concentrated under vacuum. The residue was applied onto a silica gel column with EtOAc/hexane (1/4). This resulted in the title compound as a yellow solid (1.2 g, 76%).

Intermediate B-2: Methyl 4-(3-methoxyphenyl)-2,4-dioxobutanoate

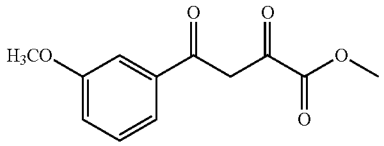 [SMILES: COC(=O)C(=O)CC(=O)c1cccc(OC)c1]

To a solution of 1-(3-methoxyphenyl)ethan-1-one (10 g, 66.59 mmol, 1.00 equiv) in MeOH (200 mL) was added sequentially NaOMe (30 mL), and dimethyl oxalate (10.2 g, 86.38 mmol, 1.3 equiv). The resulting solution was stirred for 8 h at room temperature. The reaction mixture was cooled to 0° C. with a water/ice bath. The resulting solution was diluted with 200 mL of EtOAc. The pH value of the solution was adjusted to 3 with aq HCl (3 mol/L). The resulting solution was extracted with 2×300 mL of EtOAc, and the organic layers were combined and dried over anhydrous $Na_2SO_4$ and concentrated under vacuum. This resulted in the title compound as a yellow solid (11 g, 70%).

Intermediate B-3: Methyl 4-[3-(oxetan-3-ylmethoxy)phenyl]-2,4-dioxobutanoate

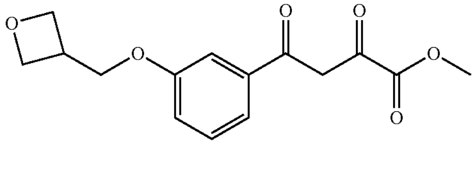 [SMILES: COC(=O)C(=O)CC(=O)c1cccc(OCC2COC2)c1]

In a 100-mL flask were combined a solution of 1-[3-(oxetan-3-ylmethoxy)-phenyl]ethan-1-one (Int. A-10, 3 g, 14.55 mmol, 1.00 equiv) in MeH (40 mL), dimethyl oxalate (3.42 g, 28.96 mmol, 2.00 equiv), and a solution of MeONa (2.36 g, 43.70 mmol, 3.00 equiv) in MeH (8 mL). The resulting solution was stirred for 12 h at rt, then poured onto ice/water. The pH was adjusted to 3 with HCl. The solids that formed were collected by filtration, affording 3.2 g (75%) of the title compound as a light yellow solid. LC-MS: (ES, m/z): 293.0. $^1$H-NMR: 6H (300 MHz, DMSO-$d_6$) 7.68 (1H, d, J=7.7 Hz), 7.53 (2H, in), 7.30 (1H, m), 7.14 (1H, s), 4.72 (2H, dd, J 7.9, 6.0 Hz), 4.45 (2H, t, J 6.0, 6.0 Hz), 4.30 (2H, d, J 6.7 Hz), 3.86 (3H, s), 3.40 (1H, tt, J=8.0, 8.0, 6.3, 6.3 Hz).

The following substituted 4-aryl-2,4-dioxobutanoate esters were obtained from Claisen condensation of an 1-aryl-ethanone with an oxalic ester.

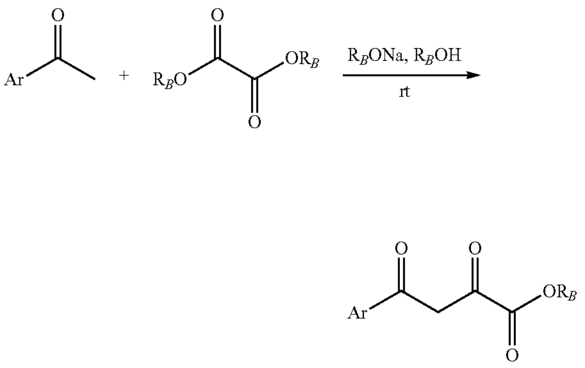

TABLE 3

Claisen synthesis of 4-aryl-2,4-dioxobutanoate esters.

| $R_BOH$/ time/ temp | Aryl ethanone | Product 4-aryl-2,4-dioxobutanoate ester | | Spectral |
|---|---|---|---|---|
| MeOH/ 12 hr/rt | 1-(3-nitrophenyl)-ethan-1-one | Methyl 4-(3-nitrophenyl)-2,4-dioxobutanoate | B-4 | |
| MeOH/ 12 hr/rt | 1-(Pyridin-2-yl)ethan-1-one | Methyl 2,4-dioxo-4-(pyridin-2-yl)butanoate | B-5 | LC-MS: (ES, m/z): 291.25. |
| MeOH/ 12 hr/ 30° C. | 1-(2,3-Dihydro-1,4-benzodioxin-6-yl)ethan-1-one | Methyl 4-(2,3-dihydro-1,4-benzodioxin-6-yl)-2,4-dioxobutanoate | B-6 | LC-MS: (ES, m/z): 265. |
| MeOH/ 16 hr/rt | 1-(2H-1,3-Benzo-dioxol-5-yl)ethan-1-one | Methyl 4-(2H-1,3-benzodioxol-5-yl)-2,4-dioxobutanoate | B-7 | LC-MS: (ES, m/z): 251. |
| MeOH/ 16 hr/ 40° C. | 1-(1-Methyl-1H-pyrazol-4-yl)-ethan-1-one | Methyl 4-(1-methyl-1H-pyrazol-4-yl)-2,4-dioxo-butanoate | B-8 | LC-MS: (ES, m/z): 211 |
| EtOH/5 hr/ rt | 1-(1-Benzothio-phen-2-yl)ethan-1-one | Ethyl 4-(1-benzothiophen-2-yl)-2,4-dioxobutanoate | B-9 | LC-MS: (ES, m/z): 277 |
| MeOH/ 2 hr/ 60° C. | 1-(4-Bromothien-2-yl)ethanone | Methyl 4-(4-bromothien-2-yl)-2,4-dioxobutanoate | B-10 | |
| EtOH/ 16 hr/rt | A-1 | Ethyl 4-(1-methyl-1H-indol-6-yl)-2,4-dioxobutanoate | B-11 | LC-MS: (ES, m/z): 273. |
| EtOH/ 16 hr/rt | A-2 | Ethyl 4-(1-methyl-1H-indazol-6-yl)-2,4-dioxobutanoate | B-12 | LC-MS: (ES, m/z): 274. |
| MeOH/ 16 hr/rt | A-3 | Methyl 4-[3-(propan-2-yl)-phenyl]2,4-dioxobutanoate | B-13 | |
| MeOH/ 16 hr/rt | A-4 | Methyl 4-(1-ethyl-1H-indazol-6-yl)-2,4-dioxobutanoate | B-14 | LC-MS: (ES, m/z): 275. |
| EtOH/ 16 hr/rt | A-4 | Ethyl 4-(1-ethyl-1H-indazol-6-yl)-2,4-dioxobutanoate | B-15 | LC-MS: (ES, m/z): 288. |
| MeOH/ 16 hr/rt | A-5 | Methyl 4-(3-chloro-5-methoxyphenyl)-2,4-dioxobutanoate | B-16 | LC-MS: (ES, m/z): 271 |
| EtOH/ 16 hr/rt | A-6 | Ethyl 4-(1-methyl-1H-indazol-5-yl)-2,4-dioxobutanoate | B-17 | LC-MS: (ES, m/z): 274. |
| EtOH/ 16 hr/rt | A-7 | Ethyl 4-(1-methyl-1H-indazol-4-yl)-2,4-dioxobutanoate | B-18 | LC-MS: (ES, m/z): 274. |
| MeOH/ 16 h/rt | A-8 | Methyl 4-(1-ethyl-1H-1,2,3-benzotriazol-6-yl)-2,4-dioxobutanoate | B-19 | LC-MS: (ES, m/z): 275 |
| EtOH/ 16 hr/rt | A-9 | Ethyl 4-(3-cyclo-butoxyphenyl)-2,4-dioxobutanoate | B-20 | LC-MS: (ES, m/z): 291. |
| EtOH/ 12 hr/rt | A-11 | Ethyl 4-[3-(oxetan-3-yloxy)-phenyl]-2,4-dioxobutanoate | B-21 | LC-MS: (ES, m/z): 293. |

TABLE 3-continued

Claisen synthesis of 4-aryl-2,4-dioxobutanoate esters.

| $R_B$OH/ time/ temp | Aryl ethanone | Product 4-aryl-2,4-dioxobutanoate ester | | Spectral |
|---|---|---|---|---|
| MeOH/ 12 hr/rt | A-12 | Methyl 4-(3-cyclopropoxy-phenyl)-2,4-dioxobutanoate | B-22 | LC-MS: (ES, m/z): 262.85. |
| MeOH/ 12 hr/rt | A-13 | Methyl 4-[3-(2,2-dimethyl-propoxy)phenyl]-2,4-dioxo-butanoate | B-23 | LC-MS: (ES, m/z): 292.95. |
| MeOH/ 12 hr/rt | A-14 | Methyl 4-[3-(cyclobutyl-methoxy)phenyl]-2,4-dioxo-butanoate | B-24 | LC-MS: (ES, m/z): 290.95. |
| MeOH/ 16 hr/rt | A-15 | Methyl 4-[3-(cyclopropyl-methoxy)phenyl]-2,4-dioxo-butanoate | B-25 | LC-MS: (ES, m/z): 276. |
| EtOH/ 16 hr/rt | A-16 | Ethyl 4-(3-ethoxyphenyl)-2,4-dioxobutanoate | B-26 | LC-MS: (ES, m/z): 264. |
| MeOH/ 12 hr/rt | A-17 | Methyl 4-[3-(benzyloxy)-phenyl]-2,4-dioxobutanoate | B-27 | LC-MS: (ES, m/z): 313.1. |
| MeOH/ 16 hr/rt | A-18 | Methyl 4-[3-(2-methyl-propoxy)phenyl]-2,4-dioxobutanoate | B-28 | LC-MS: (ES, m/z): 279. |
| MeOH/ 16 hr/rt | A-19 | Methyl 4-(3,5-dimethoxyphenyl)-2,4-dioxobutanoate | B-29 | LC-MS: (ES, m/z): 267. |
| MeOH/ 12 hr/rt | A-20 | Methyl 4-(3,5-diethoxy-phenyl)-2,4-dioxobutanoate | B-30 | LC-MS: (ES, m/z): 295.2. |
| MeOH/ 16 hr/rt | A-21 | Methyl 4-(3-ethoxy-5-methoxyphenyl)-2,4-dioxobutanoate | B-31 | LC-MS: (ES, m/z): 281 |
| EtOH/ 5 hr/rt | A-22 | Ethyl 2,4-dioxo-4-[2-(propan-2-yloxy)-1,3-oxazol-5-yl]-butanoate | B-32 | LC-MS: (ES, m/z): 270 |
| MeOH/ 16 h/rt | A-23 | Methyl 4-[1,3-dimethyl-1H-thieno[2,3-c]pyrazol-5-yl]-2,4-dioxobutanoate | B-33 | LC-MS: (ES, m/z): 281 |
| MeOH/ 16 h/rt | A-24 | Methyl 4-(5-2-methoxythien-2-yl)-2,4-dioxobutanoate | B-34 | |
| MeOH/ 16 h/rt | A-26 | Methyl 4-(5-(2-methylpropoxy)thien-2-yl)-2,4-dioxobutanoate | B-35 | |
| EtOH/ 5 h/rt | A-28 | 4-[2-(2-Methylpropyl)-1,3-oxazol-5-yl]-2,4-dioxobutanoate | B-36 | |
| MeOH/ 16 h/rt | A-29 | Methyl 4-(1-methyl-1H-1,3-benzodiazol-6-yl)-2,4-dioxobutanoate | B-37 | LC-MS: (ES, m/z): [M + 1] = 261 |
| MeOH/ 16 h/rt | A-30 | Methyl 4-[3-[(propan-2-yl)-carbamoyl]phenyl]-2,4-butanedioate | B-38 | |

Intermediate B-39: Ethyl 4-[2-(2-methylpropoxy)-1,3-thiazol-5-yl]-2,4-dioxobutanoate

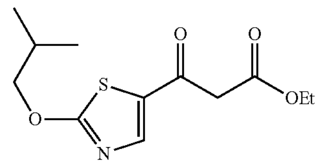 [SMILES: CCOC(=O)CC(=O)c1cnc(OCC(C)C)s1]

To a solution of It. A-25 (500 mg, 2.51 mmol, 1.00 equiv) in THF (10 mL) was added sequentially diethyl oxalate (1100 mg, 7.53 mmol, 2.00 equiv), and t-BuOK (850 mg, 7.58 mmol, 3.00 equiv). The resulting solution was stirred for 4 h at room temperature followed by dilution with 20 mL of $H_2O$, extraction with 2×30 mL of EtOAc and the organic layers were combined and dried over anhydrous $Na_2SO_4$ and concentrated under vacuum. The residue was applied onto a silica gel column with EtOAc/petroleum ether (1:4). This resulted in the title compound as a yellow solid (400 mg, 53%)

Intermediate B-40: Ethyl 2,4-dioxo-5-phenylpentanoate

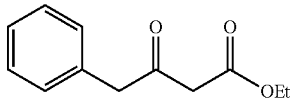 [SMILES: CCOC(=O)CC(=O)Cc1ccccc1]

To a solution of 1-phenyl-2-propanone (1 g, 8.32 mmol, 1.00 equiv) in THF (25 mL) was added NaH (269 mg, 11.21 mmol, 1.50 equiv), in portions at 0° C. in 30 min, followed by the addition of diethyl oxalate (1.64 g, 11.22 mmol, 1.50 equiv). The resulting solution was stirred for 1 h at room temperature, then cooled to 0° C. The reaction was then quenched by the addition of 20 mL of water. The resulting solution was extracted with 3×50 mL of EtOAc, and the combined organic layers were dried over anhydrous $Na_2SO_4$, concentrated under vacuum, and purified with silica gel chromatography using EtOAc/petroleum ether (1:40) to afford 700 mg (36%) of the title product as a yellow liquid.

The following substituted ketoesters were also used in the synthesis of pyrazoles.

Intermediate B-41: Methyl 2,4-dioxo-4-(1-propyl-1H-indazol-6-yl)butanoate

Intermediate B-42: Methyl 4-(3-cyclobutoxyphenyl)-2,4-dioxobutanoate

The following arylhydrazine intermediates were synthesized for use in preparing the compounds of this disclosure, including, but not limited to, use in Scheme I.

Intermediate C-1: 2-(Difluoromethoxy)phenyl]hydrazine trifluoroacetate

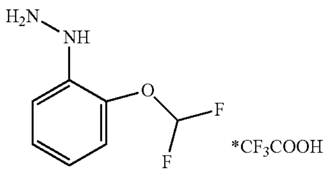 [SMILES: NNc1ccccc1OC(F)F]

Boc-protected 2-(difluoromethoxy)phenyl]hydrazine To a solution of 1-bromo-2-(difluoromethoxy)benzene (8.0 g, 35.87 mmol, 1.00 equiv), (tert-butoxy)-carbohydrazide (5.68 g, 42.98 mmol, 1.20 equiv), and BrettPhos Pd G3 (1.74 g, 1.92 mmol, 0.05 equiv) in dioxane (60 mL) under $N_2$ was added $Cs_2CO_3$ (11.70 g, 35.91 mmol, 1.00 equiv), in portions at room temperature. The resulting solution was stirred for 16 h at 100° C., then cooled, diluted with 200 mL of EtOAc, washed with 200 mL of brine, dried over $Na_2SO_4$ and concentrated under vacuum. The crude product was purified with silica gel chromatography using EtOAc/petroleum ether (1:5) to afford 8.0 g (81%) of the title compound as an orange solid. LC-MS: (ES, m/z): 275. $^1$H NMR (400 MHz, DMSO-$d_6$) δ 8.83 (s, 1H), 7.29-7.22 (m, 1H), 7.07 (q, J=7.7 Hz, 2H), 6.80-6.68 (m, 2H), 1.42 (s, 9H).

2-(Difluoromethoxy)phenyl]hydrazine trifluoroacetate A solution of the product from the previous step (2.0 g, 7.29 mmol, 1.00 equiv) and TFA (10 mL) in $CH_2Cl_2$ (20 mL) was stirred for 2 h at room temperature, then concentrated under vacuum, to afford 1.0 g (48%) of the title compound as a brown oil. LC-MS: (ES, m/z): 175.

The following arylhydrazines were synthesized from the corresponding aryl halides using similar procedures.

TABLE 4

Synthesis of aryl hydrazines from aryl bromides. The compounds were isolated as trifluoroacetate salts.

| Aryl bromide | Product | | Spectral |
|---|---|---|---|
| 1-Bromo-2-ethoxy-benzene | (2-Ethoxyphenyl)hydrazine | C-2 | LC-MS: (ES, m/z): 152. |

TABLE 4-continued

Synthesis of aryl hydrazines from aryl bromides. The compounds were isolated as trifluoroacetate salts.

| Aryl bromide | Product | | Spectral |
|---|---|---|---|
| 7-Bromo-1-methyl-1H-indazole | 7-Hydrazinyl-1-methyl-1H-indazole | C-3 | LC-MS: (ES, m/z): 163. |
| 4-Bromo-1-methyl-1H-indazole | 4-Hydrazinyl-1-methyl-1H-indazole | C-4 | LC-MS: (ES, m/z): 162. |
| 7-Bromo-1-ethyl-1H-indazole | 1-Ethyl-7-hydrazinyl-1H-indazole | C-5 | LC-MS: (ES, m/z): 277. |
| 1-Bromo-2-(propan-2-yloxy)benzene | [2-(Propan-2-yloxy)-phenyl]hydrazine | C-6 | LC-MS: (ES, m/z): 274. |

The free amino groups of the following reactants were first protected with SEM groups (NaH; SEM-Cl). Treatment of the coupling product with TFA for removal of the Boc groups also accomplished removal of the SEM protecting groups.

TABLE 5

Synthesis of aryl hydrazines from aryl bromides.

| Aryl bromide | Product | | Spectral |
|---|---|---|---|
| 4-Bromo-1H-indazole | 4-Hydrazinyl-1H-indazole | C-7 | LC-MS: (ES, m/z): 148.9. |
| 7-Bromo-1H-indazole | 7-Hydrazinyl-1H-indazole | C-8 | LC-MS: (ES, m/z): 379. |
| 4-Bromo-3-methyl-1H-indazole | 4-Hydrazinyl-3-methyl-1H-indazole | C-9 | LC-MS: (ES, m/z): 163.2. |
| 7-Bromo-1-methyl-1H-1,3-benzodiazole | 7-Hydrazinyl-1-methyl-1H-1,3-benzodiazole trifluoroacetate | C-10 | |
| 7-Bromo-1,3-dimethyl-1H-indazole | 7-Hydrazinyl-1,3-dimethyl-1H-indazole | C-11 | LC-MS: (ES, m/z): 177.1. |

Intermediate C-12: 7-Hydrazinyl-1-methyl-1H-1,2,3-benzotriazole trifluoroacetate

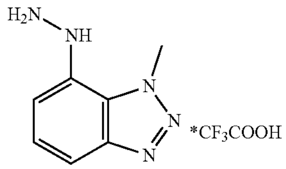

2-Bromo-N-methyl-6-nitroaniline A mixture of 1-bromo-2-fluoro-3-nitrobenzene (7 g, 31.82 mmol, 1.00 equiv), $K_2CO_3$ (8.8 g, 63.21 mmol, 2.00 equiv), and $CH_3NH_2$ (10 mL, 33%) in $CH_2Cl_2$ (50 mL) was stirred 16 h at rt, then diluted with 100 mL of water. The resulting solution was extracted with 2×200 mL of $CH_2Cl_2$. The combined organic layers were washed with 50 mL of brine, dried over $Na_2SO_4$, and concentrated under vacuum to afford 7 g (95%) of the title compound as a red oil. LC-MS: (ES, m/z): 230. $^1$H NMR (400 MHz, DMSO-$d_6$) δ 7.77 (ddd, J=9.8, 8.0, 1.6 Hz, 2H), 6.70 (t, J=8.0 Hz, 1H), 6.43-6.19 (m, 1H), 2.71 (d, J=5.3 Hz, 3H).

6-Bromo-1-N-methylbenzene-1,2-diamine A mixture of the product from the previous step (8 g, 34.62 mmol, 1.00 equiv) and Zn (4 g, 62.50 mmol, 2.00 equiv) in AcOH (120 mL) was stirred for 16 h at rt. The solids were removed by filtration, and the filtrate was concentrated under vacuum. The residue was dissolved in 300 mL of $CH_2Cl_2$, washed with 100 mL of $NaHCO_3$, dried over $Na_2SO_4$, and concentrated under vacuum, to afford 4 g (57%) of the title compound as a black oil. LC-MS: (ES, m/z): 201.

7-Bromo-1-methyl-1H-1,2,3-benzotriazole To a solution of the product from the previous step (4 g, 19.89 mmol, 1.00 equiv) in HBr/$H_2O$ (60 mL) at 5° C. was added a solution of $NaNO_2$ (2.07 g, 1.50 equiv) in $H_2O$ (10 mL) dropwise with stirring. The solution was stirred for 4 h at 15-20° C. The pH was adjusted to 8 with $NaHCO_3$ (3 mol/L). The resulting solution was extracted with 2×200 mL of EtOAc. The combined organic layers were washed with 100 mL of brine, dried over anhydrous $Na_2SO_4$, concentrated under vacuum, and purified with silica gel chromatography using EtOAc/petroleum ether (1:5), to afford 4 g (95%) of the title compound as a black solid. LC-MS: (ES, m/z): 212. $^1H$ NMR (400 MHz, DMSO-$d_6$) δ 8.06 (dd, J=8.3, 0.8 Hz, 1H), 7.84-7.73 (m, 1H), 7.31 (dd, J=8.4, 7.5 Hz, 1H), 4.51 (s, 3H).

7-Hydrazinyl-1-methyl-1H-1,2,3-benzotriazole trifluoroacetate was prepared from the previous compound by using the procedure of C-1. LC-MS: (ES, m/z): 163.

Intermediate C-13: [(2-Chlorophenyl)methyl]hydrazine dihydrochloride

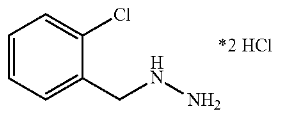

To a solution of hydrazine hydrate (85%) (31 g, 8.50 equiv) in EtOH (100 mL) was added dropwise a solution of 1-chloro-2-(chloromethyl)benzene (10 g, 62.10 mmol, 1.00 equiv) in EtOH (50 mL) over 1 hr at 70° C. The resulting solution was stirred for 1 h at 70° C., concentrated under vacuum diluted with water, and extracted with EtOAc three times. The combined organic layers were chilled to 0° C., then a solution of 4N HCl in dioxane was added. The solids that formed were collected by filtration, affording 6.1 g (63%) of the title product as a white solid.

Intermediate D-1: Ethyl 5-[[(tert-butoxy)carbonyl](phenyl)amino]-1-[(2-chlorophenyl)methyl]-1H-pyrazole-3-carboxylate

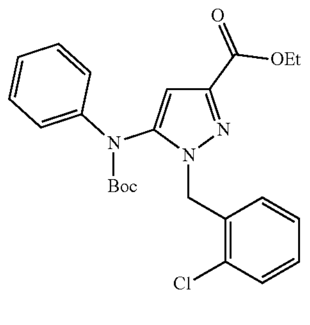 [SMILES: CCOC(=O)c1cc(N(C(=O)OC(C)(C)C)c2ccccc2)n(Cc2ccccc2Cl)n1]

Ethyl 3-cyano-2-(potassiooxy)prop-2-enoate To a solution of diethyl oxalate (5.06 g, 34.62 mmol, 1.00 equiv) in $CH_3CN$ (20 mL) was added t-BuOK (3.90 g, 34.76 mmol, 1.12 equiv), in portions at rt. The resulting solution was stirred for 1.5 h at rt. The solids that formed were collected by filtration. This resulted in 5.09 g (82%) of the title product as a yellow solid.

Ethyl 5-amino-1-[(2-chlorophenyl)methyl]-1H-pyrazole-3-carboxylate To a solution of the product from the previous step (2.0 g, 11.16 mmol, 1.00 equiv) in 1,4-dioxane (20 mL) was added TFA (2 mL) dropwise with stirring at rt. The resulting mixture was stirred at rt for 30 min. To this was added Int. C-13 (2.0 g, 12.77 mmol, 1.15 equiv), in portions at rt. The resulting solution was stirred overnight at rt, then diluted with 200 mL of EtOAc, washed with 2×200 mL of brine, dried over anhydrous $Na_2SO_4$, concentrated under vacuum, and purified with silica gel chromatography using EtOAc/petroleum ether (1:3) to afford 1.8 g (58%) of the title compound as a yellow oil.

Ethyl 1-[(2-chlorophenyl)methyl]-5-(phenylamino)-1H-pyrazole-3-carboxylate

A solution of the product from the previous step (1.0 g, 3.57 mmol, 1.00 equiv), iodobenzene (768 mg, 3.76 mmol, 1.05 equiv), Brettphos Pd G3 precatalyst (326 mg, 0.36 mmol, 0.10 equiv), and $Cs_2CO_3$ (1.4 g, 4.30 mmol, 1.20 equiv) in 1,4-dioxane (20 mL). The resulting solution was stirred in a sealed tube under $N_2$ at 90° C. for 3 h. The resulting solution was diluted with 200 mL of EtOAc, washed with 2×200 mL of brine, dried over $Na_2SO_4$, concentrated under vacuum, and purified with silica gel chromatography using petroleum ether:EtOAc:DCM (3:1:0.1) to afford 1.3 g (102%) of the title product as a yellow solid.

Ethyl 5-[[(tert-butoxy)carbonyl](phenyl)amino]-1-[(2-chlorophenyl)methyl]-1H-pyrazole-3-carboxylate To a solution of the product from the previous step (800 mg, 2.25 mmol, 1.00 equiv) and DMAP (548 mg, 4.49 mmol, 2.00 equiv) in toluene (20 mL) was added di-tert-butyl dicarbonate (980 mg, 4.49 mmol, 2.00 equiv), in portions at rt. The resulting solution was heated at reflux overnight. The resulting solution was diluted with 200 mL of EtOAc, washed with 2×100 mL of brine, dried over anhydrous $Na_2SO_4$, concentrated under vacuum, and purified with silica gel chromatography using EtOAc/petroleum ether (1:3) to afford 1.0 g (101%) of the title product as a colorless oil.

Intermediate D-2: Methyl 5-(3-cyclopropoxyphenyl)-1H-pyrazole-3-carboxylate

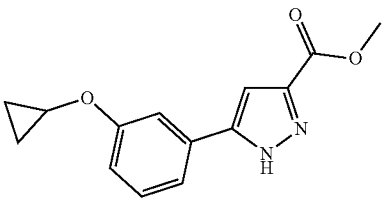 [SMILES: COC(=O)c1cc(-c2cccc(OC3CC3)c2)[nH]n1]

A solution of Int. B-22 (2 g, 7.63 mmol, 1.00 equiv) and hydrazine hydrate (540 mg, 10.00 mmol, 1.30 equiv) in AcOH (20 mL) was stirred for 2 h at 100° C., then cooled. The pH was adjusted to 7 with satd $NaHCO_3$, and the resulting solution was extracted with 3×100 mL EtOAc. The combined organic layers were dried over $Na_2SO_4$, concentrated under vacuum, and purified with silica gel chromatography using EtOAc/hexane (1/1) to afford 1.5 g (76%) of the title compound as a light yellow solid. LC-MS: (ES, m/z): 259. $^1H$ NMR (300 MHz, MeOD) δ 7.35 (m, 3H), 7.13 (d, J=21.3 Hz, 2H), 3.92 (s, 3H), 3.84 (dp, J=6.4, 3.0, 3.0, 2.9, 2.9 Hz, 1H), 0.82 (m, 2H), 0.72 (m, 2H).

The following substituted 3-pyrazolecarboxylic esters were obtained from condensation of methyl 4-(aryl)-2,4-dioxobutanoate with hydrazine:

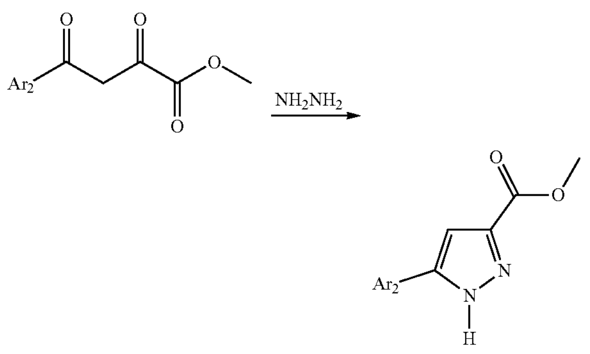

TABLE 6

Pyrazole synthesis with hydrazine.

| Diketone | Product | | Spectral |
|---|---|---|---|
| B-2 | Methyl 5-(3-methoxyphenyl)-1H-pyrazole-3-carboxylate | D-3 | |
| B-4 | Methyl 5-(3-nitrophenyl)-1H-pyrazole-3-carboxylate | D-4 | |
| B-6 | Methyl 5-(2,3-dihydro-1,4-benzodioxin-6-yl)-1H-pyrazole-3-carboxylate | D-5 | LC-MS: (ES, m/z): 261. |
| B-7 | Methyl 5-(2H-1,3-benzodioxol-5-yl)-1H-pyrazole-3-carboxylate | D-6 | LC-MS: (ES, m/z): 247. |
| B-8 | Methyl 5-(1-methyl-1H-pyrazol-4-yl)-1H-pyrazole-3-carboxylate | D-7 | LC-MS: (ES, m/z): 207. |
| B-9 | Ethyl 5-(1-benzothiophen-2-yl)-1H-pyrazole-3-carboxylate | D-8 | LC-MS: (ES, m/z): 272. |
| B-11 | Ethyl 5-(1-methyl-1H-indol-6-yl)-1H-pyrazole-3-carboxylate | D-9 | LC-MS: (ES, m/z): 269. |
| B-12 | Ethyl 5-(1-methyl-1H-indazol-6-yl)-1H-pyrazole-3-carboxylate | D-10 | LC-MS: (ES, m/z): 271. |
| B-14 | Methyl 5-(1-ethyl-1H-indazol-6-yl)-1H-pyrazole-3-carboxylate | D-11 | LC-MS: (ES, m/z): 271. |
| B-16 | Methyl 5-(3-chloro-5-methoxyphenyl)-1H-pyrazole-3-carboxylate | D-12 | LC-MS: (ES, m/z): 252. |
| B-17 | Ethyl 5-(1-methyl-1H-indazol-5-yl)-1H-pyrazole-3-carboxylate | D-13 | LC-MS: (ES, m/z): 270. |
| B-18 | Ethyl 5-(1-methyl-1H-indazol-4-yl)-1H-pyrazole-3-carboxylate | D-14 | LC-MS: (ES, m/z): 270. |
| B-19 | Methyl 5-(1-ethyl-1H-1,2,3-benzotriazol-6-yl)-1H-pyrazole-3-carboxylate | D-15 | LC-MS: (ES, m/z): 271. |
| B-20 | Ethyl 5-(3-cyclobutoxyphenyl)-1H-pyrazole-3-carboxylate | D-16 | LC-MS: (ES, m/z): 286. |
| B-23 | Methyl 5-[3-(2,2-dimethylpropoxy)phenyl]-1H-pyrazole-3-carboxylate | D-17 | LC-MS: (ES, m/z): 289.1. |
| B-26 | Ethyl 5-(3-ethoxyphenyl)-1H-pyrazole-3-carboxylate | D-18 | LC-MS: (ES, m/z): 260. |
| B-27 | Methyl 5-[3-(benzyloxy)phenyl]-1H-pyrazole-3-carboxylate | D-19 | LC-MS: (ES, m/z): 309.1. |
| B-28 | Methyl 5-[3-(2-methylpropoxy)phenyl]-1H-pyrazole-3-carboxylate | D-20 | |
| B-29 | Methyl 5-(3,5-dimethoxyphenyl)-1H-pyrazole-3-carboxylate | D-21 | LC-MS: (ES, m/z): 263. |
| B-30 | Methyl 5-(3,5-diethoxyphenyl)-1H-pyrazole-3-carboxylate | D-22 | LC-MS: (ES, m/z): 290.95. |
| B-31 | Methyl 5-(3-ethoxy-5-methoxyphenyl)-1H-pyrazole-3-carboxylate | D-23 | LC-MS: (ES, m/z): 277. |
| B-32 | Ethyl 5-[2-(propan-2-yloxy)-1,3-oxazol-5-yl]-1H-pyrazole-3-carboxylate | D-24 | LC-MS: (ES, m/z): 266. |
| B-33 | Methyl 5-[1,3-dimethyl-1H-thieno[2,3-c]pyrazol-5-yl]-1H-pyrazole-3-carboxylate | D-25 | LC-MS: (ES, m/z): 277. |
| B-38 | Methyl 5-[3-[(propan-2-yl)carbamoyl]phenyl]-1H-pyrazol-3-carboxylate | D-26 | |

Intermediate D-27: Methyl 1-[(2-chlorophenyl)methyl]-5-(3-(propan-2-yl)phenyl)-1H-pyrazole-3-carboxylate

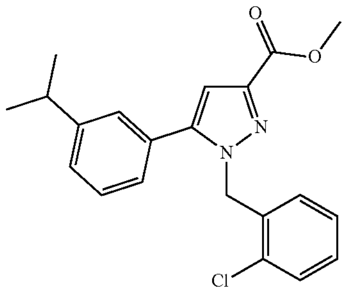 [SMILES: COC(=O)c1cc(-c2cccc(C(C)C)c2)n(Cc2ccccc2Cl)n1]

A solution of Int. B-13 (1.0 g, 4.03 mmol, 1.00 equiv) and Int. C-13 (1.38 g, 6.01 mmol, 1.50 equiv) in AcOH (20 mL) was stirred for 2 h at 100° C., then concentrated under vacuum, diluted with 200 mL of EtOAc, washed with 2×100 mL of sat $NaHCO_3$, dried over anhydrous $Na_2SO_4$ and concentrated under vacuum. The crude product was purified with silica gel chromatography using EtOAc/petroleum ether (1:5) to afford 1.05 g (71%) of the title product as a yellow solid.

Intermediate D-28: Methyl 1-[(2-Chlorophenyl)methyl]-5-(3-methoxyphenyl)-1H-pyrazole-3-carboxylate

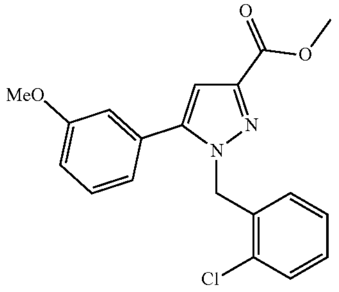 [SMILES: COC(=O)c1cc(-c2cccc(OC)c2)n(Cc2ccccc2Cl)n1]

To a solution of Int. B-2 (3.8 g, 16.09 mmol, 1.00 equiv) in MeOH (80 mL) was added Int. C-13 (4.8 g, 20.91 mmol, 1.30 equiv). The resulting solution was stirred for 3 h at 65° C., then concentrated under vacuum, and purified with silica gel chromatography using EtOAc/petroleum ether (1:2), to afford the title compound as a white solid (5.5 g, 96%).

The following substituted 3-pyrazolecarboxylic esters were obtained from condensation of methyl 4-(aryl)-2,4-dioxobutanoate with various substituted hydrazines:

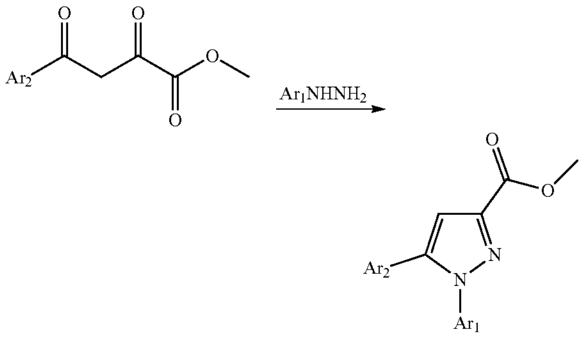

TABLE 7

Pyrazole synthesis with substituted hydrazines.

| $Ar_1NHNH_2$ | Diketone | Product | | Spectral |
|---|---|---|---|---|
| Phenylhydrazine | B-28 | Methyl 5-[3-(2-methylpropoxy)-phenyl]-1-phenyl-1H-pyrazole-3-carboxylate | D-29 | LC-MS: (ES, m/z): 357. |
| (2-Bromo-phenyl)hydrazine | B-14 | Methyl 1-(2-bromophenyl)-5-(1-ethyl-1H-indazol-6-yl)-1H-pyrazole-3-carboxylate | D-30 | LC-MS: (ES, m/z): 425.1. |
| (2-Bromo-phenyl)hydrazine | B-18 | Ethyl 1-(2-bromophenyl)-5-(1-methyl-1H-indazol-6-yl)-1H-pyrazole-3-carboxylate | D-31 | LC-MS: (ES, m/z): 425. |
| (2-Bromo-phenyl)hydrazine | B-23 | Methyl 1-(2-bromophenyl)-5-[3-(2,2-dimethylpropoxy)phenyl]-1H-pyrazole-3-carboxylate | D-32 | LC-MS: (ES, m/z): 443.1. |
| (2-Bromo-phenyl)hydrazine | B-29 | Methyl 1-(2-bromophenyl)-5-(3,5-dimthoxyphenyl)-1H-pyrazole-3-carboxylate | D-33 | LC-MS: (ES, m/z): 417. |
| (2-Bromo-phenyl)hydrazine | B-41 | Methyl 1-(2-bromophenyl)-5-(1-propyl-1H-indazol-6-yl)-1H-pyrazole-3-carboxylate | D-34 | LC-MS: (ES, m/z): 439.1. |
| (2-Bromo-phenyl)hydrazine | B-42 | Methyl 1-(2-bromophenyl)-5-(3-cyclobutoxyphenyl)-1H-pyrazole-3-carboxylate | D-35 | LC-MS: (ES, m/z): 441.2. |

TABLE 7-continued

Pyrazole synthesis with substituted hydrazines.

| | | | | |
|---|---|---|---|---|
| (2-Fluorophenyl)-hydrazine | B-3 | Methyl 1-(2-fluorophenyl)-5-[3-(oxetan-3-ylmethoxy)phenyl]-1H-pyrazole-3-carboxylate | D-36 | LC-MS: (ES, m/z): 383.1. |
| (2-Fluorophenyl)-hydrazine | B-20 | Ethyl 5-(3-cyclobutoxyphenyl)-1-(2-fluorophenyl)-1H-pyrazole-3-carboxylate | D-37 | LC-MS: (ES, m/z): 381. |
| (2-Fluorophenyl)-hydrazine | B-21 | Ethyl 1-(2-fluorophenyl)-5-[3-(oxetan-3-yloxy)phenyl]-1H-pyrazole-3-carboxylate | D-38 | LC-MS: (ES, m/z): 383. |
| (2-Fluorophenyl)-hydrazine | B-28 | Methyl 1-(2-fluorophenyl)-5-[3-(2-methylpropoxy)phenyl]-1H-pyrazole-3-carboxylate | D-39 | LC-MS: (ES, m/z): 369. |
| (2-Methyl-phenyl)hydrazine | B-20 | Ethyl 5-(3-cyclobutoxyphenyl)-1-(2-methylphenyl)-1H-pyrazole-3-carboxylate | D-40 | LC-MS: (ES, m/z): 376. |
| (2-Methyl-phenyl)hydrazine | B-30 | Methyl 5-(3,5-diethoxyphenyl)-1-(2-methylphenyl)-1H-pyrazole-3-carboxylate | D-41 | LC-MS: (ES, m/z): 381.05. |
| (2-Nitrophenyl)-hydrazine | B-14 | Methyl 5-(1-ethyl-1H-indazol-6-yl)-1-(2-nitrophenyl)-1H-pyrazole-3-carboxylate | D-42 | LC-MS: (ES, m/z): 392.30. |
| Quinolin-8-yl-hydrazine | B-23 | Methyl 5-[3-(2,2-dimethyl-propoxy)phenyl]-1-(quinolin-8-yl)-1H-pyrazole-3-carboxylate | D-43 | LC-MS: (ES, m/z): [M + 1] = 416. |
| C-2 | B-29 | Methyl 5-(3,5-dimethoxyphenyl)-1-(2-ethoxyphenyl)-1H-pyrazole-3-carboxylate | D-44 | LC-MS: (ES, m/z): 383. |
| C-3 | B-15 | Ethyl 5-(1-ethyl-1H-indazol-6-yl)-1-(1-methyl-1H-indazol-7-yl)-1H-pyrazole-3-carboxylate | D-45 | LC-MS: (ES, m/z): 414. |
| C-3 | B-20 | Ethyl 5-(3-cyclobutoxyphenyl)-1-(1-methyl-1H-indazol-7-yl)-1H-pyrazole-3-carboxylate | D-46 | LC-MS: (ES, m/z): 416. |
| C-3 | B-23 | Methyl 5-[3-(2,2-dimethyl-propoxy)phenyl]-1-(1-methyl-1H-indazol-7-yl)-1H-pyrazole-3-carboxylate | D-47 | LC-MS: (ES, m/z): 419.10. |
| C-3 | B-24 | Methyl 5-[3-(cyclobutylmethoxy)phenyl]-1-(1-methyl-1H-indazol-7-yl)-1H-pyrazole-3-carboxylate | D-48 | LC-MS: (ES, m/z): 417. |
| C-3 | B-25 | Methyl 5-[3-(cyclopropyl-methoxy)phenyl]-1-(1-methyl-1H-indazol-7-yl)-1H-pyrazole-3-carboxylate | D-49 | LC-MS: (ES, m/z): 402. |
| C-3 | B-28 | Methyl 1-(1-methyl-1H-indazol-7-yl)-5-[3-(2-methylpropoxy)-phenyl]-1H-pyrazole-3-carboxylate | D-50 | LC-MS: (ES, m/z): 405. |
| C-3 | B-29 | Methyl 5-(3,5-dimethoxyphenyl)-1-(1-methyl-1H-indazol-7-yl)-1H-pyrazole-3-carboxylate | D-51 | LC-MS: (ES, m/z): 393. |
| C-3 | B-30 | Methyl 5-(3,5-diethoxyphenyl)-1-(1-methyl-1H-indazol-7-yl)-1H-pyrazole-3-carboxylate | D-52 | LC-MS: (ES, m/z): 421.05. |
| C-5 | B-23 | Methyl 5-[3-(2,2-dimethylpropoxy)phenyl]-1-(1-ethyl-1H-indazol-7-yl)-1H-pyrazole-3-carboxylate | D-53 | LC-MS: (ES, m/z): 432. |
| C-6 | B-2 | Methyl 5-(3-methoxyphenyl)-1-[2-(propan-2-yloxy)phenyl]-1H-pyrazole-3-carboxylate | D-54 | LC-MS: (ES, m/z): 367. |
| C-11 | B-23 | Methyl 1-(1,3-dimethyl-1H-indazol-7-yl)-5-[3-(2,2-dimethyl-propoxy)phenyl]-1H-pyrazole-3-carboxylate | D-55 | LC-MS: (ES, m/z): 433.3. |
| C-12 | B-23 | Methyl 5-[3-(2,2-dimethyl-propoxy)phenyl]-1-(1-methyl-1H-1,2,3-benzotriazol-7-yl)-1H-pyrazole-3-carboxylate | D-56 | LC-MS: (ES, m/z): 420. |
| C-13 | B-37 | Methyl 1-[(2-chlorophenyl)-methyl]-5-(1-methyl-1H-1,3-benzodiazol-6-yl)-1H-pyrazole-3-carboxylate | D-57 | LC-MS: (ES, m/z): [M + 1] = 381. |

TABLE 7-continued

| Pyrazole synthesis with substituted hydrazines. | | | |
|---|---|---|---|
| $Ar_1NHNH_2$ | Diketone | Product | |
| (4-Nitro-phenyl)-hydrazine | B-28 | Methyl-5-[3-(2-methylpropoxy)phenyl]-1-[(4-nitrophenyl)methyl]-1H-pyrazole-3-carboxylate | D-58 |
| (Pyridin-3-yl)-hydrazine | B-2 | Methyl 5-(3-methoxyphenyl)-1-(pyridin-3-yl)-1H-pyrazole-3-carboxylate | D-59 |
| C-13 | B-1 | Methyl 1-[(2-chlorophenyl)methyl]-5-(2-methoxyphenyl)-1H-pyrazole-3-carboxylate | D-60 |
| C-13 | B-10 | Methyl 5-(4-bromothien-2-yl)-1-[(2-chloro-phenyl)methyl]-1H-pyrazole-3-carboxylate | D-61 |
| C-13 | B-35 | Methyl 1-[(2-chlorophenyl)methyl]-5-[5-(2-methylpropoxy)thien-2-yl]1H-pyrazole-3-carboxylate | D-62 |
| C-13 | B-36 | Methyl 1-[(2-chlorophenyl)-5-[2-(2-methyl-propyl)-1,3-oxazol-5-yl]-1H-pyrazole-3-carboxylate | D-63 |
| C-13 | B-39 | Methyl 1-[(2-chlorophenyl)methyl]-5-[2-(2-methylpropoxy)-1,3-thiazol-5-yl]-1H-pyrazole-3-carboxylate | D-64 |

The following substituted 3-pyrazolecarboxylic esters were obtained from condensation of various methyl 4-aryl-2,4-dioxobutanoates with (2-chlorophenyl) hydrazine:

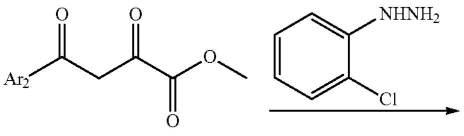

-continued

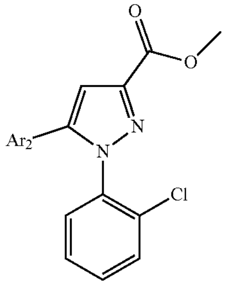

TABLE 8

| Pyrazole synthesis with 2-chlorophenyl hydrazine. | | | |
|---|---|---|---|
| Diketone | Product | | Spectral |
| B-2 | Methyl 5-(3-methoxyphenyl)-1-(2-methylphenyl)-1H-pyrazole-3-carboxylate (This product from reaction with 2-methylhydrazine) | D-65 | LC-MS: (ES, m/z): 322. |
| B-3 | Methyl 1-(2-chlorophenyl)-5-[3-(oxetan-3-yl-methoxy)phenyl]-1H-pyrazole-3-carboxylate | D-66 | LC-MS: (ES, m/z): 399.0 |
| B-5 | Methyl 1-(2-chlorophenyl)-5-(pyridin-2-yl)-1H-pyrazole-3-carboxylate | D-67 | LC-MS: (ES, m/z): 314.20. |
| B-12 | Ethyl 1-(2-chlorophenyl)-5-(1-methyl-1H-indazol-6-yl)-1H-pyrazole-3-carboxylate | D-68 | LC-MS: (ES, m/z): 381. |
| B-14 | Methyl 1-(2-chlorophenyl)-5-(1-ethyl-1H-indazol-6-yl)-1H-pyrazole-3-carboxylate | D-69 | LC-MS: (ES, m/z): 381. |
| B-20 | Ethyl 1-(2-chlorophenyl)-5-(3-cyclobutoxy-phenyl)-1H-pyrazole-3-carboxylate | D-70 | LC-MS: (ES, m/z): 396. |
| B-21 | Ethyl 1-(2-chlorophenyl)-5-[3-(oxetan-3-yloxy)phenyl]-1H-pyrazole-3-carboxylate | D-71 | LC-MS: (ES, m/z): 398.95. |
| B-22 | Methyl 1-(2-chlorophenyl)-5-(3-cyclopropoxyphenyl)-1H-pyrazole-3-carboxylate | D-72 | LC-MS: (ES, m/z): 369.25. |
| B-23 | Methyl 1-(2-chlorophenyl)-5-[3-(2,2-dimethylpropoxy)phenyl]-1H-pyrazole-3-carboxylate | D-73 | LC-MS: (ES, m/z): 398.95. |
| B-24 | Methyl 1-(2-chlorophenyl)-5-[3-(cyclobutyl-methoxy)phenyl]-1H-pyrazole-3-carboxylate | D-74 | LC-MS: (ES, m/z): 396.95. |
| B-28 | Methyl 1-(2-chlorophenyl)-5-[3-(2-methyl-propoxy)phenyl]-1H-pyrazole-3-carboxylate | D-75 | |
| B-29 | Methyl 1-(2-chlorophenyl)-5-(3,5-dimethoxy-phenyl)-1H-pyrazole-3-carboxylate | D-76 | LC-MS: (ES, m/z): 373. |
| B-30 | Methyl 1-(2-chlorophenyl)-5-(3,5-diethoxy-phenyl)-1H-pyrazole-3-carboxylate | D-77 | LC-MS: (ES, m/z): 401.3. |

TABLE 8-continued

| Pyrazole synthesis with 2-chlorophenyl hydrazine. | | | |
|---|---|---|---|
| Diketone | Product | | Spectral |
| B-40 | Ethyl [5-benzyl-1-[(2-chlorophenyl)methyl]-1H-pyrazole-3-carboxylate | D-78 | |

The following substituted 3-pyrazolecarboxylic esters were obtained from condensation of Int. B-22 with various substituted hydrazines:

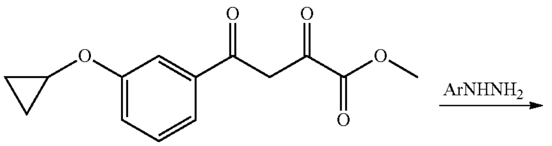

-continued

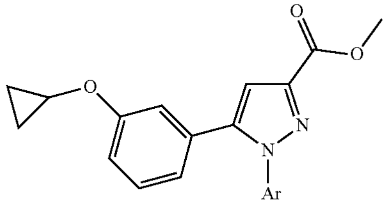

TABLE 9

| Pyrazole synthesis with methyl 4-(3-cyclopropoxyphenyl)-2,4-dioxobutanoate (Int. B-22). | | | |
|---|---|---|---|
| $ArNHNH_2$, solvent | Product | | Spectral |
| (2-Fluoro-phenyl)hydrazine hydrochloride, EtOH | Methyl 5-(3-cyclopropoxyphenyl)-1-(2-fluorophenyl)-1H-pyrazole-3-carboxylate | D-79 | LC-MS: (ES, m/z): 353.0. |
| (2-Bromophenyl)-hydrazine, MeOH | Methyl 1-(2-bromophenyl)-5-(3-cyclopropoxyphenyl)-1H-pyrazole-3-carboxylate | D-80 | LC-MS: (ES, m/z): 413. |
| (2-Bromo-4-fluoro-phenyl)hydrazine, MeOH | Methyl 1-(2-bromo-4-fluorophenyl)-5-(3-cyclopropoxyphenyl)-1H-pyrazole-3-carboxylate | D-81 | LC-MS: (ES, m/z): 430.90. |
| (2,4-Dichloro-phenyl)hydrazine, MeOH | Methyl 5-(3-cyclopropoxyphenyl)-1-(2,4-dichlorophenyl)-1H-pyrazole-3-carboxylate | D-82 | LC-MS: (ES, m/z): 402.95. |
| (2,5-Dichloro-phenyl)hydrazine, MeOH | Methyl 5-(3-cyclopropoxyphenyl)-1-(2,5-dichlorophenyl)-1H-pyrazole-3-carboxylate | D-83 | LC-MS: (ES, m/z): 402.90. |
| [2-(Difluoro-methoxy)phenyl]-hydrazine, $CF_3COOH$/MeOH | Methyl 5-(3-cyclopropoxyphenyl)-1-[2-(difluoromethoxy)phenyl]-1H-pyrazole-3-carboxylate | D-84 | LC-MS (ES, m/z): 401 |
| (2-Ethoxyphenyl)-hydrazine, MeOH | Methyl 5-(3-cyclopropoxyphenyl)-1-(2-ethoxyphenyl)-1H-pyrazole-3-carboxylate | D-85 | LC-MS: (ES, m/z): 378. |
| (2-Methoxyphenyl)-hydrazine | Methyl 5-(3-cyclopropoxyphenyl)-1-(2-methoxyphenyl)-1H-pyrazole-3-carboxylate | D-86 | LC-MS: (ES, m/z): 364.9. |
| (2-Methylphenyl)-hydrazine dihydro-chloride, MeOH | Methyl 5-(3-cyclopropoxyphenyl)-1-(2-methylphenyl)-1H-pyrazole-3-carboxylate | D-87 | LC-MS (ES, m/z): 349. |
| (2-Nitrophenyl)-hydrazine, EtOH | Methyl 5-(3-cyclopropoxyphenyl)-1-(2-nitrophenyl)-1H-pyrazole-3-carboxylate | D-88 | LC-MS: (ES, m/z): 380. |
| (2-(Propan-2-yl)-phenyl)hydrazine HCl, MeOH | Methyl 5-(3-cyclopropoxyphenyl)-1-[2-(propan-2-yl)phenyl]-1H-pyrazole-3-carboxylate | D-89 | |
| [2-(Trifluoromethyl)-phenyl]hydrazine $(HCl)_2$, MeOH | Methyl 5-(3-cyclopropoxyphenyl)-1-[2-(trifluoromethyl)phenyl]-1H-pyrazole-3-carboxylate | D-90 | LC-MS: (ES, m/z): 403. |
| C-3, MeOH | Methyl 5-(3-cyclopropoxyphenyl)-1-(1-methyl-1H-indazol-7-yl)-1H-pyrazole-3-carboxylate | D-91 | LC-MS (ES, m/z): 389 |
| C-4, MeOH | Methyl 5-(3-cyclopropoxyphenyl)-1-(1-methyl-1H-indazol-4-yl)-1H-pyrazole-3-carboxylate | D-92 | LC-MS: (ES, m/z): 388. |
| C-5, MeOH | Methyl 5-(3-cyclopropoxyphenyl)-1-(1-ethyl-1H-indazol-7-yl)-1H-pyrazole-3-carboxylate | D-93 | LC-MS: (ES, m/z): 402. |
| C-7, MeOH | Methyl 5-(3-cyclopropoxyphenyl)-1-(1H-indazol-4-yl)-1H-pyrazole-3-carboxylate | D-94 | LC-MS: (ES, m/z): 375.1. |

TABLE 9-continued

| Pyrazole synthesis with methyl 4-(3-cyclopropoxyphenyl)-2,4-dioxobutanoate (Int. B-22). | | | |
|---|---|---|---|
| $ArNHNH_2$, solvent | Product | | Spectral |
| C-8, MeOH | Methyl 5-(3-cyclopropoxyphenyl)-1-(1H-indazol-7-yl)-1H-pyrazole-3-carboxylate | D-95 | LC-MS: (ES, m/z): 375. |
| C-9, MeOH | Methyl 5-(3-cyclopropoxyphenyl)-1-(3-methyl-1H-indazol-4-yl)-1H-pyrazole-3-carboxylate | D-96 | LC-MS: (ES, m/z): 388.95. |
| C-10, MeOH | Methyl 5-(3-cyclopropoxyphenyl)-1-(1-methyl-1H-1,3-benzodiazol-7-yl)-1H-pyrazole-3-carboxylate | D-97 | LC-MS: (ES, m/z): 389.0. |

Intermediate E-1: 1-(Bromomethyl)-2-ethoxybenzene

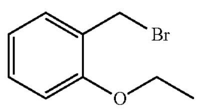

To a solution of (2-ethoxyphenyl)methanol (15.2 g, 99.87 mmol, 1.00 equiv) and $CBr_4$ (50.1 g, 150.00 mmol, 1.50 equiv) in $CH_2Cl_2$ (200 mL), was added $PPh_3$ (39.45 g, 150.41 mmol, 1.50 equiv), in portions at 0° C. The resulting solution was stirred for 16 h at rt, concentrated under vacuum, and purified with silica gel chromatography using with EtOAc/petroleum ether (1:10) to afford 14 g (65%) of the title compound as a colorless oil. $^1$H-NMR: ($CDCl_3$, ppm): δ: 7.51-7.25 (m, 1H), 7.06-6.86 (m, 1H), 4.65 (s, 1H), 4.16 (q, J=7.0 Hz, 1H), 1.53 (t, J=7.0 Hz, 1H).

Intermediate E-2: 1-(Bromomethyl)-2-cyclopropoxybenzene

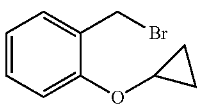 [SMILES: BrCc1ccccc1OC1CC1]

Methyl 2-cyclopropoxybenzoate To a mixture of methyl 2-hydroxybenzoate (5.0 g, 32.86 mmol, 1.00 equiv) $Cs_2CO_3$ (32 g, 98.21 mmol, 3.00 equiv) in DMA (100 mL) was added dropwise bromocyclopropane (39.8 g, 328.99 mmol, 10.00 equiv) with stirring at rt. The resulting solution was stirred for 16 h at 130° C., cooled, diluted with 200 mL of EtOAc, washed with 2×200 mL of water and 2×200 mL of brine, dried over $Na_2SO_4$, and concentrated under vacuum. The residue was purified by silica gel chromatography using EtOAc/petroleum ether (1:6) to afford 1.6 g (25%) of the title compound as a yellow oil. LC-MS: (ES, m/z): 193. 1H NMR (400 MHz, $CDCl_3$) δ 7.80 (dd, J=7.8, 1.8 Hz, 1H), 7.49 (ddd, J=8.9, 7.3, 1.8 Hz, 1H), 7.38 (dd, J=8.4, 1.1 Hz, 1H), 7.01 (td, J=7.5, 7.5, 1.2 Hz, 1H), 3.89 (s, 3H), 3.83 (tt, J=5.9, 5.9, 3.2, 3.2 Hz, 1H), 0.86 (m, 4H).

(2-Cyclopropoxyphenyl)methanol To a solution of methyl 2-cyclopropoxybenzoate (1.5 g, 7.80 mmol, 1.00 equiv) in THF (100 mL) was added $LiAlH_4$ (594 mg, 15.65 mmol, 2.00 equiv), in portions at 0° C. The resulting mixture was stirred for 2 h at 0° C. in an ice/salt bath, then quenched by the addition of $Na_2SO_4$/10 $H_2O$. The solids were removed by filtration. The resulting solution was concentrated under vacuum and purified with silica gel chromatography using EtOAc/petroleum ether (1:5) to afford 750 mg (59%) of the title compound as a yellow oil. LC-MS: (ES, m/z): 187. $^1$H NMR: (400 MHz, $CDCl_3$) δ 7.30 (m, 3H), 6.98 (tdd, J=7.5, 7.5, 3.7, 1.5 Hz, 1H), 4.65 (s, 2H), 3.80 (m, 1H), 0.82 (m, 4H).

1-(Bromomethyl)-2-cyclopropoxybenzene To a solution of (2-cyclopropoxy-phenyl)methanol (750 mg, 4.57 mmol, 1.00 equiv) and $CBr_4$ (3.06 g, 9.16 mmol, 2.00 equiv) in $CH_2Cl_2$ (30 mL) was added $PPh_3$ (2.40 g, 9.15 mmol, 2.00 equiv) in portions at 0° C. The resulting solution was stirred for 2 h at room temperature, concentrated under vacuum, and purified with silica gel chromatography using with EtOAc/petroleum ether (1:5) to afford 1.0 g (96%) of the title compound as colorless oil. $^1$H NMR (300 MHz, CDCl3) δ 7.30 (m, 3H), 6.96 (dt, J=7.6, 1.8, 1.8 Hz, 1H), 4.52 (s, 2H), 3.84 (m, 1H), 0.83 (m, 4H).

Intermediate E-3 2-(bromomethyl)-1-ethoxy-3-fluorobenzene

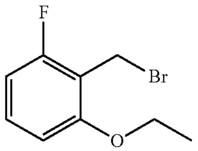

Methyl 2-ethoxy-6-fluorobenzoate A mixture of methyl 2-fluoro-hydroxybenzoate (500 mg, 2.94 mmol, 1.00 equiv), $K_2CO_3$ (811 mg, 5.87 mmol, 2.00 equiv), EtI (911 mg, 5.84 mmol, 2.00 equiv) in DMF (15 mL) was stirred overnight at 80° C., cooled to rt, and extracted with 3×20 mL of EtOAc. The combined organic layers were dried over $Na_2SO_4$ and concentrated under vacuum to afford 500 mg (86%) of the title compound as light yellow oil.

LC-MS: (ES, m/z): 199.3. $^1$H NMR (300 MHz, CDCl3) δ 7.29 (m, 1H), 6.70 (m, 2H), 4.08 (q, J=7.0, 7.0, 7.0 Hz, 2H), 3.92 (s, 3H), 1.40 (t, J=7.0, 7.0 Hz, 3H).

2-Ethoxy-6-fluorobenzoic acid A solution of the product from the previous step (2.6 g, 13.12 mmol, 1.00 equiv) and NaOH (2 g, 50.00 mmol, 4.00 equiv) in MeOH/$H_2O$ (20/10 mL) was stirred overnight at 40° C. The pH value of the solution was adjusted to 5 with 1 M HCl. The resulting solution was extracted with 3×50 mL of EtOAc. The combined organic layers were dried over $Na_2SO_4$ and concentrated under vacuum to afford 1.9 g (79%) of the title compound as a colorless oil.

LC-MS: (ES, m/z): 185.3.

(2-Ethoxy-6-fluorophenyl)methanol To a solution of the product from the previous step (1.9 g, 10.32 mmol, 1.00 equiv) and isobutyl chloroformate (2.1 g, 15.38 mmol, 1.50 equiv) in THF (50 mL) at 0° C. was added TEA (4.5 mL, 3.00 equiv). The reaction was stirred for 2 h at 0° C., then filtered. To the filtrate was added $NaBH_4$ (780 mg, 20.62 mmol, 2.00 equiv) at 0° C. The resulting solution was stirred for 3 h at room temperature. The reaction was then quenched by the addition of 10 mL of water/ice. The resulting solution was extracted with 3×50 mL of EtOAc. The combined organic layers were dried over $Na_2SO_4$, concentrated under vacuum, and purified with silica gel chromatography using EtOAc/petroleum ether (2/1) to afford 0.7 g (40%) of the title compound as a light yellow oil.

$^1$H NMR (300 MHz, DMSO) δ 7.27 (td, J=8.3, 8.3, 7.0 Hz, 1H), 6.77 (m, 2H), 4.75 (t, J=5.5, 5.5 Hz, 1H), 4.48 (dd, J=5.5, 1.9 Hz, 2H), 4.06 (q, J=7.0, 7.0, 7.0 Hz, 2H), 1.35 (t, J=6.9, 6.9 Hz, 3H).

2-(Bromomethyl)-1-ethoxy-3-fluorobenzene A solution of the product from the previous step (700 mg, 4.11 mmol, 1.00 equiv), $PPh_3$ (2.16 g, 8.24 mmol, 2.00 equiv), and $CBr_4$ (2.7 g, 2.00 equiv) in $CH_2Cl_2$ (30 mL) was stirred for 2 h at rt. The resulting solution was extracted with 3×30 mL of EtOAc. The combined organic layers were dried over $Na_2SO_4$, concentrated under vacuum, and purified with silica gel chromatography using EtOAc/petroleum ether (5/1) to afford 0.4 g (42%) of the title compound as a light yellow oil.

$^1$H NMR (300 MHz, $CDCl_3$) δ 7.24 (m, 1H), 6.69 (m, 2H), 4.67 (dd, J=32.8, 1.5 Hz, 2H), 4.13 (qd, J=7.0, 7.0, 7.0, 2.5 Hz, 2H), 1.48 (td, J=7.0, 6.9, 3.2 Hz, 3H).

Intermediate E-4
1-(Bromomethyl)-2-(propan-2-yloxy)benzene

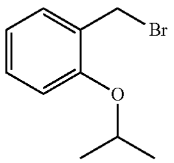

[2-(Propan-2-yloxy)phenyl]methanol To a solution of 2-(hydroxymethyl)phenol (2 g, 16.11 mmol, 1.00 equiv) in DMF (10 mL) was added sequentially 2-iodopropane (5.48 g, 32.24 mmol, 2.00 equiv) then $Cs_2CO_3$ (10.5 g, 32.23 mmol, 2.00 equiv). The resulting solution was stirred overnight at 85° C. The reaction mixture was cooled to room temperature. The resulting solution was extracted with 3×50 mL of EtOAc, and the organic layers were combined, dried over anhydrous $Na_2SO_4$, and concentrated under vacuum. The residue was applied onto a silica gel column with EtOAc/hexane (1/4). This resulted in the title compound as a light yellow oil (2.1 g, 78%).

1-(Bromomethyl)-2-(propan-2-yloxy)benzene To a solution of the product from the previous step (3 g, 18.05 mmol, 1.00 equiv) in $CH_2Cl_2$ (50 mL) were added sequentially $CBr_4$ (12.84 g, 36.17 mmol, 2.00 equiv) and $PPh_3$ (9.48 g, 36.14 mmol, 2.00 equiv) in an ice bath. The resulting solution was stirred for 5 h at room temperature. The resulting solution was extracted with 3×100 mL of $CH_2Cl_2$, and the organic layers were combined, dried over anhydrous $Na_2SO_4$, and concentrated under vacuum. The residue was applied onto a silica gel column with EtOAc/hexane (1/4). This resulted in the title compound as a light yellow oil (1.6 g, 39%).

The following alkylating agents were reacted with pyrazoles as disclosed below:
Intermediate E-5 1-(Chloromethyl)-2-nitrobenzene
Intermediate E-6 1-Bromo-2-(bromomethyl)-benzene
Intermediate E-7 1-(Bromomethyl)-2-chlorobenzene
Intermediate E-8 2-(Bromomethyl)-1-fluoro-3-nitrobenzene
Intermediate E-9 (2-Bromoethyl)benzene
Intermediate E-10 1-(Chloromethyl)-2-chlorobenzene
Intermediate E-11 2-(Bromomethyl)pyridine
Intermediate E-12 7-(Bromomethyl)-1-methyl-1H-indazole
Intermediate E-13 1-bromo-2-methylpropane
Intermediate E-14 4-(bromomethyl)tetrahydropyran Intermediate D-98: Methyl 1-[(3-chlorophenyl) methyl]-5-phenyl-1H-pyrazole-3-carboxylate

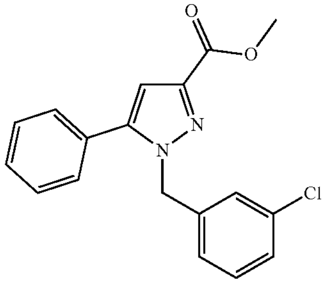 [SMILES: COC(=O)c1cc(-c2ccccc2)n(Cc2cccc(Cl)c2)n1]

To a suspension of methyl 5-phenyl-1H-pyrazole-3-carboxylate (1) (1.0 g, 4.94 mmol) in toluene was added NaH (60%) (0.394 g, 9.88 mmol) portionwise under $N_2$ at room temperature, and stirring was continued for 30 min. To the above mixture a solution of 3-chlorobenzyl bromide (0.96 ml, 7.42 mmol) in toluene (3 mL) was added dropwise at 60° C. The reaction mixture was stirred at 110° C. for 16 h. The mixture was cooled to room temperature and quenched with aq. $NH_4Cl$ solution. The mixture was partitioned with EtOAc (100 mL) and the organic layer was separated. The EtOAc layer was washed with brine (2×25 mL) and dried over $Na_2SO_4$, and the solvent was evaporated. The residue was chromatographed over $SiO_2$ (ISCO CombiFlash® Rf 200) using 0-50% gradient of EtOAc in hexane to afford title compound (1.2 g, 75%). $^1$H NMR ($CDCl_3$, 400 MHz) δ 3.95 (s, 3H), 5.36 (s, 2H), 6.85-6.92 (m, 2H), 6.95-6.99 (m, 1H), 7.17-7.29 (m, 4H). 7.35-7.48 (m, 3H).

Intermediate D-99: Methyl 1-[(2-cyclopropoxyphenyl)methyl]-5-(3-methoxyphenyl)-1H-pyrazole-3-carboxylate

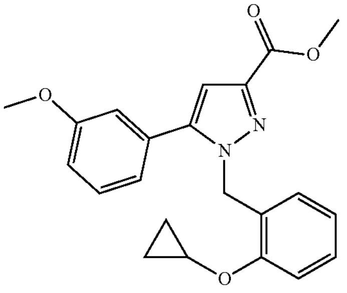

To a solution of Int. D-3 (793 mg, 3.41 mmol, 1.00 equiv) in toluene (10 mL) was added NaH (164 mg, 6.83 mmol, 2.00 equiv). The resulting solution was stirred at rt for 30 min, then warmed to 60° C. To this was added a solution of Int. E-2 (1 g, 4.40 mmol, 1.30 equiv) in toluene (10 mL). The resulting solution was stirred at 60° C. for 1 h, then the solution was heated to 110° C. and stirred for 6 h at this temperature. The reaction mixture was then cooled to rt, quenched by the addition of 10 mL of water/ice, and extracted with 3×100 mL of EtOAc. The combined organic layers were dried over $Na_2SO_4$, and concentrated under vacuum, and purified with silica gel column using EtOAc/hexane (1/3) to afford 1 g (77%) of the title compound as a yellow oil. LC-MS: (ES, m/z): 379.

Intermediate D-100: Methyl 1-[(2-chlorophenyl)methyl]-5-(3,5-dimethoxyphenyl)-1H-pyrazole-3-carboxylate

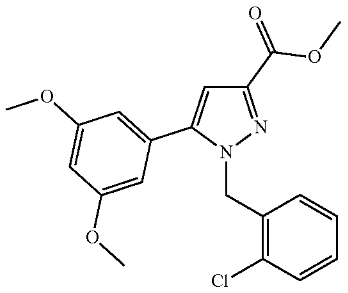

To a solution of methyl Int. D-21 (1.0 g, 3.81 mmol, 1.00 equiv) in toluene (50 mL) was added NaH (304 mg, 7.60 mmol, 2.00 equiv) in portions at rt. The mixture was stirred at rt for 30 min, then Int. E-7 (1.56 g, 7.59 mmol, 2.00 equiv) was added dropwise with stirring at 60° C. The resulting solution was stirred for 1 h at 60° C., then warmed to 110° C. and stirred for an additional 3 h. The reaction was then quenched by the addition of water/ice. The resulting solution was extracted with 200 mL of EtOAc, and the combined organic layers were washed with 2×100 mL of brine, dried over $Na_2SO_4$, concentrated under vacuum, and purified with silica gel chromatography using EtOAc/petroleum ether (1:3) to afford 800 mg (54%) of the title compound as a colorless oil. LC-MS: (ES, m/z): 387. $^1$H-NMR: ($CDCl_3$, ppm): δ: 7.42-7.29 (m, 1H), 7.29-7.13 (m, 2H), 6.97 (s, 1H), 6.77-6.67 (m, 1H), 6.42 (dd, J=30.5, 2.3 Hz, 3H), 5.55 (s, 2H), 3.97 (d, J=1.0 Hz, 3H), 3.69-3.60 (in, 6H).

The following substituted pyrazoles were obtained from alkylation with an alkyl halide:

TABLE 10

Pyrazole alkylation.

| Pyrazole | Alkyl halide | Product | | Spectral |
|---|---|---|---|---|
| D-2 | E-1 | Methyl 5-(3-cyclopropoxyphenyl)-1-[(2-ethoxyphenyl)methyl]-1H-pyrazole-3-carboxylate | D-101 | LC-MS: (ES, m/z): 393. |
| D-2 | E-2 | Methyl 5-(3-cyclopropoxyphenyl)-1-[(2-nitrophenyl)methyl]-1H-pyrazole-3-carboxylate | D-102 | LC-MS: (ES, m/z): 394. |
| D-2 | E-6 | Methyl 1-[(2-bromophenyl)methyl]-5-(3-cyclopropoxyphenyl)-1H-pyrazole-3-carboxylate | D-103 | LC-MS: (ES, m/z): 429.2. |
| D-5 | E-7 | Methyl 1-[(2-chlorophenyl)methyl]-5-(2,3-dihydro-1,4-benzodioxin-6-yl)-1H-pyrazole-3-carboxylate | D-104 | LC-MS: (ES, m/z): 385. |
| D-6 | E-7 | Methyl 5-(2H-1,3-benzodioxol-5-yl)-1-[(2-chlorophenyl)methyl]-1H-pyrazole-3-carboxylate | D-105 | LC-MS: (ES, m/z): 371. |
| D-7 | E-7 | Methyl 1-[(2-chlorophenyl)methyl]-5-(1-methyl-1H-pyrazol-4-yl)-1H-pyrazole-3-carboxylate | D-106 | LC-MS: (ES, m/z): 331. |
| D-8 | E-7 | Ethyl 5-(1-benzothiophen-2-yl)-1-[(2-chlorophenyl)methyl]-1H-pyrazole-3-carboxylate | D-107 | LC-MS: (ES, m/z): 397. |
| D-9 | E-7 | Ethyl 1-[(2-chlorophenyl)methyl]-5-(1-methyl-1H-indol-6-yl)-1H-pyrazole-3-carboxylate | D-108 | LC-MS: (ES, m/z): 393. |
| D-10 | E-1 | Ethyl 1-[(2-ethoxyphenyl)methyl]-5-(1-methyl-1H-indazol-6-yl)-1H-pyrazole-3-carboxylate | D-109 | LC-MS: (ES, m/z): 404. |
| D-10 | E-7 | Ethyl 1-[(2-chlorophenyl)methyl]-5-(1-methyl-1H-indazol-6-yl)-1H-pyrazole-3-carboxylate | D-110 | LC-MS: (ES, m/z): 394. |
| D-11 | E-7 | Methyl 1-[(2-chlorophenyl)methyl]-5-(1-ethyl-1H-indazol-6-yl)-1H-pyrazole-3-carboxylate | D-111 | LC-MS: (ES, m/z): 395. |
| D-11 | E-11 | Methyl 5-(1-ethyl-1H-indazol-6-yl)-1-([pyridin-2-yl]methyl)-1H-pyrazole-3-carboxylate | D-112 | LC-MS: (ES, m/z): 362.3. |
| D-12 | E-1 | Methyl 5-(3-chloro-5-methoxyphenyl)-1-[(2-ethoxyphenyl)methyl]-1H-pyrazole-3-carboxylate | D-113 | LC-MS: (ES, m/z): 401. |

TABLE 10-continued

| Pyrazole alkylation. | | | | |
|---|---|---|---|---|
| D-13 | E-7 | Ethyl 1-[(2-chlorophenyl)methyl]-5-(1-methyl-1H-indazol-5-yl)-1H-pyrazole-3-carboxylate | D-114 | LC-MS: (ES, m/z): 394. |
| D-11 | E-1 | Methyl 1-[(2-ethoxyphenyl)methyl]-5-(1-ethyl-1H-indazol-6-yl)-1H-pyrazole-3-carboxylate | D-115 | LC-MS: (ES, m/z): 404. |
| D-14 | E-7 | Ethyl 1-[(2-chlorophenyl)methyl]-5-(1-methyl-1H-indazol-4-yl)-1H-pyrazole-3-carboxylate | D-116 | LC-MS: (ES, m/z): 381. |
| D-15 | E-7 | Methyl 1-[(2-chlorophenyl)methyl]-5-(1-ethyl-1H-1,2,3-benzotriazol-6-yl)-1H-pyrazole-3-carboxylate | D-117 | LC-MS: (ES, m/z): 396. |
| D-16 | E-1 | Ethyl 5-(3-cyclobutoxyphenyl)-1-[(2-ethoxyphenyl)methyl]-1H-pyrazole-3-carboxylate | D-118 | LC-MS: (ES, m/z): 421. |
| D-16 | E-6 | Ethyl 1-[(2-bromophenyl)methyl]-5-(3-cyclobutoxyphenyl)-1H-pyrazole-3-carboxylate | D-119 | LC-MS: (ES, m/z): 454. |
| D-17 | E-12 | Methyl 5-[3-(2,2-dimethylpropoxy)-phenyl]-1-[(1-methyl-1H-indazol-7-yl)methyl]-1H-pyrazole-3-carboxylate | D-120 | LC-MS: (ES, m/z): 433.3. |
| D-18 | E-1 | Methyl 5-(3-ethoxyphenyl)-1-[(2-ethoxy-phenyl)methyl]-1H-pyrazole-3-carboxylate | D-121 | LC-MS: (ES, m/z): 394. |
| D-19 | E-7 | Methyl 5-[3-(benzyloxy)phenyl]-1-[(2-chlorophenyl)methyl]-1H-pyrazole-3-carboxylate | D-122 | LC-MS: (ES, m/z): 433.05. |
| D-20 | E-11 | Methyl 5-[3-(2-methylpropoxy)phenyl]-1-([pyridin-2-yl]methyl)-1H-pyrazole-3-carboxylate | D-123 | LC-MS: (ES, m/z): 366. |
| D-21 | E-1 | Methyl 5-(3,5-dimethoxyphenyl)-1-[(2-ethoxyphenyl)methyl]-1H-pyrazole-3-carboxylate | D-124 | LC-MS: (ES, m/z): 397 |
| D-21 | E-9 | 5-(3,5-Dimethoxyphenyl)-1-(2-phenyl-ethyl)-1H-pyrazole-3-carboxylate | D-125 | LC-MS: (ES, m/z): 366. |
| D-21 | E-3 | Methyl 5-(3,5-dimethoxyphenyl)-1-[(2-ethoxy-6-fluorophenyl)methyl]-1H-pyrazole-3-carboxylate | D-126 | LC-MS: (ES, m/z): 415.10. |
| D-21 | E-11 | Methyl 5-(3,5-dimethoxyphenyl)-1-([pyridin-2-yl]methyl)-1H-pyrazole-3-carboxylate | D-127 | LC-MS: (ES, m/z): 354. |
| D-22 | E-1 | Methyl 5-(3,5-diethoxyphenyl)-1-[(2-ethoxyphenyl)methyl]-1H-pyrazole-3-carboxylate | D-128 | LC-MS: (ES, m/z): 425.1. |
| D-22 | E-7 | Methyl 1-[(2-chlorophenyl)methyl]-5-(3,5-diethoxyphenyl)-1H-pyrazole-3-carboxylate | D-129 | LC-MS: (ES, m/z): 415.15. |
| D-23 | E-1 | Methyl 5-(3-ethoxy-5-methoxyphenyl)-1-[(2-ethoxyphenyl)methyl]-1H-pyrazole-3-carboxylate | D-130 | LC-MS: (ES, m/z): 411. |
| D-24 | E-10 | Ethyl 1-[(2-chlorophenyl)methyl]-5-[2-(propan-2-yloxy)-1,3-oxazol-5-yl]-1H-pyrazole-3-carboxylate | D-131 | LC-MS: (ES, m/z): 389. |
| D-25 | E-7 | Methyl 1-[(2-chlorophenyl)methyl]-5-[1,3-dimethyl-1H-thieno[2,3-c]pyrazol-5-yl]-1H-pyrazole-3-carboxylate | D-132 | LC-MS: (ES, m/z): 401 |

| Pyrazole | Alkyl Halide | Product | |
|---|---|---|---|
| D-3 | E-8 | Methyl 1-[(2-fluoro-6-nitrophenyl)methyl]-5-(3-methoxyphenyl)-1H-pyrazole-3-carboxylate | D-133 |
| D-3 | E-4 | Methyl 5-(3-methoxyphenyl)-1-[[2-(propan-2-yloxy)phenyl]methyl]-1H-pyrazole-3-carboxylate | D-134 |
| D-3 | E-13 | Methyl 5-(3-methoxyphenyl)-1-(2-methylpropyl)-1H-pyrazole-3-carboxylate | D-135 |
| D-3 | E-14 | Methyl 5-(3-methoxyphenyl)-1-([oxan-4-yl]methyl)-1H-pyrazole-3-carboxylate | D-136 |
| D-4 | E-7 | Methyl 1-[(2-chlorophenyl)methyl]-5-(3-nitrophenyl)-1H-pyrazole-3-carboxylate | D-137 |
| D-26 | E-7 | Methyl 1-[(2-chlorophenyl)methyl]-5-[3-[(propan-2-yl)carbamoyl]phenyl]-1H-pyrazol-3-carboxylate | D-138 |

Intermediate D-139: Methyl 1-[(2,6-dimethoxyphenyl)methyl]-5-[3-(2-methylpropoxy)phenyl]-1H-pyrazole-3-carboxylate

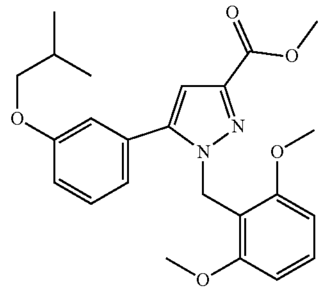 [SMILES: COC(=O)c1cc(-c2cccc(OCC(C)C)c2)n(Cc2c(OC)cccc2OC)n1]

To a solution of Int. D-20 (1.37 g, 4.99 mmol, 1.00 equiv) in THF (50 mL) under $N_2$ at 0° C. was added (2,6-dimethoxyphenyl)methanol (1.26 g, 7.49 mmol, 1.50 equiv) followed by $PPh_3$ (1.81 g, 6.90 mmol, 1.30 equiv). Subsequently DIAD (1.75 g, 8.65 mmol, 1.50 equiv) was added dropwise and the resulting solution was stirred for 16 h at 25° C. The residue was applied onto a silica gel column with EtOAc/petroleum ether (1:19). This resulted in the title compound as a yellow solid (890 mg, 42%).

Intermediate D-140: Methyl 1-[(3-chloropyridin-2-yl)methyl]-5-(3-methoxyphenyl)-1H-pyrazole-3-carboxylate

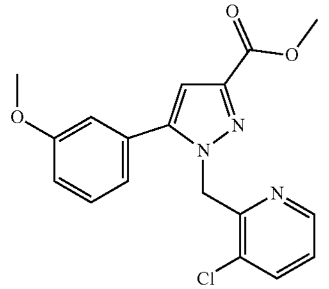 [SMILES: COC(=O)c1cc(-c2cccc(OC)c2)n(Cc2ncccc2Cl)n1]

(3-Chloropyridin-2-yl)methanol To a solution of 3-chloropyridine-2-carboxylic acid (2.1 g, 13.33 mmol, 1.00 equiv) in THF (40 mL) was added $Et_3N$ (2.7 g, 26.68 mmol, 2.00 equiv), followed by the addition of chloro(propan-2-yloxy)methanone (2.45 g, 19.99 mmol, 1.50 equiv) dropwise with stirring at 0° C. The solution was stirred for 1 h at room temperature. The solid was removed by filtration. To the filtrate was added $NaBH_4$ (1.53 g, 40.44 mmol, 3.00 equiv). The resulting solution was stirred for 2 h at rt, then diluted with 50 mL of $H_2O$ and extracted with 2×100 mL of EtOAc. The combined organic layers were washed with 50 mL of saturated NaCl, dried over $Na_2SO_4$, concentrated under vacuum, and purified with silica gel chromatography using with EtOAc/petroleum ether (1:6) to afford 0.9 g (47%) of the title compound as a colorless oil.

Methyl 1-[(3-chloropyridin-2-yl)methyl]-5-(3-methoxyphenyl)-1H-pyrazole-3-carboxylate To a solution of the product from the previous step (850 mg, 5.92 mmol, 1.00 equiv) in THF (8.5 mL), under $N_2$, was added Int. D-3 (1.4 g, 6.03 mmol, 1.00 equiv) and $Ph_3P$ (3.1 g, 11.82 mmol, 2.00 equiv), followed by the addition of DIAD (1.8 g, 8.91 mmol, 1.50 equiv) dropwise with stirring at 0° C. The resulting solution was stirred for 5 h at rt, diluted with 30 mL of $H_2O$, and extracted with 2×50 mL of EtOAc. The combined organic layers were washed with 20 mL of saturated NaCl, dried over $Na_2SO_4$, concentrated under vacuum, and purified with silica gel chromatography using EtOAc/petroleum ether (1:10) to afford 1.7 g (80%) of the title compound as a white solid. $^1$H-NMR (400 MHz, DMSO-$d_6$) δ 8.90 (s, 1H), 8.35 (dd, J=4.7, 1.5 Hz, 1H), 7.99 (dd, J=8.1, 1.5 Hz, 1H), 7.51 (s, 1H), 7.45 (dt, J=7.7, 1.2 Hz, 1H), 7.41 (dd, J=2.6, 1.5 Hz, 1H), 7.36-7.30 (m, 1H), 6.91 (ddd, J=8.2, 2.7, 1.0 Hz, 1H), 5.99 (s, 2H), 3.80 (s, 3H), 3.77 (s, 3H).

Intermediate D-141: Methyl 1-[[4-(dimethylamino)phenyl]methyl]-5-[3-(2-methylpropoxy)phenyl]-1H-pyrazole-3-carboxylate

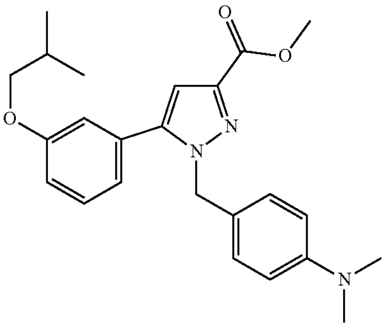 [SMILES: COC(=O)c1cc(-c2cccc(OCC(C)C)c2)n(Cc2ccc(N(C)C)cc2)n1]

Methyl 1-[(4-aminophenyl)methyl]-5-[3-(2-methylpropoxy)phenyl]-1H-pyrazole-3-carboxylate To a solution of Int. D-58 (2 g, 4.88 mmol, 1.00 equiv) in AcOH/$H_2O$ (100/40 mL) was added Zn (1 g, 15.29 mmol, 3.00 equiv), and the resulting solution was stirred for 5 h at 25° C. The solids were collected by filtration. The pH value of the solution was adjusted to 7 with (sat) $NaHCO_3$ (aq) and the resulting solution was extracted with 200 mL of EtOAc. The combined organic layers were concentrated under vacuum to afford 1.5 g (81%) of the title compound as a yellow oil.

Methyl 1-[[4-(dimethylamino)phenyl]methyl]-5-[3-(2-methylpropoxy)phenyl]-1H-pyrazole-3-carboxylate To a solution of the product from the previous step (1.35 g, 3.56 mmol, 1.00 equiv) in MeOH (50 mL) was added formaldehyde (5 mL, 1.50 equiv) in 30 min. To this was added $NaCNBH_3$ (800 mg, 12.73 mmol, 3.00 equiv), and the resulting solution was stirred for 5 min at 25° C. The resulting solution was extracted with 200 mL of EtOAc, and the combined organic layers were purified with silica gel chromatography using EtOAc/petroleum ether (1:7) to afford 810 mg (56%) of the title compound as a yellow liquid.

Intermediate D-142: Methyl 1-[[2-(dimethylamino)-6-fluorophenyl]methyl]-5-(3-methoxyphenyl)-1H-pyrazole-3-carboxylate

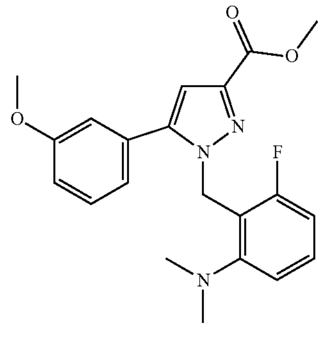 [SMILES: COC(=O)c1cc(-c2cccc(OC)c2)n(Cc2c(F)cccc2N(C)C)n1]

Intermediate D-142 was obtained from Int. D-133 by a zinc reduction/reduction amination sequence similar to that used to prepare Int. D-141.

Intermediate D-143: Methyl 1-[(2-chlorophenyl)methyl]-5-[3-(oxetan-3-ylmethoxy)phenyl]-1H-pyrazole-3-carboxylate

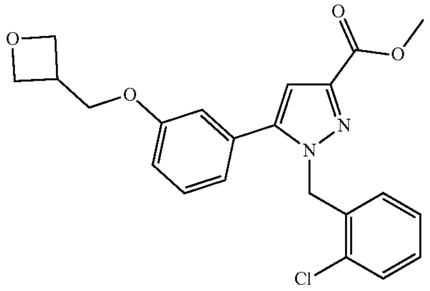 [SMILES: COC(=O)c1cc(-c2cccc(OCC3COC3)c2)n(Cc2ccccc2Cl)n1]

1-[(2-Chlorophenyl)methyl]-5-(3-hydroxyphenyl)-1H-pyrazole-3-carboxylic acid A solution of Int. D-122 (3.2 g, 7.39 mmol, 1.00 equiv) in AcOH/HCl (15/5 mL) was stirred for 2 h at 90° C., then cooled, concentrated under vacuum, and purified with silica gel chromatography using EtOAc/petroleum ether (2/1) to afford 2 g (82%) of the title compound as a light yellow oil. LC-MS: (ES, m/z): 329.0. $^{1}H$ NMR: (300 MHz, DMSO) δ 12.83 (s, 1H), 9.72 (s, 1H), 7.46 (m, 1H), 7.29 (m, 3H), 6.81 (m, 5H), 5.48 (s, 2H).

Methyl 1-[(2-chlorophenyl)methyl]-5-(3-hydroxyphenyl)-1H-pyrazole-3-carboxylate A solution of the product from the previous step (2 g, 6.08 mmol, 1.00 equiv) and $H_2SO_4$ (1 mL) in MeOH (20 mL) was stirred for 2 h at 65° C. The pH was adjusted to 7 with saturated $NaHCO_3$. The resulting solution was extracted with 3×30 mL of EtOAc, and the combined organic layers were dried over $Na_2SO_4$, concentrated under vacuum, and purified with silica gel chromatography using EtOAc/petroleum ether (2/1) to afford 1.7 g (82%) of the title compound as a white solid. LC-MS: (ES, m/z): 343.1. 1H NMR: (400 MHz, DMSO) δ 9.74 (s, 1H), 7.46 (m, 1H), 7.31 (m, 3H), 6.93 (s, 1H), 6.83 (m, 4H), 5.50 (s, 2H), 3.82 (s, 3H).

Methyl 1-[(2-chlorophenyl)methyl]-5-[3-(oxetan-3-ylmethoxy)phenyl]-1H-pyrazole-3-carboxylate To a solution of the product from the previous step (1.7 g, 4.96 mmol, 1.00 equiv), $PPh_3$ (2.62 g, 9.99 mmol, 2.00 equiv), and (oxetan-3-yl)methanol (870 mg, 9.87 mmol, 2.00 equiv) in THF (30 mL) at −10° C. under an $N_2$ atmosphere was added DTAD (1.82 g, 9.01 mmol, 1.80 equiv). The resulting solution was stirred overnight at rt and extracted with 3×30 mL of EtOAc. The combined organic layers were dried over $Na_2SO_4$, concentrated under vacuum, and purified with silica gel chromatography using EtOAc/petroleum ether (1/3) to afford 1.1 g (54%) of the title compound as a white solid. LC-MS: (ES, m/z): 413.1.

Intermediate D-144: Methyl 5-(3-cyclopropoxyphenyl)-1-(1-[[2-(trimethylsilyl)ethoxy]methyl]-1H-indazol-7-yl)-1H-pyrazole-3-carboxylate

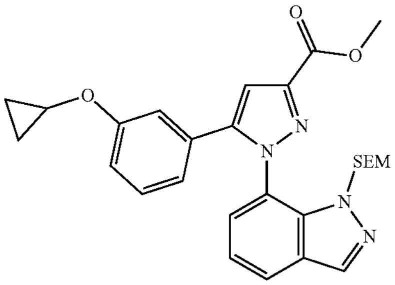 [SMILES: COC(=O)c1cc(-c2cccc(OC3CC3)c2)n(-c2cccc3cnn(COCC[Si](C)(C)C)c23)n1]

To a solution of Int. D-95 (600 mg, 1.60 mmol, 1.00 equiv) in $CH_2Cl_2$ (15 mL) was added NaH (128 mg, 5.33 mmol, 2.00 equiv). The solution was stirred 10 min, then SEMCl (664 mg, 2.50 equiv) was added. The resulting solution was stirred for 16 h at rt, then quenched by the addition of water, and extracted with 2×100 mL of EtOAc. The combined organic layers were washed with 100 mL of brine, dried over $Na_2SO_4$, concentrated under vacuum, and purified with silica gel column using EtOAc/petroleum ether (1:2) to afford 300 mg (37%) of the title compound as a yellow oil. LC-MS: (ES, m/z): 504.

Intermediate D-145: Methyl 5-(3-cyclopropoxyphenyl)-1-(1-[[2-(trimethylsilyl)ethoxy]methyl]-1H-indazol-4-yl)-1H-pyrazole-3-carboxylate

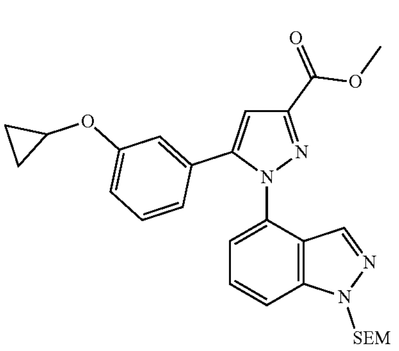 [SMILES: COC(=O)c1cc(-c2cccc(OC3CC3)c2)n(-c2cccc3c2cnn3COCC[Si](C)(C)C)n1]

To a solution of Int. D-94 (460 mg, 1.23 mmol, 1.00 equiv) in $CH_2Cl_2$ (10 mL) was added NaH (57.5 mg, 2.40 mmol, 2.00 equiv) at 0° C. The resulting solution was stirred for 30 min, then SEMCl (253 mg, 0.69 mmol, 1.30 equiv) was added. The resulting solution was stirred for 5 h at rt, then quenched with $H_2O$ and extracted with 3×20 mL of EtOAc. The combined organic layers were dried over $Na_2SO_4$, concentrated under vacuum, and purified with silica gel chromatography using EtOAc/petroleum ether (1/3) to afford 300 mg (48%) of the title compound as a colorless oil. LC-MS: (ES, m/z): 505.1.

Intermediate D-146: methyl 5-(3-cyclopropoxyphenyl)-1-(3-methyl-1-[[2-(trimethylsilyl)-ethoxy]methyl]-1H-indazol-4-yl)-1H-pyrazole-3-carboxylate

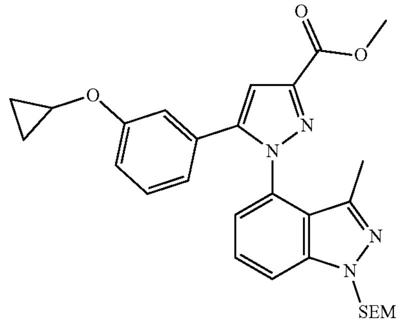 [SMILES: COC(=O)c1cc(-c2cccc(OC3CC3)c2)n(-c2cccc3c2c(C)nn3COCC[Si](C)(C)C)n1]

To a solution of Int. D-96 (500 mg, 1.29 mmol, 1.00 equiv) in $CH_2Cl_2$ (10 mL) was added NaH (62 mg, 2.58 mmol, 2.00 equiv). The resulting solution was stirred for 30 min at 0° C., then [2-(chloromethoxy)ethyl]trimethylsilane (278 mg, 1.67 mmol, 1.30 equiv) was added. The resulting solution was stirred for 5 h at rt, then quenched with $H_2O$ and extracted with 3×20 mL of $CH_2Cl_2$. The combined organic layers were dried over $Na_2SO_4$, concentrated under vacuum, and purified with prep-TLC using EtOAc/petroleum ether (1/3) to afford 250 mg (36%) of the title compound as a colorless oil. LC-MS: (ES, m/z): 519.40.

Intermediate D-147: Ethyl 1-[(2-chlorophenyl)methyl]-5-phenoxy-1H-pyrazole-3-carboxylate

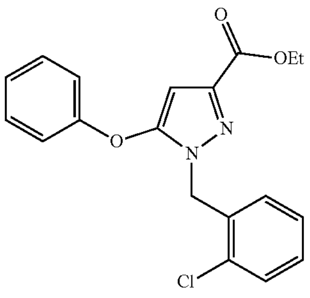 [SMILES: CCOC(=O)c1cc(Oc2ccccc2)n(Cc2ccccc2Cl)n1]

Ethyl 1-[(2-chlorophenyl)methyl]-5-oxo-4,5-dihydro-1H-pyrazole-3-carboxylate

A solution of Int. C-13 (4 g, 17.54 mmol, 1.00 equiv) and 1,4-diethyl 2-oxo-butanedioate (0 mg, 1.30 equiv) in EtOH (120 mL) was heated to reflux overnight, then concentrated under vacuum. The crude product was purified using silica gel chromatography using EtOAc/petroleum ether (1:20~1:5), to afford 2.8 g (57%) of the title product as a yellow syrup.

Ethyl 1-[(2-chlorophenyl)methyl]-5-(2-nitrophenoxy)-1H-pyrazole-3-carboxylate

A solution of the product from the previous step (2.8 g, 9.97 mmol, 1.00 equiv), 1-fluoro-2-nitrobenzene (2.8 g, 19.84 mmol, 2.00 equiv), and $K_2CO_3$ (2.7 g, 19.57 mmol, 2.00 equiv) in DMF (20 mL) was stirred overnight at 90° C. The resulting solution was diluted with EtOAc, washed with water and brine, dried over anhydrous $Na_2SO_4$, and concentrated under vacuum. The crude product was purified with silica gel chromatography using EtOAc/petroleum ether (1:50-1:10) to afford 0.8 g (20%) of the title product as a yellow oil.

Ethyl 5-(2-aminophenoxy)-1-[(2-chlorophenyl)methyl]-1H-pyrazole-3-carboxylate A solution of the product from the previous step (800 mg, 1.99 mmol, 1.00 equiv) in AcOH/$H_2O$(3:1) (8 mL) was stirred over Zn (600 mg, 9.38 mmol, 5.00 equiv) for 3 h at 60° C. The solids were removed by filtration, and the filtrate was concentrated under vacuum. The crude product was purified by silica gel chromatography using EtOAc/petroleum ether (1:30~1:5) to afford 540 mg (73%) of the title product as a yellow solid.

Ethyl 1-[(2-chlorophenyl)methyl]-5-phenoxy-1H-pyrazole-3-carboxylate To a solution of the product from the previous step (540 mg, 1.45 mmol, 1.00 equiv) in THF (15 mL) was added tert-butyl nitrite (450 mg, 4.36 mmol, 3.00 equiv). The resulting solution was stirred for 30 min at 60° C., then concentrated under vacuum. The residue was purified with Prep-TLC (EtOAc:PE=1:3) to afford 220 mg (42%) of the title product as a solid.

Intermediate F-1: [1-[(3-Chlorophenyl)methyl]-5-phenyl-1H-pyrazol-3-yl]methanol

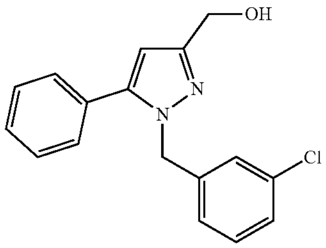 [SMILES: OCc1cc(-c2ccccc2)n(Cc2cccc(Cl)c2)n1]

A solution of Int. D-98 (0.80 g, 2.45 mmol) in anhydrous THF was cooled to 0° C. To the above mixture $LiAlH_4$ (0.14 g, 3.67 mmol) was added portionwise, and stirring was continued at 0° C. for 1.30 h. The mixture was quenched with water (0.15 mL) and 30% aq. NaOH solution (0.3 mL) at 0° C., and stirring was continued for 30 min. The reaction mixture was filtered, the filter cake was washed with THF (2×10 mL), and the filtrates were combined and evaporated to dryness. The residue was chromatographed over $SiO_2$ (ISCO CombiFlash® Rf200) using 0-40% gradient of EtOAc in DCM to afford the title product (0.58 g 79%). $^1H$ NMR ($CDCl_3$, 400 MHz) δ 4.64-4.81 (d, 2H), 5.31 (s, 2H), 6.35 (s, 1H), 6.86-6.94 (m, 1H), 6.98-7.05 (m, 1H), 7.19-7.23 (m, 2H), 7.26-7.35 (m, 2H), 7.39-7.46 (m 3H).

The following substituted 3-(hydroxymethyl)pyrazoles were obtained from $LiAlH_4$ reduction of the corresponding methyl esters:

TABLE 11

| LiAlH$_4$ reduction of pyrazole carboxylic esters. | | | |
|---|---|---|---|
| Ester | Product | | Spectral |
| D-57 | [1-[(2-chlorophenyl)methyl]-5-(1-methyl-1H-1,3-benzodiazol-6-yl)-1H-pyrazol-3-yl]methanol | F-2 | LC-MS: (ES, m/z): [M + 1] = 353. |
| D-59 | [5-(3-Methoxyphenyl)-1-pyridin-3-yl)-1H-pyrazol-3-yl]methanol | F-3 | |
| D-65 | [5-(3-Methoxyphenyl)-1-(2-methylphenyl)-1H-pyrazol-3-yl]methanol | F-4 | |
| D-117 | [1-[(2-chlorophenyl)methyl]-5-(1-ethyl-1H-1,2,3-benzotriazol-6-yl)-1H-pyrazol-3-yl]methanol | F-5 | LC-MS: (ES, m/z): 368. |
| D-132 | [1-[(2-chlorophenyl)methyl]-5-[1,3-dimethyl-1H-thieno[2,3-c]pyrazol-5-yl]-1H-pyrazol-3-yl]methanol | F-6 | LC-MS: (ES, m/z): 373. |
| D-137 | [1-[(2-chlorophenyl)methyl]-5-(3-nitrophenyl)-1H-pyrazole-3-yl]methanol | F-7 | |

Intermediate F-8: [1-[(2-Chlorophenyl)methyl]-5-(3-methoxyphenyl)-1H-pyrazol-3-yl]methanol

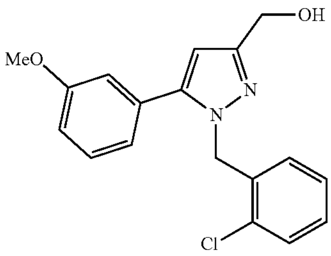 [SMILES: COc1cccc(-c2cc(CO)nn2Cc2ccccc2Cl)c1]

(iii) To a solution of Int. D-28 (5.5 g, 15.41 mmol, 1.00 equiv) in THF (100 mL) was added LiBH$_4$ (20 mL) dropwise with stirring at 0° C. in 5 min. The resulting solution was stirred for 16 h at room temperature. The reaction was then quenched by the addition of 5 mL of water, diluted with 200 mL of H$_2$O, extracted with 2×200 mL of EtOAc, and the organic layers were combined. The resulting mixture was washed with 1×100 mL of brine then dried over anhydrous Na$_2$SO$_4$ and concentrated under vacuum. The residue was applied onto a silica gel column with EtOAc/petroleum ether (1:8). This resulted in the title compound as a white solid (4.3 g, 85%).

The following substituted 3-(hydroxymethyl)pyrazoles were obtained from LiBH$_4$ reduction of the corresponding methyl esters:

TABLE 12

| LiBH$_4$ reduction of pyrazole carboxylic esters. | | | |
|---|---|---|---|
| Ester | Product | | Spectral |
| D-29 | [5-[3-(2-Methylpropoxy)phenyl]-1-phenyl-1H-pyrazol-3-yl]methanol | F-9 | LC-MS: (ES, m/z): 323. |
| D-30 | [1-(2-Bromophenyl)-5-(1-ethyl-1H-indazol-6-yl)-1H-pyrazol-3-yl]methanol | F-10 | LC-MS: (ES, m/z): 398.9. |
| D-31 | [1-(2-Bromophenyl)-5-(1-methyl-1H-indazol-6-yl)-1H-pyrazol-3-yl]methanol | F-11 | LC-MS: (ES, m/z): 383. |
| D-32 | [1-(2-Bromophenyl)-5-[3-(2,2-dimethylpropoxy)-phenyl]-1H-pyrazol-3-yl]methanol | F-12 | LC-MS: (ES, m/z): 417.00. |
| D-33 | [1-(2-Bromophenyl)-5-(3,5-dimethoxyphenyl)-1H-pyrazol-3-yl]methanol | F-13 | LC-MS: (ES, m/z): 389. |
| D-34 | [1-(2-bromophenyl)-5-(1-propyl-1H-indazol-6-yl)-1H-pyrazol-3-yl]methanol | F-14 | LC-MS: (ES, m/z): 413.0. |
| D-35 | [1-(2-bromophenyl)-5-(3-cyclobutoxyphenyl)-1H-pyrazol-3-yl]methanol | F-15 | LC-MS: (ES, m/z): 399.2. |
| D-36 | [1-(2-Fluorophenyl)-5-[3-(oxetan-3-ylmethoxy)-phenyl]-1H-pyrazol-3-yl]methanol | F-16 | LC-MS: (ES, m/z): 355.2. |
| D-37 | [5-(3-Cyclobutoxyphenyl)-1-(2-fluorophenyl)-1H-pyrazol-3-yl]methanol | F-17 | LC-MS: (ES, m/z): 339. |
| D-38 | [1-(2-Fluorophenyl)-5-[3-(oxetan-3-yloxy)-phenyl]-1H-pyrazol-3-yl]methanol | F-18 | LC-MS: (ES, m/z): 341. |
| D-39 | [1-(2-Fluorophenyl)-5-[3-(2-methylpropoxy)-phenyl]-1H-pyrazol-3-yl]methanol | F-19 | LC-MS: (ES, m/z): 341. |
| D-40 | [5-(3-cyclobutoxyphenyl)-1-(2-methylphenyl)-1H-pyrazol-3-yl]methanol | F-20 | LC-MS: (ES, m/z): 334. |
| D-41 | [5-(3,5-Diethoxyphenyl)-1-(2-methylphenyl)-1H-pyrazol-3-yl]methanol | F-21 | LC-MS: (ES, m/z): 353.00. |
| D-42 | [5-(1-Ethyl-1H-indazol-6-yl)-1-(2-nitrophenyl)-1H-pyrazol-3-yl]methanol | F-22 | LC-MS: (ES, m/z): 364.3. |
| D-43 | [5-[3-(2,2-dimethylpropoxy)phenyl]-1-(quinolin-8-yl)-1H-pyrazol-3-yl]methanol | F-23 | LC-MS: (ES, m/z): [M + 1] = 388. |
| D-44 | [5-(3,5-Dimethoxyphenyl)-1-(2-ethoxyphenyl)-1H-pyrazol-3-yl]methanol | F-24 | LC-MS: (ES, m/z): 355. |

TABLE 12-continued

| LiBH$_4$ reduction of pyrazole carboxylic esters. | | | |
|---|---|---|---|
| D-45 | [5-(1-Ethyl-1H-indazol-6-yl)-1-(1-methyl-1H-indazol-7-yl)-1H-pyrazol-3-yl]methanol | F-25 | LC-MS: (ES, m/z): 372. |
| D-46 | [5-(3-Cyclobutoxyphenyl)-1-(1-methyl-1H-indazol-7-yl)-1H-pyrazol-3-yl]methanol | F-26 | LC-MS: (ES, m/z): 375. |
| D-47 | [5-[3-(2,2-dimethylpropoxy)phenyl]-1-(1-methyl-1H-indazol-7-yl)-1H-pyrazol-3-yl]methanol | F-27 | LC-MS: (ES, m/z): 391.10. |
| D-48 | [5-[3-(Cyclobutylmethoxy)phenyl]-1-(1-methyl-1H-indazol-7-yl)-1H-pyrazol-3-yl]methanol | F-28 | LC-MS: (ES, m/z): 389. |
| D-49 | [5-[3-(Cyclopropylmethoxy)phenyl]-1-(1-methyl-1H-indazol-7-yl)-1H-pyrazol-3-yl]methanol | F-29 | LC-MS: (ES, m/z): 375. |
| D-50 | [1-(1-Methyl-1H-indazol-7-yl)-5-[3-(2-methylpropoxy)phenyl]-1H-pyrazol-3-yl]-methanol | F-30 | LC-MS: (ES, m/z): 377. |
| D-51 | [5-(3,5-dimethoxyphenyl)-1-(1-methyl-1H-indazol-7-yl)-1H-pyrazol-3-yl]methanol | F-31 | LC-MS: (ES, m/z): 365. |
| D-52 | [5-(3,5-Diethoxyphenyl)-1-(1-methyl-1H-indazol-7-yl)-1H-pyrazol-3-yl]methanol | F-32 | LC-MS: (ES, m/z): 393.05. |
| D-53 | [5-[3-(2,2-Dimethylpropoxy)phenyl]-1-(1-ethyl-1H-indazol-7-yl)-1H-pyrazol-3-yl]methanol | F-33 | LC-MS: (ES, m/z): 404. |
| D-54 | [5-(3-Methoxyphenyl)-1-[2-(propan-2-yloxy)-phenyl]-1H-pyrazol-3-yl]methanol | F-34 | LC-MS: (ES, m/z): 339. |
| D-55 | [1-(1,3-dimethyl-1H-indazol-7-yl)-5-[3-(2,2-dimethylpropoxy)phenyl]-1H-pyrazol-3-yl]methanol | F-35 | LC-MS: (ES, m/z): 405.35. |
| D-56 | [5-[3-(2,2-dimethylpropoxy)phenyl]-1-(1-methyl-1H-1,2,3-benzotriazol-7-yl)-1H-pyrazol-3-yl]methanol | F-36 | |
| D-66 | [1-(2-chlorophenyl)-5-[3-(oxetan-3-yl-methoxy)phenyl]-1H-pyrazol-3-yl]methanol | F-37 | LC-MS: (ES, m/z): 371.0. |
| D-67 | [1-(2-chlorophenyl)-5-(pyridin-2-yl)-1H-pyrazol-3-yl]methanol | F-38 | LC-MS: (ES, m/z): 285.85. |
| D-68 | [1-(2-Chlorophenyl)-5-(1-methyl-1H-indazol-6-yl)-1H-pyrazol-3-yl]methanol | F-39 | LC-MS: (ES, m/z): 339. |
| D-69 | [1-(2-chlorophenyl)-5-(1-ethyl-1H-indazol-6-yl)-1H-pyrazol-3-yl]methanol | F-40 | LC-MS: (ES, m/z): 353. |
| D-70 | [1-(2-Chlorophenyl)-5-(3-cyclobutoxyphenyl)-1H-pyrazol-3-yl]methanol | F-41 | LC-MS: (ES, m/z): 355. |
| D-71 | [1-(2-Chlorophenyl)-5-[3-(oxetan-3-yloxy)-phenyl]-1H-pyrazol-3-yl]methanol | F-42 | LC-MS: (ES, m/z): 357. |
| D-72 | [1-(2-chlorophenyl)-5-(3-cyclopropoxyphenyl)-1H-pyrazol-3-yl]methanol | F-43 | LC-MS: (ES, m/z): 369.25. |
| D-73 | [1-(2-Chlorophenyl)-5-[3-(2,2-dimethylpropoxy)-phenyl]-1H-pyrazol-3-yl]methanol | F-44 | LC-MS: (ES, m/z): 371.00. |
| D-74 | [1-(2-Chlorophenyl)-5-[3-(cyclobutylmeth-oxy)phenyl]-1H-pyrazol-3-yl]methanol | F-45 | LC-MS: (ES, m/z): 368.95. |
| D-76 | [1-(2-Chlorophenyl)-5-(3,5-dimethoxyphenyl)-1H-pyrazol-3-yl]methanol | F-46 | LC-MS: (ES, m/z): 345. |
| D-77 | [1-(2-Chlorophenyl)-5-(3,5-diethoxyphenyl)-1H-pyrazol-3-yl]methanol | F-47 | LC-MS: (ES, m/z): 373.1. |
| D-79 | [5-(3-cyclopropoxyphenyl)-1-(2-fluorophenyl)-1H-pyrazol-3-yl]methanol | F-48 | LC-MS: (ES, m/z): 325.25. |
| D-80 | [1-(2-Bromophenyl)-5-(3-cyclopropoxyphenyl)-1H-pyrazol-3-yl]methanol | F-49 | LC-MS: (ES, m/z): 387. |
| D-81 | [1-(2-Bromo-4-fluorophenyl)-5-(3-cyclopropoxy-phenyl)-1H-pyrazol-3-yl]methanol | F-50 | LC-MS: (ES, m/z): 405.0. |
| D-82 | [5-(3-Cyclopropoxyphenyl)-1-(2,4-dichloro-phenyl)-1H-pyrazol-3-yl]methanol | F-51 | LC-MS: (ES, m/z): 375.00. |
| D-83 | [5-(3-Cyclopropoxyphenyl)-1-(2,5-dichloro-phenyl)-1H-pyrazol-3-yl]methanol | F-52 | LC-MS: (ES, m/z): 375.05. |
| D-84 | [5-(3-Cyclopropoxyphenyl)-1-[2-(difluoro-methoxy)phenyl]-1H-pyrazol-3-yl]methanol | F-53 | LC-MS: (ES, m/z): 373. |
| D-85 | [5-(3-Cyclopropoxyphenyl)-1-(2-ethoxyphenyl)-1H-pyrazol-3-yl]methanol | F-54 | LC-MS: (ES, m/z): 350. |
| D-86 | [5-(3-Cyclopropoxyphenyl)-1-(2-methoxy-phenyl)-1H-pyrazol-3-yl]methanol | F-55 | LC-MS: (ES, m/z): 337. |
| D-87 | [5-(3-Cyclopropoxyphenyl)-1-(2-methylphenyl)-1H-pyrazol-3-yl]methanol | F-56 | LC-MS: (ES, m/z): 321. |
| D-88 | [5-(3-Cyclopropoxyphenyl)-1-(2-nitrophenyl)-1H-pyrazol-3-yl]methanol | F-57 | LC-MS: (ES, m/z): 352. |
| D-89 | [5-(3-Cyclopropoxyphenyl)-1-[2-(propan-2-yl)-phenyl]-1H-pyrazol-3-yl]methanol | F-58 | LC-MS: (ES, m/z): 349. |
| D-90 | [5-(3-Cyclopropoxyphenyl)-1-[2-(trifluoro-methyl)phenyl]-1H-pyrazol-3-yl]methanol | F-59 | LC-MS: (ES, m/z): 375. |
| D-91 | [5-(3-cyclopropoxyphenyl)-1-(1-methyl-1H-indazol-7-yl)-1H-pyrazol-3-yl]methanol | F-60 | LC-MS: (ES, m/z): 361. |
| D-92 | [5-(3-Cyclopropoxyphenyl)-1-(1-methyl-1H-indazol-4-yl)-1H-pyrazol-3-yl]methanol | F-61 | LC-MS: (ES, m/z): 361. |

TABLE 12-continued

| LiBH$_4$ reduction of pyrazole carboxylic esters. | | | |
|---|---|---|---|
| D-93 | [5-(3-Cyclopropoxyphenyl)-1-(1-ethyl-1H-indazol-7-yl)-1H-pyrazol-3-yl]methanol | F-62 | LC-MS: (ES, m/z): 375. |
| D-97 | [5-(3-Cyclopropoxyphenyl)-1-(1-methyl-1H-1,3-benzodiazol-7-yl)-1H-pyrazol-3-yl]methanol | F-63 | LC-MS: (ES, m/z): 361.2. |
| D-99 | [1-[(2-Cyclopropoxyphenyl)methyl]-5-(3-methoxyphenyl)-1H-pyrazol-3-yl]methanol | F-64 | LC-MS: (ES, m/z): 351. |
| D-100 | [1-[(2-chlorophenyl)methyl]-5-(3,5-dimethoxyphenyl)-1H-pyrazol-3-yl]methanol | F-65 | LC-MS: (ES, m/z): 359. |
| D-107 | [5-(1-Benzothiophen-2-yl)-1-[(2-chlorophenyl)-methyl]-1H-pyrazol-3-yl]methanol | F-66 | LC-MS: (ES, m/z): 354. |
| D-110 | [1-[(2-chlorophenyl)methyl]-5-(1-methyl-1H-indazol-6-yl)-1H-pyrazol-3-yl]methanol | F-67 | LC-MS: (ES, m/z): 353. |
| D-113 | [5-(3-Chloro-5-methoxyphenyl)-1-[(2-ethoxyphenyl)methyl]-1H-pyrazol-3-yl]methanol | F-68 | LC-MS: (ES, m/z): 373. |
| D-116 | [1-[(2-Chlorophenyl)methyl]-5-(1-methyl-1H-indazol-4-yl)-1H-pyrazol-3-yl]methanol | F-69 | LC-MS: (ES, m/z): 353. |
| D-115 | [1-[(2-Ethoxyphenyl)methyl]-5-(1-ethyl-1H-indazol-6-yl)-1H-pyrazol-3-yl]methanol | F-70 | LC-MS: (ES, m/z): 377. |
| D-121 | [5-(3-Ethoxyphenyl)-1-[(2-ethoxyphenyl)-methyl]-1H-pyrazol-3-yl]methanol | F-71 | LC-MS: (ES, m/z): 352. |
| D-130 | [5-(3-Ethoxy-5-methoxyphenyl)-1-[(2-ethoxyphenyl)methyl]-1H-pyrazol-3-yl]methanol | F-72 | LC-MS: (ES, m/z): 383. |
| D-101 | [5-(3-Cyclopropoxyphenyl)-1-[(2-ethoxyphenyl)-methyl]-1H-pyrazol-3-yl]methanol | F-73 | LC-MS: (ES, m/z): 364. |
| D-102 | [5-(3-cyclopropoxyphenyl)-1-[(2-nitrophenyl)-methyl]-1H-pyrazol-3-yl]methanol | F-74 | LC-MS: (ES, m/z): 366. |
| D-103 | [1-[(2-Bromophenyl)methyl]-5-(3-cyclopropoxy-phenyl)-1H-pyrazol-3-yl]methanol | F-75 | LC-MS: (ES, m/z): 399. |
| D-104 | [1-[(2-chlorophenyl)methyl]-5-(2,3-dihydro-1,4-benzodioxin-6-yl)-1H-pyrazol-3-yl]methanol | F-76 | LC-MS: (ES, m/z): 357. |
| D-105 | [5-(2H-1,3-benzodioxol-5-yl)-1-[(2-chloro-phenyl)methyl]-1H-pyrazol-3-yl]methanol | F-77 | LC-MS: (ES, m/z): 343. |
| D-106 | [1-[(2-Chlorophenyl)methyl]-5-(1-methyl-1H-pyrazol-4-yl)-1H-pyrazol-3-yl]methanol | F-78 | LC-MS: (ES, m/z): 303. |
| D-108 | [1-[(2-chlorophenyl)methyl]-5-(1-methyl-1H-indol-6-yl)-1H-pyrazol-3-yl]methanol | F-79 | LC-MS: (ES, m/z): 351. |
| D-109 | [1-[(2-Ethoxyphenyl)methyl]-5-(1-methyl-1H-indazol-6-yl)-1H-pyrazol-3-yl]methanol | F-80 | LC-MS: (ES, m/z): 363. |
| D-128 | [5-(3,5-Diethoxyphenyl)-1-[(2-ethoxyphenyl)-methyl]-1H-pyrazol-3-yl]methanol | F-81 | LC-MS: (ES, m/z): 397.05. |
| D-111 | [1-[(2-Chlorophenyl)methyl]-5-(1-ethyl-1H-indazol-6-yl)-1H-pyrazol-3-yl]methanol | F-82 | LC-MS: (ES, m/z): 367. |
| D-112 | [5-(1-Ethyl-1H-indazol-6-yl)-1-([pyridin-2-yl]methyl)-1H-pyrazol-3-yl]methanol | F-83 | LC-MS: (ES, m/z): 334. |
| D-114 | [1-[(2-Chlorophenyl)methyl]-5-(1-methyl-1H-indazol-5-yl)-1H-pyrazol-3-yl]methanol | F-84 | LC-MS: (ES, m/z): 352. |
| D-118 | [5-(3-Cyclobutoxyphenyl)-1-[(2-ethoxyphenyl)-methyl]-1H-pyrazol-3-yl]methanol | F-85 | LC-MS: (ES, m/z): 379. |
| D-119 | [1-[(2-Bromophenyl)methyl]-5-(3-cyclobutoxy-phenyl)-1H-pyrazol-3-yl]methanol | F-86 | LC-MS: (ES, m/z): 412. |
| D-120 | [5-[3-(2,2-dimethylpropoxy)phenyl]-1-[(1-methyl-1H-indazol-7-yl)methyl]-1H-pyrazol-3-yl]methanol | F-87 | LC-MS: (ES, m/z): 405.3. |
| D-123 | [5-[3-(2-methylpropoxy)phenyl]-1-([pyridin-2-yl]methyl)-1H-pyrazol-3-yl]methanol | F-88 | LC-MS: (ES, m/z): 338. |
| D-124 | [5-(3,5-Dimethoxyphenyl)-1-[(2-ethoxyphenyl)-methyl]-1H-pyrazol-3-yl]methanol | F-89 | LC-MS: (ES, m/z): 369. |
| D-125 | [5-(3,5-Dimethoxyphenyl)-1-(2-phenylethyl)-1H-pyrazol-3-yl]methanol | F-90 | LC-MS: (ES, m/z): 339. |
| D-126 | [5-(3,5-dimethoxyphenyl)-1-[(2-ethoxy-6-fluorophenyl)methyl]-1H-pyrazol-3-yl]methanol | F-91 | LC-MS: (ES, m/z): 387.1. |
| D-127 | [5-(3,5-dimethoxyphenyl)-1-([pyridin-2-yl]methyl)-1H-pyrazol-3-yl]methanol | F-92 | LC-MS: (ES, m/z): 326. |
| D-129 | [1-[(2-Chlorophenyl)methyl]-5-(3,5-diethoxy-phenyl)-1H-pyrazol-3-yl]methanol | F-93 | LC-MS: (ES, m/z): 387.00. |
| D-131 | [1-[(2-Chlorophenyl)methyl]-5-[2-(propan-2-yloxy)-1,3-oxazol-5-yl]-1H-pyrazol-3-yl]methanol | F-94 | LC-MS: (ES, m/z): 348. |
| D-143 | [1-[(2-Chlorophenyl)methyl]-5-[3-(oxetan-3-yl-methoxy)phenyl]-1H-pyrazol-3-yl]methanol | F-95 | LC-MS: (ES, m/z): 385.1. |
| D-144 | [5-(3-Cyclopropoxyphenyl)-1-(1-[[2-(trimethyl-silyl)ethoxy]methyl]-1H-indazol-7-yl)-1H-pyrazol-3-yl]methanol | F-96 | LC-MS: (ES, m/z): 477. |

TABLE 12-continued

| LiBH$_4$ reduction of pyrazole carboxylic esters. | | | |
|---|---|---|---|
| D-145 | [5-(3-Cyclopropoxyphenyl)-1-(1-[[2-(trimethylsilyl)ethoxy]methyl]-1H-indazol-4-yl)-1H-pyrazol-3-yl]methanol | F-97 | LC-MS: (ES, m/z): 477.2. |
| D-146 | [5-(3-Cyclopropoxyphenyl)-1-(3-methyl-1-[[2-(trimethylsilyl)ethoxy]methyl]-1H-indazol-4-yl)-1H-pyrazol-3-yl]methanol | F-98 | LC-MS: (ES, m/z): 491.4. |

| Ester | Product | |
|---|---|---|
| D-60 | [1-[(2-chlorophenyl)methyl]-5-(2-methoxyphenyl)-1H-pyrazol-3-yl]methanol | F-99 |
| D-61 | [5-(4-bromothien-2-yl)-1-[(2-chlorophenyl)-methyl]-1H-pyrazol-3-yl]methanol | F-100 |
| D-62 | [1-[(2-chlorophenyl)methyl]-5-[5-(2-methylpropoxy)thien-2-yl]-1H-pyrazol-3-yl]methanol | F-101 |
| D-63 | 1-[(2-chlorophenyl)-5-[2-(2-methylpropyl)-1,3-oxazol-5-yl]-1H-pyrazol-3-yl]methanol | F-102 |
| D-64 | [1-[(2-chlorophenyl)methyl]-5-[2-(2-methyl-propoxy)-1,3-thiazol-5-yl]-1H-pyrazol-3-yl]methanol | F-103 |
| D-75 | [1-(2-Chlorophenyl)-5-[3-(2-methyl-propoxy)phenyl]-1H-pyrazol-3-yl]methanol | F-104 |
| D-78 | (5-Benzyl-1-[(2-chlorophenyl)methyl]-1H-pyrazol-3-yl)-methanol | F-105 |
| D-134 | (5-(3-methoxyphenyl)-1-[[2-(propan-2-yloxy)-phenyl]methyl]-1H-pyrazol-3-yl)-methanol | F-106 |
| D-135 | (5-(3-methoxyphenyl)-1-(2-methylpropyl)-1H-pyrazol-3-yl)methanol | F-107 |
| D-136 | (5-(3-methoxyphenyl)-1-([oxan-4-yl]methyl)-1H-pyrazol-3-yl)methanol | F-108 |
| D-138 | (1-[(2-chlorophenyl)methyl]-5-[3-[(propan-2-yl)-carbamoyl]phenyl]-1H-pyrazol-3-yl)-methanol | F-109 |
| D-139 | (1-[(2,6-dimethoxyphenyl)methyl]-5-[3-(2-methyl-propoxy)phenyl]-1H-pyrazol-3-yl)methanol | F-110 |
| D-141 | (1-[[4-(Dimethylamino)phenyl]methyl]-5-[3-(2-methylpropoxy)phenyl]-1H-pyrazol-3-yl)methanol | F-111 |
| D-142 | (1-[[2-(dimethylamino)-6-fluorophenyl]methyl]-5-(3-methoxyphenyl)-1H-pyrazol-3-yl)methanol | F-112 |
| D-147 | (1-[(2-chlorophenyl)methyl]-5-phenoxy-1H-pyrazol-3-yl)methanol | F-113 |
| D-1 | (5-[[(tert-Butoxy)carbonyl](phenyl)amino]-1-[(2-chlorophenyl)methyl]-1H-pyrazol-3-yl)methanol | F-114 |
| D-140 | (1-[(3-chloropyridin-2-yl)methyl]-5-(3-methoxy-phenyl)-1H-pyrazol-3-yl)methanol | F-115 |

Intermediate F-116: [5-(3-Cyclopropoxyphenyl)-1-[[2-(dimethylamino)phenyl]methyl]-1H-pyrazol-3-yl]methanol

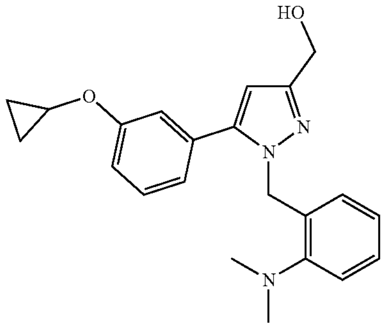 [SMILES: CN(C)c1ccccc1Cn1nc(CO)cc1-c1cccc(OC2CC2)c1]

[1-[(2-Aminophenyl)methyl]-5-(3-cyclopropoxyphenyl)-1H-pyrazol-3-yl]-methanol In a 25-mL flask were combined Int. F-74 [5-(3-cyclopropoxyphenyl)-1-[(2-nitro-phenyl) methyl]-1H-pyrazol-3-yl]methanol (350 mg, 0.96 mmol, 1.00 equiv), AcOH (7.5 mL), $H_2O$ (2.5 mL), and Zn (350 mg, 5.38 mmol, 5.60 equiv). The resulting mixture was stirred for 3 h at rt. The solids were removed. The resulting solution was extracted with 3×30 mL of EtOAc. The combined organic layers were dried over $Na_2SO_4$ and concentrated under vacuum to afford 300 mg (93%) of the title compound as a yellow oil. LC-MS (ES, m/z): 336.

[5-(3-Cyclopropoxyphenyl)-1-[[2-(dimethylamino)phenyl]methyl]-1H-pyrazol-3-yl]methanol Into a 15-mL flask were combined the product from the previous step (300 mg, 0.89 mmol, 1.00 equiv) MeOH (5 mL), AcOH (0.25 mL), HCHO (358 mg, 11.92 mmol, 4.00 equiv), and $NaCNBH_3$ (225 mg, 3.57 mmol, 4.00 equiv). The resulting solution was stirred for 2 h at 40° C., quenched by the addition of 5 mL of water/ice, and extracted with 3×30 mL of EtOAc. The combined organic layers were dried over $Na_2SO_4$, concentrated under vacuum, and purified by prep-TLC with EtOAc/hexane (1/1) to afford 300 mg (92%) of the title compound as a yellow oil. LC-MS: (ES, m/z): 365. $^1H$ NMR: (300 MHz, DMSO) δ 7.30 (dd, J=8.8, 7.6 Hz, 1H), 7.22 (td, J=7.6, 7.2, 1.6 Hz, 1H), 7.14 (dd, J=8.1, 1.4 Hz, 1H), 7.00 (m, 2H), 6.88 (dd, J=6.9, 1.5 Hz, 2H), 6.73 (dd, J=7.7, 1.5 Hz, 1H), 6.42 (s, 1H), 5.35 (s, 2H), 4.46 (s, 2H), 3.67 (dt, J=5.9, 3.1, 3.1 Hz, 1H), 2.55 (s, 6H), 0.62 (ddd, J=5.9, 3.5, 1.3 Hz, 2H), 0.57 (m, 2H).

The following compounds were obtained via a similar zinc reduction/alkylation sequence.

TABLE 13

| Nitro Cpd | Product | | Spectral |
|---|---|---|---|
| Zn reduction/alkylation of (nitroaryl) pyrazoles | | | |
| F-22 | [1-[2-(Dimethylamino)phenyl]-5-(1-ethyl-1H-indazol-6-yl)-1H-pyrazol-3-yl]methanol | F-117 | LC-MS: (ES, m/z): 362.40. |
| F-57 | [5-(3-cyclopropoxyphenyl)-1-[2-(dimethylamino)phenyl]-1H-pyrazol-3-yl]methanol | F-118 | LC-MS: (ES, m/z): 350. |

Intermediate G-1: 3-(Bromomethyl)-1-[(2-chlorophenyl)methyl]-5-(3-methoxyphenyl)-1H-pyrazole

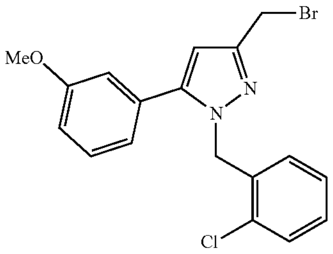 [SMILES: COc1cccc(-c2cc(CBr)nn2Cc2ccccc2Cl)c1]

To a solution of Int. F-8 (4.3 g, 13.08 mmol, 1.00 equiv) in $CH_2Cl_2$ (100 mL) was added $CBr_4$ (6.5 g, 1.50 equiv). This was followed by the addition of a solution of $PPh_3$ (7 g, 26.69 mmol, 2.00 equiv) in $CH_2Cl_2$ (10 mL) dropwise with stirring at 0° C. in 5 min. The resulting solution was stirred for 4 h at rt. The resulting mixture was concentrated under vacuum. The residue was applied onto a silica gel column with EtOAc/petroleum ether (1:5). This resulted in the title compound as a yellow oil (3.5 g, 68%).

The following substituted 3-(bromomethyl)pyrazoles were obtained from reaction of the corresponding (hydroxymethyl)pyrazole with $PPh_3$/$CBr_4$:

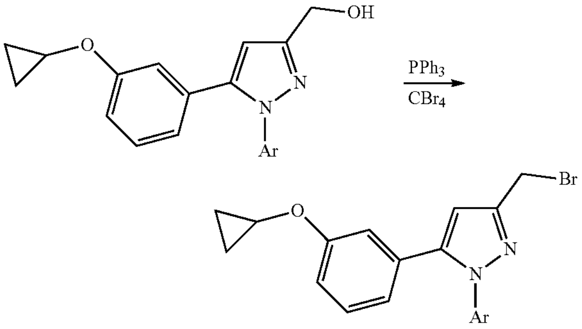

TABLE 14

| Alcohol | Bromo cpd | | Spectral |
|---|---|---|---|
| CBr4 bromination of (hydroxymethyl) pyrazoles. | | | |
| F-6 | 3-(Bromomethyl)-1-[(2-chlorophenyl)methyl]-5-[1,3-dimethyl-1H-thieno[2,3-c]pyrazol-5-yl]-1H-pyrazole | G-2 | LC-MS: (ES, m/z) 435. |
| F-9 | 3-(bromomethyl)-5-[3-(2-methylpropoxy)phenyl]-1-phenyl-1H-pyrazole | G-3 | LC-MS: (ES, m/z): 385. |
| F-10 | 6-[3-(bromomethyl)-1-(2-bromophenyl)-1H-pyrazol-5-yl]-1-ethyl-1H-indazole | G-4 | LC-MS: (ES, m/z): 459. |
| F-14 | 6-[3-(bromomethyl)-1-(2-bromophenyl)-1H-pyrazol-5-yl]-1-propyl-1H-indazole | G-5 | LC-MS: (ES, m/z): 475.2. |
| F-19 | 3-(Bromomethyl)-1-(2-fluorophenyl)-5-[3-(2-methylpropoxy)phenyl]-1H-pyrazole | G-6 | LC-MS: (ES, m/z): 403. |
| F-27 | 7-[3-(bromomethyl)-5-[3-(2,2-dimethylpropoxy)phenyl]-1H-pyrazol-1-yl]-1-methyl-1H-indazole | G-7 | LC-MS: (ES, m/z): 453. |
| F-30 | 7-[3-(bromomethyl)-5-[3-(2-methylpropoxy)phenyl]-1H-pyrazol-1-yl]-1-methyl-1H-indazole | G-8 | LC-MS: (ES, m/z): 441.3. |
| F-34 | 3-(Bromomethyl)-5-(3-methoxyphenyl)-1-[2-(propan-2-yloxy)phenyl]-1H-pyrazole | G-9 | LC-MS: (ES, m/z): 401. |
| F-43 | 3-(bromomethyl)-1-(2-chlorophenyl)-5-(3-cyclopropoxyphenyl)-1H-pyrazole | G-10 | LC-MS: (ES, m/z): 405.15. |
| F-46 | 3-(bromomethyl)-1-(2-chlorophenyl)-5-(3,5-dimethoxyphenyl)-1H-pyrazole | G-11 | LC-MS: (ES, m/z): 406. $^1$H-NMR: (300 MHz, DMSO-$d_6$) δ 7.63 (dt, J = 7.5, 2.0 Hz, 2H), 7.59-7.41 (m, 2H), 6.87 (s, 1H), 6.44 (t, J = 2.3 Hz, 1H), 6.34 (d, J = 2.3 Hz, 2H), 4.70 (s, 2H), 3.61(s, 6H). |

TABLE 14-continued

| CBr4 bromination of (hydroxymethyl) pyrazoles. | | | |
|---|---|---|---|
| F-49 | 3-(Bromomethyl)-1-(2-bromo-phenyl)-5-(3-cyclopropoxyphenyl)-1H-pyrazole | G-12 | LC-MS: (ES, m/z): 447. $^1$H NMR (300 MHz, DMSO-d6) δ 7.76 (dd, J = 7.8, 1.5 Hz, 1H), 7.50 (dddd, J = 29.7, 15.0, 7.5, 1.9 Hz, 3H), 7.23 (t, J = 8.0 Hz, 1H), 6.97-6.85 (m, 2H), 6.85-6.75 (m, 2H), 4.78 (s, 1H), 4.68 (s, 1H), 3.55 (tt, J = 6.0, 3.0 Hz, 1H), 0.69-0.58 (m, 2H), 0.49 (q, J = 2.7, 2.2 Hz, 2H). |
| F-55 | 3-(Bromomethyl)-5-(3-cyclopropoxyphenyl)-1-(2-methoxyphenyl)-1H-pyrazole | G-13 | LC-MS: (ES, m/z): 399 |
| F-60 | 7-[3-(bromomethyl)-5-(3-cyclopropoxyphenyl)-1H-pyrazol-1-yl]-1-methyl-1H-indazole | G-14 | LC-MS: (ES, m/z): 425. |
| F-64 | 3-(Bromomethyl)-1-[(2-cyclo-propoxyphenyl)methyl]-5-(3-methoxyphenyl)-1H-pyrazole | G-15 | LC-MS: (ES, m/z): 414. |
| F-65 | 3-(Bromomethyl)-1-[(2-chlorophenyl)methyl]-5-(3,5-dimethoxyphenyl)-1H-pyrazole | G-16 | LC-MS: (ES, m/z): 423. $^1$H-NMR: (CDCl3, ppm): δ: 7.42-7.30 (m, 2H), 7.29-7.16 (m, 4H), 6.83-6.71 (m, 2H), 6.52-6.36 (m, 8H), 5.45 (d, J = 1.0 Hz, 4H), 5.31 (s, 1H), 4.57 (s, 4H), 3.66 (s, 12H). |
| F-67 | 6-[3-(Bromomethyl)-1-[(2-chlorophenyl)methyl]-1H-pyrazol-5-yl]-1-methyl-1H-indazole | G-17 | LC-MS: (ES, m/z): 417. $^1$H NMR: (300 MHz, $CDCl_3$) δ 8.01 (d, J = 1.0 Hz, 1H), 7.74 (dd, J = 8.3, 0.8 Hz, 1H), 7.42-7.33 (m, 1H), 7.28 (s, 1H), 7.26 (dd, J = 3.8, 1.5 Hz, 2H), 7.10 (dd, J = 8.4, 1.4 Hz, 1H), 6.95-6.84 (m, 1H), 6.58 (s, 1H), 5.48 (d, J = 0.8 Hz, 2H), 4.61 (s, 2H), 3.99 (s, 3H). |
| F-82 | 6-[3-(bromomethyl)-1-[(2-chlorophenyl)methyl]-1H-pyrazol-5-yl]-1-ethyl-1H-indazole | G-18 | LC-MS: (ES, m/z): 431. |
| F-89 | 3-(Bromomethyl)-5-(3,5-dimethoxyphenyl)-1-[(2-ethoxyphenyl)methyl]-1H-pyrazole | G-19 | LC-MS: (ES, m/z): 431.0. |
| F-94 | 5-[3-(Bromomethyl)-1-[(2-chloro-phenyl)methyl]-1H-pyrazol-5-yl]-2-(propan-2-yloxy)-1,3-oxazole | G-20 | LC-MS: (ES, m/z): 411. |
| F-118 | 2-[3-(Bromomethyl)-5-(3-cyclo-propoxyphenyl)-1H-pyrazol-1-yl]-N,N-dimethylaniline | G-21 | LC-MS: (ES, m/z): 413. |

| Alcohol | Bromo cpd | |
|---|---|---|
| F-99 | 3-(Bromomethyl)-1-[(2-chlorophenyl)methyl]-5-(2-methoxyphenyl)-1H-pyrazole | G-22 |
| F-100 | 3-(bromomethyl)-5-(4-bromothien-2-yl)-[1-[(2-chloro-phenyl)methyl]-1H-pyrazole | G-23 |
| F-106 | 3-(Bromomethyl)-(5-(3-methoxyphenyl)-1-[[2-(propan-2-yloxy)phenyl]methyl]-1H-pyrazole | G-24 |
| F-107 | 3-(Bromomethyl)-(5-(3-methoxyphenyl)-1-(2-methyl-propyl)-1H-pyrazole | G-25 |
| F-108 | 3-(Bromomethyl)-(5-(3-methoxyphenyl)-1-([oxan-4-yl]-methyl)-1H-pyrazole | G-26 |
| F-116 | 2-([3-(Bromomethyl)-5-(3-cyclopropoxyphenyl)-1H-pyrazol-1-yl]methyl)-N,N-dimethylaniline | G-27 |

Intermediate H-1: Methyl 2-([1-[(3-chlorophenyl) methyl]-5-phenyl-1H-pyrazol-3-yl]methoxy)-2-methylpropanoate

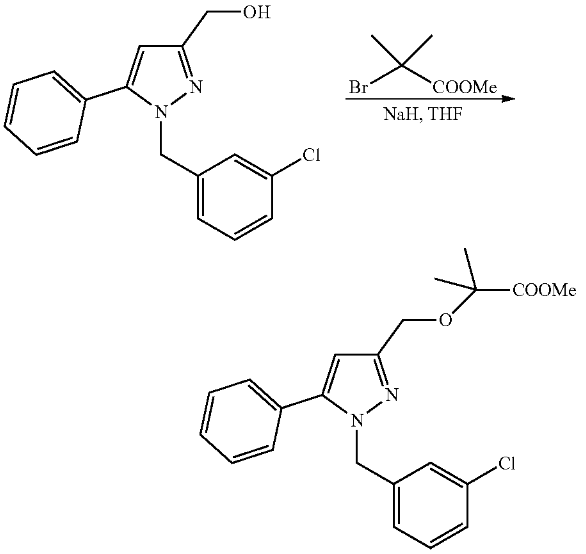

To a solution of It. F-1 (0.288 g, 0.964 mmol) DMF was added NaH (60%) (0.077 g, 1.93 mmol) portionwise under $N_2$ at room temperature, and stirring was continued for 30 min. The mixture was cooled to 0° C. and methyl 2-bromo-2-methyl-propanoate (0.16 mL, 1.25 mmol) was added dropwise followed by NaI (0.143 g, 0.964 mmol). The reaction mixture was warmed to room temperature gradually and stirred overnight. At the end of this period aq. $NH_4Cl$ solution was added, and the mixture was partitioned with EtOAc (40 mL). The aqueous layer was extracted with EtOAc (2×20 mL). The combined EtOAc layers were washed with brine and dried over $Na_2SO_4$, and the solvent was evaporated. The residue was chromatographed over $SiO_2$ (ISCO CombiFlash® Rf 200) using 0-50% gradient of EtOAc in hexanes to afford the title product as an oil (0.068 g, 38%). $^1$H NMR ($CDCl_3$, 400 MHz): δ 1.56 (s, 6H). 3.68 (s, 3H), 4.58 (s, 2H), 5.25 (s, 2H), 6.45 (s, 1H), 6.87-6.93 (m, 1H), 7.00 (s, 1H), 7.16-7.22 (m, 2H), 7.26-7.34 (m, 2H), 7.34-7.42 (m, 3H).

The following substituted pyrazole carboxylic esters were obtained from Williamson ether synthesis of the corresponding (hydroxymethyl)pyrazole with $BrC(CH_3)_2COOMe$:

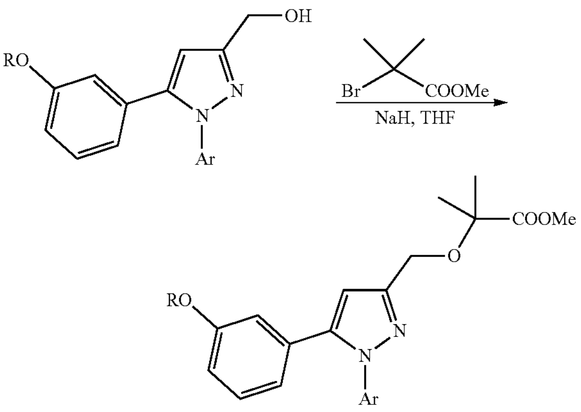

TABLE 15

Ether synthesis from (hydroxymethyl) pyrazoles.

| Alcohol | Product | | Spectral |
|---|---|---|---|
| F-10 | Methyl 2-([1-(2-bromo-phenyl)-5-(1-ethyl-1H-indazol-6-yl)-1H-pyrazol-3-yl]methoxy)-2-methylpropanoate | H-2 | LC-MS: (ES, m/z): 499.1. $^1$H NMR: (300 MHz, DMSO) δ 8.01 (d, J = 1.0 Hz, 1H), 7.74 (dd, J = 8.0, 1.5 Hz, 1H), 7.66 (dd, J = 8.4, 0.8 Hz, 1H), 7.62 (dd, J = 7.8, 1.8 Hz, 1H), 7.53 (td, J = 7.7, 7.6, 1.5 Hz, 1H), 7.48 (dd, J = 1.5, 0.8 Hz, 1H), 7.44 (m, 1H), 6.96 (dd, J = 8.4, 1.4 Hz, 1H), 6.79 (s, 1H), 4.50 (s, 2H), 4.32 (q, J = 7.2, 7.2, 7.2 Hz, 2H), 3.72 (s, 3H), 1.47 (s, 6H), 1.24 (t, J = 7.2, 7.2 Hz, 3H). |
| F-11 | Methyl 2-([1-(2-bromo-phenyl)-5-(1-methyl-1H-indazol-6-yl)-1H-pyrazol-3-yl]methoxy)-2-methylpropanoate | H-3 | LC-MS: (ES, m/z): 483. $^1$H NMR: (300 MHz, DMSO-$d_6$) δ 7.99 (d, J = 1.0 Hz, 1H), 7.73 (dd, J = 7.9, 1.5 Hz, 1H), 7.67-7.47 (m, 4H), 7.42 (td, J = 7.6, 1.9 Hz, 1H), 6.86 (dd, J = 8.4, 1.4 Hz, 1H), 6.78 (s, 1H), 4.49 (s, 2H), 3.94 (s, 3H), 3.71 (s, 3H), 1.46 (s, 6H). |
| F-12 | Methyl 2-([1-(2-bromo-phenyl)-5-[3-(2,2-dimethyl-propoxy)phenyl]-1H-pyrazol-3-yl]methoxy)-2-methylpropanoate | H-4 | LC-MS: (ES, m/z): 517.05. $^1$H NMR (300 MHz, DMSO) δ 7.76 (dd, J = 7.7, 1.3 Hz, 1H), 7.53 (m, 2H), 7.44 (ddd, J = 7.8, 6.6, 2.6 Hz, 1H), 7.18 (t, J = 8.0, 8.0 Hz, 1H), 6.81 (m, 2H), 6.70 (d, J = 2.4 Hz, 2H), 4.45 (s, 2H), 3.70 (s, 3H), 3.39 (s, 2H), 1.45 (s, 6H), 0.93 (s, 9H). |

TABLE 15-continued

| Ether synthesis from (hydroxymethyl) pyrazoles. | | | |
|---|---|---|---|
| F-20 | Methyl 2-([5-(3-cyclo-butoxyphenyl)-1-(2-methylphenyl)-1H-pyrazol-3-yl]methoxy)-2-methylpropanoate | H-5 | LC-MS: (ES, m/z): 434. $^1$H NMR: (300 MHz, DMSO-$d_6$) δ 12.68 (s, 1H), 7.38-7.20 (m, 2H), 7.05-6.94 (m, 2H), 6.92-6.82 (m, 2H), 6.75-6.62 (m, 2H), 6.42 (s, 1H), 5.26 (s, 2H), 4.50 (q, J = 7.1 Hz, 1H), 4.42 (s, 2H), 4.02 (q, J = 6.9 Hz, 2H), 2.30-2.15 (m, 2H), 2.03-1.86 (m, 2H), 1.79-1.65 (m, 1H), 1.63-1.47 (m, 1H), 1.40 (s, 6H), 1.24 (t, J = 6.9 Hz, 3H). |
| F-25 | Methyl 2-([5-(1-ethyl-1H-indazol-6-yl)-1-(1-methyl-1H-indazol-7-yl)-1H-pyrazol-3-yl]methoxy)-2-methylpropanoate | H-6 | LC-MS: (ES, m/z): 472. $^1$H NMR: (400 MHz, DMSO-$d_6$) δ 8.18 (s, 1H), 7.97 (d, J = 0.9 Hz, 1H), 7.90 (dd, J = 8.1, 1.0 Hz, 1H), 7.59 (dd, J = 8.4, 0.8 Hz, 1H), 7.54 (q, J = 1.1 Hz, 1H), 7.46 (dd, J = 7.3, 1.0 Hz, 1H), 7.18 (dd, J = 8.1, 7.3 Hz, 1H), 6.95 (dd, J = 8.4, 1.4 Hz, 1H), 6.91 (s, 1H), 4.55 (s, 2H), 4.26 (t, J = 7.2 Hz, 2H), 3.72 (s, 3H), 3.48 (s, 3H), 1.48 (s, 6H), 1.17 (t, J = 7.1 Hz, 3H). |
| F-26 | Methyl 2-([5-(3-cyclo-butoxyphenyl)-1-(1-methyl-1H-indazol-7-yl)-1H-pyrazol-3-yl]-methoxy)-2-methyl-propanoate | H-7 | LC: (ES, m/z): 475. $^1$H NMR: (300 MHz, DMSO-$d_6$) δ 8.21 (s, 1H), 7.93 (dd, J = 8.1, 1.0 Hz, 1H), 7.38 (dd, J = 7.3, 1.0 Hz, 1H), 7.28-7.09 (m, 2H), 6.94-6.86 (m, 1H), 6.79 (s, 1H), 6.75-6.66 (m, 1H), 6.45 (dd, J = 2.5, 1.6 Hz, 1H), 4.50 (s, 2H), 4.19-4.05 (m, 1H), 3.70 (s, 3H), 3.43 (s, 3H), 2.10-1.95 (m, 2H), 1.89-1.74 (m, 2H), 1.67 (dd, J = 11.6, 8.3 Hz, 1H), 1.52 (d, J = 8.3 Hz, 2H), 1.45 (s, 6H). |
| F-27 | Methyl 2-([5-[3-(2,2-dimethylpropoxy)-phenyl]-1-(1-methyl-1H-indazol-7-yl)-1H-pyrazol-3-yl]methoxy)-2-methylpropanoate | H-8 | LC-MS: (ES, m/z): 491.3. $^1$H NMR: (300 MHz, DMSO) δ 8.19 (s, 1H), 7.92 (dd, J = 8.1, 1.0 Hz, 1H), 7.39 (dd, J = 7.3, 1.0 Hz, 1H), 7.16 (m, 2H), 6.81 (m, 3H), 6.62 (m, 1H), 4.51 (s, 2H), 3.70 (s, 3H), 3.42 (s, 3H), 3.17 (d, J = 6.6 Hz, 2H), 1.46 (s, 6H), 0.87 (s, 9H). |
| F-28 | Methyl 2-([5-[3-(cyclo-butylmethoxy)phenyl]-1-(1-methyl-1H-indazol-7-yl)-1H-pyrazol-3-yl]-methoxy)-2-methyl-propanoate | H-9 | LC-MS: (ES, m/z): 489. $^1$H NMR: (300 MHz, DMSO-$d_6$) δ 8.19 (s, 1H), 7.92 (dd, J = 8.1, 1.0 Hz, 1H), 7.39 (dd, J = 7.3, 1.0 Hz, 1H), 7.28-7.02 (m, 2H), 6.94-6.71 (m, 3H), 6.65 (dd, J = 2.6, 1.6 Hz, 1H), 4.50 (s, 2H), 3.70 (s, 3H), 3.56 (d, J = 6.8 Hz, 2H), 3.43 (s, 3H), 3.16 (s, 1H), 2.04-1.91 (m, 2H), 1.89-1.77 (m, 2H), 1.66 (dt, J = 11.0, 7.6 Hz, 2H), 1.45 (s, 6H). |
| F-30 | Methyl 2-methyl-2-([1-(1-methyl-1H-indazol-7-yl)-5-[3-(2-methyl-propoxy)phenyl]-1H-pyrazol-3-yl]methoxy]-propanoate | H-10 | LC-MS: (ES, m/z): 477. $^1$H NMR (400 MHz, DMSO-$d_6$): δ 8.20 (s, 1H), 7.92 (dd, J = 8.1, 1.0 Hz, 1H), 7.40 (dd, J = 7.4, 1.0 Hz, 1H), 7.26-7.08 (m, 2H), 6.91-6.74 (m, 3H), 6.64 (dd, J = 2.5, 1.5 Hz, 1H), 4.52 (s, 2H), 3.71 (s, 3H), 3.44 (s, 3H), 3.35 (d, J = 6.6 Hz, 2H), 1.81 (dh, J = 13.4, 6.8 Hz, 1H), 1.47 (s, 6H), 0.85 (d, J = 6.6 Hz, 6H). |
| F-33 | Methyl 2-([5-[3-(2,2-di-methylpropoxy)phenyl]-1-(1-ethyl-1H-indazol-7-yl)-1H-pyrazol-3-yl]-methoxy)-2-methyl-propanoate | H-11 | LC-MS: (ES, m/z): 504. $^1$H NMR (400 MHz, DMSO-$d_6$) δ 8.25 (s, 1H), 7.93 (dd, J = 8.1, 1.0 Hz, 1H), 7.33 (dd, J = 7.3, 1.0 Hz, 1H), 7.27-7.07 (m, 2H), 6.87 (s, 1H), 6.84-6.72 (m, 2H), 6.61 (dd, J = 2.5, 1.6 Hz, 1H), 4.52 (s, 2H), 3.71 (s, 2H), 3.18 (s, 3H), 3.16 (s, 2H), 1.47 (s, 6H), 1.10 (t, J = 7.1 Hz, 3H), 0.87 (s, 9H). |
| F-47 | Methyl 2-([1-(2-chloro-phenyl)-5-(3,5-diethoxy-phenyl)-1H-pyrazol-3-yl]methoxy)-2-methyl-propanoate | H-12 | LC-MS: (ES, m/z): 473.05. $^1$H NMR: (300 MHz, DMSO) δ 7.57 (m, 4H), 6.70 (s, 1H), 6.38 (t, J = 2.3, 2.3 Hz, 1H), 6.30 (d, J = 2.2 Hz, 2H), 4.45 (s, 2H), 3.85 (q, J = 7.0, 7.0, 7.0 Hz, 4H), 3.71 (s, 3H), 1.45 (s, 6H), 1.22 (t, J = 7.0, 7.0 Hz, 6H). |

TABLE 15-continued

| Ether synthesis from (hydroxymethyl) pyrazoles. | | | |
|---|---|---|---|
| F-48 | Methyl 2-([5-(3-cyclopropoxyphenyl)-1-(2-fluorophenyl)-1H-pyrazol-3-yl]methoxy]-2-methylpropanoate | H-13 | LC-MS: (ES, m/z): 425.2. $^1$H-NMR: $\delta_H$(300 MHz, DMSO-$D_6$) 7.54 (2 H, m), 7.31 (3 H, m), 6.90 (3 H, m), 6.67 (1 H, s), 4.45 (2 H, s), 3.69 (3 H, s), 3.61 (1 H, dp, J = 6.1, 3.1, 3.1, 3.0, 3.0 Hz), 1.44 (6 H, s), 0.54 (4 H, m). |
| F-61 | Methyl 2-([5-(3-cyclopropoxyphenyl)-1-(1-methyl-1H-indazol-4-yl)-1H-pyrazol-3-yl]-methoxy)-2-methyl-propanoate | H-14 | LC-MS: (ES, m/z): 461. $^1$H NMR (300 MHz, DMSO-$d_6$) δ 7.77-7.62 (m, 2H), 7.42 (dd, J = 8.6, 7.3 Hz, 1H), 7.23 (t, J = 7.9 Hz, 1H), 7.01-6.84 (m, 4H), 6.72 (s, 1H), 4.52 (s, 2H), 4.08 (s, 3H), 3.71 (s, 3H), 3.57 (tt, J = 6.2, 3.0 Hz, 1H), 1.48 (s, 6H), 0.60-0.46 (m, 2H), 0.40 (dq, J = 6.8, 3.4 Hz, 2H). |
| F-62 | Methyl 2-([5-(3-cyclopropoxyphenyl)-1-(1-ethyl-1H-indazol-7-yl)-1H-pyrazol-3-yl]-methoxy)-2-methyl-propanoate | H-15 | LC-MS: (ES, m/z): 475. $^1$H NMR (300 MHz, DMSO-$d_6$) δ 8.24 (s, 1H), 7.91 (dd, J = 8.0, 1.0 Hz, 1H), 7.30 (dd, J = 7.3, 1.0 Hz, 1H), 7.27-7.05 (m, 2H), 6.93 (dt, J = 7.8, 1.2 Hz, 1H), 6.89-6.80 (m, 2H), 6.76 (dd, J = 2.5, 1.6 Hz, 1H), 4.51 (s, 2H), 3.70 (s, 3H), 3.35 (d, J = 4.6 Hz, 2H), 3.33-3.29 (m, 1H), 1.45 (s, 6H), 1.10 (t, J = 7.1 Hz, 3H), 0.52-0.28 (m, 4H). |
| F-66 | Methyl 2-([5-(1-benzothiophen-2-yl)-1-[(2-chlorophenyl)methyl]-1H-pyrazol-3-yl]methoxy)-2-methylpropanoate | H-16 | LC-MS: (ES, m/z): 454. $^1$H NMR: (300 MHz, DMSO-$d_6$) δ 8.04-7.96 (m, 1H), 7.90-7.82 (m, 1H), 7.59 (d, J = 0.8 Hz, 1H), 7.53-7.47 (m, 1H), 7.46-7.39 (m, 2H), 7.32 (tt, J = 7.4, 5.5 Hz, 2H), 6.78-6.70 (m, 1H), 6.69 (s, 1H), 5.63 (s, 2H), 4.43 (s, 2H), 3.71 (s, 3H), 1.44 (s, 6H). |
| F-69 | Methyl 2-([1-[(2-chlorophenyl)methyl]-5-(1-methyl-1H-indazol-4-yl)-1H-pyrazol-3-yl]-methoxy)-2-methyl-propanoate | H-17 | LC-MS: (ES, m/z): 453. $^1$H NMR (300 MHz, DMSO-$d_6$) δ 7.94 (d, J = 1.0 Hz, 1H), 7.79-7.65 (m, 1H), 7.45 (dd, J = 8.5, 7.1 Hz, 1H), 7.41-7.32 (m, 1H), 7.29-7.21 (m, 2H), 7.10 (dd, J = 7.1, 0.8 Hz, 1H), 6.85-6.73 (m, 1H), 6.58 (s, 1H), 5.40 (s, 2H), 4.45 (s, 2H), 4.09 (s, 3H), 3.69 (s, 3H), 1.44 (s, 6H). |
| F-70 | Methyl 2-([1-[(2-ethoxyphenyl)methyl]-5-(1-ethyl-1H-indazol-6-yl)-1H-pyrazol-3-yl]-methoxy)-2-methyl-propanoate | H-18 | LC-MS: (ES, m/z): 477. $^1$H NMR: (400 MHz, DMSO-$d_6$) δ 8.09 (d, J = 1.0 Hz, 1H), 7.80 (dd, J = 8.3, 0.8 Hz, 1H), 7.68 (q, J = 1.0 Hz, 1H), 7.27-7.19 (m, 1H), 7.16 (dd, J = 8.4, 1.4 Hz, 1H), 6.95 (dd, J = 8.2, 1.1 Hz, 1H), 6.86 (td, J = 7.5, 1.1 Hz, 1H), 6.72 (dd, J = 7.5, 1.7 Hz, 1H), 6.51 (s, 1H), 5.33 (s, 2H), 4.41 (s, 2H), 4.40-4.35 (m, 2H), 3.93 (d, J = 7.0 Hz, 2H), 3.70 (s, 3H), 1.44 (s, 6H), 1.33 (t, J = 7.2 Hz, 3H), 1.12 (t, J = 6.9 Hz, 3H). |
| F-71 | Methyl 2-([5-(3-ethoxyphenyl)-1-[(2-ethoxyphenyl)methyl]-1H-pyrazol-3-yl]methoxy)-2-methylpropanoate | H-19 | LC-MS: (ES, m/z): 452. $^1$H NMR (400 MHz, DMSO-$d_6$) δ 7.33 (t, J = 7.9 Hz, 1H), 7.24 (ddd, J = 8.2, 7.3, 1.7 Hz, 1H), 7.04-6.91 (m, 3H), 6.90-6.79 (m, 2H), 6.69 (dd, J = 7.6, 1.7 Hz, 1H), 6.43 (s, 1H), 5.77 (s, 1H), 5.26 (s, 2H), 4.38 (s, 2H), 3.96 (dq, J = 26.5, 6.9 Hz, 4H), 3.69 (s, 3H), 1.42 (s, 6H), 1.25 (dt, J = 18.7, 7.0 Hz, 6H). |
| F-75 | Methyl 2-([1-[(2-bromophenyl)methyl]-5-(3-cyclopropoxyphenyl)-1H-pyrazol-3-yl]-methoxy)-2-methylpropanoate | H-20 | LC-MS: (ES, m/z): 499.3. $^1$H NMR: (300 MHz, DMSO) δ 7.62 (dd, J = 7.9, 1.3 Hz, 1H), 7.35 (tdd, J = 7.5, 7.5, 2.6, 1.0 Hz, 2H), 7.23 (td, J = 7.6, 7.6, 1.8 Hz, 1H), 7.01 (m, 3H), 6.69 (dd, J = 7.7, 1.7 Hz, 1H), 6.47 (s, 1H), 5.34 (s, 2H), 4.40 (s, 2H), 3.68 (s, 4H), 1.42 (s, 6H), 0.59 (tt, J = 5.8, 5.8, 2.4, 2.4 Hz, 4H). |

TABLE 15-continued

Ether synthesis from (hydroxymethyl) pyrazoles.

| | | | |
|---|---|---|---|
| F-79 | Methyl 2-([1-[(2-chloro-phenyl)methyl]-5-(1-methyl-1H-indol-6-yl)-1H-pyrazol-3-yl]-methoxy)-2-methyl-propanoate | H-21 | LC-MS: (ES, m/z): 451. $^1$H NMR (400 MHz, DMSO-$d_6$) δ 7.59 (d, J = 8.1 Hz, 1H), 7.48-7.42 (m, 2H), 7.41 (d, J = 3.1 Hz, 1H), 7.34-7.29 (m, 2H), 7.03 (dd, J = 8.2, 1.5 Hz, 1H), 6.84-6.76 (m, 1H), 6.49-6.42 (m, 2H), 5.44 (s, 2H), 4.42 (s, 2H), 3.74 (s, 3H), 3.70 (s, 3H), 1.44 (s, 6H). |
| F-80 | Methyl 2-([1-[(2-ethoxy-phenyl)methyl]-5-(1-methyl-1H-indazol-6-yl)-1H-pyrazol-3-yl]-methoxy)-2-methyl-propanoate | H-22 | LC-MS: (ES, m/z): 463. $^1$H NMR: (400 MHz, DMSO-$d_6$) δ 8.09 (d, J = 0.9 Hz, 1H), 7.80 (dd, J = 8.3, 0.8 Hz, 1H), 7.69 (q, J = 1.0 Hz, 1H), 7.28-7.20 (m, 1H), 7.16 (dd, J = 8.4, 1.4 Hz, 1H), 6.95 (dd, J =8.4, 1.1 Hz, 1H), 6.86 (td, J = 7.5, 1.0 Hz, 1H), 6.75 (dd, J = 7.5, 1.7 Hz, 1H), 6.49 (s, 1H), 5.32 (s, 2H), 4.41 (s, 2H), 4.01 (s, 3H), 3.93 (q, J = 7.0 Hz, 2H), 3.70 (s, 3H), 1.43 (s, 6H), 1.12 (t, J = 6.9 Hz, 3H). |
| F-90 | Methyl 2-([5-(3,5-di-methoxyphenyl)-1-(2-phenylethyl)-1H-pyrazol-3-yl]methoxy)-2-methyl-propanoate | H-23 | LC-MS: (ES, m/z): 439. $^1$H NMR (400 MHz, DMSO-$d_6$) δ 7.29-7.11 (m, 3H), 7.04-6.94 (m, 2H), 6.54 (t, J = 2.3 Hz, 1H), 6.37 (d, J = 2.3 Hz, 2H), 6.26 (s, 1H), 4.39 (s, 2H), 4.25 (dd, J = 8.1, 6.6 Hz, 2H), 3.74 (s, 6H), 3.70 (s, 3H), 3.05 (t, J = 7.3 Hz, 2H), 1.43 (s, 6H). |
| F-13 | Methyl 2-([1-(2-bromophenyl)-5-(3,5-dimethoxy-phenyl)-1H-pyrazol-3-yl]methoxy)-2-methylpropanoate | H-24 | LC-MS: (ES, m/z): 489. |
| F-14 | Methyl 2-([1-(2-bromophenyl)-5-(1-propyl-1H-indazol-6-yl)-1H-pyrazol-3-yl]methoxy)-2-methylpropanoate | H-25 | LC-MS: (ES, m/z): 535.1. |
| F-15 | Methyl 2-([1-(2-bromophenyl)-5-(3-cyclobutoxy-phenyl)-1H-pyrazol-3-yl]methoxy)-2-methylpropanoate | H-26 | LC-MS: (ES, m/z): 499.3. |
| F-16 | Methyl 2-([1-(2-fluorophenyl)-5-[3-(oxetan-3-yl-methoxy)phenyl]-1H-pyrazol-3-yl]methoxy)-2-methyl-propanoate | H-27 | LC-MS: (ES, m/z): 455.3. |
| F-17 | Methyl 2-([5-(3-cyclo-butoxyphenyl)-1-(2-fluoro-phenyl)-1H-pyrazol-3-yl]methoxy)-2-methylpropanoate | H-28 | LC-MS: (ES, m/z): 439. |
| F-18 | Methyl 2-([1-(2-fluorophenyl)-5-[3-(oxetan-3-yloxy)-phenyl]-1H-pyrazol-3-yl]methoxy)-2-methyl-propanoate | H-29 | LC-MS: (ES, m/z): 440. |
| F-21 | Methyl 2-([5-(3,5-diethoxy-phenyl)-1-(2-methylphenyl)-1H-pyrazol-3-yl]methoxy)-2-methylpropanoate | H-30 | LC-MS: (ES, m/z): 453.25. |
| F-24 | Methyl 2-([5-(3,5-dimethoxy-phenyl)-1-(2-ethoxyphenyl)-1H-pyrazol-3-yl]methoxy)-2-methylpropanoate | H-31 | LC-MS: (ES, m/z): 455. |
| F-29 | Methyl 2-([5-[3-(cyclo-propylmethoxy)phenyl]-1-(1-methyl-1H-indazol-7-yl)-1H-pyrazol-3-yl]methoxy)-2-methylpropanoate | H-32 | LC-MS: (ES, m/z): 475. |
| F-31 | Methyl 2-([5-(3,5-dimethoxy-phenyl)-1-(1-methyl-1H-indazol-7-yl)-1H-pyrazol-3-yl]methoxy)-2-methyl-propanoate | H-33 | LC-MS: (ES, m/z): 465. |
| F-32 | Methyl 2-([5-(3,5-diethoxy-phenyl)-1-(1-methyl-1H-indazol-7-yl)-1H-pyrazol-3-yl]methoxy)-2-methyl-propanoate | H-34 | LC-MS: (ES, m/z): 493.15. |

TABLE 15-continued

| Ether synthesis from (hydroxymethyl) pyrazoles. | | | |
|---|---|---|---|
| F-35 | Methyl 2-([1-(1,3-dimethyl-1H-indazol-7-yl)-5-[3-(2,2-dimethylpropoxy)phenyl]-1H-pyrazol-3-yl]methoxy)-2-methylpropanoate | H-35 | LC-MS: (ES, m/z): 505.3. |
| F-36 | Methyl 2-([5-[3-(2,2-dimethyl-propoxy)phenyl]-1-(1-methyl-1H-1,2,3-benzotriazol-7-yl)-1H-pyrazol-3-yl]methoxy)-2-methylpropanoate | H-36 | LC-MS: (ES, m/z): 492 |
| F-37 | Methyl 2-([1-(2-chlorophenyl)-5-[3-(oxetan-3-yl-methoxy)phenyl]-1H-pyrazol-3-yl]methoxy)-2-methylpropanoate | H-37 | LC-MS: (ES, m/z): 471.3. |
| F-38 | Methyl 2-([1-(2-chlorophenyl)-5-(pyridin-2-yl)-1H-pyrazol-3-yl]methoxy)-2-methylpropanoate | H-38 | LC-MS: (ES, m/z): 386.00. |
| F-39 | Methyl 2-([1-(2-chlorophenyl)-5-(1-methyl-1H-indazol-6-yl)-1H-pyrazol-3-yl]methoxy)-2-methylpropanoate | H-39 | LC-MS: (ES, m/z): 455. |
| F-40 | Methyl 2-([1-(2-chlorophenyl)-5-(1-ethyl-1H-indazol-6-yl)-1H-pyrazol-3-yl]methoxy)-2-methylpropanoate | H-40 | LC-MS: (ES, m/z): 453. |
| F-41 | Methyl 2-([1-(2-chlorophenyl)-5-(3-cyclo-butoxyphenyl)-1H-pyrazol-3-yl]methoxy)-2-methylpropanoate | H-41 | LC-MS: (ES, m/z): 455. |
| F-42 | Methyl 2-([1-(2-chlorophenyl)-5-[3-(oxetan-3-yloxy)-phenyl]-1H-pyrazol-3-yl]methoxy)-2-methylpropanoate | H-42 | LC-MS: (ES, m/z): 457. |
| F-44 | Methyl 2-([1-(2-chlorophenyl)-5-[3-(2,2-dimethyl-propoxy)phenyl]-1H-pyrazol-3-yl]methoxy)-2-methyl-propanoate | H-43 | LC-MS: (ES, m/z): 471.10. |
| F-45 | methyl 2-([1-(2-chlorophenyl)-5-[3-(cyclobutyl-methoxy)phenyl]-1H-pyrazol-3-yl]methoxy)-2-methyl-propanoate | H-44 | LC-MS: (ES, m/z): 469.15. |
| F-46 | Methyl 2-([1-(2-chlorophenyl)-5-(3,5-dimethoxy-phenyl)-1H-pyrazol-3-yl]methoxy)-2-methylpropanoate | H-45 | LC-MS: (ES, m/z): 445. |
| F-49 | Methyl 2-([1-(2-bromophenyl)-5-(3-cycloprop-oxyphenyl)-1H-pyrazol-3-yl]methoxy)-2-methyl-propanoate | H-46 | LC-MS: (ES, m/z): 486.95 |
| F-50 | Methyl 2-([1-(2-bromo-4-fluorophenyl)-5-(3-cyclo-propoxyphenyl)-1H-pyrazol-3-yl]methoxy)-2-methylpropanoate | H-47 | LC-MS: (ES, m/z): 503.1. |
| F-51 | Methyl 2-([5-(3-cyclo-propoxyphenyl)-1-(2,4-dichloro-phenyl)-1H-pyrazol-3-yl]methoxy)-2-methylpropanoate | H-48 | LC-MS: (ES, m/z): 475.05. |
| F-52 | Methyl 2-([5-(3-cyclo-propoxyphenyl)-1-(2,5-dichloro-phenyl)-1H-pyrazol-3-yl]methoxy)-2-methylpropanoate | H-49 | LC-MS: (ES, m/z): 475.1. |
| F-53 | Methyl 2-([5-(3-cyclo-propoxyphenyl)-1-[2-(difluoro-methoxy)phenyl]-1H-pyrazol-3-yl]methoxy)-2-methyl-propanoate | H-50 | LC-MS: (ES, m/z): 473. |
| F-54 | Methyl 2-([5-(3-cyclo-propoxyphenyl)-1-(2-ethoxyphenyl)-1H-pyrazol-3-yl]methoxy)-2-methylpropanoate | H-51 | LC-MS: (ES, m/z): 450. |
| F-56 | Methyl 2-([5-(3-cyclo-propoxyphenyl)-1-(2-methyl-phenyl)-1H-pyrazol-3-yl]methoxy)-2-methylpropanoate | H-52 | LC-MS: (ES, m/z): 421. |

TABLE 15-continued

| Ether synthesis from (hydroxymethyl) pyrazoles. | | | |
|---|---|---|---|
| F-58 | Methyl 2-([5-(3-cyclopropoxyphenyl)-1-[2-(propan-2-yl)phenyl]-1H-pyrazol-3-yl]methoxy)-2-methylpropanoate | H-53 | LC-MS: (ES, m/z): 449. |
| F-59 | Methyl 2-([5-(3-cyclopropoxyphenyl)-1-[2-(trifluoromethyl)phenyl]-1H-pyrazol-3-yl]methoxy)-2-methylpropanoate | H-54 | LC-MS: (ES, m/z): 475. |
| F-60 | Methyl 2-([5-(3-cyclopropoxyphenyl)-1-(1-methyl-1H-indazol-7-yl)-1H-pyrazol-3-yl]methoxy)-2-methylpropanoate | H-55 | LC-MS: (ES, m/z): 461. |
| F-63 | Methyl 2-([5-(3-cyclopropoxyphenyl)-1-(1-methyl-1H-1,3-benzodiazol-7-yl)-1H-pyrazol-3-yl]methoxy)-2-methylpropanoate | H-56 | LC-MS: (ES, m/z): 461.1. |
| F-68 | Methyl 2-([5-(3-chloro-5-methoxyphenyl)-1-[(2-ethoxyphenyl)methyl]-1H-pyrazol-3-yl]methoxy)-2-methylpropanoate | H-57 | LC-MS: (ES, m/z): 473 |
| F-72 | Methyl 2-([5-(3-ethoxy-5-methoxyphenyl)-1-[(2-ethoxyphenyl)methyl]-1H-pyrazol-3-yl]methoxy)-2-methylpropanoate | H-58 | LC-MS: (ES, m/z): 483. |
| F-73 | Methyl 2-([5-(3-cyclopropoxyphenyl)-1-[(2-ethoxyphenyl)methyl]-1H-pyrazol-3-yl]methoxy)-2-methylpropanoate | H-59 | LC-MS: (ES, m/z): 465. |
| F-76 | Methyl 2-([1-[(2-chlorophenyl)methyl]-5-(2,3-dihydro-1,4-benzodioxin-6-yl)-1H-pyrazol-3-yl]methoxy)-2-methylpropanoate | H-60 | LC-MS: (ES, m/z): 457. |
| F-77 | Methyl 2-([5-(2H-1,3-benzodioxol-5-yl)-1-[(2-chlorophenyl)methyl]-1H-pyrazol-3-yl]methoxy)-2-methylpropanoate | H-61 | LC-MS: (ES, m/z): 443. |
| F-78 | Methyl 2-([1-[(2-chlorophenyl)methyl]-5-(1-methyl-1H-pyrazol-4-yl)-1H-pyrazol-3-yl]methoxy)-2-methylpropanoate | H-62 | LC-MS: (ES, m/z): 403. |
| F-81 | Methyl 2-([5-(3,5-diethoxyphenyl)-1-[(2-ethoxyphenyl)methyl]-1H-pyrazol-3-yl]methoxy)-2-methylpropanoate | H-63 | LC-MS: (ES, m/z): 497.25. |
| F-82 | Methyl 2-([1-[(2-chlorophenyl)methyl]-5-(1-ethyl-1H-indazol-6-yl)-1H-pyrazol-3-yl]methoxy)-2-methylpropanoate | H-64 | LC-MS: (ES, m/z): 467. |
| F-83 | Methyl 2-([5-(1-ethyl-1H-indazol-6-yl)-1-([pyridin-2-yl]methyl)-1H-pyrazol-3-yl]methoxy)-2-methylpropanoate | H-65 | LC-MS: (ES, m/z): 434. |
| F-84 | Methyl 2-([1-[(2-chlorophenyl)methyl]-5-(1-methyl-1H-indazol-5-yl)-1H-pyrazol-3-yl]methoxy)-2-methylpropanoate | H-66 | LC-MS: (ES, m/z): 452. |
| F-85 | Methyl 2-([5-(3-cyclobutoxyphenyl)-1-[(2-ethoxyphenyl)methyl]-1H-pyrazol-3-yl]methoxy)-2-methylpropanoate | H-67 | LC-MS: (ES, m/z): 479. |

TABLE 15-continued

| Ether synthesis from (hydroxymethyl) pyrazoles. | | | |
|---|---|---|---|
| F-86 | Methyl 2-([1-[(2-bromophenyl)methyl]-5-(3-cyclobutoxyphenyl)-1H-pyrazol-3-yl]methoxy)-2-methylpropanoate | H-68 | LC-MS: (ES, m/z): 512. |
| F-87 | Methyl 2-([5-[3-(2,2-dimethylpropoxy)phenyl]-1-[(1-methyl-1H-indazol-7-yl)methyl]-1H-pyrazol-3-yl]methoxy)-2-methylpropanoate | H-69 | LC-MS: (ES, m/z): 505. |
| F-88 | Methyl 2-methyl-2-([5-[3-(2-methylpropoxy)phenyl]-1-([pyridin-2-yl]methyl)-1H-pyrazol-3-yl]methoxy)-propanoate | H-70 | LC-MS: (ES, m/z): 438. |
| F-89 | Methyl 2-([5-(3,5-dimethoxyphenyl)-1-[(2-ethoxyphenyl)methyl]-1H-pyrazol-3-yl]methoxy)-2-methylpropanoate | H-71 | LC-MS: (ES, m/z): 469. |
| F-91 | Methyl 2-([5-(3,5-dimethoxyphenyl)-1-[(2-ethoxy-6-fluorophenyl)methyl]-1H-pyrazol-3-yl]methoxy)-2-methylpropanoate | H-72 | LC-MS: (ES, m/z): 487.2. |
| F-92 | Methyl 2-([5-(3,5-dimethoxyphenyl)-1-([pyridin-2-yl]methyl)-1H-pyrazol-3-yl]methoxy)-2-methylpropanoate | H-73 | LC-MS: (ES, m/z): 426. |
| F-93 | Methyl 2-([1-[(2-chlorophenyl)methyl]-5-(3,5-diethoxyphenyl)-1H-pyrazol-3-yl]methoxy)-2-methylpropanoate | H-74 | LC-MS: (ES, m/z): 487.2. |
| F-95 | Methyl 2-([1-[(2-chlorophenyl)methyl]-5-[3-(oxetan-3-ylmethoxy)phenyl]-1H-pyrazol-3-yl]methoxy)-2-methylpropanoate | H-75 | LC-MS: (ES, m/z): 485.2. |
| F-96 | Methyl 2-([5-(3-cyclopropoxyphenyl)-1-(1-[[2-(trimethylsilyl)ethoxy]methyl]-1H-indazol-7-yl)-1H-pyrazol-3-yl]methoxy)-2-methylpropanoate | H-76 | LC-MS: (ES, m/z): 577. |
| F-97 | Methyl 2-([5-(3-cyclopropoxyphenyl)-1-(1-[[2-(trimethylsilyl)ethoxy]methyl]-1H-indazol-4-yl)-1H-pyrazol-3-yl]methoxy)-2-methylpropanoate | H-77 | LC-MS: (ES, m/z): 577.3. |
| F-98 | Methyl 2-([5-(3-cyclopropoxyphenyl)-1-(3-methyl-1-[[2-(trimethylsilyl)ethoxy]methyl]-1H-indazol-4-yl)-1H-pyrazol-3-yl]methoxy)-2-methylpropanoate | H-78 | LC-MS: (ES, m/z): 591.3. |
| F-4 | Methyl 2-([5-(3-methoxyphenyl)-1-(2-methylphenyl)-1H-pyrazol-3-yl]methoxy)-2-methylpropanoate | H-79 | LC-MS: (ES, m/z): 394. |
| F-2 | Methyl 2-([1-[(2-chlorophenyl)methyl]-5-(1-methyl-1H-1,3-benzodiazol-6-yl)-1H-pyrazol-3-yl]methoxy)-2-methylpropanoate | H-80 | LC-MS: (ES, m/z): 453. |
| F-5 | Methyl 2-([1-[(2-chlorophenyl)methyl]-5-(1-ethyl-1H-1,2,3-benzotriazol-6-yl)-1H-pyrazol-3-yl]methoxy)-2-methylpropanoate | H-81 | LC-MS: (ES, m/z): 468. |
| F-117 | Methyl 2-([1-[2-(dimethylamino)phenyl]-5-(1-ethyl-1H-indazol-6-yl)-1H-pyrazol-3-yl]methoxy)-2-methylpropanoate | H-82 | LC-MS: (ES, m/z): 478.3. |

TABLE 15-continued

| Ether synthesis from (hydroxymethyl) pyrazoles. | | |
|---|---|---|
| Alcohol | Product | |
| F-23 | Methyl 2-([5-[3-(2,2-dimethylpropoxy)phenyl]-1-(quinolin-8-yl)-1H-pyrazol-3-yl]methoxy)-2-methylpropanoate | H-83 |
| F-101 | Methyl 2-([1-[(2-chlorophenyl)methyl]-5-[5-(2-Methylpropoxy)thien-2-yl]-1H-pyrazol-3-yl]methoxy)-2-methylpropanoate | H-84 |
| F-102 | Methyl 2-(1-[(2-chlorophenyl)-5-[2-(2-methylpropyl)-1,3-oxazol-5-yl]-1H-pyrazol-3-yl]methoxy)-2-methylpropanoate | H-85 |
| F-103 | Methyl 2-(1-[(2-chlorophenyl)methyl]-5-[2-(2-methyl-propoxy)-1,3-thiazol-5-yl]-1H-pyrazol-3-yl]methoxy)-2-methylpropanoate | H-86 |
| F-104 | Methyl 2-([1-(2-chlorophenyl)-5-[3-(2-methyl-propoxy)phenyl]-1H-pyrazol-3-yl]methoxy)-2-methylpropanoate | H-87 |
| F-105 | 2-([5-Benzyl-1-[(2-chlorophenyl)methyl]-1H-pyrazol-3-yl]methoxy)-2-methylpropanoic acid | H-88 |
| F-110 | Methyl 2-[1-[(2,6-dimethoxyphenyl)methyl]-5-[3-(2-methylpropoxy)phenyl]-1H-pyrazol-3-yl)methoxy)-2-methylpropanoate | H-89 |
| F-111 | Methyl 2-[(1-[[4-(dimethylamino)phenyl]methyl]-5-[3-(2-methylpropoxy)phenyl]-1H-pyrazol-3-yl)methoxy)-2-methylpropanoate | H-90 |
| F-112 | Methyl 2-(1-[[2-(dimethylamino)-6-fluorophenyl]-methyl]-5-(3-methoxyphenyl)-1H-pyrazol-3-yl)methoxy)-2-methyl propanoate | H-91 |
| F-113 | Methyl (1-[(2-chlorophenyl)methyl]-5-phenoxy-1H-pyrazol-3-yl)methoxy)-2-methyl-propanoate | H-92 |
| F-114 | Methyl 2-[(5-[[(tert-Butoxy)carbonyl](phenyl)amino]-1-[(2-chlorophenyl)methyl]-1H-pyrazol-3-yl)methoxy)-2-methylpropanoate | H-93 |
| F-115 | Methyl 2-[(1-[(3-chloropyridin-2-yl)methyl]-5-(3-methoxyphenyl)-1H-pyrazol-3-yl)methoxy)-2-methylpropanoate | H-94 |
| F-7 | Methyl 2-([1-[(2-chlorophenyl)methyl]-5-(3-nitro-phenyl)-1H-pyrazole-3-yl]methoxy)-2-methylpropanoate | H-95 |

The following esters of 2-hydroxy-2-methylbutanoic acid were prepared.

Methyl 2-hydroxy-2-methylbutanoate To a solution of 2-hydroxy-2-methylbutanoic acid (3.0 g, 25.40 mmol, 1.00 equiv) in MeOH (100 mL) was added $H_2SO_4$ (3 mL) dropwise with stirring at 0° C. The resulting solution was heated to reflux for 16 h, cooled, concentrated under vacuum, diluted with 200 mL of EtOAc, washed with 1×100 mL of (sat)NaHCO3(aq), dried over $Na_2SO_4$, and concentrated under vacuum to afford 780 mg (23%) of the title compound as a colorless oil.

Methyl (2R)-2-hydroxy-2-methylbutanoate To a solution of (2R)-2-hydroxy-2-methylbutanoic acid (1.0 g, 8.47 mmol, 1.00 equiv) in MeOH (50 mL) was added $SOCl_2$ (2.0 g, 2.00 equiv) dropwise with stirring at 0° C. The resulting solution was heated to reflux for 16 h, then concentrated under vacuum, diluted with 100 mL of $CH_2Cl_2$. The mixture was dried over $Na_2SO_4$ and concentrated under vacuum, affording 700 mg (63%) of the title compound as a colorless oil. $^1$H-NMR: (300 MHz, $CDCl_3$) δ: 3.79 (s, 3H), 3.04 (s, 1H), 1.89-1.61 (m, 2H), 1.41 (s, 3H), 0.88 (t, J=7.4 Hz, 3H).

Methyl (2S)-2-hydroxy-2-methylbutanoate To a solution of (2S)-2-hydroxy-2-methylbutanoic acid (500 mg, 4.23 mmol, 1.00 equiv) in MeOH (30 mL) was added $SOCl_2$ (1.03 mg, 0.01 mmol, 2.00 equiv) dropwise with stirring at 0° C. The resulting solution was stirred for 16 h at 60° C., then concentrated under vacuum, diluted with 200 mL of $CH_2Cl_2$, washed with 1×100 mL of (sat)NaHCO3(aq), and evaporated under reduced pressure. The solid that formed was dried in an oven under reduced pressure, affording 400 mg (72%) of the title compound as colorless oil. LC-MS: (ES, m/z): 132. $^1$H NMR (DMSO) δ: 5.10 (s, 1H), 3.62 (s, 3H), 1.73-1.44 (m, 2H), 1.24 (s, 3H), 0.78 (t, J=7.4 Hz, 3H).

The following substituted pyrazole carboxylic esters were obtained from Williamson ether synthesis of the corresponding (bromomethyl)pyrazole with HO—$C(CH_3)_2$COOMe:

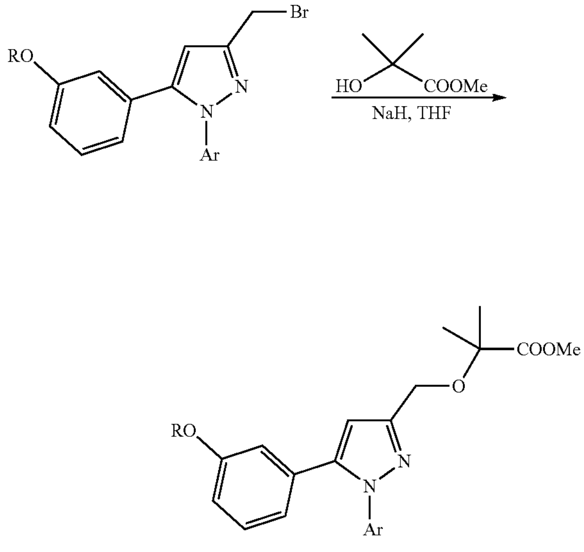

TABLE 16

Ether synthesis from (bromomethyl) pyrazoles.

| Bromo cpd | Product | | Spectral |
|---|---|---|---|
| G-3 | Methyl 2-methyl-2-([5-[3-(2-methylpropoxy)-phenyl]-1-phenyl-1H-pyrazol-3-yl]methoxy)-propanoate | H-96 | LC-MS: (ES, m/z): 423. |
| G-5 | Ethyl (2R)-2-([1-(2-bromophenyl)-5-(1-propyl-1H-indazol-6-yl)-1H-pyrazol-3-yl]methoxy)-2-methylbutanoate (This reaction was performed with Methyl (2R)-2-hydroxy-2-methylbutanoate) | H-97 | LC-MS: (ES, m/z): 541.1. |
| G-6 | Methyl 2-([1-(2-fluorophenyl)-5-[3-(2-methyl-propoxy)phenyl]-1H-pyrazol-3-yl]methoxy)-2-methylpropanoate | H-98 | LC-MS: (ES, m/z): 441. |
| G-9 | Methyl 2-([5-(3-methoxyphenyl)-1-[2-(propan-2-yloxy)phenyl]-1H-pyrazol-3-yl]methoxy)-2-methylpropanoate | H-99 | LC-MS: (ES, m/z): 439. |
| G-22 | Methyl 2-[3-(bromomethyl)-1-[(2-chlorophenyl)-methyl]-5-(2-methoxyphenyl)-1H-pyrazol-3-yl]-methoxy)-2-methylpropanoate | H-100 | |
| G-10 | Methyl 2-([1-(2-chlorophenyl)-5-(3-cyclopropoxyphenyl)-1H-pyrazol-3-yl]methoxy)-2-methylpropanoate | H-101 | |
| G-12 | Methyl (2R)-2-([1-(2-bromophenyl)-5-(3-cyclo-propoxyphenyl)-1H-pyrazol-3-yl]methoxy)-2-methylbutanoate | H-102 | LC-MS: (ES, m/z): 499.3. |
| G-13 | Methyl 2-([5-(3-cyclopropoxyphenyl)-1-(2-methoxyphenyl)-1H-pyrazol-3-yl]methoxy)-2-methylpropanoate | H-103 | LC-MS: (ES, m/z): 437. |
| G-25 | Methyl 2-([5-(3-methoxyphenyl)-1-(2-methyl-propyl)-1H-pyrazol-3-yl]methoxy)-2-methylpropanoate | H-104 | |
| G-26 | Methyl 2-([5-(3-methoxyphenyl)-1-([oxan-4-yl]-methyl)-1H-pyrazol-3-yl]methoxy)-2-methyl-propanoate | H-105 | |
| G-15 | Methyl 2-([1-[(2-cyclopropoxyphenyl)methyl]-5-(3-methoxyphenyl)-1H-pyrazol-3-yl]methoxy)-2-methylpropanoate | H-106 | LC-MS: (ES, m/z): 451. |
| G-16 | Methyl 2-([1-[(2-chlorophenyl)methyl]-5-(3,5-dimethoxyphenyl)-1H-pyrazol-3-yl]methoxy)-2-methylpropanoate | H-107 | LC-MS: (ES, m/z): 459. |
| G-17 | Methyl 2-([1-[(2-chlorophenyl)methyl]-5-(1-methyl-1H-indazol-6-yl)-1H-pyrazol-3-yl]-methoxy)-2-methylpropanoate | H-108 | LC-MS: (ES, m/z): 453. |
| G-20 | Methyl 2-([1-[(2-chlorophenyl)methyl]-5-[2-(propan-2-yloxy)-1,3-oxazol-5-yl]-1H-pyrazol-3-yl]methoxy)-2-methylpropanoate | H-109 | LC-MS: (ES, m/z): 448. |
| G-2 | Methyl 2-([1-[(2-chlorophenyl)methyl]-5-[1,3-dimethyl-1H-thieno[2,3-c]pyrazol-5-yl]-1H-pyrazol-3-yl]methoxy)-2-methylpropanoate | H-110 | LC-MS: (ES, m/z): 473. |
| G-27 | Methyl 2-([5-(3-cyclopropoxyphenyl)-1-[[2-(dimethylamino)phenyl]methyl]-1H-pyrazol-3-yl]methoxy)-2-methylpropanoate | H-111 | LC-MS: (ES, m/z): 464. |
| G-21 | Methyl 2-([5-(3-cyclopropoxyphenyl)-1-[2-(dimethylamino)phenyl]-1H-pyrazol-3-yl]-methoxy)-2-methylpropanoate | H-112 | LC-MS: (ES, m/z): 450 |
| G-24 | Methyl 2-([5-(3-methoxyphenyl)-1-[[2-(propan-2-yloxy)phenyl]methyl]-1H-pyrazol-3-yl]-methoxy)-2-methylpropanoate | H-113 | |

Intermediate H-114: Methyl 2-([1-[(2-chlorophenyl)methyl]-5-(4-cyclopropoxythien-2-yl)-1H-pyrazol-3-yl]methoxy)-2-methylpropanoate

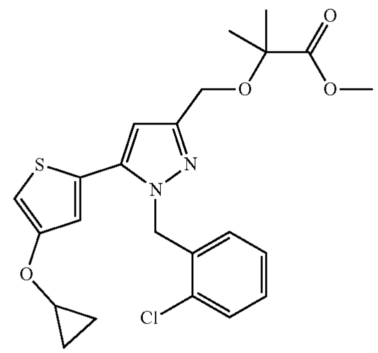 [SMILES: COC(=O)C(C)(C)OCc1cc(-c2cc(OC3CC3)cs2)n(Cc2ccccc2Cl)n1]

tert-Butyl 2-([1-[(2-chlorophenyl)methyl]-5-(4-bromothien-2-yl)-1H-pyrazol-3-yl]methoxy)-2-methylpropanoate To a solution of tert-butyl 2-hydroxy-2-methylpropanoate (2.14 g, 13.36 mmol, 3.00 equiv) in THF (50 mL) was added NaH (535 mg, 13.38 mmol, 3.00 equiv), in portions at 0° C. The mixture was stirred at 0° C. for 20 min. To this was added Int G-23 (2 g, 4.48 mmol, 1.00 equiv) at 0° C. and $Bu_4NI$ (1.0 g, 2.72 mmol, 0.50 equiv). The resulting solution was stirred for 16 h at rt then quenched by the addition of water/ice. The resulting solution was extracted with 500 mL of EtOAc, and the organic layers were combined and dried over anhydrous $Na_2SO_4$ and concentrated under vacuum. The residue was applied onto a silica gel column with EtOAc/petroleum ether (1:2). This resulted in the title compound as a yellow oil (400 mg, 17%).

Methyl 2-([5-(4-bromothien-2-yl)-1-[(2-chlorophenyl)methyl]-1H-pyrazol-3-yl]methoxy)-2-methylpropanoate. To a solution of the product from the previous step (400 mg, 0.76 mmol, 1.00 equiv) in MeOH (20 mL) was added aq HCl (1 mL) dropwise with stirring at rt. The resulting solution was stirred for 3 h at 65° C., concentrated under vacuum, and diluted with 100 mL of EtOAc. The pH value of the solution was adjusted to 7-8 with (sat) $NaHCO_3$ (aq). The mixture was dried over anhydrous $Na_2SO_4$ and concentrated under vacuum. This resulted in the title compound as a yellow oil (350 mg, 95%).

Methyl 2-([1-[(2-chlorophenyl)methyl]-5-(4-cyclopropoxythien-2-yl)-1H-pyrazol-3-yl]methoxy)-2-methylpropanoate To a solution of the product from the previous step (350 mg, 0.72 mmol, 1.00 equiv) in dioxane (10 mL) was added stepwise $Cs_2CO_3$ (473 mg, 1.45 mmol, 2.00 equiv), 2nd Generation XantPhos precatalyst (322 mg, 0.36 mmol, 0.50 equiv), and cyclopropanol (168 mg, 2.89 mmol, 4.00 equiv). The final reaction mixture was irradiated with microwave radiation for 1 h at 85° C. The resulting solution was diluted with 100 mL of EtOAc. The resulting mixture was washed with 2×100 mL of brine. The mixture was dried over anhydrous $Na_2SO_4$ and concentrated under vacuum. The residue was applied onto a silica gel column with EtOAc/petroleum ether (1:2). This resulted in the title compound as a yellow oil (150 mg, 45%).

Intermediate H-115: Methyl 2-([5-(3-aminophenyl)-1-[(2-chlorophenyl)methyl]-1H-pyrazol-3-yl]methoxy)-2-methylpropanoate

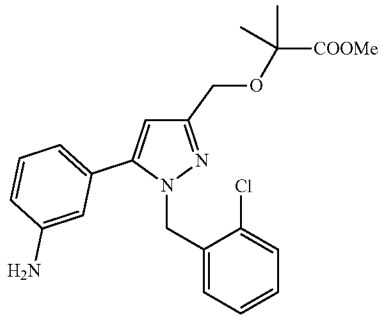 [SMILES: COC(=O)C(C)(C)OCc1cc(-c2cccc(N)c2)n(Cc2ccccc2Cl)n1]

To a solution of Int. H-95 (400 mg, 0.90 mmol, 1.00 equiv) in AcOH/$H_2O$ (10/1 mL) was added Zn (400 mg, 6.15 mmol), in portions at room temperature. The resulting mixture was stirred for 2 h at room temperature. The solids were removed by filtration. The pH value of the solution was adjusted to 7-8 with sat $NaHCO_3$. The resulting solution was extracted with 100 mL of EtOAc, and the organic layers were combined, washed with 2×200 mL of brine, dried over anhydrous $Na_2SO_4$ and concentrated under vacuum. The residue was purified by Prep-TLC with DCM/MeOH (30:1), affording 230 mg (62%) of the title product as a yellow oil.

Intermediate H-116: Methyl 2-([1-[(2-chlorophenyl)methyl]-5-[3-(2-methylpropanamido)-phenyl]-1H-pyrazol-3-yl]methoxy)-2-methylpropanoate

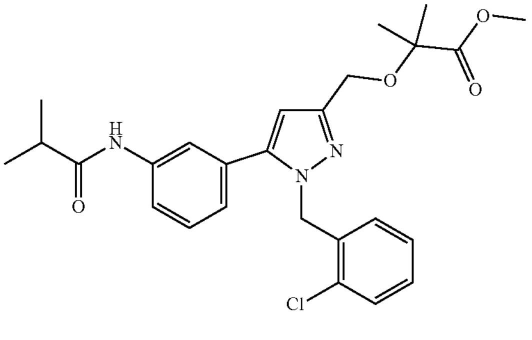 [SMILES: COC(=O)C(C)(C)OCc1cc(-c2cccc(NC(=O)C(C)C)c2)n(Cc2ccccc2Cl)n1]

A solution of Int. H-115 (200 mg, 0.48 mmol, 1.00 equiv), HATU (276 mg, 0.73 mmol, 1.50 equiv), 2-methylpropanoic acid (130 mg, 1.48 mmol, 3.00 equiv) and DIEA (187 mg, 1.45 mmol, 3.00 equiv) in DMF (20 mL) was stirred overnight at rt, then diluted with 200 mL of EtOAc, washed with 2×100 mL of brine, dried over anhydrous $Na_2SO_4$ and concentrated under vacuum. The residue was purified by Prep-TLC with DCM/MeOH (30:1), to afford 155 mg (66%) of the title product as a yellow solid.

Intermediate H-117: Methyl 2-([1-[(2-chlorophenyl) methyl]-5-[3-(methylsulfanyl)phenyl]-1H-pyrazol-3-yl]methoxy)-2-methylpropanoate

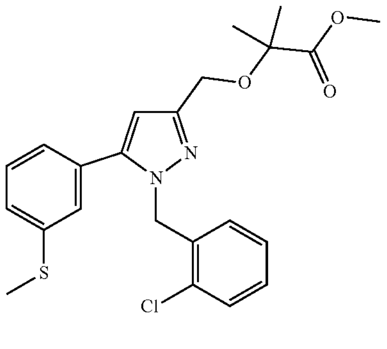 [SMILES: COC(=O)C(C)(C)OCc1cc(-c2cccc(SC)c2)n(Cc2ccccc2Cl)n1]

To a solution of Int. H-115 (700 mg, 1.69 mmol, 1.00 equiv) in MeCN (10 mL). was added dimethyl disulfide (319 mg, 3.39 mmol, 2.00 equiv). The resulting mixture was heated 60° C. for 1 h, then cooled to rt. tert-Butyl nitrite (350 mg, 3.40 mmol, 2.00 equiv) was then added dropwise with stirring, and the resulting solution was stirred for 3 h at 60° C., then diluted with 200 mL of EtOAc, washed with 2×100 mL of brine, dried over anhydrous $Na_2SO_4$ and concentrated under vacuum. The residue was applied onto Prep-TLC with EtOAc/petroleum ether (1:2). This resulted in 300 mg (40%) of the title product as a yellow oil.

Intermediate H-118: Methyl 2-([1-[(2-chlorophenyl) methyl]-5-(3-methanesulfonylphenyl)-1H-pyrazol-3-yl]methoxy)-2-methylpropanoate

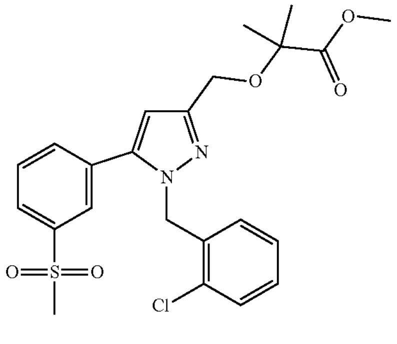 [SMILES: COC(=O)C(C)(C)OCc1cc(-c2cccc(S(C)(=O)=O)c2)n(Cc2ccccc2Cl)n1]

To a solution of Int. H-117 (300 mg, 0.67 mmol, 1.00 equiv) in MeOH/$H_2O$ (10/5 mL) was added $K_2S_2O_8$ (233 mg, 1.53 mmol, 1.00 equiv), in portions at rt. The resulting solution was stirred for 2 h, then diluted with 200 mL of EtOAc, washed with 2×100 mL of brine, dried over anhydrous $Na_2SO_4$ and concentrated under vacuum. The residue was applied onto Prep-TLC with EtOAc/petroleum ether (1:3). This resulted in 180 mg (58%) of the title product as a yellow solid.

Intermediate H-119: Methyl 2-([1-[(2-chlorophenyl) methyl]-5-(3-methanesulfonamidophenyl)-1H-pyrazol-3-yl]methoxy)-2-methylpropanoate

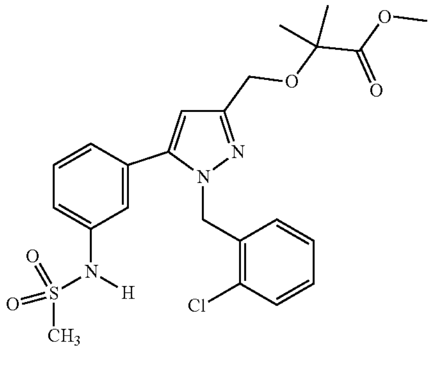 [SMILES: COC(=O)C(C)(C)OCc1cc(-c2cccc(NS(C)(=O)=O)c2)n(Cc2ccccc2Cl)n1]

To a solution of Int. H-115 (200 mg, 0.48 mmol, 1.00 equiv), pyridine (75 mg, 0.95 mmol, 2.00 equiv), and DMAP (6 mg, 0.05 mmol, 0.10 equiv) in DCM (10 mL). was added methanesulfonyl chloride (83 mg, 0.72 mmol, 1.50 equiv) dropwise with stirring at 0° C. The resulting solution was stirred overnight at rt, then diluted with 100 mL of DCM, washed with 2×100 mL of brine, dried over anhydrous $Na_2SO_4$ and concentrated under vacuum. The residue was applied onto Prep-TLC with EtOAc/petroleum ether (1:4). This resulted in 100 mg (42%) of the title product as a yellow oil.

Intermediate H-120: Methyl 2-([1-[(2-chlorophenyl) methyl]-5-[3-(methylamino)phenyl]-1H-pyrazol-3-yl]methoxy)-2-methylpropanoate

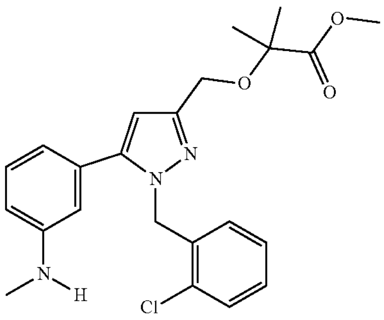 [SMILES: CNc1cccc(-c2cc(COC(C)(C)C(=O)OC)nn2Cc2ccccc2Cl)c1]

To a solution of Int. H-115 (200 mg, 0.48 mmol, 1.00 equiv) in MeOH (10 mL) was added paraformaldehyde (107 mg, 2.43 mmol, 5.00 equiv), followed by the addition of MeONa (0.45 mL, 5.00 equiv, 5.4M) dropwise with stirring at room temperature. The resulting solution was stirred for 2 h at 60° C., then cooled to 0° C. $NaBH_4$ (92 mg, 2.43 mmol, 5.00 equiv) was added, and the solution was stirred for 1 h at 60° C., then cooled, diluted with 100 mL of EtOAc, washed with 2×50 mL of brine, dried over anhydrous $Na_2SO_4$ and concentrated under vacuum. The residue was applied onto Prep-TLC with EtOAc/petroleum ether (1:4). This resulted in 100 mg (48%) of the title product as a yellow oil.

Intermediate H-121: Methyl 2-([1-[(2-chlorophenyl) methyl]-5-(3-methoxyphenyl)-1H-pyrazol-3-yl] methoxy)-2-ethylbutanoate

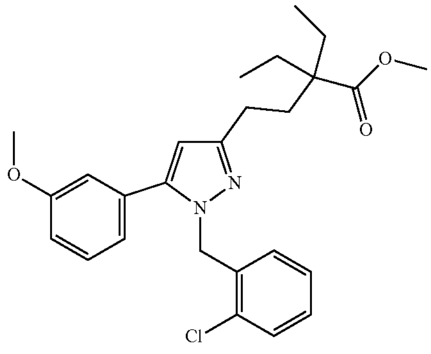 [SMILES: CCC(CC)(CCc1cc(-c2cccc(OC)c2)n(Cc2ccccc2Cl)n1)C(=O)OC]

Methyl 2-ethyl-2-hydroxybutanoate To a solution of 2-ethyl-2-hydroxybutanoic acid (2.0 g, 15.13 mmol, 1.00 equiv) in MeOH (100 mL) was added $H_2SO_4$ (3 mL) dropwise with stirring at rt. The resulting solution was heated to reflux for 16 h, then concentrated under vacuum, diluted with 200 mL of EtOAc, washed with 2×100 mL of sat $NaHCO_3$, dried over anhydrous $Na_2SO_4$ and concentrated under vacuum, affording 800 mg (36%) of the title product as a colorless oil.

Methyl 2-([1-[(2-chlorophenyl)methyl]-5-(3-methoxyphenyl)-1H-pyrazol-3-yl]methoxy)-2-ethylbutanoate To a solution of methyl 2-ethyl-2-hydroxybutanoate (371 mg, 2.54 mmol, 2.00 equiv) in DMF/THF (7/7 mL) was added NaH (100 mg, 4.17 mmol, 2.00 equiv) at 0° C. in 30 min. To this was added NaI (140 mg) and Int. G-1 (500 mg, 1.28 mmol, 1.00 equiv). The resulting solution was stirred for 16 h at rt. The residue was applied onto a Prep-TLC with EtOAc/petroleum ether (1:10). The collected fractions were combined and concentrated under vacuum. This resulted in 210 mg (38%) of the title product as a white liquid.

Intermediate H-122: Methyl (2R)-2-([5-(3-cyclopropoxyphenyl)-1-(1-methyl-1H-indazol-7-yl)-1H-pyrazol-3-yl]methoxy)-2-methylbutanoate

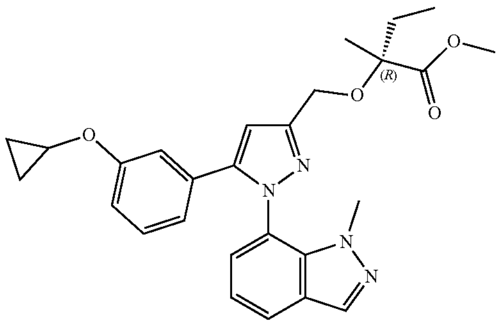

Methyl (2R)-2-([5-(3-cyclopropoxyphenyl)-1-(1-methyl-1H-indazol-7-yl)-1H-pyrazol-3-yl]methoxy)-2-methylbutanoate To a solution of methyl (2R)-2-hydroxy-2-methylbutanoate (250 mg, 1.89 mmol, 2.00 equiv) in THF (20 mL) was added NaH (76 mg, 1.90 mmol, 2.00 equiv), in portions at 0° C. The mixture was stirred at 0° C. for 20 min, then Int. F-10 (400 mg, 0.94 mmol, 1.00 equiv) at 0° C., Bu4NI (200 mg, 0.54 mmol, 0.50 equiv) was added. The resulting solution was stirred for 16 h at rt, then quenched by the addition of water/ice. The resulting solution was extracted with 100 mL of ethyl acetate, and the combined organic layers were dried over $Na_2SO_4$, concentrated under vacuum, and purified with Prep-TLC using EtOAc/petroleum ether (1:1) to afford 160 mg (36%) of the title compound as a yellow solid. LC-MS: (ES, m/z): 475.

The following substituted pyrazole carboxylic esters were obtained from Williamson ether synthesis of the corresponding (bromomethyl)pyrazole with HO—$C(CH_3)(Et)COOMe$:

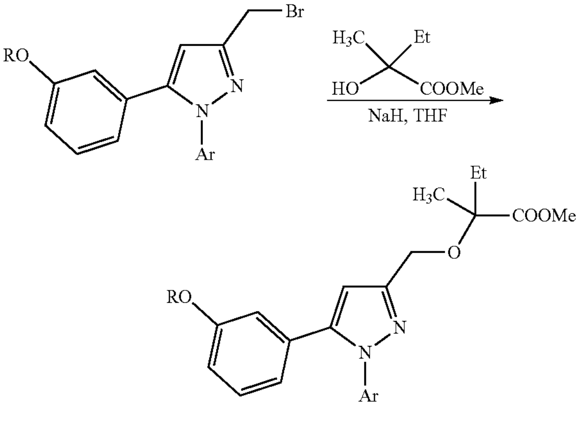

TABLE 17

Ether synthesis from (bromomethyl) pyrazoles.

| Bromo cpd | Product | | Spectral |
|---|---|---|---|
| G-1 | Methyl (2S)-2-([1-[(2-chlorophenyl)methyl]-5-(3-methoxyphenyl)-1H-pyrazol-3-yl]methoxy)-2-methylbutanoate | H-123 | LC-MS: (ES, m/z): 443. |
| G-1 | Methyl (2R)-2-([1-[(2-chlorophenyl)methyl]-5-(3-methoxyphenyl)-1H-pyrazol-3-yl]methoxy)-2-methylbutanoate | H-124 | LC-MS: (ES, m/z): 443. |

TABLE 17-continued

Ether synthesis from (bromomethyl) pyrazoles.

| Bromo cpd | Product | | Spectral |
|---|---|---|---|
| G-4 | Ethyl (2R)-2-([1-(2-bromophenyl)-5-(1-ethyl-1H-indazol-6-yl)-1H-pyrazol-3-yl]methoxy)-2-methylbutanoate | H-125 | LC-MS: (ES, m/z): 525. |
| G-7 | Methyl (2R)-2-([5-[3-(2,2-dimethylpropoxy)phenyl]-1-(1-methyl-1H-indazol-7-yl)-1H-pyrazol-3-yl]methoxy)-2-methylbutanoate | H-126 | LC-MS: (ES, m/z): 505. |
| G-8 | Ethyl (2R)-2-methyl-2-([1-(1-methyl-1H-indazol-7-yl)-5-[3-(2-methylpropoxy)phenyl]-1H-pyrazol-3-yl]methoxy]butanoate | H-127 | LC-MS: (ES, m/z): 505.15. |
| G-10 | Ethyl (2R)-2-([1-(2-chlorophenyl)-5-(3-cyclopropoxyphenyl)-1H-pyrazol-3-yl]methoxy)-2-methylbutanoate | H-128 | LC-MS: (ES, m/z): 469.1. |
| G-11 | Methyl (2R)-2-([1-(2-chlorophenyl)-5-(3,5-dimethoxyphenyl)-1H-pyrazol-3-yl]methoxy)-2-methylbutanoate | H-129 | LC-MS: (ES, m/z): 459. |
| G-18 | Methyl (2R)-2-([1-[(2-chlorophenyl)methyl]-5-(1-ethyl-1H-indazol-6-yl)-1H-pyrazol-3-yl]methoxy)-2-methylbutanoate | H-130 | LC-MS: (ES, m/z): 481. |
| G-18 | Methyl (2S)-2-([1-[(2-chlorophenyl)methyl]-5-(1-ethyl-1H-indazol-6-yl)-1H-pyrazol-3-yl]methoxy)-2-methylbutanoate | H-131 | |
| G-19 | Ethyl (2R)-2-([5-(3,5-dimethoxyphenyl)-1-[(2-ethoxyphenyl)methyl]-1H-pyrazol-3-yl]methoxy)-2-methylbutanoate | H-132 | LC-MS: (ES, m/z): 497.5. |

Intermediate H-133: Methyl 2-([1-[2-(azetidin-1-yl) phenyl]-5-(1-ethyl-1H-indazol-6-yl)-1H-pyrazol-3-yl]methoxy)-2-methylpropanoate

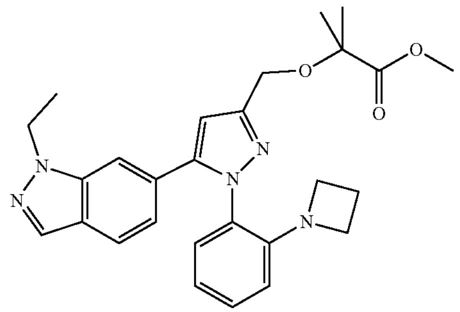 [SMILES: CCn1ncc2ccc(-c3cc(COC(C)(C)C(=O)OC)nn3-c3ccccc3N3CCC3)cc21]

Into a 20-mL sealed tube were combined methyl 2-([1-(2-bromophenyl)-5-(1-ethyl-1H-indazol-6-yl)-1H-pyrazol-3-yl]methoxy)-2-methylpropanoate (200 mg, 0.40 mmol, 1.00 equiv) L-proline (46 mg, 0.40 mmol, 1.00 equiv), CuI (38 mg, 0.20 mmol, 0.50 equiv), $K_2CO_3$ (166 mg, 1.20 mmol, 3.00 equiv), azetidine (69 mg, 1.21 mmol, 3.00 equiv), and DMSO (10 mL). The resulting solution was stirred overnight at 70° C. The reaction mixture was cooled to room temperature. The resulting solution was extracted with 3×20 mL of EtOAc and the organic layers combined and dried over $Na_2SO_4$ and concentrated under vacuum. The residue was purified by prep-TLC with EtOAc/petroleum ether (1/3). This resulted in 50 mg (26%) of the title compound as light yellow oil. LC-MS: (ES, m/z): 474. $^1$H NMR: (300 MHz, $CDCl_3$) δ 7.90 (s, 1H), 7.62 (d, J=8.4 Hz, 1H), 7.34 (s, 1H), 7.24 (m, 2H), 7.07 (dd, J=7.8, 1.5 Hz, 1H), 6.76 (s, 1H), 6.69 (td, J=7.6, 7.5, 1.3 Hz, 1H), 6.45 (dd, J=8.2, 1.3 Hz, 1H), 4.63 (s, 2H), 4.25 (q, J=7.3, 7.3, 7.3 Hz, 2H), 3.79 (s, 3H), 3.58 (dq, J=24.9, 7.4, 7.3, 7.3 Hz, 4H), 2.10 (p, J=7.3, 7.3, 7.3, 7.3 Hz, 2H), 1.56 (s, 6H), 1.34 (q, J=8.2, 8.2, 7.2 Hz, 3H).

Intermediate H-134: Methyl 2-([1-[2-(azetidin-1-yl) phenyl]-5-[3-(2,2-dimethylpropoxy)-phenyl]-1H-pyrazol-3-yl]methoxy)-2-methylpropanoate

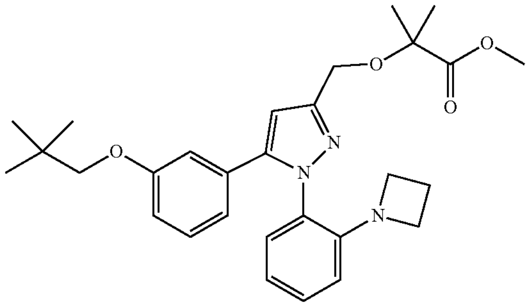 [SMILES: COC(=O)C(C)(C)OCc1cc(-c2cccc(OCC(C)(C)C)c2)n(-c2ccccc2N2CCC2)n1]

Into a 30-mL sealed tube were combined Int. H-4 (200 mg, 0.39 mmol, 1.00 equiv), L-proline (44 mg, 0.38 mmol, 1.00 equiv), CuI (40 mg, 0.21 mmol, 0.50 equiv), $K_2CO_3$ (160 mg, 1.16 mmol, 3.00 equiv), azetidine (66 mg, 1.16 mmol, 3.00 equiv), and DMSO (10 mL). The resulting solution was stirred overnight at 70° C., cooled, and extracted with 3×15 mL of EtOAc. The combined organic layers were dried over $Na_2SO_4$, concentrated under vacuum, and purified with by prep-TLC using EtOAc/petroleum ether (1/3) to afford 70 mg (37%) of the title compound as a light yellow oil. LC-MS: (ES, m/z): 492.30. $^1$H NMR: (300 MHz, DMSO) δ 7.28 (ddd, J=8.5, 7.4, 1.6 Hz, 1H), 7.20 (t, J=7.9, 7.9 Hz, 1H), 6.98 (ddd, J=9.9, 7.2, 1.5 Hz, 2H), 6.84 (m, 2H), 6.69 (m, 2H), 6.51 (dd, J=8.3, 1.3 Hz, 1H), 4.44 (s, 2H), 3.71 (s, 3H), 3.50 (m, 2H), 3.42 (m, 2H), 2.07 (m, 2H), 1.45 (s, 6H), 0.94 (s, 9H).

The following amino substituted aryl compounds were obtained through use of similar copper(I) mediated coupling procedures.

TABLE 18

Arylamine synthesis from (bromoaryl) pyrazoles.

| Aryl halide | Amine | Product | | Spectral |
|---|---|---|---|---|
| H-2 | Pyrrolidine | Methyl 2-([5-(1-ethyl-1H-indazol-6-yl)-1-[2-(pyrrolidin-1-yl)phenyl]-1H-pyrazol-3-yl]methoxy)-2-methylpropanoate | H-135 | LC-MS: (ES, m/z): 488.15. |
| H-3 | Pyrrolidine | Methyl 2-methyl-2-([5-(1-methyl-1H-indazol-6-yl)-1-[2-(pyrrolidin-1-yl)-phenyl]-1H-pyrazol-3-yl]methoxy]-propanoate | H-136 | LC-MS: (ES, m/z): 474. |
| H-24 | Pyrrolidine | Methyl 2-([5-(3,5-dimethoxyphenyl)-1-[2-(pyrrolidin-1-yl)phenyl]-1H-pyrazol-3-yl]methoxy)-2-methylpropanoate | H-137 | LC-MS: (ES, m/z): 480. |
| H-24 | Azetidine | Methyl 2-([1-[2-(azetidin-1-yl)phenyl]-5-(3,5-dimethoxyphenyl)-1H-pyrazol-3-yl]methoxy)-2-methylpropanoate | H-138 | LC-MS: (ES, m/z): 466. |
| H-25 | Azetidine | Methyl 2-([1-[2-(azetidin-1-yl)phenyl]-5-(1-propyl-1H-indazol-6-yl)-1H-pyrazol-3-yl]methoxy)-2-methylpropanoate | H-139 | LC-MS: (ES, m/z): 488.1. |
| H-25 | Pyrrolidine | Methyl 2-methyl-2-([5-(1-propyl-1H-indazol-6-yl)-1-[2-(pyrrolidin-1-yl)phenyl]-1H-pyrazol-3-yl]methmoxy]propanoate | H-140 | LC-MS: (ES, m/z): 502.2. |
| H-26 | Azetidine | Methyl 2-([1-[2-(azetidin-1-yl)phenyl]-5-(3-cyclobutoxyphenyl)-1H-pyrazol-3-yl]methoxy)-2-methylpropanoate | H-141 | LC-MS: (ES, m/z): 476.5. |
| H-46 | Pyrrolidine | Methyl 2-([5-(3-cyclopropoxyphenyl)-1-[2-(pyrrolidin-1-yl)phenyl]-1H-pyrazol-3-yl]methoxy)-2-methylpropanoate | H-142 | LC-MS: (ES, m/z): 476.4. |
| H-46 | Azetidine | methyl 2-([1-[2-(azetidin-1-yl)phenyl]-5-(3-cyclopropoxyphenyl)-1H-pyrazol-3-yl]methoxy)-2-methylpropanoate | H-143 | LC-MS: (ES, m/z): 462.15. |
| H-46 | (3S)-3-hydroxy-pyrrolidine | Methyl 2-([5-(3-cyclopropoxyphenyl)-1-[2-[(3S)-3-hydroxypyrrolidin-1-yl]-phenyl]-1H-pyrazol-3-yl]methoxy)-2-methylpropanoate | H-144 | LC-MS: (ES, m/z): 492. |
| H-46 | Morpholine | Methyl 2-([5-(3-cyclopropoxyphenyl)-1-[2-(morpholin-4-yl)phenyl]-1H-pyrazol-3-yl]methoxy)-2-methylpropanoate | H-145 | LC-MS: (ES, m/z): 492.5. |
| H-46 | 2-Oxo-pyrrolidine | Methyl 2-([5-(3-cyclopropoxyphenyl)-1-[2-(2-oxopyrrolidin-1-yl)phenyl]-1H-pyrazol-3-yl]methoxy)-2-methylpropanoate | H-146 | LC-MS: (ES, m/z): 490.1. |
| H-46 | Pyrazole | Methyl 2-([5-(3-cyclopropoxyphenyl)-1-[2-(1H-pyrazol-1-yl)phenyl]-1H-pyrazol-3-yl]methoxy)-2-methylpropanoate | H-147 | LC-MS: (ES, m/z): 473.25. |
| H-46 | (3R)-3-hydroxy-pyrrolidine | Methyl 2-([5-(3-cyclopropoxyphenyl)-1-[2-[(3R)-3-hydroxypyrrolidin-1-yl]-phenyl]-1H-pyrazol-3-yl]methoxy)-2-methylpropanoate | H-148 | LC-MS: (ES, m/z): 492. |
| H-47 | Azetidine | Methyl 2-([1-[2-(azetidin-1-yl)-4-fluorophenyl]-5-(3-cyclopropoxy-phenyl)-1H-pyrazol-3-yl]methoxy)-2-methylpropanoate | H-149 | LC-MS: (ES, m/z): 480.40. |
| H-20 | Pyrrolidine | Methyl 2-([5-(3-cyclopropoxyphenyl)-1-[[2-(pyrrolidin-1-yl)phenyl]methyl]-1H-pyrazol-3-yl]methoxy)-2-methyl-propanoate | H-150 | LC-MS: (ES, m/z): 490.15. |

TABLE 18-continued

Arylamine synthesis from (bromoaryl) pyrazoles.

| Aryl halide | Amine | Product | | Spectral |
|---|---|---|---|---|
| H-68 | Pyrrolidine | Methyl 2-([5-(3-cyclobutoxyphenyl)-1-[[2-(pyrrolidin-1-yl)phenyl]methyl]-1H-pyrazol-3-yl]methoxy)-2-methylpropanoate | H-151 | LC-MS: (ES, m/z): 504. |
| H-97 | Azetidine | Ethyl (2R)-2-([1-[2-(azetidin-1-yl)phenyl]-5-(1-propyl-1H-indazol-6-yl)-1H-pyrazol-3-yl]methoxy)-2-methylbutanoate | H-152 | LC-MS: (ES, m/z): 516.5. |
| H-102 | Azetidine | Methyl (2R)-2-([1-[2-(azetidin-1-yl)phenyl]-5-(3-cyclopropoxyphenyl)-1H-pyrazol-3-yl]methoxy)-2-methylbutanoate | H-153 | LC-MS: (ES, m/z): 476.2. |
| H-125 | Pyrrolidine | Ethyl (2R)-2-([5-(1-ethyl-1H-indazol-6-yl)-1-[2-(pyrrolidin-l-yl)phenyl]-1H-pyrazol-3-yl]methoxy)-2-methylbutanoate | H-154 | LC-MS: (ES, m/z): 516. |
| H-125 | Azetidine | Ethyl (2R)-2-([1-[2-(azetidin-1-yl)phenyl]-5-(1-ethyl-1H-indazol-6-yl)-1H-pyrazol-3-yl]methoxy)-2-methylbutanoate | H-155 | LC-MS: (ES, m/z): 502. |

Intermediate H-156: Methyl 2-([1-(2-cyanophenyl)-5-(3-cyclopropoxyphenyl)-1H-pyrazol-3-yl]methoxy)-2-methylpropanoate

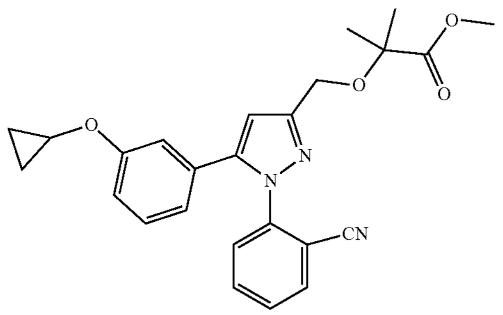 [SMILES: COC(=O)C(C)(C)OCc1cc(-c2cccc(OC3CC3)c2)n(-c2ccccc2C#N)n1]

To a solution of Int. H-46 (150 g, 309.04 mmol, 1.00 equiv) and $Zn(CN)_2$ (72 mg, 0.62 mmol, 2.00 equiv) in DMF (15 mL) was added $Pd(PPh_3)_4$ (36 mg, 0.03 mmol, 0.10 equiv), in portions at rt. The resulting solution was stirred for 16 h at 100° C., diluted with 100 mL of EtOAc, washed with 2×50 mL of (sat)$FeSO_4$(aq), dried over $Na_2SO_4$ and concentrated under vacuum. The residue was applied onto a Prep-TLC with EtOAc/petroleum ether (1:2). This resulted in 100 mg of the title compound as colorless oil. LC-MS: (ES, m/z): 432.

Chromatographic Procedures

All chromatography was performed on an 2#-Analy-seHPLC-SHIMADZU(HPLC-10) instrument, with detection at 254/220 nm. Columns used for purification include:

"Xselect": XSelect CSH Prep C18 OBD Column, 19*250 mm, 5 um.

"XBridge": XBridge Prep C18 OBD Column, 19*150 mm 5 um.

EXAMPLES

The invention is further illustrated by the following examples.

Example 1: 2-([1-[(3-Chlorophenyl)methyl]-5-phenyl-1H-pyrazol-3-yl]methoxy)-2-methylpropanoic acid

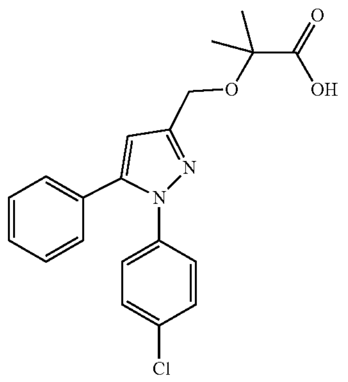 [SMILES: CC(C)(OCc1cc(-c2ccccc2)n(-c2ccc(Cl)cc2)n1)C(=O)O]

To a solution of It. H-1 (0.068 g, 0.170 mmol) in THF:MeOH:$H_2O$ (2:1:1) (8 mL) was added LiOH*$H_2O$ (0.035 g, 0.85 mmol) at RT and stirring was continued for further 3 h. The solvent was then evaporated and to the residue water (2 mL) was added and acidified with 1M citric acid. The mixture was extracted with EtOAc (25 mL) and washed with water (10 mL) followed by brine (10 mL). The EtOAc layer was dried over $Na_2SO_4$, and solvent was removed by evaporation. The crude product was chromatographed over $SiO_2$ (ISCO CombiFlash® Rf 200) using 0-30% gradient of MeOH in DCM to afford the title product as white solid (0.032 g). $^1$HNMR($CDCl_3$): δ 1.56 (s, 6H), 4.61 (s, 2H), 5.34 (s, 2H), 6.38 (s, 1H), 6.87-6.97 (m, 1H), 7.04 (s, 1H), 7.18-7.24 (m, 2H), 7.26-7.35 (m, 2H), 7.35-7.45 (m, 3H).

Examples 2-50 were prepared analogously as described in Example 1.

TABLE 19

Examples 2-50.

| Ex. | Structure | IUPAC Name<br>Analytical data |
|---|---|---|
| 2 | 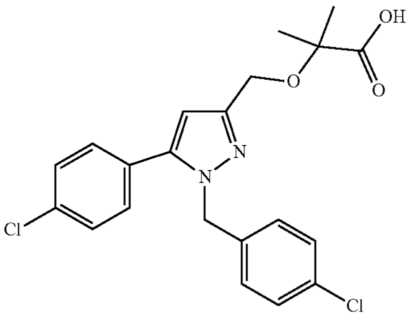 [SMILES: CC(C)(OCc1cc(-c2ccc(Cl)cc2)n(Cc2ccc(Cl)cc2)n1)C(=O)O] | 2-([5-(4-Chlorophenyl)-1-[(4-chlorophenyl)-methyl]1H-pyrazol-3-yl]methoxy)-2-methylpropanoic acid<br>$^1$H NMR ($CD_3OD$, 400 MHz) δ 1.52 (s, 6H), 4.54(s, 2H0, 5.329s, 2H), 6.48 (s, 1H), 6.91-7.00 (m, 1H), 7.21-7.30-(m, 2H), 7.31-7.38 (m, 2H), 7.40-7.48 (m 3H). |
| 3 | 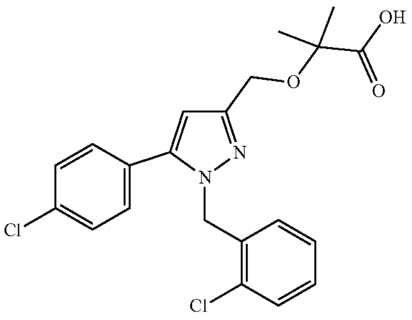 [SMILES: CC(C)(OCc1cc(-c2ccc(Cl)cc2)n(Cc2ccccc2Cl)n1)C(=O)O] | 2-([5-(4-Chlorophenyl)-1-[(2-chlorophenyl)-methyl]1H-pyrazol-3-yl]methoxy)-2-methyl-propanoic acid<br>$^1$H NMR ($CD_3OD$, 400 MHz) δ 1.50 (s, 6H), 4.58 (s, 2H), 5.41 (s, 2H), 6.56 (s, 1H), 6.72-6.80 (m, 1H), 7.20-7.34 (m, 2H), 7.34-50 (m, 5H). |
| 4 | 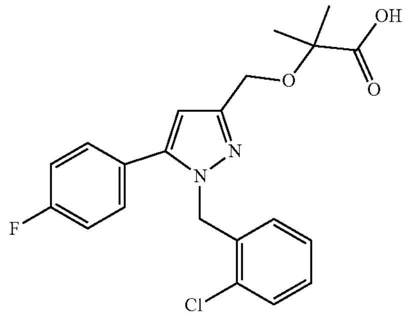 [SMILES: CC(C)(OCc1cc(-c2ccc(F)cc2)n(Cc2ccccc2Cl)n1)C(=O)O] | 2-([1-[(2-Chlorophenyl)methyl]-5-(4-fluorophenyl)1H-pyrazol-3-yl]methoxy)-2-methylpropanoic acid<br>$^1$H NMR ($CD_3OD$, 400 MHz) δ 1.51 (s, 6H), 4.58 (s, 2H), 5.40 (s, 2H), 6.55 (s, 1H), 6.70-6.78 (m, 1H), 7.14-7.18 (m, 2H), 7-20-7.29 (m, 2H), 7.32-7.40 (m, 3H). |
| 5 | 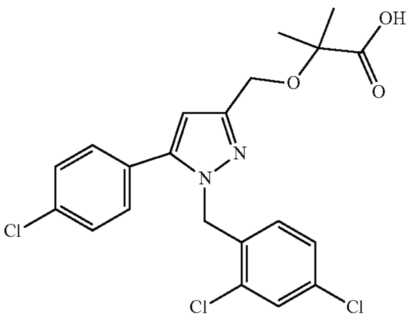 [SMILES: CC(C)(OCc1cc(-c2ccc(Cl)cc2)n(Cc2ccc(Cl)cc2Cl)n1)C(=O)O] | 2-([5-(4-Chlorophenyl)-1-[(2,4-dichlorophenyl)methyl]1H-pyrazol-3-yl]methoxy)-2-methylpropanoic acid<br>$^1$H NMR ($CD_3OD$, 400 MHz) δ 1.48 (s, 6H), 4.58 (s, 2H), 5.40 (s, 2H), 6.54 (s, 1H), 6.73 (d, 1H), 7.20-7.38 (m, 3H), 7.40-48 (m, 3H). |

TABLE 19-continued

| Examples 2-50. | | |
|---|---|---|
| Ex. | Structure | IUPAC Name<br>Analytical data |
| 6 | 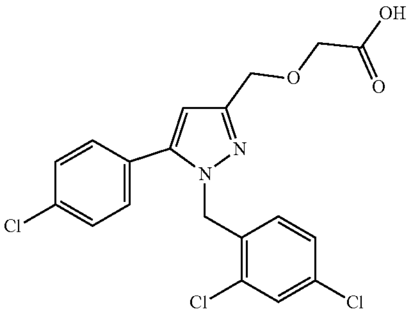 [SMILES: O=C(O)COCc1cc(-c2ccc(Cl)cc2)n(Cc2ccc(Cl)cc2Cl)n1] | 2-([5-(4-Chlorophenyl)-1-[(2,4-dichlorophenyl)methyl]1H-pyrazol-3-yl]methoxy]acetic acid<br>$^1$H NMR (DMSO-$d_6$, 400 MHz) δ 3.80 (s, 2H), 4.50 9s, 2H), 5.30 (s, 2H), 6.50 (s, 1H), 6.60-80 (m, 1H), 7.20-70 (m, 6H). |
| 7 | 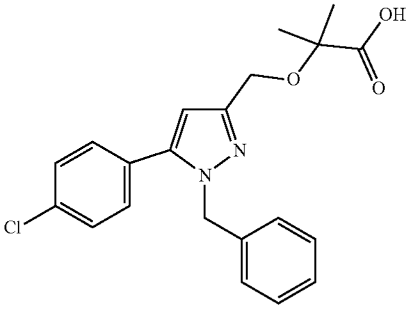 [SMILES: CC(C)(OCc1cc(-c2ccc(Cl)cc2)n(Cc2ccccc2)n1)C(=O)O] | 2-([1-Benzyl-5-(4-Chlorophenyl)1H-pyrazol-3-yl]methoxy)-2-methylpropanoic acid<br>$^1$H NMR ($CD_3OD$, 400 MHz) δ 1.53 (s, 6H), 4.58 (s, 2H), 5.38 (s, 2H), 6.51 (s, 1H), 6.90 (d, 2H), 7.18-7.50 (m, 7H). |
| 8 | 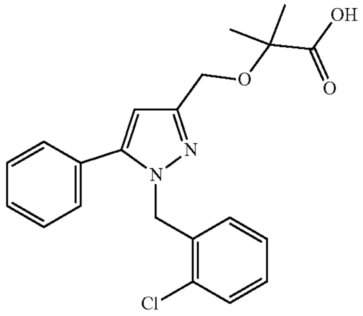 [SMILES: CC(C)(OCc1cc(-c2ccccc2)n(Cc2ccccc2Cl)n1)C(=O)O] | 2-([1-[(2-Chlorophenyl)methyl]-5-phenyl-1H-pyrazol-3-yl]methoxy)-2-methylpropanoic acid<br>$^1$H NMR (DMSO-$d_6$, 400 MHz) δ1.56 (s, 6H), 4.58 (s, 2H), 5.41 (s, 2H), 6.56 (s, 1H), 6.75-6.78 (m, 1H), 7.20-7.30 (m, 4H), 7.32-7.43 (m, 4H).<br>1H NMR (CD3OD, 400 MHz) δ 1.54 (s, 6H), 4.589s, 2H), 5.40 (s, 2H), 6.55 (s, 1H), 6.68-6.74 (m, 1H), 7.20-7.42 (m, 8H). |
| 9 | 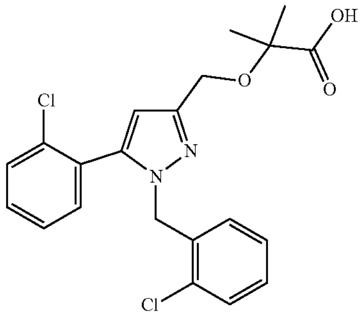 [SMILES: CC(C)(OCc1cc(-c2ccccc2Cl)n(Cc2ccccc2Cl)n1)C(=O)O] | 2-([5-(2-Chlorophenyl)-1-[(2-chlorophenyl)methyl]1H-pyrazol-3-yl]methoxy)-2-methylpropanoic acid<br>$^1$H NMR ($CD_3OD$, 400 MHz) δ 1.53 (s, 6H), 4.58 (s, 2H), 5.28 (s, 2H), 6.43 (s, 1H), 6.78-7.81 (m, 1H), 7.16-34 (m, 5H), 7.38-7.42 (m, 1H), 7.50-7.56 (m, 1H). |

TABLE 19-continued

Examples 2-50.

| Ex. | Structure | IUPAC Name<br>Analytical data |
|---|---|---|
| 10 | 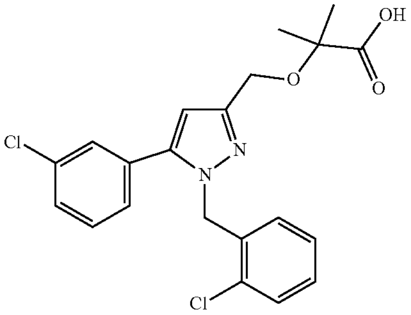 [SMILES: CC(C)(OCc1cc(-c2cccc(Cl)c2)n(Cc2ccccc2Cl)n1)C(=O)O] | 2-([5-(3-Chlorophenyl)-1-[(2-chlorophenyl)methyl]1H-pyrazol-3-yl]methoxy)-2-methylpropanoic acid<br>$^{1}$H NMR ($CD_3OD$, 400 MHz) δ1.32 (S, 6h) 4.58 (s, 2H), 5.42 (s, 2H), 6.57 (s, 1H), 6.67-6.80 (m, 1H), 7.22-7.30 (m, 3H), 7.32-42 (m, 4H). |
| 11 | 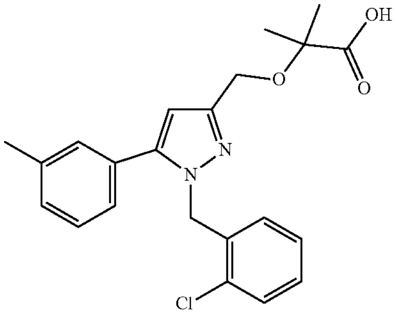 [SMILES: Cc1cccc(-c2cc(COC(C)(C)C(=O)O)nn2Cc2ccccc2Cl)c1] | 2-([1-[(2-Chlorophenyl)methyl]-5-(m-tolyl)1H-pyrazol-3-yl]methoxy)-2-methylpropanoic acid<br>$^{1}$H NMR ($CDCl_3$, 400 MHz) δ 1.58 (s, 6H), 2.35 (s, 3H), 4.61 (s, 2H), 5.42 (s, 2H), 6.39 (s, 1H), 6.75-6.84 (m, 1H), 7.00-7.12 (m, 2H), 7.18-7.29 (4H), 7.29-7.38 (m, 1H). |
| 12 | 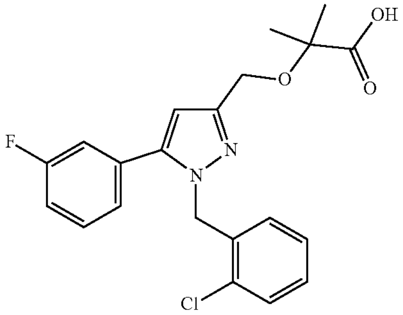 | 2-([1-[(2-Chlorophenyl)methyl]-5-(3-fluorophenyl)1H-pyrazol-3-yl]methoxy)-2-methylpropanoic acid<br>$^{1}$H NMR ($CDCl_3$, 400 MHz) δ 1.58 (s, 6H), 4.64 (s, 2H), 5.48 (s, 2H), 6.42 (s, 1H), 6.72-6.85 (m, 1H), 6.88-7.14 (m, 3H), 7.14-7.40 (m, 4H). |
| 13 | 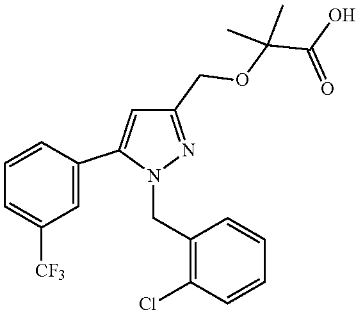 | 2-([1-[(2-Chlorophenyl)methyl]-5-[3-(trifluoromethyl)phenyl]1H-pyrazol-3-yl]methoxy)-2-methylpropanoic acid<br>$^{1}$H NMR ($CDCl_3$, 400 MHz) δ 1.58 (s, 6H), 4.62 (s, 2H), 5.41 (s, 2H), 6.46 (s, 1H), 6.80-6.88 (m, 1H), 7.17-7.24 (m, 2H), 7.29-7.38 (m, 1H), 7.39-7.47 (m, 1H), 7.49-7.54 (m, 2H), 7.59-7.68 (m, 1H). |

TABLE 19-continued

| Examples 2-50. | | |
|---|---|---|
| Ex. | Structure | IUPAC Name<br>Analytical data |
| 14 | 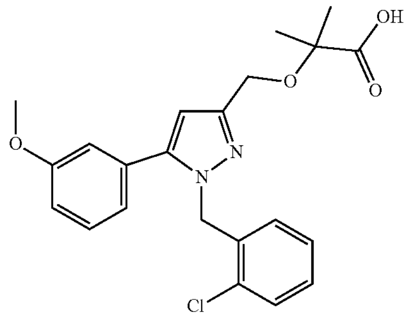 [SMILES: CC(C)(OCc1cc(-c2cccc(F)c2)n(Cc2ccccc2Cl)n1)C(=O)O] | 2-([1-[(2-Chlorophenyl)methyl]-5-(3-methoxyphenyl)1H-pyrazol-3-yl]methoxy)-2-methylpropanoic acid<br>$^1$H NMR ($CDCl_3$, 400 MHz) δ 1.58 (s, 6H), 3.68 (s, 3H), 4.62 (s, 2H), 5.46 (s, 2H), 6.42 (s, 1H), 6.74-6.81 (m, 2H), 6.82-6.88 (m, 1H), 6.89-6.94 (m, 1H), 7.15-7023 (m, 2H), 7.26-7.37 (m, 2H). |
| 15 | 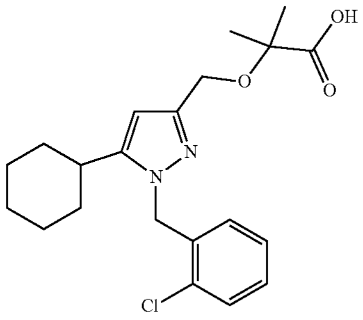 [SMILES: CC(C)(OCc1cc(C2CCCCC2)n(Cc2ccccc2Cl)n1)C(=O)O] | 2-([1-[(2-Chlorophenyl)methyl]-5-cyclohexyl-1H-pyrazol-3-yl]methoxy)-2-methylpropanoic acid<br>$^1$H NMR ($CDCl_3$, 400 MHz) δ1.16-1.42 (m, 4H), 1.54 (s, 6H), 1.57-1.81 (m, 5H), 2.36-2051 (m, 1H), 2.76-2.91 (m, 1H), 4.56 (s, 2H), 5.39 (s, 2H), 6.15 (s, 1H), 6.54-6.68 (m, 1H), 7.08-7.25 (m, 2H), 7.31-7.44 (m, 1H). |
| 16 | 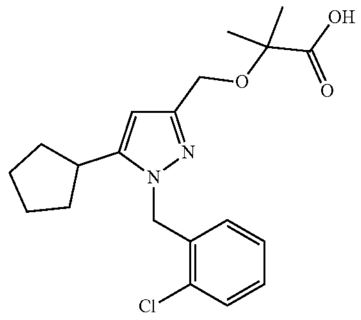 [SMILES: CC(C)(OCc1cc(C2CCCC2)n(Cc2ccccc2Cl)n1)C(=O)O] | 2-([1-[(2-Chlorophenyl)methyl]-5-cyclopentyl-1H-pyrazol-3-yl]methoxy)-2-methylpropanoic acid<br>$^1$H NMR ($CDCl_3$, 400 MHz) δ 1.22-1.64 (m, 10H), 1.64-1.80 (m, 2H), 1.82-2.00 (m, 2H), 2.80-2.92 (m, 1H), 4.74 (s, 2H), 5.40 (s, 2H), 6.10 (s, 1H), 6.58-6.62 (m, 1H), 7.10-7.22 (m, 2H), 7.38 (d, 1H). |
| 17 | 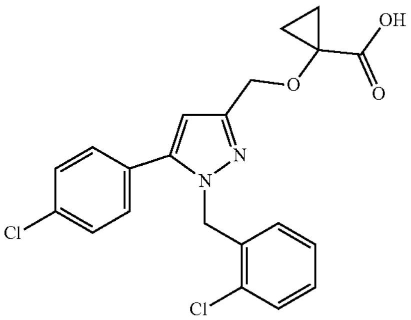 [SMILES: O=C(O)C1(OCc2cc(-c3ccc(Cl)cc3)n(Cc3ccccc3Cl)n2)CC1] | 1-[[5-(4-Chlorophenyl)-1-[(2-chlorophenyl)methyl]1H-pyrazol-3-yl]methoxy]cyclopropanecarboxylic acid<br>$^1$H NMR ($CD_3OD$, 400 MHz) δ1.18-1.32 (m, 3H), 1.64-1.80 (m, 1H), 4.61 (s, 2H), 5.42 (s, 2H), 6.52 (s, 1H), 6.60-6.80 (m, 1H), 7.20-52 (m, 7H). |

TABLE 19-continued

| Examples 2-50. | | |
|---|---|---|
| Ex. | Structure | IUPAC Name<br>Analytical data |
| 18 | 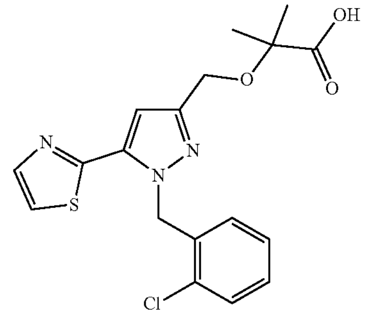 [SMILES: CC(C)(OCc1cc(-c2nccs2)n(Cc2ccccc2Cl)n1)C(=O)O] | 2-([1-[(2-Chlorophenyl)methyl]-5-thiazol-2-yl-1H-pyrazol-3-yl]methoxy)-2-methylpropanoic acid<br>$^{1}H$ NMR ($CDCl_3$, 400 MHz) δ 1.38 (m, 6H), 4.48 (s, 2H), 5.61 (s, 2H), 6.55-6.65 (m, 1H), 7.03 (s, 1H), 7.09-7.16 (m, 1H), 7.17-7.23 (m, 1H), 7.27-7.33 (d, 1H), 7.34-7.42 (m, 1H), 7.88-7.96 (d, 1H). |
| 19 | 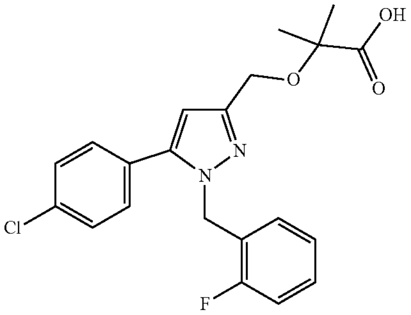 | 2-([5-(4-Chlorophenyl)-1-[(2-fluorophenyl)methyl]1H-pyrazol-3-yl]methoxy)-2-methylpropanoic acid<br>$^{1}H$ NMR ($CD_3OD$, 400 MHz) δ 1.48 (s, 6H), 4.53 (s, 2H) 5.38 (s, 2H), 6.50 (s, 1H), 6.81-6.92 (m 1H), 7.00-7.13 (m, 2H), 7.21-7.31 (m 1H), 7.34-7.48 (m 4H) |
| 20 | 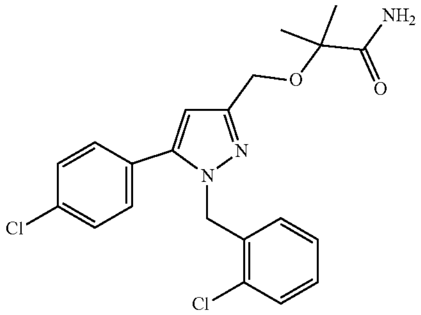 [SMILES: CC(C)(OCc1cc(-c2ccc(Cl)cc2)n(Cc2ccccc2Cl)n1)C(N)=O] | 2-([5-(4-Chlorophenyl)-1-[(2-chlorophenyl)methyl]1H-pyrazol-3-yl]methoxy)-2-methyl-propanamide<br>$^{1}H$ NMR ($CD_3OD$ 400 MHz) δ 1.46 (s, 6H), 4.58 (s, 2H), 5.40 (s, 2H), 6.52 (s, 1H), 6.71-6.76 (m, 1H), 7.20-7.58 (m, 6H) |
| 21 | 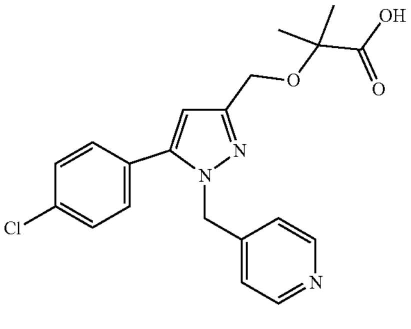 [SMILES: CC(C)(OCc1cc(-c2ccc(Cl)cc2)n(Cc2ccncc2)n1)C(=O)O] | 2-([5-(4-chlorophenyl)-1-([pyridin-4-yl]methyl)1H-pyrazol-3-yl]methoxy)-2-methylpropanoic acid<br>$^{1}H$ NMR ($CD_3OD$ 400 MHz) δ 1.52 (s, 6H), 4.58 (s, 2H), 5.56 (s, 2H), 6.59 (s, 1H), 7.21-7.52 (m, 6H), 8.50 (bs, 2H) |

TABLE 19-continued

| Ex. | Structure | IUPAC Name Analytical data |
| --- | --- | --- |
| | Examples 2-50. | |
| 22 | 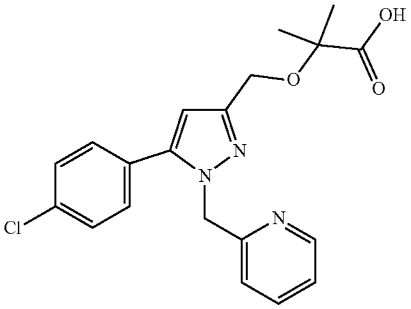 [SMILES: CC(C)(OCc1cc(-c2ccc(Cl)cc2)n(Cc2ccccn2)n1)C(=O)O] | 2-([5-(4-Chlorophenyl)-1-([pyridin-2-yl]methyl)1H-pyrazol-3-yl]methoxy)-2-methylpropanoic acid $^{1}H$ NMR (DMSO-$d_6$, 400 MHz) δ 1.38 (s, 6H), 4.40 (s, 2H), 5.38 (s, 2H), 6.41 (s, 1H), 6.90-7.10 (m, 1H), 7.20-7.85 (m, 6H), 8.51 (bs, 1H) |
| 23 | 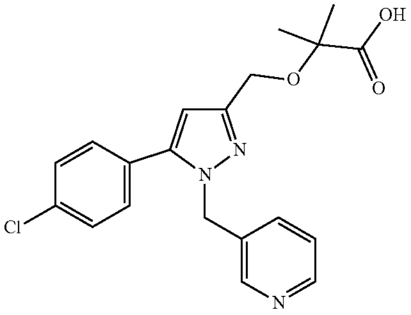 [SMILES: CC(C)(OCc1cc(-c2ccc(Cl)cc2)n(Cc2cccnc2)n1)C(=O)O] | 2-([5-(4-Chlorophenyl)-1-([pyridin-3-yl]methyl)1H-pyrazol-3-yl]methoxy)-2-methylpropanoic acid $^{1}H$ NMR ($CD_3OD$ 400 MHz) δ 1.52 (s, 6H), 4.58 (s, 2H), 5.10 (s, 2H), 6.55 (s, 1H), 7.30-7.41 (m, 3H), 7.42-7.51 (m, 3H), 8.19 (s, 1H), 8.41 (d, 1H). |
| 24 | 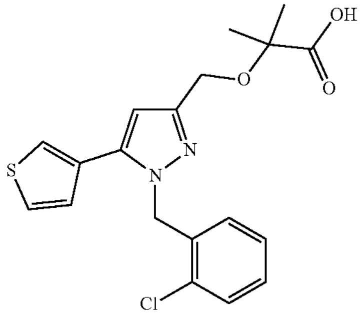 [SMILES: CC(C)(OCc1cc(-c2ccsc2)n(Cc2ccccc2Cl)n1)C(=O)O] | 2-([1-[(2-Chlorophenyl)methyl]-5-(thien-3-yl)1H-pyrazol-3-yl]methoxy)-2-methylpropanoic acid. $^{1}HNMR(CDCl_3)$: δ1.37 (s, 6H), 4.38 (s, 2H), 5.43 (s, 2H), 6.48 (s, 1H), 6.62-6.64 (m, 1H), 7.17-7.31 (m, 3H), 7.44-7.46 (m, 1H), 7.57-7.64 (m, 2H). |
| 25 | 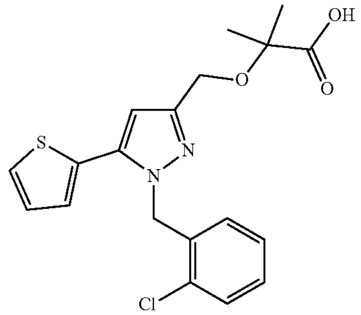 [SMILES: CC(C)(OCc1cc(-c2cccs2)n(Cc2ccccc2Cl)n1)C(=O)O] | 2-([1-[(2-Chlorophenyl)methyl]-5-(thien-2-yl)1H-pyrazol-3-yl]methoxy)-2-methylpropanoic acid. $^{1}HNMR$ ($CDCl_3$): δ 1.37 (s, 6H), 4.39 (s, 2H), 5.47 (s, 2H), 6.53 (s, 1H), 6.59-6.61 (m, 1H), 7.09-7.14 (m, 2H), 7.24-7.31 (m, 2H), 7.45-7.47 (m, 1H), 7.62-7.64 (m, 1H). |

TABLE 19-continued

| Examples 2-50. | | |
|---|---|---|
| Ex. | Structure | IUPAC Name<br>Analytical data |
| 26 | 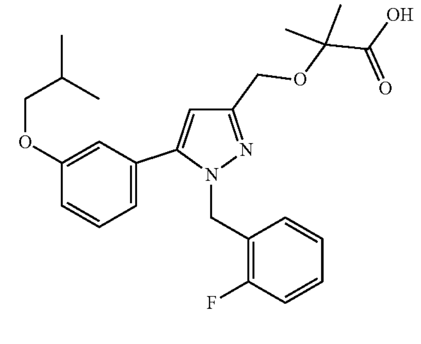 [SMILES: CC(C)COc1cccc(-c2cc(COC(C)(C)C(=O)O)nn2Cc2ccccc2F)c1] | 2-([1-[(2-Fluorophenyl)methyl]-5-(3-(2-methylpropoxy)phenyl)1H-pyrazol-3-yl]methoxy)-2-methylpropanoic acid<br>$^1$HNMR($CDCl_3$): δ 0.97 (s, 3H), 0.99 (s, 3H), 1.55 (s, 6H), 2.00-2.06 (m, 1H), 3.70 (d, 2H), 4.62 (s, 2H), 5.39 (s, 2H), 6.37 (s, 1H), 6.79-6.80 (m, 1H), 6.87-7.09 (M, 5H), 7.22-7.30 (m, 2H) |
| 27 | 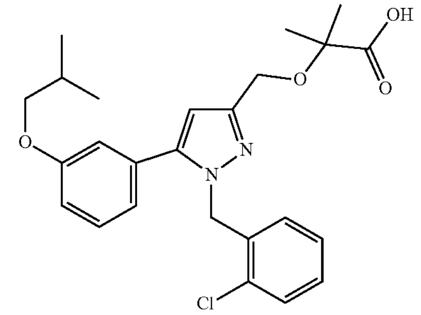 [SMILES: CC(C)COc1cccc(-c2cc(COC(C)(C)C(=O)O)nn2Cc2ccccc2Cl)c1] | 2-([1-[(2-Chlorophenyl)methyl]-5-(3-(2-methylpropoxy)phenyl)1H-pyrazol-3-yl]methoxy)-2-methylpropanoic acid.<br>$^1$HNMR ($CDCl_3$): δ 0.95 (s, 3H)(, 0.96 (s, 3H), 1.56 (s, 6H), 1.97-2.03 (m, 1H), 3.49 (d, 2H), 4.63 (s, 2H), 5.43 (s, 2H), 6.41 (s, 1H), 6.73-6.80 (m, 2H), 6.84-6.92 (m, 2H), 7.19-7.28 (m, 3H), 7.33-7.35 (m, 1H). |
| 28 | 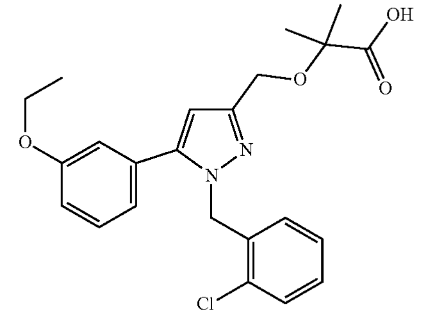 [SMILES: CCOc1cccc(-c2cc(COC(C)(C)C(=O)O)nn2Cc2ccccc2Cl)c1] | 2-([1-[(2-Chlorophenyl)methyl]-5-(3-ethoxyphenyl)1H-pyrazol-3-yl]methoxy)-2-methylpropanoic acid.<br>$^1$HNMR ($CDCl_3$): δ 1.34 (t, 3H),, 1.56 (s, 6H), 3.86 (q, 2H), 4.62 (s, 2H), 5.43 (s, 2H), 6.40 (s, 1H), 6.76-6.78 (m, 2H), 6.83-6.85 (m, 1H), 6.89-6.91 (m, 1H), 7.19-7.28 (m, 3H), 7.33-7.35 (m, 1H). |
| 29 | 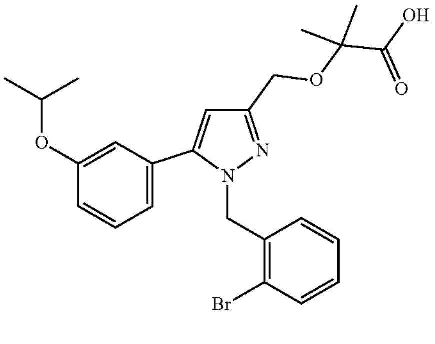 [SMILES: CC(C)Oc1cccc(-c2cc(COC(C)(C)C(=O)O)nn2Cc2ccccc2Br)c1] | 2-([1-[(2-Bromophenyl)methyl]-5-(3-isopropoxyphenyl)1H-pyrazol-3-yl]methoxy)-2-methylpropanoic acid.<br>$^1$HNMR ($CDCl_3$): 1.21 (s, 3H), 1.23 (s, 3H), 4.28-4.32 (m, 1H), 4.62 (s, 2H), 5.39 (s, 2H).6.42 (s, 1H), 6.71-6.74 (m, 2H), 6.82-6.89 (m, 2H), 7.11-7.15 (m, 1H), 7.22-7.27 (m, 2H), 7.51-7.54 (m, 1H). |

TABLE 19-continued

| Examples 2-50. | | |
|---|---|---|
| Ex. | Structure | IUPAC Name<br>Analytical data |
| 30 | 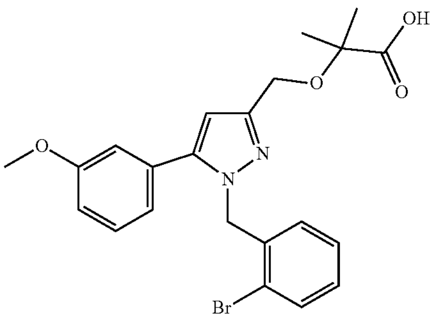 [SMILES: COc1cccc(-c2cc(COC(C)(C)C(=O)O)nn2Cc2ccccc2Br)c1] | 2-([1-[(2-Bromophenyl)methyl]-5-(3-methoxyphenyl)-1H-pyrazol-3-yl]methoxy)-2-methylpropanoic acid<br>$^1$HNMR ($CDCl_3$): δ 1.56 (s, 6H), 3.65 (s, 3H), 4.62 (s, 2H), 5.39 (s, 2H), 6.41 (s, 1H), 6.73-6.76 (m 2H), 6.84-6.92 (m, 2H), 7.15 (t, 1H), 7.13-7.29 (m, 2H), 7.52-7.54 (m, 1H). |
| 31 | 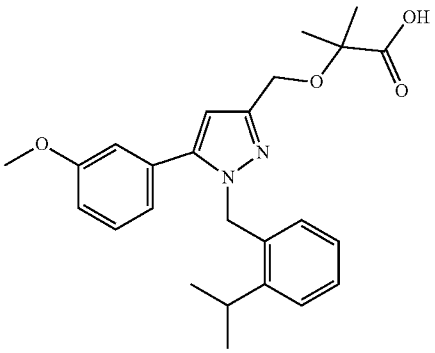 [SMILES: COc1cccc(-c2cc(COC(C)(C)C(=O)O)nn2Cc2ccccc2C(C)C)c1] | 2-([1-[(2-Isopropylphenyl)methyl]-5-(3-methoxyphenyl)1H-pyrazol-3-yl]methoxy)-2-methylpropanoic acid.<br>$^1$HNMR ($CDCl_3$): δ1.13 (s, 3H), 1.15 (s, 3H), 1.55 (s 6H), 2.94-2.97 (m, 1H), 3.62 (s, 3H), 4.63 (s, 2H), 5.42 (s, 2H), 6.39 (s, 1H), 6.65-6.67 (m, 1H), 6.75-6.76 (m, 1H), 6.85-6.91 (m, 2H), 7.07-7.11 (m, 1H), 7.21-7.28 (m, 3H) |
| 32 | 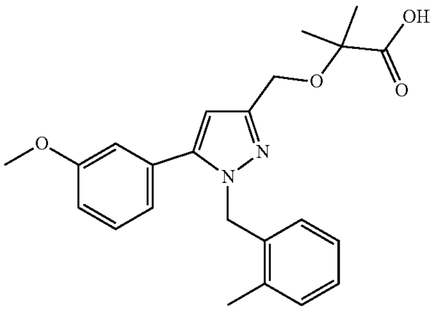 [SMILES: COc1cccc(-c2cc(COC(C)(C)C(=O)O)nn2Cc2ccccc2C)c1] | 2-([5-(3-Methoxyphenyl)-1-(o-tolylmethyl)1H-pyrazol-3-yl]methoxy)-2-methylpropanoic acid.<br>$^1$HNMR ($CDCl_3$): δ 1.55 (s, 6H), 2.18 (s, 3H), 3.64 (s, 3H), 4.62 9s, 2H), 5.31 (s, 2H), 6.38 (s, 1H), 6.69-6.31 (m, 1H), 6.77-6.78 (m, 1H), 6.86-6.92 (m, 2H), 7.10-7.15 (m, 3H), 7.25-7.29 (m, 1H). |
| 33 | 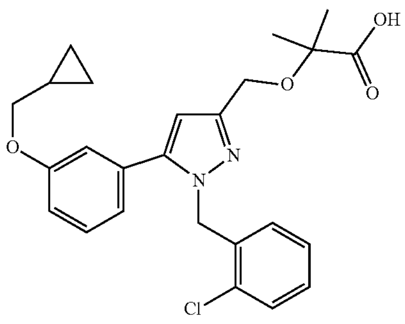 [SMILES: CC(C)(OCc1cc(-c2cccc(OCC3CC3)c2)n(Cc2ccccc2Cl)n1)C(=O)O] | 2-([1-[(2-Chlorophenyl)methyl]-5-[3-(cyclopropylmethoxy)phenyl]1H-pyrazol-3-yl]methoxy)-2-methylpropanoic acid.<br>$^1$HNMR ($CDCl_3$): δ 0.25-0.29 (m, 2H), 0.58-0.63 (m, 2H), 14.16-1.20 (m, 1H), 1.55 (s, 6H), 5.58 (d, 2H), 4.63 (s, 2H), 5.42 (s, 2H), 6.40 (s, 1H), 6.374-6.78 (m, 2H), 6.84-6.93 (m, 2H), 7.18-7.28 (m, 3H), 7.33-7.35 (m, 1H). |

TABLE 19-continued

| Examples 2-50. | | |
|---|---|---|
| Ex. | Structure | IUPAC Name<br>Analytical data |
| 34 | 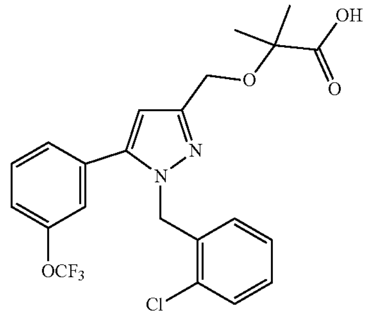 [SMILES: CC(C)(OCc1cc(-c2cccc(OC(F)(F)F)c2)n(Cc2ccccc2Cl)n1)C(=O)O] | 2-([1-[(2-Chlorophenyl)methyl]-5-[3-(trifluoromethoxy)phenyl]1H-pyrazol-3-yl]methoxy)-2-methylpropanoic acid.<br>$^1$HNMR ($CDCl_3$): δ1.56 (6H), 4.63 (s, 2H), 5.41 (s, 2H), 6.46 (s, 1H), 6.77-6.79 (m, 1H), 7.12-7.25 (m, 5H), 7.32-7.35 (m, 1H), 7.38-7.42 (m, 1H). |
| 35 | 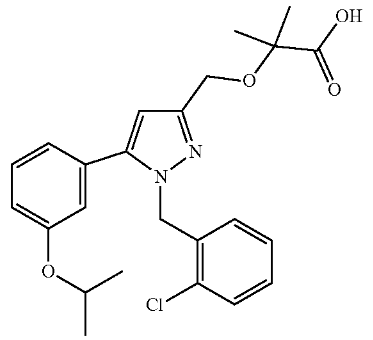 [SMILES: CC(C)Oc1cccc(-c2cc(COC(C)(C)C(=O)O)nn2Cc2ccccc2Cl)c1] | 2-([1-[(2-Chlorophenyl)methyl]-5-(3-isopropoxyphenyl)1H-pyrazol-3-yl]methoxy)-2-methylpropanoic acid.<br>$^1$HNMR ($CDCl_3$): δ 1.22 (s, 3H)(, 1.23 (s, 3H), 1.55 (s, 6H), 4.30-4.33 (m, 1H), 4.62 (s, 2H), 5.43 (s, 2H), 6.41 (s, 1H), 6.75-6.90 (4H), 7.19-7.35 (m, 4H). |
| 36 | 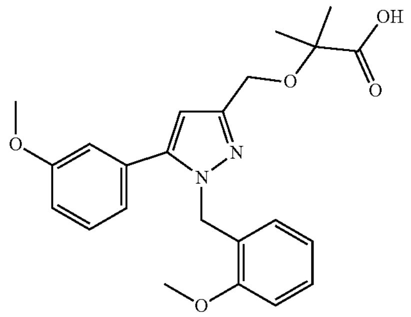 [SMILES: COc1cccc(-c2cc(COC(C)(C)C(=O)O)nn2Cc2ccccc2OC)c1] | 2-([5-(3-Methoxyphenyl)-1-[(2-methoxyphenyl)methyl]1H-pyrazol-3-yl]methoxy)-2-methylpropanoic acid.<br>$^1$HNMR ($CDCl_3$): δ 1.55 (s. 6H), 3.70 (s, 3H), 3.73 (s, 3H), 4.62 (s, 2H), 5.34 (s, 2H), 6.35 (s, 1H), 6.77-6.392 (m, 6H), 7.22-7.29 (m, 2H). |
| 37 | 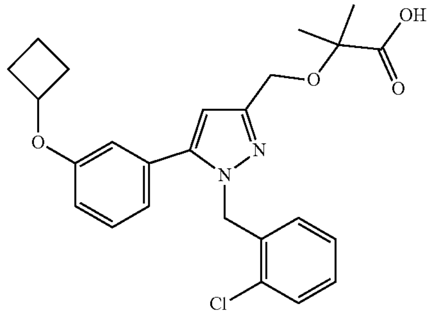 [SMILES: CC(C)(OCc1cc(-c2cccc(OC3CCC3)c2)n(Cc2ccccc2Cl)n1)C(=O)O] | 2-([1-[(2-Chlorophenyl)methyl]-5-[3-(cyclobuloxy)phenyl]1H-pyrazol-3-yl]methoxy)-2-methylpropanoic acid.<br>$^1$HNMR ($CDCl_3$): δ 1.49-1.61 (m, 7H), m1.75-1.82 (m 1H), 2.01-2.11 (m 2H), 2.17-2.24 (m 2H), 4.37-4.45 (m 1H), 4.62 (s, 2H), 5.42 (s, 2H), 6.39 (s, 1H), 6.64 (s, 1H), 6.75-6.86 (m, 3H), 7.19-7.35 (m 4H). |

TABLE 19-continued

| Examples 2-50. | | |
|---|---|---|
| Ex. | Structure | IUPAC Name<br>Analytical data |
| 38 | 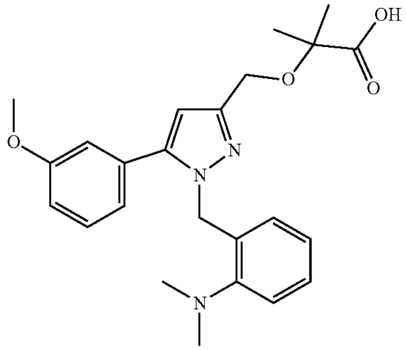 [SMILES: COc1cccc(-c2cc(COC(C)(C)C(=O)O)nn2Cc2ccccc2N(C)C)c1] | 2-([1-[[2-(Dimethylamino)phenyl]methyl]-5-(3-methoxyphenyl)1H-pyrazol-3-yl]methoxy)-2-methylpropanoic acid.<br>$^1$HNMR ($CDCl_3$): δ 1.56 (s, 6H), 2.60 (s, 6H), 6.64 (s, 3H), 4.63 (s, 2H), 5.44 (s, 2H). 6.30 (s, 1H), 6.71-7.11 (m 6H), 7.20-7.25 (m, 2H). |
| 39 | 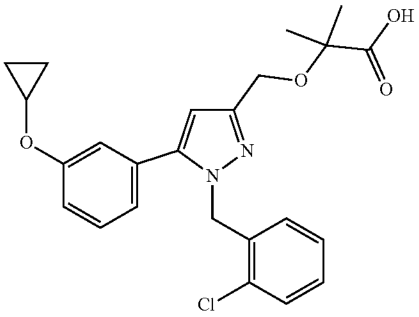 [SMILES: CC(C)(OCc1cc(-c2cccc(OC3CC3)c2)n(Cc2ccccc2Cl)n1)C(=O)O] | 2-([1-[(2-Chlorophenyl)methyl]-5-[3-(cyclopropoxy)phenyl]1H-pyrazol-3-yl]methoxy)-2-methylpropanoic acid.<br>$^1$HNMR ($CDCl_3$): δ 0.55-0.68 (m 4H), 1.55 (s, 6H), 3.50-3.54 (m 1H), 4.63 (s, 2H), 5.44 (s, 2H), 6.42 (s, 1H), 6.76-7.02 (m, 4H), 7.17-7.35 (m, 4H). |
| 40 | 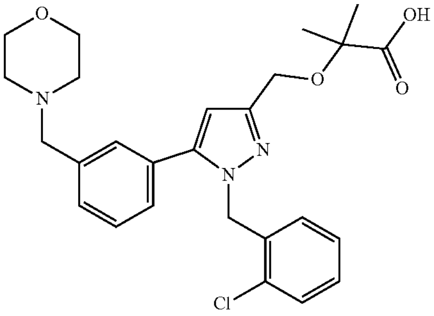 [SMILES: CC(C)(OCc1cc(-c2cccc(CN3CCOCC3)c2)n(Cc2ccccc2Cl)n1)C(=O)O] | 2-([1-[(2-Chlorophenyl)methyl]-5-[3-(morpholinomethyl)phenyl]1H-pyrazol-3-yl]methoxy)-2-methylpropanoic acid.<br>$^1$HNMR ($CD_3OD$): δ 1.50 (s, 6H), 3.15-3.23 (bs, 4H), 3.60-3.81 (bs, 2H), 3.85-4.16 (bs, 2H), 4.35 (s, 2H), 4.57 (s, 2H), 5.45 (s, 2H), 6.60 (s, 1H), 6.75 (d, 1H), 7.20-7.55 (m, 7H). |
| 41 | 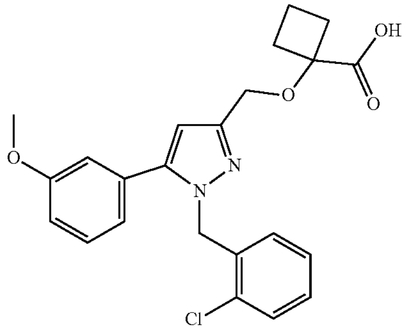 [SMILES: COc1cccc(-c2cc(COC3(C(=O)O)CCC3)nn2Cc2ccccc2Cl)c1] | 1-[[1-[(2-Chlorophenyl)methyl]-5-(3-methoxyphenyl)1H-pyrazol-3-yl]methoxy]cyclobutanecarboxylic acid.<br>$^1$HNMR ($CDCl_3$): δ 1.78-1.85 (m 1H), 1.95-2.04 (m, 2H), 2.18-2.25 (m, 1H), 3.09-3.14 (m, 1H), 3.66 (s, 3H), 4.27-4.32 (m, 1H), 4.55-4.65 (dd, 2H), 5.43 (s, 2H), 6.44 (s, 1H), 6.73-6.91 (m, 4H), 7.17-7.34 (m 4). |

TABLE 19-continued

| Examples 2-50. | | |
|---|---|---|
| Ex. | Structure | IUPAC Name<br>Analytical data |
| 42 | 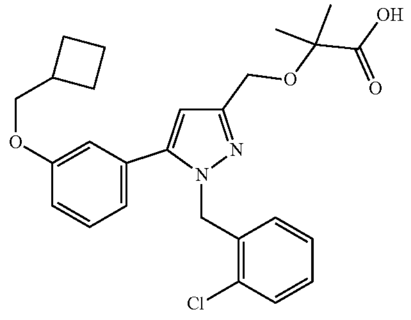 [SMILES: CC(C)(OCc1cc(-c2cccc(OCC3CCC3)c2)n(Cc2ccccc2Cl)n1)C(=O)O] | 2-([1-[(2-Chlorophenyl)methyl]-5-[3-(cyclobutylmethoxy)phenyl]1H-pyrazol-3-yl]methoxy)-2-methylpropanoic acid.<br>$^1$HNMR ($CDCl_3$): δ 1.55 (s, 6H), 1.75-1.82 (m, 2H), 1.85-1.98 (m, 2H), 2.06-2.14 (m, 2H), 2.64-2.70 (m, 1H), 3.71 (d, 2H), 4.63 (s, 2H), 5.43 (s, 2H), 6.42 (s, 1H), 6.75-6.92 (m, 4H), 7.20-7.36 (m, 4). |
| 43 | 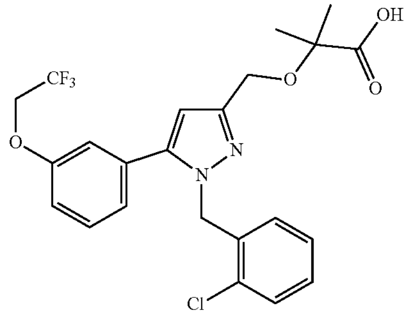 [SMILES: CC(C)(OCc1cc(-c2cccc(OCC(F)(F)F)c2)n(Cc2ccccc2Cl)n1)C(=O)O] | 2-([1-[(2-Chlorophenyl)methyl]-5-[3-(2,2,2-trifluoroethoxy)phenyl]1H-pyrazol-3-yl]methoxy)-2-methylpropanoic acid.<br>$^1$HNMR ($CDCl_3$): δ 1.55 (s, 6H), 4.16 (q, 2H), 4.63 (s, 2H), 5.42 (s, 2H), 6.43 (s, 1H), 6.77-6.81 (m, 2H), 6.96-6.98 (m, 2H), 7.19-7.36 (m, 4H). |
| 44 | 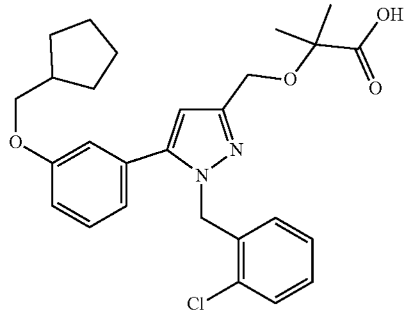 [SMILES: CC(C)(OCc1cc(-c2cccc(OCC3CCCC3)c2)n(Cc2ccccc2Cl)n1)C(=O)O] | 2-([1-[(2-Chlorophenyl)methyl]-5-[3-(cyclopentylmethoxy)phenyl]1H-pyrazol-3-yl]methoxy)-2-methylpropanoic acid.<br>$^1$HNMR ($CDCl_3$): δ 1.25-1.29 (m, 2H), 1.55-1.61 (m, 10H), 1.76-1.79 (m, 2H), 2.24-2.31 (m, 1H), 3.59 (d, 2H), 4.62 (s, 2H), 5.43 (s, 2H), 6.41 (s, 1H), 6.73-6.91 (m, 4H), 7.19-7.35 (m, 4H). |
| 45 | 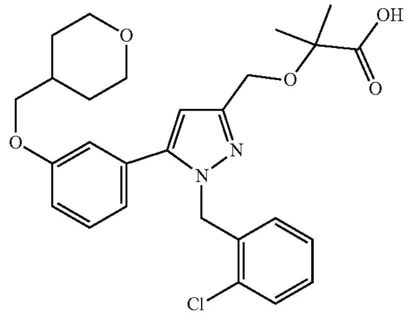 [SMILES: CC(C)(OCc1cc(-c2cccc(OCC3CCOCC3)c2)n(Cc2ccccc2Cl)n1)C(=O)O] | 2-([1-[(2-Chlorophenyl)methyl]-5-[3-(tetrahydropyran-4-ylmethoxy)phenyl]1H-pyrazol-3-yl]methoxy)-2-methylpropanoic acid.<br>$^1$HNMR ($CDCl_3$): δ 1.34-1.41 (m, 2H), 1.55 (s, 6H), 1.66-1.69 (m, 2H), 1.97-1.99 (m, 1H), 3.38-3.46 m, 2H), 3.56 (d, 2H), 3.98-4.01 (m, 2H), 4.62 (s, 2H), 5.42 (s, 2H), 6.42 (s, 1H), 6.71 (s, 1H), 6.77-6.95 (m, 3H), 7.19-7.35 (m, 4H). |

TABLE 19-continued

| Examples 2-50. | | |
|---|---|---|
| Ex. | Structure | IUPAC Name<br>Analytical data |
| 46 | 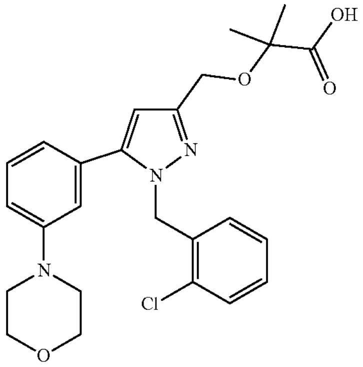 [SMILES: CC(C)(OCc1cc(-c2cccc(N3CCOCC3)c2)n(Cc2ccccc2Cl)n1)C(=O)O] | 2-([1-[(2-Chlorophenyl)methyl]-5-(3-morpholinophenyl)1H-pyrazol-3-yl]methoxy)-2-methylpropanoic acid.<br>$^{1}$HNMR ($CDCl_3$): δ 1.55 (s, 6H), 2.96 (t, 4H), 3.76 (t, 4H), 4.62 (s, 2H), 5.41 (s, 2H), 6.41 (s, 1H), 6.68 (s, 1H), 6.78-6.80 (m, 2H), 6.88-6.91 (m, 1H), 7.19-7.35 (m, 4H). |
| 47 | 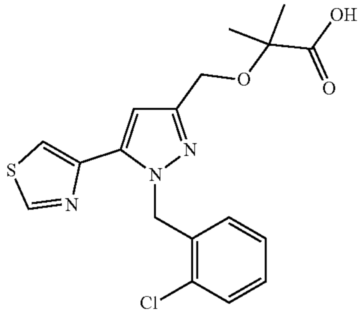 [SMILES: CC(C)(OCc1cc(-c2cscn2)n(Cc2ccccc2Cl)n1)C(=O)O] | 2-([1-[(2-Chlorophenyl)methyl]-5-(1,3-thiazol-4-yl)-1H-pyrazol-3-yl]methoxy)-2-methylpropionic acid<br>$^{1}$HNMR ($CDCl_3$): δ 1.56 (s, 6H), 4.63 (s, 2H), 5.84 (s, 2H), 6.62-6.67 (m, 2H), 7.10-7.19 (m 2H), 7.33-7.35 (m, 1H), 7.39 (d, 1H), 8.83 (d, 1H). |
| 48 | 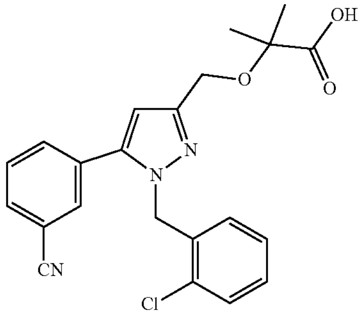 [SMILES: CC(C)(OCc1cc(-c2cccc(C#N)c2)n(Cc2ccccc2Cl)n1)C(=O)O] | 2-([1-[(2-Chlorophenyl)methyl]-5-(3-cyano-phenyl)-1H-pyrazol-3-yl]methoxy)-2-methylpropionic acid<br>$^{1}$HNMR ($CDCl_3$): δ 1.56 (s, 6H), 4.62 (s, 2H), 5.39 (s, 2H), 6.46 (s, 1H), 6.82-6.84 (m, 1H), 7.18-7.24 (m, 2H), 7.33-7.35 (m 1H), 7.46-7.55 (m, 3H), 7.65-7.68 (m, 1H). |
| 49 | 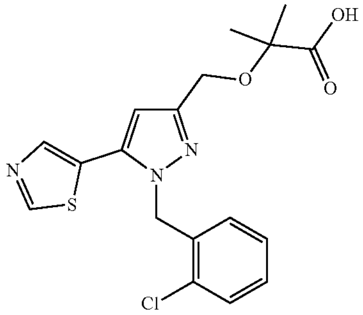 [SMILES: CC(C)(OCc1cc(-c2cncs2)n(Cc2ccccc2Cl)n1)C(=O)O] | 2-([1-[(2-Chlorophenyl)methyl]-5-(1,3-thiazol-5-yl)-1H-pyrazol-3-yl]methoxy)-2-methylpropionic acid<br>$^{1}$HNMR ($CDCl_3$): δ 1.56 (s, 6H), 4.62 (s, 2H), 5.50 (s, 2H), 6.60-6.6 (m, 2H), 7.14-7.24 (m, 2H), 7.36-7.38 (m, 1H), 7.76 (s, 1H), 8.84 (s, 1H). |

TABLE 19-continued

| Examples 2-50. | | |
|---|---|---|
| Ex. | Structure | IUPAC Name<br>Analytical data |
| 50 | 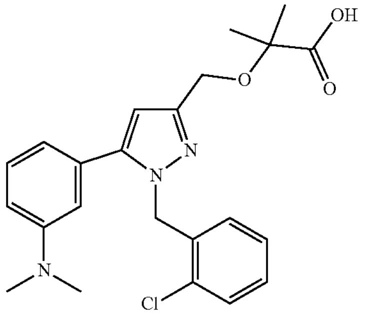 [SMILES: CN(C)c1cccc(-c2cc(COC(C)(C)C(=O)O)nn2Cc2ccccc2Cl)c1] | 2-([1-[(2-Chlorophenyl)methyl]-5-[3-(dimethylamino)phenyl]-1H-pyrazol-3-yl]methoxy)-2-methylpropionic acid<br>MS: Calculated: 427.92; Found: 428.9 [M + H]. |

Examples 51-74 were prepared using the methods disclosed in the indicated Schemes.

TABLE 30

| Examples 51-74. | | | |
|---|---|---|---|
| Ex. | Scheme | Structure | IUPAC Name<br>Analytical data |
| 51 | II | 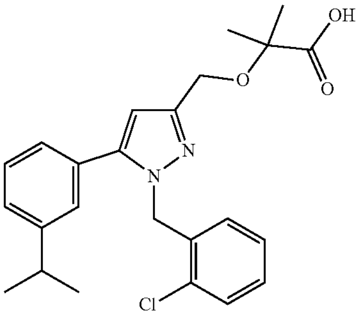 [SMILES: CC(C)c1cccc(-c2cc(COC(C)(C)C(=O)O)nn2Cc2ccccc2Cl)c1] | 2-([1-[(2-Chlorophenyl)methyl]-5-[3-(propan-2-yl)phenyl]-1H-pyrazol-3-yl]methoxy)-2-methylpropanoic acid.<br>$^1$H-NMR (300 MHz, MeOD): δ 1.12 (6 H, d), 1.53 (6 H, s), 2.83 (1 H, p), 4.60 (2 H, s), 5.40 (2 H, s), 6.54 (1 H, s), 6.72-6.81 (1 H, m), 7.05-7.45 (7 H, m). |
| 52 | II | 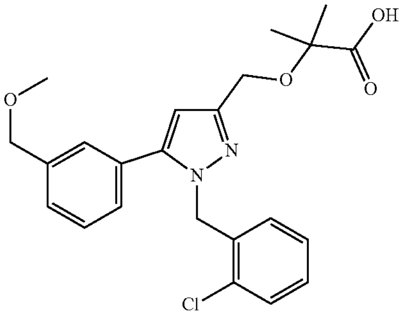 [SMILES: COCc1cccc(-c2cc(COC(C)(C)C(=O)O)nn2Cc2ccccc2Cl)c1] | 2-([1-[(2-chlorophenyl)methyl]-5-[3-(methoxymethyl)phenyl]-1H-pyrazol-3-yl]methoxy)-2-methylpropanoic acid<br>$^1$H-NMR (300 MHz, MeOD): δ 1.52 (6 H, s), 4.42 (2 H, s), 4.59 (2 H, s), 5.42 (2 H, s), 6.56 (1 H, s), 6.70-6.80 (1 H, m), 7.17-7.33 (4 H, m), 7.32-7.45 (3 H, m). |
| 53 | II | 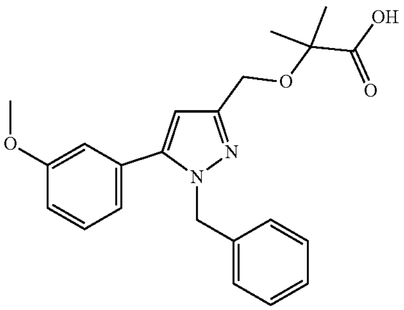 [SMILES: COc1cccc(-c2cc(COC(C)(C)C(=O)O)nn2Cc2ccccc2)c1] | 2-([1-benzyl-5-(3-methoxyphenyl)-1H-pyrazol-3-yl]methoxy)-2-methylpropanoic acid<br>$^1$H-NMR (300 MHz, MeOD) δ 1.51 (6 H, s), 3.68 (3 H, s), 4.57 (2 H, s), 5.35 (2 H, s), 6.48 (1 H, s), 6.84 (1 H, dd), 6.89-7.06 (4 H, m), 7.17-7.38 (4 H, m). |

TABLE 30-continued

| Examples 51-74. | | | |
|---|---|---|---|
| Ex. | Scheme | Structure | IUPAC Name<br>Analytical data |
| 54 | II | 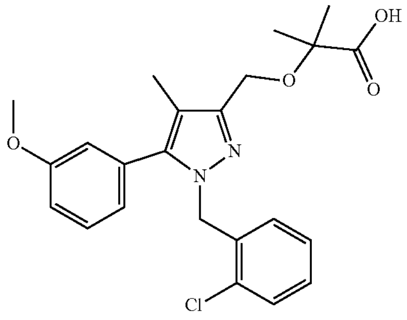 [SMILES: COc1cccc(-c2c(C)c(COC(C)(C)C(=O)O)nn2Cc2ccccc2Cl)c1] | 2-({1-[(2-Chlorophenyl)methyl]-5-(3-methoxyphenyl)-4-methyl-1H-pyrazol-3-yl}methoxy)-2-methylpropionic acid<br>$^{1}$H-NMR: (300 MHz, MeOD) 1.53 (6 H, s), 2.09 (3 H, s), 3.67 (3 H, s), 4.60 (2 H, s), 5.31 (2 H, s), 6.67-6.86 (3 H, m), 6.97 (1 H, ddd), 7.17-7.40 (4 H, m). |
| 55 | II | 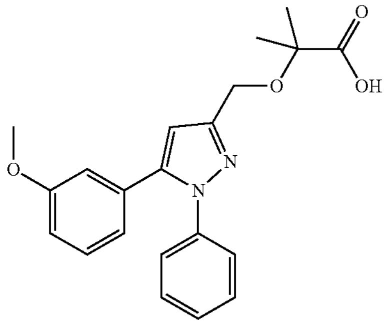 [SMILES: COc1cccc(-c2cc(COC(C)(C)C(=O)O)nn2-c2ccccc2)c1] | 2-([5-(3-methoxyphenyl)-1-phenyl-1H-pyrazol-3-yl]methoxy)-2-methyl-propanoic acid<br>$^{1}$H-NMR (300 MHz, MeOD) δ 1.53 (6 H, s), 3.64 (3 H, s), 4.61 (2 H, s), 6.63-6.77 (2 H, m), 6.77-6.93 (2 H, m), 7.16-7.36 (3 H, m), 7.40 (3 H, dddd). |
| 56 | II | 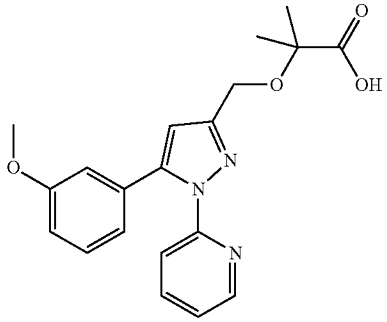 [SMILES: COc1cccc(-c2cc(COC(C)(C)C(=O)O)nn2-c2ccccn2)c1] | 2-([5-(3-methoxyphenyl)-1-(pyridin-2-yl)-1H-pyrazol-3-yl]methoxy)-2-methylpropanoic acid<br>LC-MS (ES, m/z): 367<br>$^{1}$H-NMR (400 MHz, MeOD) δ 1.54 (6 H, s), 3.69 (3 H, s), 4.65 (2 H, s), 6.70 (1 H, s), 6.76-6.78 (2 H, m), 6.89 (1 H, ddd), 7.20-7.25 (1H, d), 7.41-7.45 (2H, m), 7.91 (1 H, dt), 8.41 (1 H, t). |
| 57 | II | 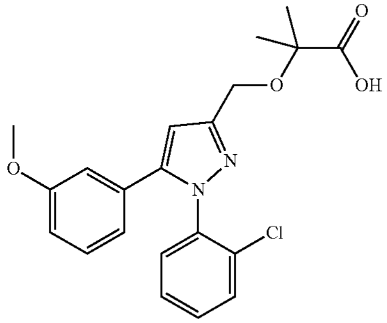 [SMILES: COc1cccc(-c2cc(COC(C)(C)C(=O)O)nn2-c2ccccc2Cl)c1] | 2-([1-(2-chlorophenyl)-5-(3-methoxyphenyl)-1H-pyrazol-3-yl]methoxy)-2-methylpropanoic acid<br>LC-MS (ES, m/z): 401<br>$^{1}$H-NMR (400 MHz, MeOD) δ 1.55 (6 H, s), 3.64 (3 H, s), 4.63 (2 H, s), 6.73 (2 H, d), 6.86 (2 H, dd), 7.20 (1 H, dd), 7.42-7.60 (4 H, m). |

TABLE 30-continued

| Examples 51-74. | | | |
|---|---|---|---|
| Ex. | Scheme | Structure | IUPAC Name<br>Analytical data |
| 58 | II | 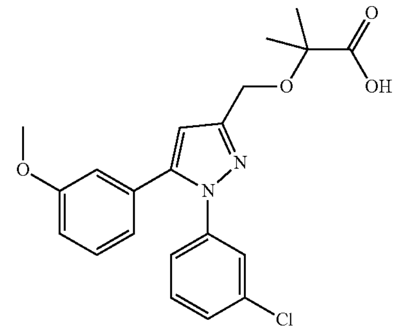 [SMILES: COc1cccc(-c2cc(COC(C)(C)C(=O)O)nn2-c2cccc(Cl)c2)c1] | 2-([1-(3-chlorophenyl)-5-(3-methoxyphenyl)-1H-pyrazol-3-yl]methoxy)-2-methylpropanoic acid<br>$^{1}$H-NMR (400 MHz, MeOD) δ 1.54 (6 H, s), 3.71 (3 H, s), 4.62 (2 H, s), 6.68 (1 H, s), 6.77-6.87 (2 H, m), 6.94 (1 H, ddd), 7.19 (1 H, dt), 7.27 (1 H, t), 7.32-7.44 (3 H, m). |
| 59 | II | 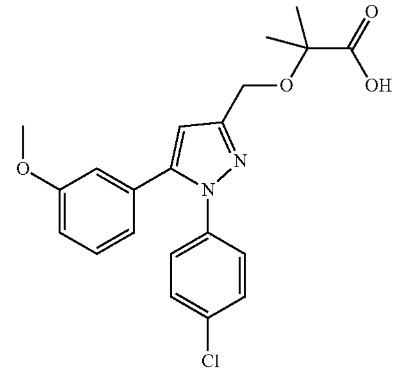 [SMILES: COc1cccc(-c2cc(COC(C)(C)C(=O)O)nn2-c2ccc(Cl)cc2)c1] | 2-([1-(4-chlorophenyl)-5-(3-methoxyphenyl)-1H-pyrazol-3-yl]methoxy)-2-methylpropanoic acid<br>LC-MS (ES, m/z): 401<br>$^{1}$H-NMR (400 MHz, MeOD) δ 1.54 (6 H, s), 3.71 (3 H, s), 4.62 (2 H, s), 6.67 (1 H, s), 6.75-6.85 (2 H, m), 6.92 (1 H, ddd), 7.21-7.32 (3 H, m), 7.37-7.46 (2 H, m). |
| 60 | VII | 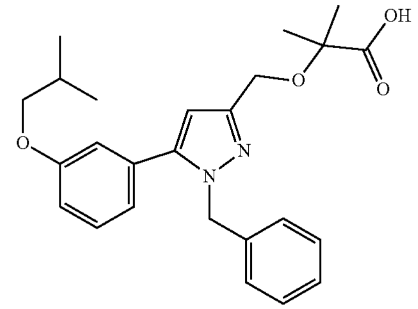 [SMILES: CC(C)COc1cccc(-c2cc(COC(C)(C)C(=O)O)nn2Cc2ccccc2)c1] | 2-([1-Benzyl-5-[3-(2-methylpropoxy)phenyl]-1H-pyrazol-3-yl]methoxy)-2-methylpropanoic acid<br>$^{1}$H-NMR (400 MHz, MeOD) δ 0.97 (6 H, d), 1.53 (6 H, s), 1.97 (1 H, dp), 3.48 (2 H, d), 3.78 (3 H, s), 4.58 (2 H, s), 5.31 (2 H, s), 6.52 (1 H, s), 6.67-6.74 (1 H, m), 6.76-6.82 (1 H, m), 6.85-7.00 (4 H, m), 7.22-7.33 (2 H, m) |
| 61 | VII | 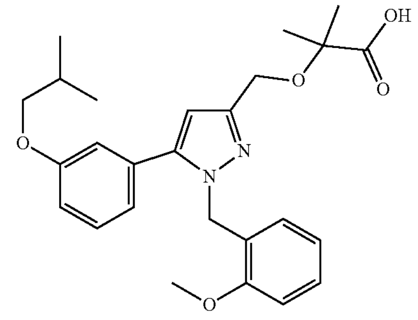 [SMILES: COc1ccccc1Cn1nc(COC(C)(C)C(=O)O)cc1-c1cccc(OCC(C)C)c1] | 2-([1-[(2-methoxyphenyl)methyl]-5-[3-(2-methylpropoxy)phenyl]-1H-pyrazol-3-yl]methoxy)-2-methylpropanoic acid<br>LC-MS (ES, m/z): 453<br>$^{1}$H-NMR (400 MHz, MeOD) δ 0.97 (6 H, d), 1.53 (6 H, s), 1.97 (1 H, dp), 3.48 (2 H, d), 3.78 (3 H, s), 4.58 (2 H, s), 5.31 (2 H, s), 6.52 (1 H, s), 6.67-6.74 (1 H, m), 6.76-6.82 (1 H, m), 6.85-7.00 (4 H, m), 7.22-7.33 (2 H, m). |

TABLE 30-continued

| Examples 51-74. | | | |
|---|---|---|---|
| Ex. | Scheme | Structure | IUPAC Name<br>Analytical data |
| 62 | VII | 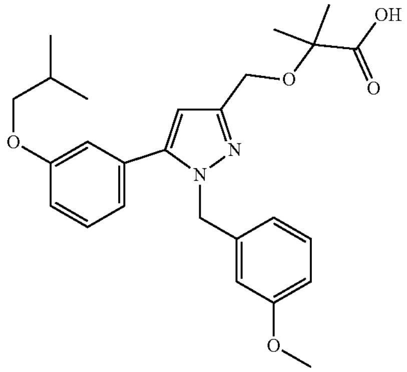 [SMILES: COc1cccc(Cn2nc(COC(C)(C)C(=O)O)cc2-c2cccc(OCC(C)C)c2)c1] | 2-([1-[(3-methoxyphenyl)methyl]-5-[3-(2-methylpropoxy)phenyl]-1H-pyrazol-3-yl]methoxy)-2-methylpropanoic acid<br>LC-MS (ES, m/z): 453<br>$^{1}$H-NMR (400 MHz, MeOD) δ 0.99 (6 H, d), 1.53 (6 H, s), 1.99 (1 H, dq), 3.55 (2 H, d), 3.73 (3 H, s), 4.59 (2 H, s), 5.33 (2 H, s), 6.50 (1 H, s), 6.56-6.65 (2 H, m), 6.78-6.86 (2 H, m), 6.92-7.00 (2 H, m), 7.22 (1 H, t), 7.33 (1 H, t). |
| 63 | VII | 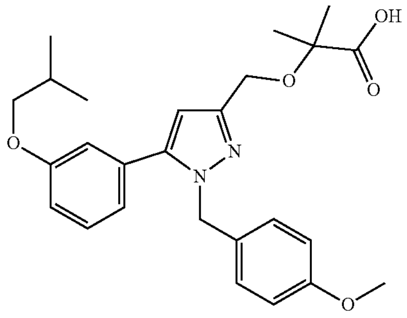 [SMILES: COc1ccc(Cn2nc(COC(C)(C)C(=O)O)cc2-c2cccc(OCC(C)C)c2)cc1] | 2-([1-[(4-methoxyphenyl)methyl]-5-[3-(2-methylpropoxy)phenyl]-1H-pyrazol-3-yl]methoxy)-2-methylpropanoic acid<br>LC-MS (ES, m/z): 453<br>$^{1}$H-NMR (400 MHz, MeOD) δ 1.00 (6 H, d), 1.53 (6 H, s), 2.01 (1 H, dp), 3.57 (2 H, d), 3.77 (3 H, s), 4.58 (2 H, s), 5.29 (2 H, s), 6.47 (1 H, s), 6.78-6.90 (3 H, m), 6.92-7.01 (4 H, m), 7.29-7.39 (1 H, m). |
| 64 | VIII | 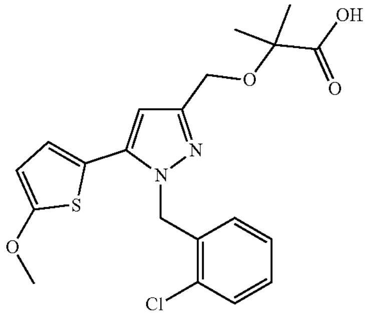 [SMILES: COc1ccc(-c2cc(COC(C)(C)C(=O)O)nn2Cc2ccccc2Cl)s1] | 2-([1-[(2-Chlorophenyl)methyl]-5-(5-methoxythien-2-yl)-1H-pyrazol-3-yl]methoxy)-2-methylpropanoic acid<br>$^{1}$H-NMR (300 MHz, MeOD) δ 1.51 (6 H, s), 3.86 (3 H, s), 4.54 (2 H, s), 5.50 (2 H, s), 6.19 (1 H, d), 6.51 (1 H, s), 6.55-6.66 (2 H, m), 7.25 (2 H, dtd), 7.43 (1 H, dd). |
| 65 | VIII | 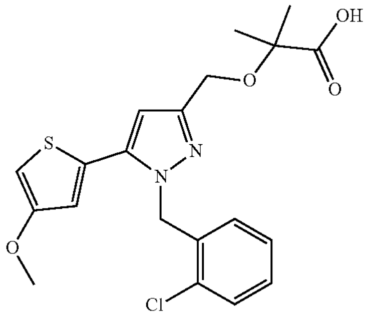 [SMILES: COc1csc(-c2cc(COC(C)(C)C(=O)O)nn2Cc2ccccc2Cl)c1] | 2-([1-[(2-Chlorophenyl)methyl]-5-(4-methoxythien-2-yl)-1H-pyrazol-3-yl]methoxy)-2-methylpropanoic acid<br>$^{1}$H-NMR (300 MHz, MeOD) δ 1.51 (6 H, s), 3.76 (3 H, s), 4.56 (2 H, s), 5.54 (2 H, s), 6.51 (1 H, d), 6.56-6.69 (3 H, m), 7.26 (2 H, dtd), 7.44 (1 H, dd). |

TABLE 30-continued

| Examples 51-74. | | | |
|---|---|---|---|
| Ex. | Scheme | Structure | IUPAC Name<br>Analytical data |
| 66 | VIII | 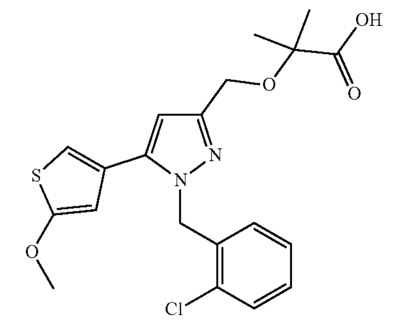 [SMILES: COc1cc(-c2cc(COC(C)(C)C(=O)O)nn2Cc2ccccc2Cl)cs1] | 2-([1-[(2-chlorophenyl)methyl]-5-(5-methoxythien-3-yl)-1H-pyrazol-3-yl]methoxy)-2-methylpropanoic acid<br>$^1$H-NMR (400 MHz, MeOD) δ 1.53 (6 H, s), 3.85 (3 H, s), 4.57 (2 H, s), 5.52 (2 H, s), 6.26 (1 H, d), 6.52-6.59 (2 H, m), 6.64-6.71 (1 H, m), 7.28 (2 H, dtd), 7.45 (1 H, dd). |
| 67 | VIII | 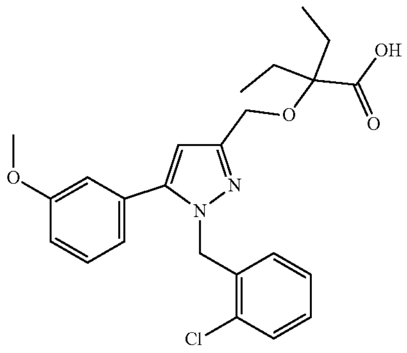 [SMILES: CCC(CC)(OCc1cc(-c2cccc(OC)c2)n(Cc2ccccc2Cl)n1)C(=O)O] | 2-([1-[(2-Chlorophenyl)methyl]-5-(3-methoxyphenyl)-1H-pyrazol-3-yl)methoxy)-2-ethylbutyric acid<br>$^1$H-NMR (400 MHz, MeOD) δ (0.91 (6 H, t), 1.87 (4 H, q), 3.68 (3 H, s), 4.52 (2 H, s), 5.43 (2 H, s), 6.67 (1 H, s), 6.72-6.86 (2 H, m), 6.88-7.00 (2 H, m), 7.21-7.36 (3 H, m), 7.37-7.48 (1 H, m). |
| 68 | VII | 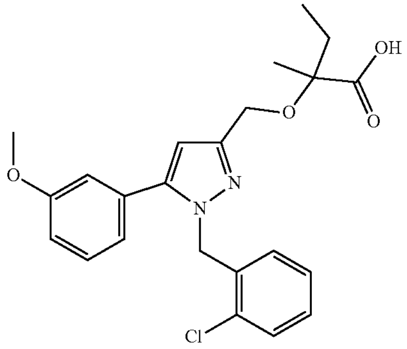 [SMILES: CCC(C)(OCc1cc(-c2cccc(OC)c2)n(Cc2ccccc2Cl)n1)C(=O)O] | 2-([1-[(2-Chlorophenyl)methyl]-5-(3-methoxyphenyl)-1H-pyrazol-3-yl]methoxy)-2-methylbutanoic acid<br>$^1$H-NMR (400 MHz, MeOD) δ 0.97 (3 H, t), 1.51 (3 H, s), 1.89 (2 H, qd), 3.68 (3 H, s), 4.59 (2 H, s), 5.44 (2 H, s), 6.56 (1 H, s), 6.71-6.79 (1 H, m), 6.83 (1 H, dd), 6.89-7.01 (2 H, m), 7.22-7.36 (3 H, m), 7.37-7.45 (1 H, m). |
| 69 | XVIII | 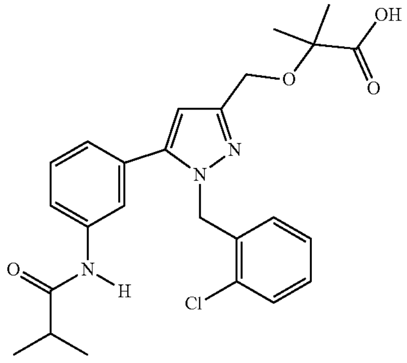 [SMILES: CC(C)C(=O)Nc1cccc(-c2cc(COC(C)(C)C(=O)O)nn2Cc2ccccc2Cl)c1] | 2-([1-[(2-Chlorophenyl)methyl]-5-[3-(2-methylpropanamido)phenyl]-1H-pyrazol-3-yl]methoxy)-2-methylpropanoic acid<br>$^1$H-NMR (400 MHz, DMSO) δ 1.09 (6 H, d), 1.39 (6 H, s), 2.57 (1 H, p), 5.39 (2 H, s), 6.40 (1 H, s), 6.69-6.79 (1 H, m), 7.00 (1 H, dt), 7.21-7.48 (4 H, m), 7.53-7.63 (1 H, m), 7.78(1 H, I), 9.93(1 H, s). |

TABLE 30-continued

| Examples 51-74. | | | |
|---|---|---|---|
| Ex. | Scheme | Structure | IUPAC Name<br>Analytical data |
| 70 | XIX | 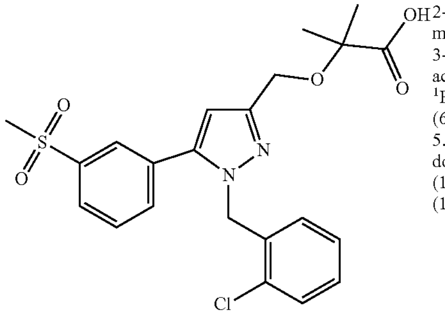 | 2-([1-[(2-Chlorophenyl)methyl]-5-(3-methanesulfonylphenyl)-1H-pyrazol-3-yl]methoxy)-2-methylpropanoic acid<br>$^1$H-NMR (400 MHz, MeOD) δ 1.54 (6 H, s), 3.10 (3 H, s), 4.61 (2 H, s), 5.48 (2 H, s), 6.67 (1 H, s), 6.82 (1 H, dd), 7.21-7.33 (2 H, m), 7.35-7.42 (1 H, m), 7.64-7.74 (2 H, m), 7.90 (1 H, q), 7.96-8.03 (1 H, m). |
| 71 | XIX | 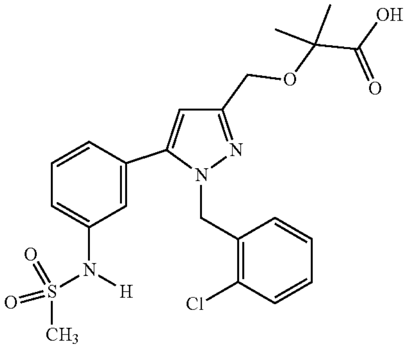 [SMILES: CC(C)(OCc1cc(-c2cccc(NS(C)(=O)=O)c2)n(Cc2ccccc2Cl)n1)C(=O)O] | 2-([1-[(2-Chlorophenyl)methyl]-5-(3-methanesulfonamidophenyl)-1H-pyrazol-3-yl]methoxy)-2-methyl-propanoic acid<br>$^1$H-NMR (300 MHz, MeOD): δ 1.52 (6 H, s), 2.04 (1 H, s), 2.87 (3 H, s), 4.58 (2 H, s), 5.44 (2 H, s), 6.56 (1 H, s), 6.66-6.76 (1 H, m), 7.12 (1 H, dt), 7.25 (4 H, dtd), 7.32-7.44 (2 H, m). |
| 72 | XIX | 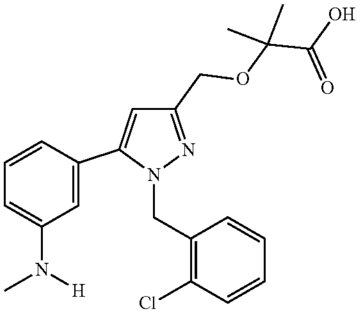 [SMILES: CNc1cccc(-c2cc(COC(C)(C)C(=O)O)nn2Cc2ccccc2Cl)c1] | 2-([1-[(2-chlorophenyl)methyl]-5-[3-(methylamino)phenyl]-1H-pyrazol-3-yl]¬methoxy)-2-methylpropanoic acid<br>$^1$H-NMR (300 MHz, MeOD): δ 1.52 (6 H, s), 2.04 (1 H, s), 2.87 (3 H, s), 4.58 (2 H, s), 5.44 (2 H, s), 6.56 (1 H, s), 6.66-6.76 (1 H, m), 7.12 (1 H, dt), 7.25 (4 H, dtd), 7.32-7.44 (2 H, m). |
| 73 | XIX | 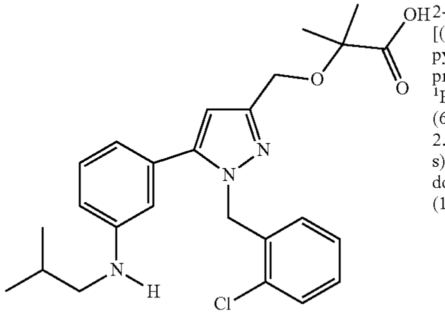 | 2-([1-[(2-chlorophenyl)methyl]-5-[3-[(2-methylpropyl)amino]phenyl]-1H-pyrazol-3-yl]methoxy)-2-methyl-propanoic acid<br>$^1$H-NMR (300 MHz, MeOD): δ 0.88 (6 H, d), 1.52 (6 H, s), 1.74 (1 H, dp), 2.66 (2 H, d), 4.57 (2 H, s), 5.42 (2 H, s), 6.40-6.77 (5 H, m), 7.11 (1 H, dd), 7.19-7.35 (2 H, m), 7.35-7.47 (1 H, m). |

TABLE 30-continued

Examples 51-74.

| Ex. | Scheme | Structure | IUPAC Name Analytical data |
|---|---|---|---|
| 74 | XII | 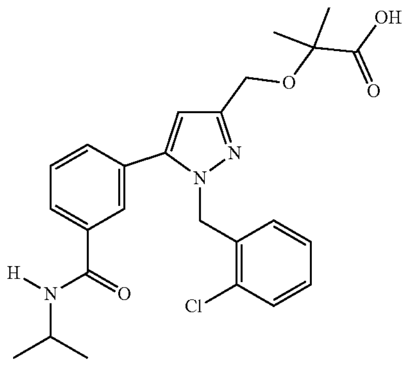 [SMILES: CC(C)NC(=O)c1cccc(-c2cc(COC(C)(C)C(=O)O)nn2Cc2ccccc2Cl)c1] | 2-([1-[(2-Chlorophenyl)methyl]-5-[3-[(propan-2-yl)carbamoyl]phenyl]-1H-pyrazol-3-yl]methoxy)-2-methyl-propanoic acid $^1$H-NMR: (400 MHz, DMSO-d$_6$) δ 1.16 (6 H, d), 1.41 (6 H, s), 3.33 (5 H, s), 4.02-4.17 (1 H, m), 4.44 (2 H, s), 5.40 (2 H, s), 6.53 (1 H, s), 6.75-6.88 (1 H, m), 7.23-7.36 (2 H, m), 7.41-7.47 (1 H, m), 7.49-7.57 (2 H, m), 7.81-7.98 (2 H, m), 8.29 (1 H, d), 12.63 (1 H, s). |

Example 75: 2-([1-[(2-chlorophenyl)methyl]-5-(phenylamino)-1H-pyrazol-3-yl]methoxy)-2-methylpropanoic acid

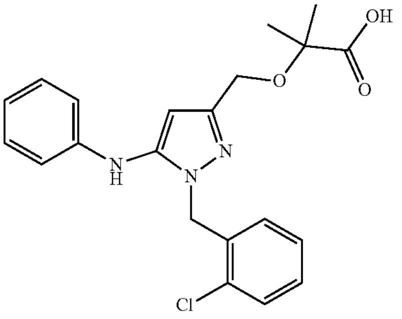 [SMILES: CC(C)(OCc1cc(Nc2ccccc2)n(Cc2ccccc2Cl)n1)C(=O)O]

2-[(?5-[[tert-Butoxy)carbonyl](phenyl)amino]-1-[(?2-chlorophenyl)methyl]-1H-pyrazol-3-yl)methoxy)-2-methyl-propanoic acid was prepared from Int. H-93 using the procedure of Example 1. This resulted in 200 mg as yellow oil.

2-([l-[(2-Chlorophenyl)methyl]-5-(phenylamino)-1H-pyrazol-3-yl]methoxy)-2-methylpropanoic acid To a solution of the product from the previous step (200 g, 400.01 mmol, 1.00 equiv) in DCM (10 mL) was added TFA (5 mL) dropwise with stirring at rt. The resulting solution was stirred for 1 h, then concentrated under vacuum. The crude product (150 mg) was purified by Prep-HPLC with the following conditions (2#-AnalyseHPLC-SHIMADZU (HPLC-10)): Column, SunFire C18 OBD Prep Column, 0.1 nM, 5 uM, 19 mm×150 mm, mobile phase, Waters (0.1% TFA) and ACN (61.0% ACN up to 74.0% in 6 min); Detector, UV 254 nm), to afford 19.2 mg of the title product as a white solid.

$^1$H-NMR (300 MHz, MeOD) δ 1.50 (6H, s), 4.48 (2H, s), 5.34 (2H, d), 6.18 (1H, s), 6.68-6.95 (4H, n), 7.11-7.30 (4H, m), 7.33-7.43 (1H, n).

The following Examples were prepared using the indicated Schemes.

TABLE 21

Examples 76-77.

| Ex. | Scheme | Structure | IUPAC Name Analytical data |
|---|---|---|---|
| 76 | XVII | 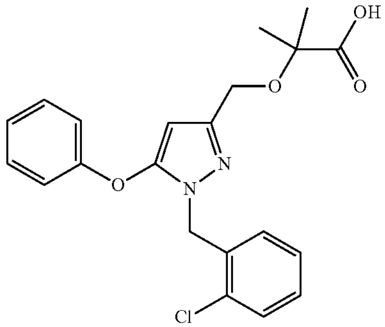 [SMILES: CC(C)(OCc1cc(Oc2ccccc2)n(Cc2ccccc2Cl)n1)C(=O)O] | 2-([1-[(2-Chlorophenyl)methyl]-5-phenoxy-1H-pyrazol-3-yl]methoxy)-2-methylpropanoic acid $^1$H-NMR (CD3OD, ppm): δ (300 MHz, MeOD) 1.46 (6H, s), 4.44 (2H, s), 5.35 (2H, s), 5.78 (1H, s), 6.90-7.00 (1H, m), 7.06-7.46 (8H, m). |

TABLE 21-continued

| Ex. | Scheme | Structure | IUPAC Name Analytical data |
|---|---|---|---|
| | | Examples 76-77. | |
| 77 | VI | 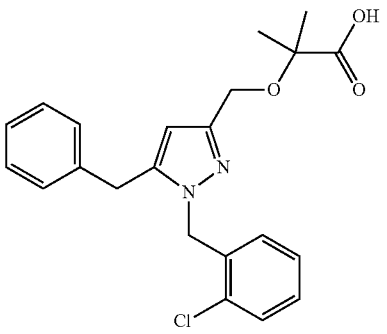 [SMILES: CC(C)(OCc1cc(Cc2ccccc2)n(Cc2ccccc2Cl)n1)C(=O)O] | 2-([5-Benzyl-1-[(2-chlorophenyl)-methyl]-1H-pyrazol-3-yl]methoxy)-2-methylpropanoic acid $^1$H-NMR (300 MHz, MeOD): δ 1.48 (6H, s), 3.92 (2H, s), 4.50 (2H, s), 5.32 (2H, s), 6.23 (1H, s), 6.42-6.52 (1H, m), 7.07-7.30 (7H, m), 7.39 (1H, dd). |

Example 78 is intentionally left blank.

Example 79: 2-([1-[(2-Chlorophenyl)methyl]-5-(3-hydroxyphenyl)1H-pyrazol-3-yl]methoxy)-2-methyl-propanoic acid

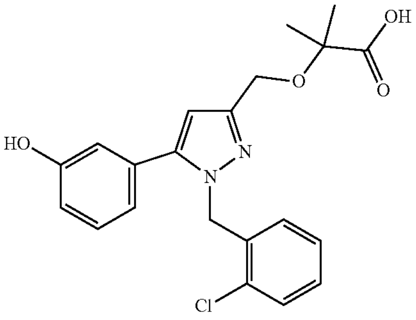 [SMILES: CC(C)(OCc1cc(-c2cccc(O)c2)n(Cc2ccccc2Cl)n1)C(=O)O]

(i) 2-([1-[(2-Chlorophenyl)methyl]-5-(3-hydroxyphenyl) 1H-pyrazol-3-yl]methoxy)-2-methylpropanoic acid: A solution of methyl 2-([5-(3-benzyloxyphenyl)-1-[(2-chlorophenyl)-methyl]1H-pyrazol-3-yl]methoxy)-2-methyl-propanoate in mixture of acetic acid and conc HCl (8 mL) (3:1, v/v) was heated at 90° C. for 6 h. At the end of this period the reaction mixture was evaporated to dryness and the residue was chromatographed over $SiO_2$ using 0-20% gradient of MeOH in DCM to afford the title product. $^1$HNMR ($CDCl_3$): δ 1.55 (s, 6H), 4.61 (s, 2H), 5.40 (s, 2H), 6.38 (s, 1H), 6.74-6.83 (m, 4H), 7.18-7.35 (m, 4H).

Example 80: 2-([1-[(2-Chlorophenyl)methyl]-5-[3-(oxetan-3-ylmethoxy)phenyl]-1H-pyrazol-3-yl]methoxy)-2-methylpropanoic acid

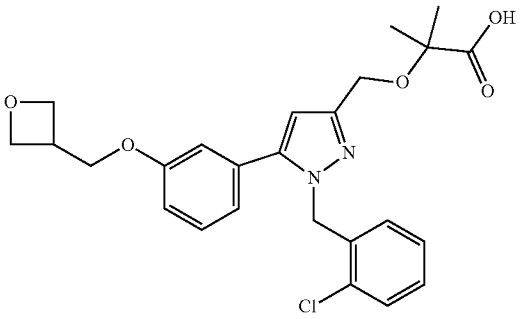 [SMILES: CC(C)(OCc1cc(-c2cccc(OCC3COC3)c2)n(Cc2ccccc2Cl)n1)C(=O)O]

(i) Methyl 2-([1-[(2-chlorophenyl)methyl]-5-(3-hydroxyphenyl)1H-pyrazol-3-yl]-methoxy)-2-methyl-propanoate: To a solution of 2-([1-[(2-chlorophenyl)methyl]-5-(3-hydroxyphenyl) 1H-pyrazol-3-yl]methoxy)-2-methylpropanoic acid (Example 79) in MeOH was added 4 drops of conc $H_2SO_4$, and the solution was refluxed for 16 h. The product was evaporated to dryness and the residue was chromatographed over $SiO_2$ using 0-25% gradient of MeOH in DCM to afford the title product.

(ii) Methyl 2-([1-[(2-chlorophenyl)methyl]-5-[3-(oxetan-3-ylmethoxy)phenyl]1H-pyrazol-3-yl]methoxy)-2-methyl-propanoate. To a solution of methyl 2-([1-[(2-chlorophenyl)-methyl]-5-(3-hydroxyphenyl)-1H-pyrazol-3-yl]methoxy)-2-methyl-propanoate (0.170 g, 0.410 mmol) in DMF was added [oxetan-3-yl]methyl 4-methylbenzenesulfonate (0.149 g, 0.615 mmol) and $K_2CO_3$ (0.113 g, 0.820 mmol) at room temperature. The mixture was heated at 60° C. for 16 h. The reaction mixture was cooled to room temperature, water was added, and the mixture was extracted with EtOAc (20 mL×2). The combined organic layers were washed with water (20 mL) and brine (20 mL), dried over $Na_2SO_4$, and concentrated under reduced pressure. The residue was chromatographed over $SiO_2$ using 0-100% gradient of EtOAc in hexane to afford the title product. $^1$HNMR ($CDCl_3$): δ 1.54 (s, 6H), 3.33-3.36 (m, 1H), 3.77 (s, 3H), 3.97 (d, 2H), 4.30 (t, 2H), 4.56 (s, 2H), 4.84 (t, 2H), 5.40 (s, 2H), 6.53 (s, 1H), 6.77-6.90 (m, 4H), 7.19-7.37 (m, 4H).

(iii) 2-([1-[(2-Chlorophenyl)methyl]-5-[3-(oxetan-3-yl-methoxy)phenyl]1H-pyrazol-3-yl]methoxy)-2-methyl-propanoic acid was prepared analogously as described in Step iv of Example 1, yielding the title product (20 mg). $^{1}$HNMR ($CDCl_3$): δ 1.55 (s, 6H), 3.34-3.74 (m, 1H), 3.98 (d, 2H), 4.49 (t, 2H), 4.63 (s, 2H), 4.83 (t, 2H), 5.43 (s, 2H), 6.44 (s, 1H), 6.76-6.93 (m, 4H), 7.20-7.37 (m, 4H).

Example 81: 2-([1-[(2-chlorophenyl)methyl]-5-(3-methoxyphenyl)1H-pyrazol-3-yl]methoxy)-2-methyl-N-methylsulfonyl-propanamide

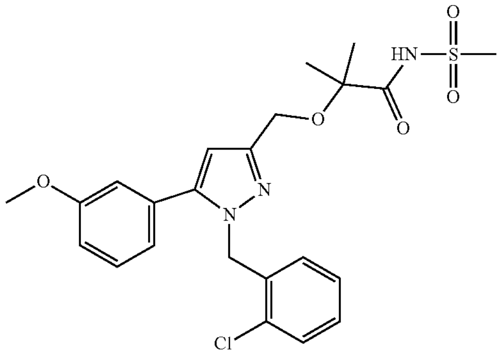

To a solution of Example 14 (2-([1-[(2-chlorophenyl)methyl]-5-(3-methoxyphenyl)-1H-pyrazol-3-yl]methoxy)-2-methylpropanoic acid) (0.08 g, 0.192 mmol) in $CH_3CN$ was added CDI (0.047 g, 0.288 mmol) and methanesulfonamide (0.022 g, 0.23 mmol) at rt. The mixture was stirred at rt for 16 h. The solvent was evaporated and the residue was chromatographed over $SiO_2$ using 0-20% gradient of MeOH in DCM to afford the title product. $^{1}$HNMR ($CDCl_3$): δ 1.55 (s, 6H), 3.21 (s, 3H), 3.67 (s, 3H), 4.58 (s, 2H), 5.48 (s, 2H), 6.36 (s, 1H), 6.75-6.92 (m, 4H), 7.18-7.35 (m, 4H).

Example 82: Methyl 2-([1-[(2-chlorophenyl)methyl]-5-(3-methoxyphenyl)1H-pyrazol-3-yl]methoxy)-2-methyl-propanoate

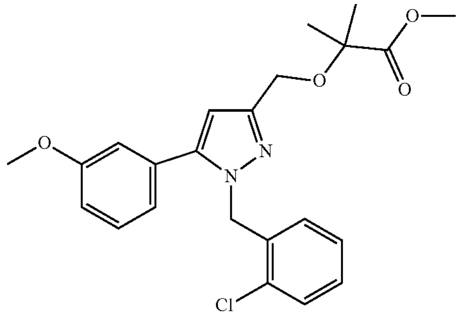

Example 82 was prepared analogously as described in Example 1, omitting Step iv. $^{1}$HNMR($CDCl_3$): δ1.54 (s, 6H), 3.65 (s, 3H), 3.77 (s, 3H), 4.56 (s, 2H), 5.37 (s, 2H), 6.53 (s, 1H), 6.71-6.78 (m, 2H), 6.85-6.90 (m 2H), 7.10-7.13 (m, 1H), 7.21-7.27 (m, 2H), 7.51-7.53 (m 1H).

Examples 83-100 are intentionally left blank.

The following Examples were prepared using the indicated Schemes.

TABLE 22

Examples 101-119.

| Ex. | Scheme | Structure | IUPAC Name<br>Analytical Data |
|---|---|---|---|
| 101 | II | 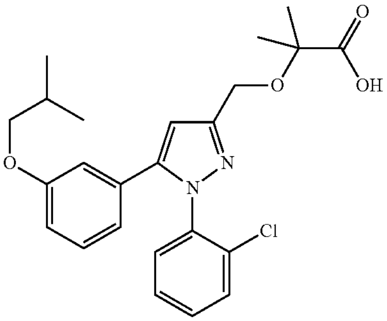 [SMILES: CC(C)COc1cccc(-c2cc(COC(C)(C)C(=O)O)nn2-c2ccccc2Cl)c1] | 2-([1-(2-Chlorophenyl)-5-[3-(2-methylpropoxy)phenyl]-1H-pyrazol-3-yl]methoxy)-2-methylpropanoic acid<br>LC-MS (ES, m/z): 443.<br>$^{1}$H-NMR (400 MHz, DMSO) δ 0.90 (6H, d), 1.25 (1H, d), 1.43 (6H, s), 1.88 (1H, hept), 3.54 (2H, d), 4.48 (2H, s), 6.65-6.73 (2H, m), 6.75-6.88 (2H, m), 7.20 (1H, t), 7.45-7.65 (4H, m). |
| 102 | II | 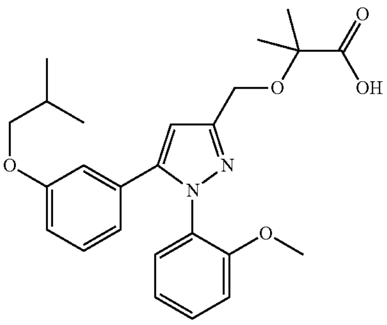 [SMILES: COc1ccccc1-n1nc(COC(C)(C)C(=O)O)cc1-c1cccc(OCC(C)C)c1] | 2-([1-(2-Methoxyphenyl)-5-[3-(2-methylpropoxy)phenyl]-1H-pyrazol-3-yl]methoxy)-2-methylpropanoic acid.<br>LC-MS (ES, m/z): 439<br>$^{1}$H-NMR (400 MHz, DMSO) δ 0.90 (6H, d), 1.43 (6H, s), 1.87 (1H, hept), 3.45-3.55 (5H, m), 4.45 (2H, s), 6.60 (1H, s), 6.67 (1H, dd), 6.76-6.86 (2H, m), 7.01-7.23 (3H, m), 7.35 (1H, dd), 7.44 (1H, ddd), 12.73 (1H, s). LC-MS (ES, m/z): 439. |

TABLE 22-continued

Examples 101-119.

| Ex. | Scheme | Structure | IUPAC Name Analytical Data |
|---|---|---|---|
| 103 | II | 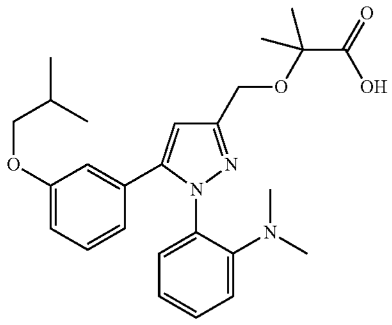 [SMILES: CC(C)COc1cccc(-c2cc(COC(C)(C)C(=O)O)nn2-c2ccccc2N(C)C)c1] | 2-([1-[2-(Dimethylamino)phenyl]-5-[3-(2-methylpropoxy)phenyl]-1H-pyrazol-3-yl]methoxy)-2-methylpropanoic acid. LC-MS (ES, m/z): 452 $^1$H-NMR (300 MHz, MeOD) δ 1.02 (6H, d), 1.53 (6H, s), 2.04 (1H, dt), 3.02 (6H, s), 3.65 (2H, d), 4.60 (2H, s), 5.48 (2H, s), 6.49 (1H, s), 6.81 (1H, d), 6.92-7.05 (3H, m), 7.26 (1H, t), 7.42 (2H, dt), 7.54 (1H, d). |
| 104 | II | 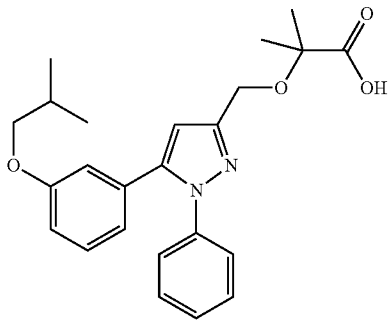 [SMILES: CC(C)COc1cccc(-c2cc(COC(C)(C)C(=O)O)nn2-c2ccccc2)c1] | 2-methyl-2-([5-[3-(2-methylpropoxy)phenyl]-1-phenyl-1H-pyrazol-3-yl]methoxy)propanoic acid LC-MS (ES, m/z): 409 1H-NMR (300 MHz, MeOD 7.48-7.32 (m, 3H), 7.35-7.14 (m, 3H), 6.91-6.78 (m, 2H), 6.73-6.63 (m, 2H), 4.61 (s, 2H), 3.54 (d, J = 6.5 Hz, 2H), 1.92 (hept, J = 6.7 Hz, 1H), 1.53 (s, 6H), 0.95 (d, J = 6.7 Hz, 6H). |
| 105 | II | 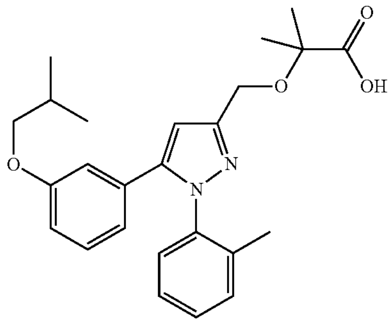 [SMILES: Cc1ccccc1-n1nc(COC(C)(C)C(=O)O)cc1-c1cccc(OCC(C)C)c1] | 2-Methyl-2-([1-(2-methylphenyl)-5-[3-(2-methylpropoxy)phenyl]-1H-pyrazol-3-yl]methoxy]propanoic acid. LC-MS (ES, m/z): 423 $^1$H-NMR (300 MHz, MeOD) δ 0.95 (d, 6H), 1.54 (s, 6H), 1.81-2.01 (m, 4H), 3.34 (s, 1H), 3.46 (d, 2H), 4.61 (s, 2H), 6.63 (dd, 1H), 6.71-6.92 (m, 3H), 7.18 (t, 1H), 7.26-7.47 (m, 4H). |
| 106 | II | 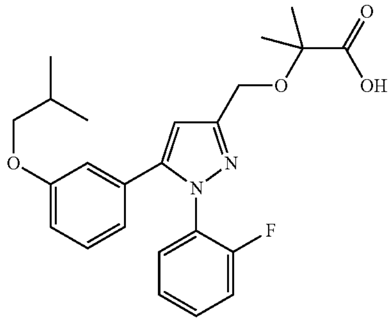 [SMILES: CC(C)COc1cccc(-c2cc(COC(C)(C)C(=O)O)nn2-c2ccccc2F)c1] | 2-([1-(2-fluorophenyl)-5-[3-(2-methylpropoxy)phenyl]-1H-pyrazol-3-yl]methoxy)-2-methylpropanoic acid. LC-MS (ES, m/z): 427 1H-NMR (300 MHz, MeOD) δ 7.57-7.46 (m, 2H), 7.38-7.29 (m, 1H), 7.28-7.16 (m, 2H), 6.91-6.81 (m, 2H), 6.72 (q, 2H), 4.63 (s, 2H), 3.56 (d, 2H), 1.98-1.93 (m, 1H), 1.55 (s, 6H), 0.98 (d, 6H). |

TABLE 22-continued

| Examples 101-119. | | | |
|---|---|---|---|
| Ex. | Scheme | Structure | IUPAC Name<br>Analytical Data |
| 107 | XIII | 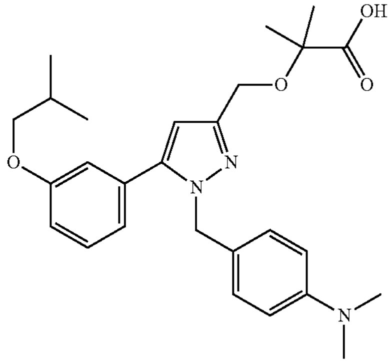 [SMILES: CC(C)COc1cccc(-c2cc(COC(C)(C)C(=O)O)nn2Cc2ccc(N(C)C)cc2)c1] | 2-[(1-[[4-(Dimethylamino)phenyl]methyl]-5-[3-(2-methylpropoxy)phenyl]-1H-pyrazol-3-yl)methoxy)-2-methylpropanoic acid<br>$^1$H-NMR (400 MHz, DMSO) δ 0.95 (7H, d), 1.21-1.27 (1H, m), 1.40 (6H, s), 1.96 (1H, dq), 2.84 (6H, s), 3.64 (2H, d), 4.40 (2H, s), 5.18 (2H, s), 6.37 (1H, s), 6.60-6.67 (2H, m), 6.83-6.92 (3H, m), 6.98 (2H, ddd), 7.36 (1H, t), 12.68 (1H, s). LC-MS (ES, m/z): 466. |
| 108 | XIII | 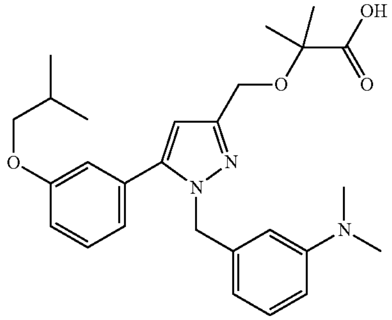 [SMILES: CC(C)COc1cccc(-c2cc(COC(C)(C)C(=O)O)nn2Cc2cccc(N(C)C)c2)c1] | 2-[(1-[[3-(Dimethylamino)phenyl]-methyl]-5-[3-(2-methylpropoxy)-phenyl]-1H-pyrazol-3-yl)methoxy)-2-methylpropanoic acid.<br>LC-MS (ES, m/z): 466<br>$^1$H-NMR (300 MHz, MeOD) δ 1.01 (6H, d), 1.54 (6H, s), 1.95-2.06 (1H, m), 3.07 (6H, s), 3.56 (2H, d), 4.59 (2H, s), 5.32 (2H, s), 6.51 (1H, s), 6.80-6.87 (3H, m), 7.10 (2H, d), 7.24 (1H, ddd), 7.32-7.37 (2H, dd). |
| 109 | XIII | 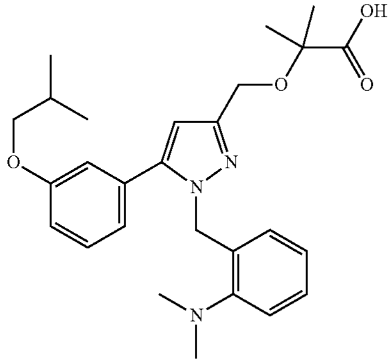 [SMILES: CC(C)COc1cccc(-c2cc(COC(C)(C)C(=O)O)nn2Cc2ccccc2N(C)C)c1] | 2-[(1-[[2-(Dimethylamino)phenyl]-methyl]-5-[3-(2-methylpropoxy)-phenyl]-1H-pyrazol-3-yl)methoxy)-2-methylpropanoic acid.<br>LC-MS (ES, m/z): 466<br>$^1$H-NMR (300 MHz, MeOD) δ 1.02 (6H, d), 1.53 (6H, s), 2.04 (1H, dt), 3.02 (6H, s), 3.65 (2H, d), 4.60 (2H, s), 5.48 (2H, s), 6.49 (1H, s), 6.81 (1H, d), 6.92-7.05 (3H, m), 7.26 (1H, t), 7.42 (2H, dt), 7.54 (1H, d). |
| 110 | VII | 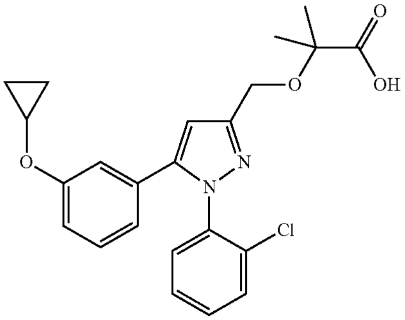 [SMILES: CC(C)(OCc1cc(-c2cccc(OC3CC3)c2)n(-c2ccccc2Cl)n1)C(=O)O] | 2-([1-(2-Chlorophenyl)-5-(3-cyclopropoxyphenyl)-1H-pyrazol-3-yl]methoxy)-2-methylpropanoic acid<br>$^1$H NMR (MeOD, ppm): δ: 0.50-0.59 (m, 2H), 0.63-0.72 (m, 2H), 1.55 (s, 6H), 3.53 (tt, 1H), 4.63 (s, 2H), 6.73 (s, 1H), 6.86-6.98 (m, 3H), 7.22 (t, 1H), 7.41-7.61 (m, 4H). LC-MS (ES, m/z): 427. |

TABLE 22-continued

| Ex. | Scheme | Structure | IUPAC Name Analytical Data |
|---|---|---|---|
| Examples 101-119. | | | |
| 111 | VII | 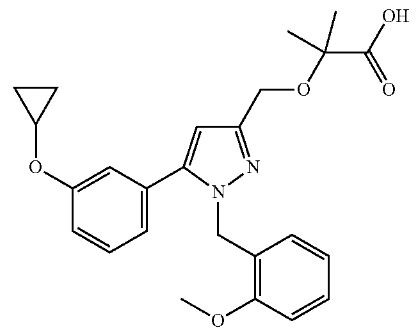 [SMILES: COc1ccccc1Cn1nc(COC(C)(C)C(=O)O)cc1-c1cccc(OC2CC2)c1] | 2-([5-(3-Cyclopropoxyphenyl)-1-[(2-methoxyphenyl)methyl]-1H-pyrazol-3-yl]methoxy)-2-methylpropanoic acid. LC-MS (ES, m/z): 437 $^1$H-NMR (300 MHz, $CDCl_3$) δ 0.54-0.61 (2H, m), 0.65 (2H, dt), 1.53 (6H, s), 3.45-3.58 (1H, m), 3.74 (3H, s), 4.63 (2H, s), 5.38 (2H, s), 6.41 (1H, s), 6.76-6.84 (2H, m), 6.85-6.92 (1H, m), 7.01 (2H, dd), 7.17-7.35 (3H, m). |
| 112 | VII | 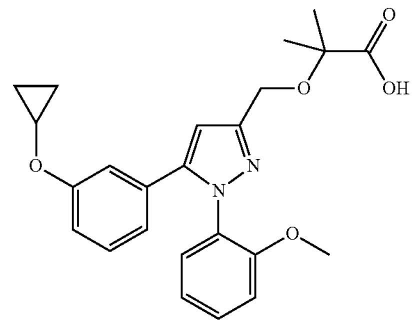 [SMILES: COc1ccccc1-n1nc(COC(C)(C)C(=O)O)cc1-c1cccc(OC2CC2)c1] | 2-([5-(3-cyclopropoxyphenyl)-1-(2-methoxyphenyl)-1H-pyrazol-3-yl]methoxy)-2-methylpropanoic acid LC-MS (ES, m/z): 423 $^1$H NMR (300 MHz, MeOD) δ 7.45 (ddd, J = 8.3, 7.5, 1.7 Hz, 1H), 7.38 (dd, J = 8.0, 1.7 Hz, 1H), 7.19 (ddd, J = 7.6, 6.9, 2.0 Hz, 1H), 7.07 (m, 2H), 6.90 (m, 3H), 6.65 (s, 1H), 4.60 (s, 2H), 3.51 (m, 4H), 1.53 (s, 6H), 0.63 (m, 2H), 0.54 (m, 2H). |
| 113 | VII | 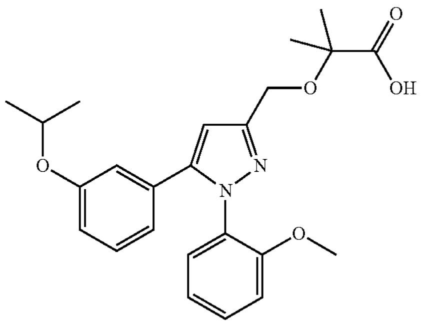 [SMILES: COc1ccccc1-n1nc(COC(C)(C)C(=O)O)cc1-c1cccc(OC(C)C)c1] | 2-([1-(2-Methoxyphenyl)-5-[3-(propan-2-yloxy)phenyl]-1H-pyrazol-3-yl]methoxy)-2-methylpropanoic acid. LC-MS (ES, m/z): 425 $^1$H-NMR (300 MHz, MeOD) δ 1.16 (6H, d), 1.53 (6H, s), 3.53 (3H, s), 4.30 (1H, p), 4.59 (2H, s), 6.64 (1H, s), 6.67-6.72 (1H, m), 6.79 (1H, ddd), 6.86 (1H, dt), 7.01-7.10 (2H, m), 7.17 (1H, t), 7.34-7.39 (1H, m), 7.43 (1H, td). |
| 114 | VII | 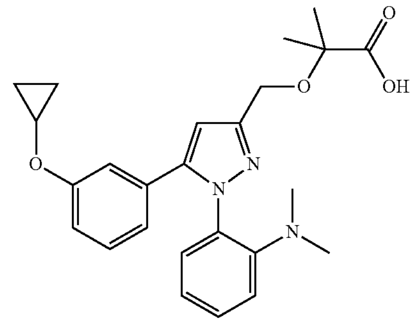 [SMILES: CN(C)c1ccccc1-n1nc(COC(C)(C)C(=O)O)cc1-c1cccc(OC2CC2)c1] | 2-([5-(3-cyclopropoxyphenyl)-1-[2-(dimethylamino)phenyl]-1H-pyrazol-3-yl]methoxy)-2-methylpropanoic acid. LC-MS (ES, m/z): 436 1H-NMR (300 MHz, CDCl3) δ 7.47-7.29 (m, 2H), 7.26-7.06 (m, 3H), 6.96-6.81 (m, 3H), 6.71 (s, 1H), 4.63 (s, 2H), 3.50 (tt, J = 6.2, 3.0 Hz, 1H), 2.44 (s, 6H), 1.54 (s, 6H), 0.70-0.47 (m, 4H). |

TABLE 22-continued

Examples 101-119.

| Ex. | Scheme | Structure | IUPAC Name Analytical Data |
|---|---|---|---|
| 115 | II | 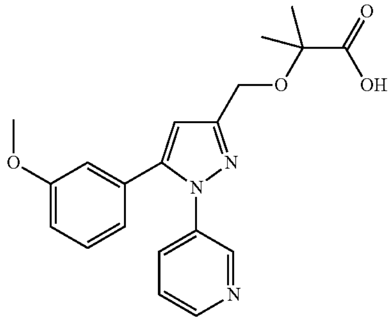 [SMILES: COc1cccc(-c2cc(COC(C)(C)C(=O)O)nn2-c2cccnc2)c1] | 2-([5-(3-Methoxyphenyl)-1-(pyridin-3-yl)-1H-pyrazol-3-yl]methoxy)-2-methylpropanoic acid $^{1}$H-NMR (400 MHz, MeOD) δ 1.55 (s, 6H), 3.72 (s, 3H), 4.65 (s, 2H), 6.73 (s, 1H), 6.79-6.88 (m, 2H), 6.96 (ddd, J = 8.4, 2.5, 0.9 Hz, 1H), 7.25-7.34 (m, 1H), 7.51 (dd, J = 8.3, 4.8 Hz, 1H), 7.82 (ddd, J = 8.3, 2.5, 1.4 Hz, 1H), 8.49 (d, J = 2.5 Hz, 1H), 8.53 (dd, J = 4.9, 1.4 Hz, 1H). LC-MS (ES, m/z): 368. |
| 116 | II | 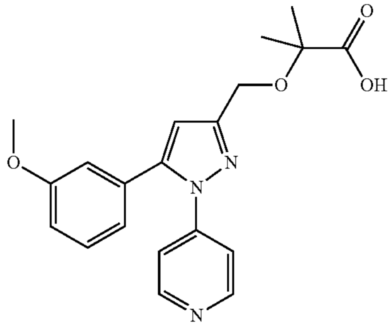 [SMILES: COc1cccc(-c2cc(COC(C)(C)C(=O)O)nn2-c2ccncc2)c1] | 2-([5-(3-Methoxyphenyl)-1-(pyridin-3-yl)-1H-pyrazol-3-yl]methoxy)-2-methylpropanoic acid. LC-MS (ES, m/z): 368. $^{1}$H-NMR (400 MHz, DMSO) δ 2.23 (s, 5H), 4.53 (s, 3H), 5.31 (s, 2H), 7.49 (s, 1H), , 7.63 (d, 1H), 7.22 (t, 1H), 7.72 (s, 1H), 7.81-7.83 (m, 1H), 8.07-8.09 (m, 2H), 8.12-8.16 (m, 1H), 9.38 (d, 2H). |
| 117 | II | 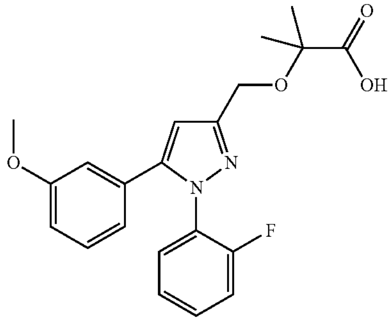 [SMILES: COc1cccc(-c2cc(COC(C)(C)C(=O)O)nn2-c2ccccc2F)c1] | 2-([1-(2-Fluorophenyl)-5-(3-methoxyphenyl)-1H-pyrazol-3-yl]methoxy)-2-methylpropanoic acid. LC-MS (ES, m/z): 384 $^{1}$H-NMR (300 MHz, MeOD) δ 1.55 (6H, d), 3.66 (3H, s), 4.63 (2H, s), 6.72 (1H, s), 6.75 (1H, dd), 6.81-6.92 (2H, m), 7.17-7.28 (2H, m), 7.28-7.37 (1H, m), 7.46-7.56 (2H, m). |
| 118 | II | 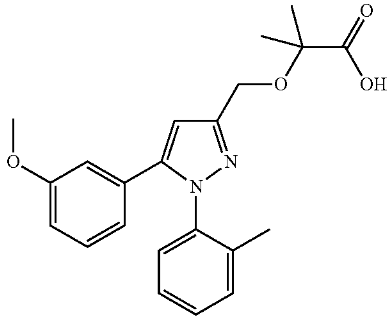 [SMILES: COc1cccc(-c2cc(COC(C)(C)C(=O)O)nn2-c2ccccc2C)c1] | 2-([5-(3-methoxyphenyl)-1-(2-methylphenyl)-1H-pyrazol-3-yl]methoxy)-2-methylpropanoic acid. LC-MS (ES, m/z): 381 1H-NMR (300 MHz, MeOD) δ 7.49-7.28 (m, 4H), 7.18 (t, 1H), 6.94-6.79 (m, 2H), 6.74 (s, 1H), 6.67 (dd, 1H), 4.61 (s, 2H), 3.59 |

TABLE 22-continued

| Examples 101-119. | | | |
|---|---|---|---|
| Ex. | Scheme | Structure | IUPAC Name Analytical Data |
| 119 | II | 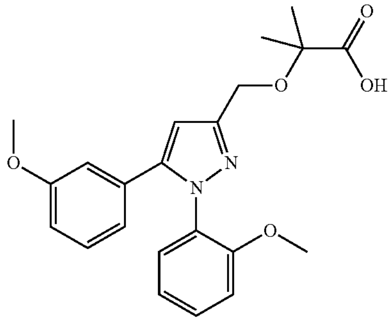 [SMILES: COc1cccc(-c2cc(COC(C)(C)C(=O)O)nn2-c2ccccc2OC)c1] | 22-([1-(2-Methoxyphenyl)-5-(3-methoxyphenyl)-1H-pyrazol-3-yl]methoxy)-2-methylpropanoic acid. LC-MS (ES, m/z): 397 $^1$H-NMR (300 MHz, $CDCl_3$) δ 1.57 (6H, s), 3.48 (3H, s), 3.62 (3H, s), 4.68 (2H, s), 6.57 (1H, s), 6.72 (1H, dd), 6.76-6.85 (2H, m), 6.88 (1H, dd), 7.01 (1H, td), 7.15 (1H, t), 7.31-7.36 (1H, m), 7.37-7.44 (1H, m). |

Examples 120/121: (2S)-2-([1-[(2-Chlorophenyl)methyl]-5-(3-methoxyphenyl)-1H-pyrazol-3-yl]methoxy)-2-methylbutanoic acid and (2R)-2-([1-[(2-Chlorophenyl)methyl]-5-(3-methoxyphenyl)-1H-pyrazol-3-yl]methoxy)-2-methylbutanoic acid

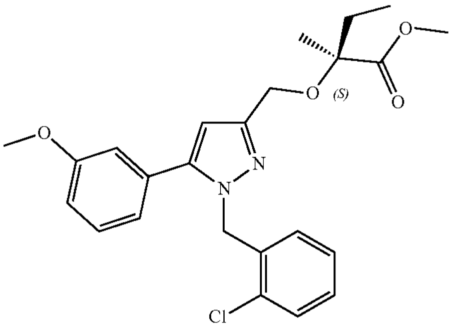

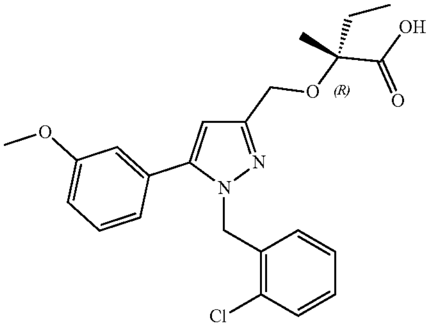

Ethyl 2-([1-[(2-chlorophenyl)methyl]-5-(3-methoxyphenyl)-1H-pyrazol-3-yl]methoxy)-2-methylbutanoate. To a solution of Int. G-1 (700 mg, 1.79 mmol, 1.00 equiv) in THF (10 mL), under $N_2$, was added NaH (200 mg, 8.33 mmol, 3.00 equiv). The solution was stirred for 10 min at 0° C. To this was added methyl 2-hydroxy-2-methylbutanoate (700 mg, 5.30 mmol, 3.00 equiv), $Bu_4NI$ (330 mg, 0.50 equiv). The resulting solution was stirred for 4 h at room temperature. The reaction was quenched by the addition of 1 mL of water. The resulting solution was diluted with 20 mL of $H_2O$, extracted with 2×30 mL of EtOAc, and the organic layers were combined. The resulting mixture was washed with 20 mL of saturated NaCl, then dried over anhydrous $Na_2SO_4$ and concentrated under vacuum. The residue was applied onto a silica gel column with EtOAc/petroleum ether (1:5). This resulted in the title compound as a yellow oil (300 mg, 38%).

(vi) Chiral separation of Ethyl 2-([1-[(2-chlorophenyl)methyl]-5-(3-methoxyphenyl)-1H-pyrazol-3-yl]methoxy)-2-methylbutanoate. The crude product of step v was purified by Chiral-Prep-HPLC with the following conditions (Prep-HPLC-004): Column, Chiralpak IC, 2*25 cm, 5 um; mobile phase, Hex- and ethanol- (hold 2.0% ethanol- in 23 min); Detector, UV 254/220 nm. 100 mg product was obtained which Alpha(25° C., 0.05 mol/L, MeOH). This resulted in ethyl (2S)-2-([1-[(2-chlorophenyl)methyl]-5-(3-methoxyphenyl)-1H-pyrazol-3-yl]methoxy)-2-methylbutanoate as colorless oil (100 mg, 36%) and ethyl (2R)-2-([1-[(2-chlorophenyl)methyl]-5-(3-methoxyphenyl)-1H-pyrazol-3-yl]methoxy)-2-methylbutanoate as colorless oil (100 mg, 36%).

(vii) (2S)-2-([1-[(2-Chlorophenyl)methyl]-5-(3-methoxyphenyl)-1H-pyrazol-3-yl]methoxy)-2-methylbutanoic acid was obtained from ethyl (2S)-2-([1-[(2-chlorophenyl)-methyl]-5-(3-methoxyphenyl)-1H-pyrazol-3-yl]methoxy)-2-methylbutanoate analogously as described in Step iv of Example 1. $^1$H-NMR (400 MHz, MeOD) δ 7.45-7.38 (m, 1H), 7.34 (d, J=7.9 Hz, 1H), 7.31-7.29 (m, 1H), 7.29-7.24 (m, 1H), 6.83 (dd, J=2.5, 1.6 Hz, 1H), 6.80-6.72 (m, 1H), 6.56 (s, 1H), 5.44 (s, 2H), 4.59 (s, 2H), 3.69 (s, 3H), 1.89 (qd, J=7.2, 5.0 Hz, 2H), 1.51 (s, 3H), 0.98 (t, J=7.5 Hz, 3H). LC-MS (ES, m/z): 429.

(viii) (2R)-2-([1-[(2-Chlorophenyl)methyl]-5-(3-methoxyphenyl)-1H-pyrazol-3-yl]methoxy)-2-methylbutanoic acid was obtained from ethyl (2R)-2-([1-[(2-chlorophenyl)methyl]-5-(3-methoxyphenyl)-1H-pyrazol-3-yl]methoxy)-2-methylbutanoate analogously as described in Step iv of Example 1. $^1$H-NMR (400 MHz, MeOD) δ 7.45-7.38 (m, 1H), 7.37-7.31 (m, 1H), 7.31-7.29 (m, 1H), 7.29-7.24 (m, 1H), 6.97 (ddd, J=8.4, 2.6, 0.9 Hz, 1H), 6.93 (dt, J=7.6, 1.2 Hz, 1H), 6.83 (dd, J=2.6, 1.6 Hz, 1H), 6.81-6.72 (m, 1H), 6.56 (s, 1H), 5.44 (s, 2H), 4.59 (s, 2H), 3.69 (s, 3H), 1.89 (qd, J=7.2, 4.9 Hz, 2H), 1.51 (s, 3H), 0.98 (t, J=7.5 Hz, 3H). LC-MS (ES, m/z): 429.

Alternative Synthesis of Examples 120/121: (2S)-2-([1-[(2-Chlorophenyl)methyl]-5-(3-methoxyphenyl)-1H-pyrazol-3-yl]methoxy)-2-methylbutanoic acid and (2R)-2-([1-[(2-Chlorophenyl)methyl]-5-(3-methoxyphenyl)-1H-pyrazol-3-yl]methoxy)-2-methylbutanoic acid

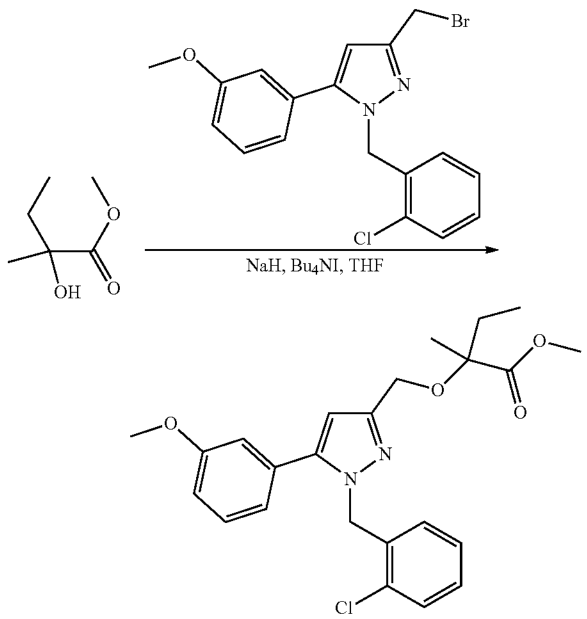

Methyl 2-([1-[(2-chlorophenyl)methyl]-5-(3-methoxyphenyl)-1H-pyrazol-3-yl]methoxy)-2-methylbutanoate To a solution of methyl 2-hydroxy-2-methylbutanoate (780 mg, 5.90 mmol, 1.00 equiv) in THF (50 mL) under $N_2$ was added NaH (236 mg, 5.90 mmol, 1.00 equiv) in portions at 0° C. The mixture was stirred at 0° C. for 30 min, then Int. G-1 (1.16 g, 2.96 mmol, 0.50 equiv) and $Bu_4NI$ (600 mg, 1.63 mmol, 0.50 equiv) were added at 0° C. The resulting solution was stirred for 16 h at rt, then then quenched by the addition of water/ice. The resulting solution was diluted with 200 mL of EtOAc, washed with 2×100 mL of brine, dried over $Na_2SO_4$, concentrated under vacuum, and purified by Prep-HPLC with the following conditions (2#-AnalyseHPLC-SHIMADZU(HPLC-10)): Column, XBridge Prep OBD C18 Column, 30??150 mm 5 um; mobile phase, Water (0.1% FA) and ACN (55.0% ACN up to 79.0% in 7 min); Detector, UV 254/220 nm, to afford 200 mg (8%) of the title compound as a colorless oil. LC-MS: (ES, m/z): 443.

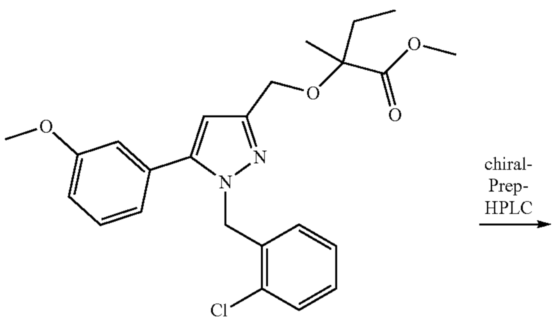

-continued

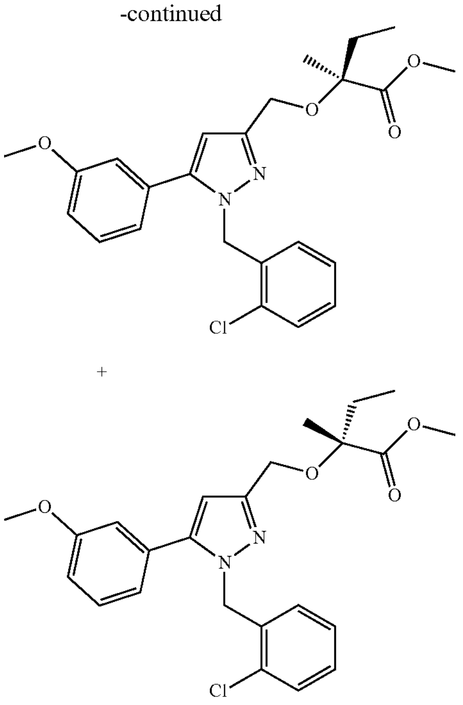

Chiral separation of (2R)- and (2S)-Methyl 2-([1-[(2-chlorophenyl)methyl]-5-(3-methoxyphenyl)-1H-pyrazol-3-yl]methoxy)-2-methylbutanoate The racemic methyl ester (200 mg, 0.45 mmol, 1.00 equiv) was separated into enantiomers by Chiral-Prep-HPLC with the following conditions Column: Chiralpak IC, 2*25 cm, 5 um; Mobile Phase A:Hex-HPLC, Mobile Phase B: EtOH-HPLC; Flow rate: 20 mL/min; Gradient: 2 B to 2 B in 24 min; 220/254 nm; RT1:18.171; RT2:20.742, affording 80 mg (40%) of methyl (2S)-2-([1-[(2-chlorophenyl)-methyl]-5-(3-methoxyphenyl)-1H-pyrazol-3-yl]methoxy)-2-methylbutanoate, and 70 mg (35%) of methyl (2R)-2-([1-[(2-chlorophenyl)methyl]-5-(3-methoxyphenyl)-1H-pyrazol-3-yl]methoxy)-2-methylbutanoate, both as colorless oils.

Alternate Synthesis of methyl (2S)-2-([1-[(2-chlorophenyl)methyl]-5-(3-methoxyphenyl)-1H-pyrazol-3-yl]methoxy)-2-methylbutanoate

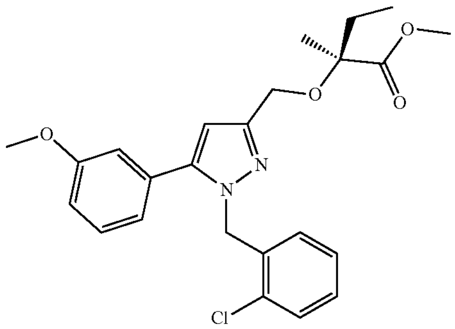

Methyl (2S)-2-([1-[(2-chlorophenyl)methyl]-5-(3-methoxyphenyl)-1H-pyrazol-3-yl]methoxy)-2-methylbutanoate To a solution of methyl (2S)-2-hydroxy-2-methylbutanoate (400 mg, 3.03 mmol, 1.00 equiv) in THF (20 mL)

was added NaH (122 mg, 3.05 mmol, 1.00 equiv) in portions at 0° C. The mixture was stirred at 0° C. for 10 min, then Int. G-1 (400 mg, 1.02 mmol, 0.34 equiv) and $Bu_4NI$ (200 mg, 0.54 mmol, 0.50 equiv) were added at 0° C. The resulting solution was stirred for 16 h at rt, quenched by the addition of water/ice, and extracted with 100 mL of EtOAc. The combined organic layers were washed with 1×100 mL of brine, dried over $Na_2SO_4$, concentrated under vacuum, and purified with Prep-TLC using EtOAc/petroleum ether (1:3) to afford 150 mg (11%) of the title compound as a colorless oil. LC-MS: (ES, m/z): 443.

Example 120. (2S)-2-([1-[(2-chlorophenyl)methyl]-5-(3-methoxyphenyl)-1H-pyrazol-3-yl]methoxy)-2-methylbutanoic acid

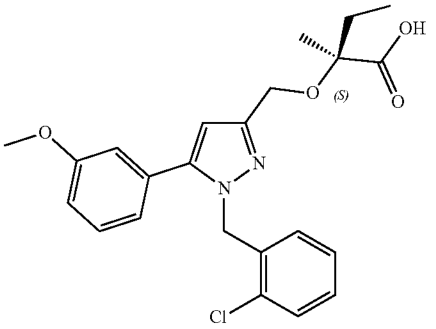

To a solution of methyl (2S)-2-([1-[(2-chlorophenyl)methyl]-5-(3-methoxyphenyl)-1H-pyrazol-3-yl]methoxy)-2-methylbutanoate (70 mg, 0.16 mmol, 1.00 equiv) in THF/$H_2O$/MeOH (4/2/2 mL) was added LiOH (23 mg, 0.96 mmol, 6.00 equiv), in portions at rt. The resulting solution was stirred for 2 h at room temperature. The pH v was adjusted to 3-4 with cone HCl. The resulting solution was extracted with 100 mL of EtOAc. The combined organic layers were dried over $Na_2SO_4$, concentrated under vacuum, and purified by Prep-HPLC with the following conditions (2#-AnalyseHPLC-SHIMADZU(HPLC-10)): Column, XBridge Prep OBD C18 Column, 30??150 mm 5 um; mobile phase, Water (0.1% FA) and ACN (40.0% ACN up to 75.0% in 7 min); Detector, UV 254/220 nm to afford 40 mg (59%) of the title compound as a colorless oil. LC-MS: (ES, m/z): 429. $^1H$ NMR: (400 MHz, DMSO-$d_6$) δ12.60 (s, 1H), 7.50-7.22 (m, 4H), 7.02-6.84 (m, 3H), 6.78-6.69 (m, 1H), 6.45 (s, 1H), 5.38 (s, 2H), 4.41 (d, J=2.2 Hz, 2H), 3.69 (s, 3H), 1.87-1.61 (m, J=7.1 Hz, 2H), 1.36 (s, 3H), 0.85 (t, J=7.4 Hz, 3H).

Example 121. (2R)-2-([1-[(2-chlorophenyl)methyl]-5-(3-methoxyphenyl)-1H-pyrazol-3-yl]methoxy)-2-methylbutanoic acid

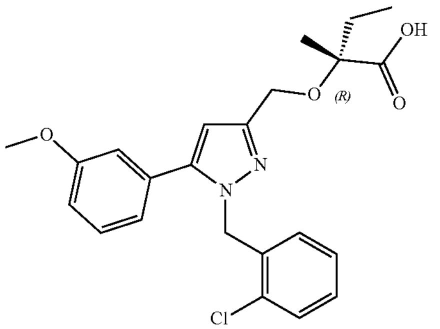

To a solution of methyl (2R)-2-([1-[(2-chlorophenyl)methyl]-5-(3-methoxyphenyl)-1H-pyrazol-3-yl]methoxy)-2-methylbutanoate (80 mg, 0.18 mmol, 1.00 equiv) in THF/$H_2O$/MeOH (4/2/2 mL) was added LiOH (26 mg, 1.09 mmol, 6.00 equiv) in portions at rt. The resulting solution was stirred for 2 h at rt. The pH value was adjusted to 3-4 with conHCl. The resulting solution was extracted with 100 mL of EtOAc, and the organic layers were combined, dried over $Na_2SO_4$, concentrated under vacuum, and purified by Prep-HPLC with the following conditions (2#-AnalyseHPLC-SHIMADZU(HPLC-10)): Column, XBridge Prep OBD C18 Column, 30??150 mm 5 um; mobile phase, Water (0.1% FA) and ACN (40.0% ACN up to 75.0% in 7 min); Detector, UV 254/220 nm to afford 46.3 mg (60%) of the title compound as a colorless oil. LC-MS: (ES, m/z): 429. $^1H$ NMR: (400 MHz, DMSO-$d_6$) δ12.61 (s, 1H), 7.49-7.22 (m, 4H), 7.02-6.84 (m, 3H), 6.78-6.69 (m, 1H), 6.46 (s, 1H), 5.38 (s, 2H), 4.41 (d, J=2.2 Hz, 2H), 3.69 (s, 3H), 1.84-1.61 (m, J=7.6 Hz, 2H), 1.36 (s, 3H), 0.85 (t, J=7.4 Hz, 3H).

The following Examples were prepared using Scheme III.

TABLE 23

Examples 122-127.

| Ex. | Structure | IUPAC Name<br>Analytical data |
|---|---|---|
| 122 | 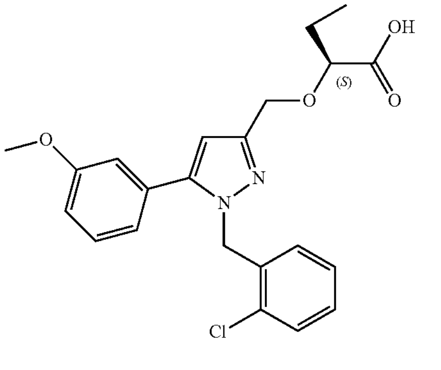 | (2S)-2-([1-[(2-Chlorophenyl)methyl]-5-(3-methoxyphenyl)-1H-pyrazol-3-yl]methoxy)-butanoic acid.<br>LC-MS (ES, m/z): 415.<br>$^1H$-NMR (400 MHz, MeOD) δ 7.46-7.37 (m, 1H), 7.36-7.21 (m, 3H), 7.00-6.88 (m, 2H), 6.82 (dd, J = 2.6, 1.5 Hz, 1H), 6.79-6.71 (m, 1H), 6.58 (s, 1H), 5.44 (s, 2H), 4.76 (d, J = 12.1 Hz, 1H), 4.47 (d, J = 12.1 Hz, 1H), 3.82 (dd, J = 7.3, 4.7 Hz, 1H), 3.68 (s, 3H), 1.89-1.66 (m, 2H), 1.00 (t, J = 7.4 Hz, 3H). |

TABLE 23-continued

| Examples 122-127. | | |
|---|---|---|
| Ex. | Structure | IUPAC Name<br>Analytical data |
| 123 | 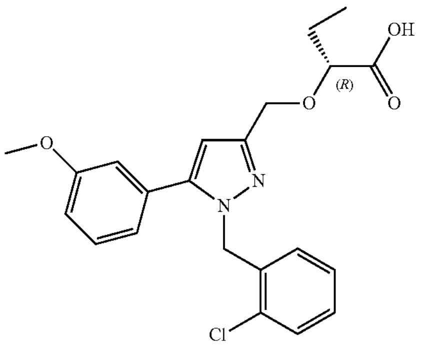 | (2R)-2-([1-[(2-Chlorophenyl)methyl]-5-(3-methoxyphenyl)-1H-pyrazol-3-yl]methoxy)-butanoic acid.<br>LC-MS (ES, m/z): 415<br>$^{1}$H-NMR (300 MHz, MeOD) δ 7.46-7.36 (m, 1H), 7.36-7.22 (m, 3H), 7.00-6.88 (m, 2H), 6.82 (dd, J = 2.6, 1.5 Hz, 1H), 6.78-6.71 (m, 1H), 6.58 (s, 1H), 5.44 (s, 2H), 4.75 (d, J = 12.1 Hz, 1H), 4.46 (d, J = 12.1 Hz, 1H), 3.82 (dd, J = 7.4, 4.8 Hz, 1H), 3.68 (s, 3H), 1.90-1.66 (m, 2H), 1.00 (t, J = 7.4 Hz, 3H). |
| 124 | 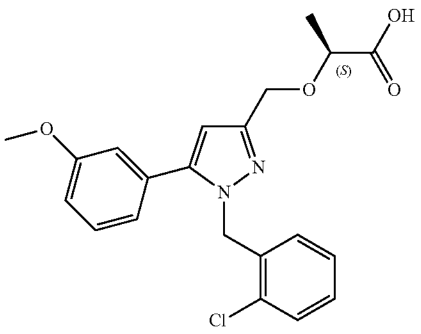 | (2S)-2-([1-[(2-Chlorophenyl)methyl]-5-(3-methoxyphenyl)-1H-pyrazol-3-yl]methoxy)-propanoic acid<br>LC-MS (ES, m/z): 401<br>$^{1}$H-NMR (300 MHz, MeOD) δ 7.49-7.36 (m, 1H), 7.34-7.22 (m, 3H), 7.01-6.89 (m, 2H), 6.83 (dd, J = 2.6, 1.6 Hz, 1H), 6.79-6.71 (m, 1H), 6.55 (s, 1H), 5.45 (s, 2H), 4.73 (d, J = 11.9 Hz, 1H), 4.56 (d, J = 11.9 Hz, 1H), 4.17 (q, J = 6.9 Hz, 1H), 3.68 (s, 3H), 1.44 (d, J = 6.9 Hz, 3H). |
| 125 | 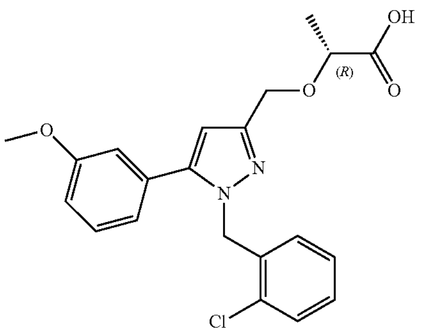 | (2R)-2-([1-[(2-Chlorophenyl)methyl]-5-(3-methoxyphenyl)-1H-pyrazol-3-yl]methoxy)-propanoic acid.<br>LC-MS (ES, m/z): 401<br>$^{1}$H-NMR (300 MHz, MeOD) δ 7.45-7.37 (m, 1H), 7.37-7.22 (m, 3H), 7.01-6.89 (m, 2H), 6.83 (dd, J = 2.6, 1.6 Hz, 1H), 6.79-6.71 (m, 1H), 6.56 (s, 1H), 5.45 (s, 2H), 4.73 (d, J = 11.9 Hz, 1H), 4.56 (d, J = 11.9 Hz, 1H), 4.17 (q, J = 6.9 Hz, 1H), 3.69 (s, 3H), 1.44 (d, J = 6.8 Hz, 3H). |
| 126 | 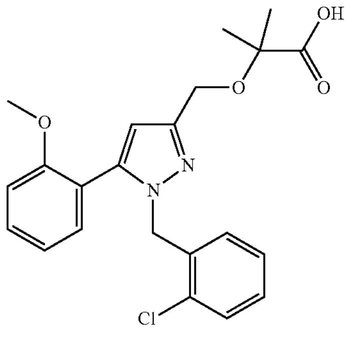 [SMILES: COc1ccccc1-c1cc(COC(C)(C)C(=O)O)nn1Cc1ccccc1Cl] | 2-([1-[(2-Chlorophenyl)methyl]-5-(2-methoxyphenyl)-1H-pyrazol-3-yl]methoxy)-2-methylpropanoic acid<br>$^{1}$H-NMR (300 MHz, MeOD) δ 1.52 (6H, s), 3.64 (3H, s), 4.57 (2H, s), 5.24 (2H, s), 6.40 (1H, s), 6.73-6.83 (1H, m), 6.89-7.10 (2H, m), 7.12-7.24 (3H, m), 7.25-7.46 (2H, m). LC-MS (ES, m/z): 415. |

TABLE 23-continued

| Examples 122-127. | | |
|---|---|---|
| Ex. | Structure | IUPAC Name<br>Analytical data |
| 127 | 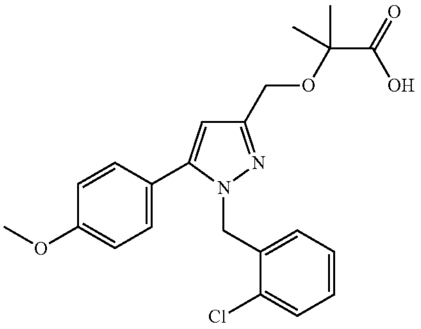 [SMILES: COc1ccc(-c2cc(COC(C)(C)C(=O)O)nn2Cc2ccccc2Cl)cc1] | 2-([1-[(2-Chlorophenyl)methyl]-5-(4-methoxyphenyl)-1H-pyrazol-3-yl]methoxy)-2-methylpropanoic acid.<br>$^{1}$H-NMR (400 MHz, MeOD) δ 7.44-7.37 (m, 1H), 7.35-7.07 (m, 4H), 7.03-6.89 (m, 2H), 6.73 (dd, J = 7.1, 2.1 Hz, 1H), 6.50 (s, 1H), 5.41 (s, 2H), 4.58 (s, 2H), 3.82 (s, 3H), 1.53 (s, 6H). LC-MS (ES, m/z): 415. |

The following Examples were prepared using the indicated Schemes.

TABLE 24

| Examples 128-142. | | | |
|---|---|---|---|
| Ex. | Scheme | Structure | IUPAC Name<br>Analytical Data |
| 128 | VIII | 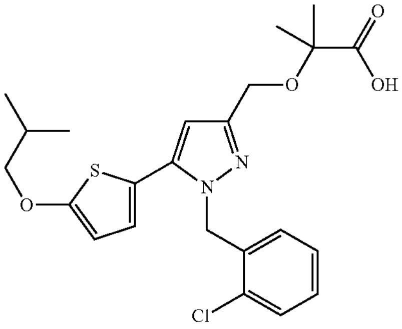 [SMILES: CC(C)COc1ccc(-c2cc(COC(C)(C)C(=O)O)nn2Cc2ccccc2Cl)s1] | 2-([1-[(2-Chlorophenyl)methyl]-5-[5-(2-methylpropoxy)thien-2-yl]-1H-pyrazol-3-yl]methoxy)-2-methylpropanoic acid<br>$^{1}$H-NMR (400 MHz, MeOD) δ 1.01 (dd, 6H), 1.52 (s, 6H), 2.07 (ddd, 1H), 3.83 (dd, 2H), 4.55 (s, 2H), 5.52 (s, 2H), 6.17-6.23 (m, 1H), 6.53 (s, 1H), 6.58-6.66 (m, 2H), 7.20-7.35 (m, 2H), 7.45 (dt, 1H). LC-MS (ES, m/z): 463. |
| 129 | VIII | 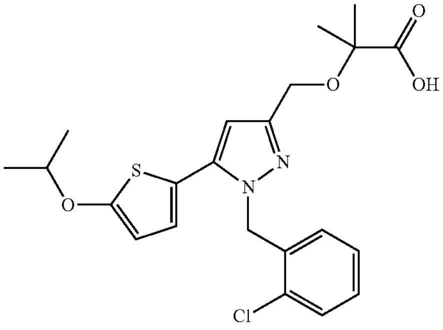 [SMILES: CC(C)Oc1ccc(-c2cc(COC(C)(C)C(=O)O)nn2Cc2ccccc2Cl)s1] | 2-([1-[(2-Chlorophenyl)methyl]-5-[5-(propan-2-yloxy)thien-2-yl]-1H-pyrazol-3-yl]methoxy)-2-methylpropanoic acid<br>$^{1}$H-NMR (400 MHz, DMSO) δ 1.34 (d, 6H), 1.52 (s, 6H), 4.42 (p, 1H), 4.56 (s, 2H), 5.52 (s, 2H), 6.22 (dd, 1H), 6.53 (s, 1H), 6.59-6.67 (m, 2H), 7.19-7.35 (m, 2H), 7.45 (dd, 1H). LC-MS (ES, m/z): 449. |

TABLE 24-continued

| Examples 128-142. | | | |
|---|---|---|---|
| Ex. | Scheme | Structure | IUPAC Name<br>Analytical Data |
| 130 | IX | 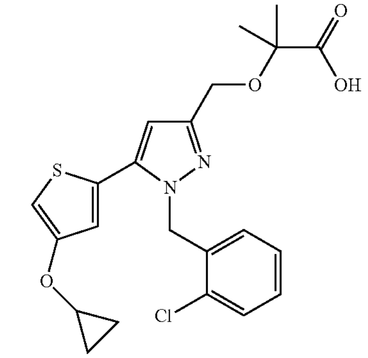 [SMILES: CC(C)(OCc1cc(-c2cc(OC3CC3)cs2)n(Cc2ccccc2Cl)n1)C(=O)O] | 2-([1-[(2-Chlorophenyl)methyl]-5-(4-cyclopropoxythien-2-yl)-1H-pyrazol-3-yl]methoxy)-2-methylpropanoic acid<br>$^{1}$H-NMR (400 MHz, DMSO) δ 1.52 (s, 6H), 1.74-1.90 (m, 2H), 2.65 (t, 2H), 4.45 (t, 1H), 4.58 (s, 2H), 5.55 (s, 2H), 6.61-6.69 (m, 2H), 6.90 (d, 1H), 7.13 (d, 1H), 7.20-7.38 (m, 3H), 7.45 (dd, 1H). LC-MS (ES, m/z): 447. |
| 131 | IX | 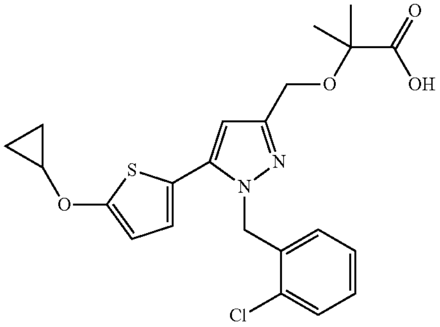 [SMILES: CC(C)(OCc1cc(-c2ccc(OC3CC3)s2)n(Cc2ccccc2Cl)n1)C(=O)O] | 2-([1-[(2-Chlorophenyl)methyl]-5-(5-cyclopropoxythien-2-yl)-1H-pyrazol-3-yl]methoxy)-2-methylpropanoic acid<br>$^{1}$H-NMR (400 MHz, MeOD) δ 1.53 (s, 6H), 1.89 (qd, 2H), 2.89 (t, 2H), 4.51 (t, 1H), 4.58 (s, 2H), 5.55 (s, 2H), 6.62 (d, 2H), 6.76-6.88 (m, 2H), 7.27 (dt, 2H), 7.45 (dd, 1H). LC-MS (ES, m/z): 447. |
| 132 | VIII | 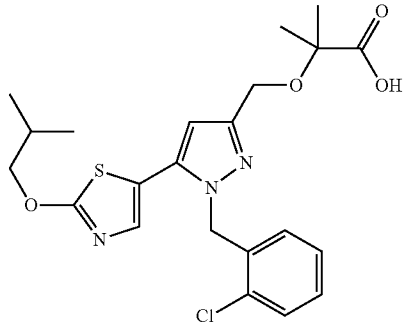 [SMILES: CC(C)COc1ncc(-c2cc(COC(C)(C)C(=O)O)nn2Cc2ccccc2Cl)s1] | 2-([1-[(2-Chlorophenyl)methyl]-5-[2-(2-methylpropoxy)-1,3-thiazol-5-yl]-1H-pyrazol-3-yl]methoxy)-2-methylpropanoic acid<br>$^{1}$H-NMR (400 MHz, DMSO) δ 7.46 (dd, J = 7.9, 1.3 Hz, 1H), 7.32 (td, J = 7.7, 1.7 Hz, 1H), 7.25 (td, J = 7.6, 1.4 Hz, 1H), 7.04 (s, 1H), 6.68-6.60 (m, 2H), 5.52 (s, 2H), 4.57 (s, 2H), 4.18 (d, J = 6.6 Hz, 2H), 2.12 (hept, J = 6.7 Hz, 1H), 1.52 (s, 6H), 1.33 (dd, J = 17.9, 3.5 Hz, 1H), 1.02 (d, J = 6.7 Hz, 6H). LC-MS (ES, m/z): 464. |
| 133 | VIII | 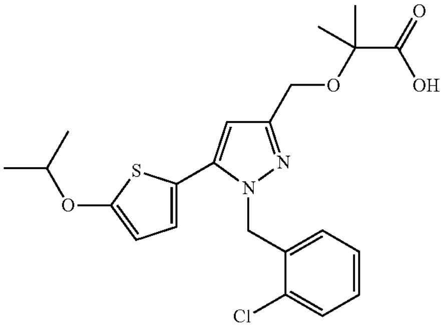 [SMILES: CC(C)Oc1ccc(-c2cc(COC(C)(C)C(=O)O)nn2Cc2ccccc2Cl)s1] | 2-([1-[(2-Chlorophenyl)methyl]-5-[2-(propan-2-yloxy)-1,3-thiazol-5-yl]-1H-pyrazol-3-yl]methoxy)-2-methylpropanoic acid<br>$^{1}$H-NMR (400 MHz, DMSO) δ 7.46 (dd, J = 7.9, 1.4 Hz, 1H), 7.31 (td, J = 7.7, 1.7 Hz, 1H), 7.25 (td, J = 7.5, 1.4 Hz, 1H), 7.03 (s, 1H), 6.64 (dd, J = 7.6, 1.7 Hz, 1H), 6.61 (s, 1H), 5.52 (s, 2H), 5.13 (dq, J = 12.3, 6.2 Hz, 1H), 4.57 (s, 2H), 1.52 (s, 6H), 1.40 (d, J = 6.2 Hz, 6H). LC-MS (ES, m/z): 450. |

TABLE 24-continued

| Ex. | Scheme | Structure | IUPAC Name Analytical Data |
|---|---|---|---|
| | | Examples 128-142. | |
| 134 | X | 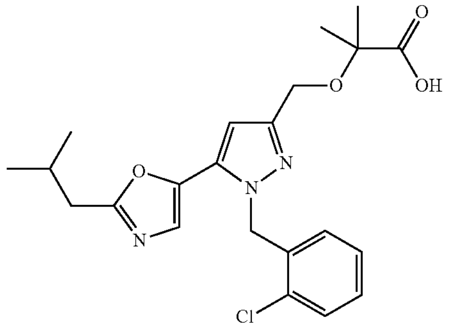 | 2-([1-[(2-Chlorophenyl)methyl]-5-[2-(2-methylpropyl)-1,3-oxazol-5-yl]-1H-pyrazol-3-yl]methoxy)-2-methylpropanoic acid $^{1}$H-NMR (400 MHz, MeOD) 7.46 (dd, J = 7.9, 1.3 Hz, 1H), 7.29 (td, J = 7.5, 1.6 Hz, 1H), 7.25-7.18 (m, 1H), 7.17 (s, 1H), 6.81 (s, 1H), 6.59 (dd, J = 7.7, 1.6 Hz, 1H), 5.65 (s, 2H), 4.59 (s, 2H), 2.64 (d, J = 7.2 Hz, 2H), 2.09-1.93 (m, 1H), 1.53 (s, 6H), 0.88 (d, J = 6.7 Hz, 6H). LC-MS (ES, m/z): 442 |
| 135 | XI | 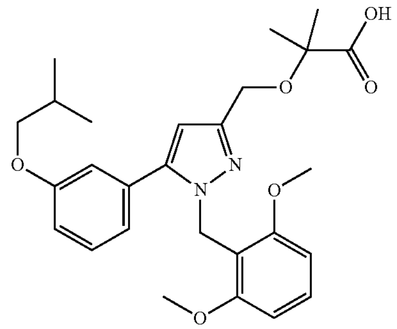 [SMILES: COc1cccc(OC)c1Cn1nc(COC(C)(C)C(=O)O)cc1-c1cccc(OCC(C)C)c1] | 2-([1-[(2,6-Dimethoxyphenyl)methyl]-5-[3-(2-methylpropoxy)phenyl] 1H-pyrazol-3-yl]methoxy)-2-methylpropanoic acid $^{1}$H-NMR (400 MHz, DMSO) δ 0.98 (6H, d), 1.44 (6H, s), 2.01 (1H, dt), 3.16 (1H, s), 3.32 (1H, s), 3.76 (8H, d), 4.66 (2H, s), 5.28 (2H, s), 6.59 (1H, s), 6.69 (2H, d), 6.79 (1H, dt), 7.16-7.35 (4H, m). LC-MS (ES, m/z): 483. |
| 136 | XIV | 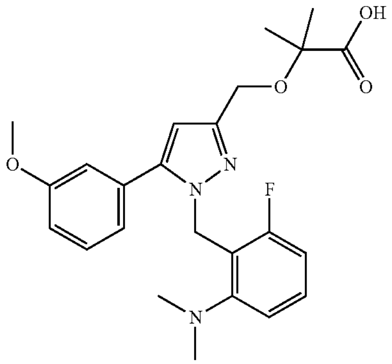 [SMILES: COc1cccc(-c2cc(COC(C)(C)C(=O)O)nn2Cc2c(F)cccc2N(C)C)c1] | 2-[(1-[[2-(Dimethylamino)-6-fluoro-phenyl]methyl]-5-(3-methoxyphenyl)-1H-pyrazol-3-yl)methoxy)-2-methylpropanoic acid $^{1}$H-NMR (400 MHz, DMSO) δ 1.44 (s, 6H), 2.48 (s, 6H), 3.83 (s, 3H), 4.49 (s, 2H), 5.44 (s, 2H), 6.43 (s, 1H), 6.75 (t, 1H), 6.87-7.06 (m, 4H), 7.23 (td, 1H), 7.35 (t, 1H). LC-MS (ES, m/z): 441. |
| 137 | XII | 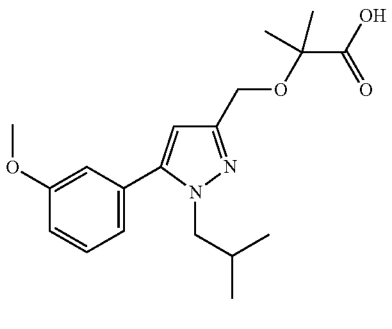 [SMILES: COc1cccc(-c2cc(COC(C)(C)C(=O)O)nn2CC(C)C)c1] | 2-([5-(3-Methoxyphenyl)-1-(2-methylpropyl)-1H-pyrazol-3-yl]methoxy)-2-methylpropanoic acid $^{1}$H-NMR (400 MHz, MeOD) δ 0.76 (d, 6H), 1.28-1.38 (m, 3H), 1.52 (s, 6H), 2.07 (dt, 1H), 3.85 (s, 3H), 3.96 (d, 2H), 4.55 (s, 2H), 6.38 (s, 1H), 6.94-7.07 (m, 3H), 7.41 (t, 1H). LC-MS (ES, m/z): 347. |

TABLE 24-continued

Examples 128-142.

| Ex. | Scheme | Structure | IUPAC Name<br>Analytical Data |
|---|---|---|---|
| 138 | XII | 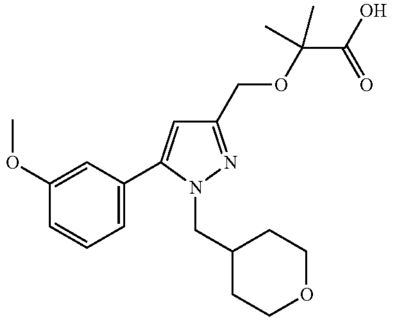 [SMILES: COc1cccc(-c2cc(COC(C)(C)C(=O)O)nn2CC2CCOCC2)c1] | 2-([5-(3-Methoxyphenyl)-1-([oxan-4-yl]methyl)-1H-pyrazol-3-yl]methoxy)-2-methylpropanoic acid<br>$^{1}$H-NMR (400 MHz, MeOD) δ 1.13 (qd, 2H), 1.28-1.41 (m, 5H), 1.52 (s, 6H), 2.06 (dq, 1H), 3.23-3.34 (m, 2H), 3.86 (s, 5H), 4.05 (d, 2H), 4.54 (s, 2H), 6.37 (d, 1H), 6.95-7.08 (m, 3H), 7.43 (t, 1H). LC-MS (ES, m/z): 389. |
| 139 | XI | 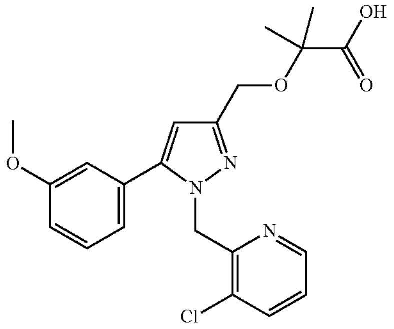 [SMILES: COc1cccc(-c2cc(COC(C)(C)C(=O)O)nn2Cc2ncccc2Cl)c1] | 2-([1-[(3-Chloropyridin-2-yl)methyl]-5-(3-methoxyphenyl)-1H-pyrazol-3-yl]methoxy)-2-methylpropanoic acid<br>$^{1}$H-NMR (400 MHz, MeOD) δ 8.37 (dd, J = 4.7, 1.4 Hz, 1H), 7.89 (dd, J = 8.1, 1.5 Hz, 1H), 7.38-7.24 (m, 4H), 6.91-6.83 (m, 1H), 6.71 (s, 1H), 5.87 (s, 2H), 4.64 (s, 2H), 3.83 (s, 3H), 1.42 (s, 6H). LC-MS (ES, m/z): 416. |
| 140 | XI | 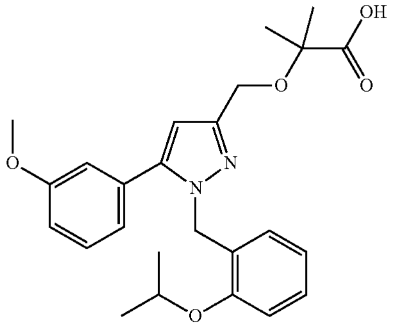 [SMILES: COc1cccc(-c2cc(COC(C)(C)C(=O)O)nn2Cc2ccccc2OC(C)C)c1] | 2-([5-(3-Methoxyphenyl)-1-[[2-(propan-2-yloxy)phenyl]methyl]-1H-pyrazol-3-yl]methoxy)-2-methylpropanoic acid<br>$^{1}$H-NMR (300 MHz, MeOD) δ 1.25 (6H, d), 1.52 (6H, s), 3.64 (3H, s), 4.57 (2H, s), 4.59-4.68 (1H, m), 5.30 (2H, s), 6.51 (1H, s), 6.67 (1H, dd), 6.78-6.88 (2H, m), 6.90-7.00 (3H, m), 7.19-7.26 (1H, m), 7.29 (1H, dd). LC-MS (ES, m/z): 439. |
| 141 | XI | 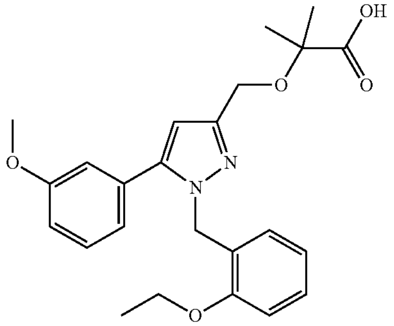 [SMILES: CCOc1ccccc1Cn1nc(COC(C)(C)C(=O)O)cc1-c1cccc(OC)c1] | 2-([1-[(2-Ethoxyphenyl)methyl]-5-(3-methoxyphenyl)-1H-pyrazol-3-yl]methoxy)-2-methylpropanoic acid.<br>LC-MS (ES, m/z): 425<br>$^{1}$H-NMR (400 MHz, $CDCl_3$) δ 1.33 (3H, t), 1.56 (6H, s), 3.68 (3H, s), 4.00 (2H, q), 4.65 (2H, s), 5.40 (2H, s), 6.43 (1H, s), 6.77-6.82 (1H, m), 6.83-6.89 (3H, m), 6.89-6.98 (2H, m), 7.16-7.24 (1H, m), 7.26-7.32 (1H, m). |

TABLE 24-continued

| Examples 128-142. | | | |
|---|---|---|---|
| Ex. | Scheme | Structure | IUPAC Name Analytical Data |
| 142 | XI | 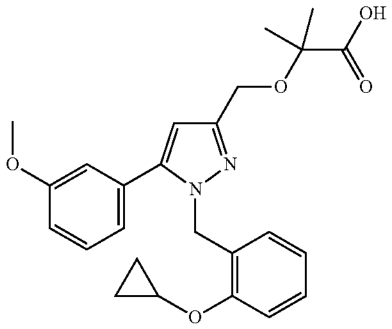 [SMILES: COc1cccc(-c2cc(COC(C)(C)C(=O)O)nn2Cc2ccccc2OC2CC2)c1] | 2-([1-[(2-Cyclopropoxyphenyl)methyl]-5-(3-methoxyphenyl)-1H-pyrazol-3-yl]methoxy)-2-methylpropanoic acid LC-MS (ES, m/z): 437 $^1$H-NMR (300 MHz, MeOD) δ 7.27 (m, 3H), 6.94 (m, 2H), 6.88 (m, 1H), 6.82 (dd, J = 2.6, 1.5 Hz, 1H), 6.72 (d, J = 7.4 Hz, 1H), 6.48 (s, 1H), 5.25 (s, 2H), 4.56 (s, 2H), 3.77 (tt, J = 6.0, 6.0, 3.0, 3.0 Hz, 1H), 3.67 (s, 3H), 1.51 (s, 6H), 0.75 (m, 2H), 0.58 (m, 2H). |

Example 143: (3E)-4-[1-[(2-Chlorophenyl)methyl]-5-(3-methoxyphenyl)-1H-pyrazol-3-yl]-2,2-dimethylbut-3-enoic acid

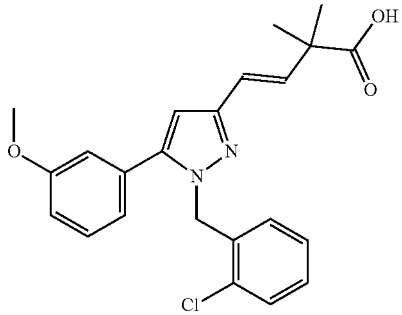 [SMILES: COc1cccc(-c2cc(/C=C/C(C)(C)C(=O)O)nn2Cc2ccccc2Cl)c1]

(ii) ([1-[(2-Chlorophenyl)methyl]-5-(3-methoxyphenyl)-1H-pyrazol-3-yl]methyl)triphenylphosphonium bromide. To a solution of Int. G-1 (2.4 g, 6.13 mmol, 1.00 equiv) in toluene (20 mL) was added $PPh_3$ (2.4 g, 9.15 mmol, 1.50 equiv) at room temperature. The resulting solution was stirred for 3 h at 110° C. The solids were collected by filtration. The solid was dried in an oven under reduced pressure. This resulted in the title compound as a white solid (2.2 g, 55%).

(iii) Methyl (3E)-4-[1-[(2-chlorophenyl)methyl]-5-(3-methoxyphenyl)-1H-pyrazol-3-yl]-2,2-dimethylbut-3-enoate. To a solution of ([1-[(2-chlorophenyl)methyl]-5-(3-methoxyphenyl)-1H-pyrazol-3-yl]methyl) triphenylphosphonium bromide (500 mg, 0.76 mmol, 1.00 equiv) in THF (20 mL) was added methyl 2,2-dimethyl-3-oxopropanoate (200 mg, 1.54 mmol, 2.00 equiv). This was followed by the addition of NaH (50 mg, 1.25 mmol, 2.00 equiv), in portions at 0° C. The resulting solution was stirred for 16 h at room temperature then quenched by the addition of water/ice. The resulting solution was diluted with 100 mL of EtOAc, then washed with 2×50 mL of brine. The mixture was dried over $Na_2SO_4$ and concentrated under vacuum. The residue was applied onto a Prep-TLC with EtOAc/petroleum ether (1:2). This resulted in the title compound as a colorless oil (125 mg, 38%).

(iv) (3E)-4-[1-[(2-Chlorophenyl)methyl]-5-(3-methoxyphenyl)-1H-pyrazol-3-yl]-2,2-dimethylbut-3-enoic acid was obtained analogously as described in Step iv of Example 101 using methyl (3E)-4-[l-[(2-chlorophenyl)methyl]-5-(3-methoxyphenyl)-1H-pyrazol-3-yl]-2,2-dimethylbut-3-enoate as starting material. $^1$H-NMR (400 MHz, MeOD) δ 1.42 (s, 6H), 3.69 (s, 3H), 5.43 (s, 2H), 6.49 (d, 1H), 6.56-6.68 (m, 2H), 6.71-6.79 (m, 1H), 6.84 (dd, 1H), 6.90-7.06 (m, 2H), 7.23-7.47 (m, 5H). LC-MS (ES, m/z): 411.

Example 144: 4-[1-[(2-chlorophenyl)methyl]-5-(3-methoxyphenyl)-1H-pyrazol-3-yl]-2,2-dimethylbutanoic acid

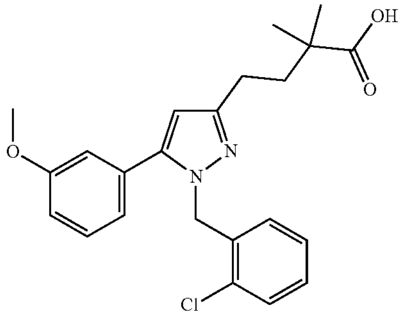 [SMILES: COc1cccc(-c2cc(CCC(C)(C)C(=O)O)nn2Cc2ccccc2Cl)c1]

(i) Methyl (3E)-4-[1-[(2-chlorophenyl)methyl]-5-(3-methoxyphenyl)-1H-pyrazol-3-yl]-2,2-dimethylbut-3-enoate was obtained as in Steps i-iii of Example 143.

(ii) Methyl 4-[1-[(2-chlorophenyl)methyl]-5-(3-methoxyphenyl)-1H-pyrazol-3-yl]-2,2-dimethylbutanoate. To a solution of methyl (3E)-4-[1-[(2-chlorophenyl) methyl]-5-(3-methoxyphenyl)-1H-pyrazol-3-yl]-2,2-dimethylbut-3-enoate (60 mg, 0.14 mmol, 1.00 equiv) in EtOAc/MeOH (10/10 mL) was added Pd/C (20 mg). The resulting solution was stirred for 3 h under $H_2$ at room temperature. The solids were removed by filtration. The resulting mixture was concentrated under vacuum. The residue was purified by Prep-TLC with 20:1 $CH_2Cl_2$: MeOH. This resulted in the title compound as a colorless oil (40 mg, 66%).

(iii) 4-[1-[(2-chlorophenyl)methyl]-5-(3-methoxyphenyl)-1H-pyrazol-3-yl]-2,2-dimethylbutanoic acid was obtained analogously as described in Step iv of Example 101 using methyl 4-[1-[(2-chlorophenyl)methyl]-5-(3-methoxyphenyl)-1H-pyrazol-3-yl]-2,2-dimethylbutanoate as starting material. $^1$H-NMR (400 MHz, MeOD) δ 1.26-1.38 (m, 6H), 1.98 (s, 2H), 2.69 (s, 2H), 3.68 (s, 3H), 5.41 (s, 2H), 6.35 (s, 1H), 6.69 (dd, 1H), 6.81 (dd, 1H), 6.87-7.00 (m, 2H), 7.23-7.36 (m, 3H), 7.38-7.45 (m, 1H). LC-MS (ES, m/z): 413.

Examples 145-149 are intentionally left blank.

Example 150: 2-([1-[(2-Chlorophenyl)methyl]-5-(1-ethyl-1H-indazol-6-yl)-1H-pyrazol-3-yl]-methoxy)-2-methylpropanoic acid

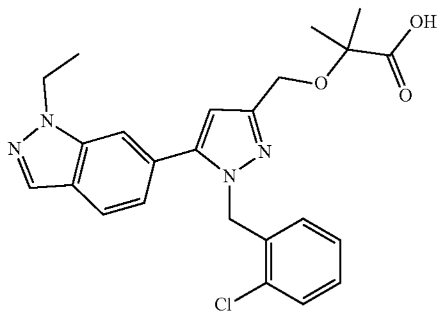 [SMILES: CCn1ncc2ccc(-c3cc(COC(C)(C)C(=O)O)nn3Cc3ccccc3Cl)cc21]

To a solution of Int. H-64 (120 mg, 0.26 mmol, 1.00 equiv) in THF/$H_2O$/MeOH (8/4/4 mL) was added LiOH (37 mg, 1.54 mmol, 6.00 equiv), in portions at room temperature. The resulting solution was stirred for 2 h at room temperature. The pH was then adjusted to 3-4 with aq HCl. The resulting solution was extracted with 100 mL EtOAc, and the combined organic layers were dried over $Na_2SO_4$ and concentrated under vacuum. The crude product (100 mg) was purified by Prep-HPLC with the following conditions (2#-AnalyseHPLC-SHIMADZU(HPLC-10)): Column, XBridge Prep OBD C18 Column, 30??150 mm 5 um; mobile phase, Water (0.1% FA) and ACN (38.0% ACN up to 65.0% in 7 min); Detector, uv 254/220 nm, to afford 42 mg (36%) of the title compound as a white solid. LC-MS: (ES, m/z): 453. $^1$H-NMR: (DMSO) δ: 12.70 (s, 1H), 8.09 (d, J=0.9 Hz, 1H), 7.80 (dd, J=8.4, 0.8 Hz, 1H), 7.70 (t, J=1.1 Hz, 1H), 7.48-7.37 (m, 1H), 7.36-7.23 (m, 2H), 7.14 (dd, J=8.4, 1.3 Hz, 1H), 6.86-6.75 (m, 1H), 6.55 (s, 1H), 5.47 (s, 2H), 4.46 (s, 2H), 4.41 (q, J=0.9 Hz, 2H), 1.42 (s, 6H), 1.36 (t, J=0.6 Hz, 3H).

Example 151: Sodium 2-([1-[(2-chlorophenyl)methyl]-5-(1-ethyl-1H-indazol-6-yl)-1H-pyrazol-3-yl]methoxy)-2-methylpropanoate

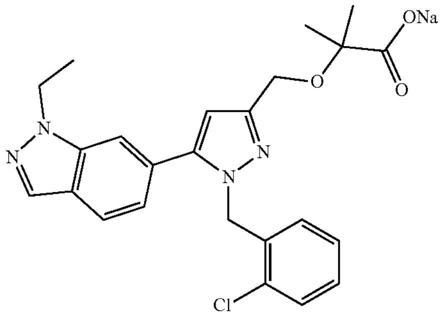

A solution of 2-([1-[(2-chlorophenyl)methyl]-5-(1-ethyl-1H-indazol-6-yl)-1H-pyrazol-3-yl]methoxy)-2-methylpropanoic acid (Example 150, 50 mg, 0.11 mmol, 1.00 equiv) and NaOH (18 mg, 0.45 mmol, 4.00 equiv) in MeOH/$H_2O$ (5/2 mL) was stirred for 3 h at rt, then purified by Prep-HPLC with the following conditions (2#-AnalyseHPLC-SHIMADZU(HPLC-10)): Column, XBridge Shield RP18 OBD Column, 5 um, 19*150 mm; mobile phase, Water (10 MMOL/L NH4HCO3) and MeOH— (15.0% MeOH— up to 95.0% in 7 min); Detector, UV 254/220 nm, to afford 20.9 mg (40%) of the title compound as a white solid. LC-MS: (ES, m/z): 453.00. $^1$H NMR (300 MHz, DMSO) δ 8.07 (s, 1H), 7.77 (d, J=8.3 Hz, 1H), 7.65 (s, 1H), 7.41 (m, 1H), 7.28 (m, 2H), 7.10 (d, J=8.4 Hz, 1H), 6.79 (m, 1H), 6.56 (s, 1H), 5.46 (s, 2H), 4.49 (s, 2H), 4.37 (q, J=7.2, 7.2, 7.2 Hz, 2H), 1.34 (d, J=17.1 Hz, 9H).

Example 152: 2-([5-(3-Cyclopropoxyphenyl)-1-(1H-indazol-7-yl)-1H-pyrazol-3-yl]methoxy)-2-methylpropanoic acid

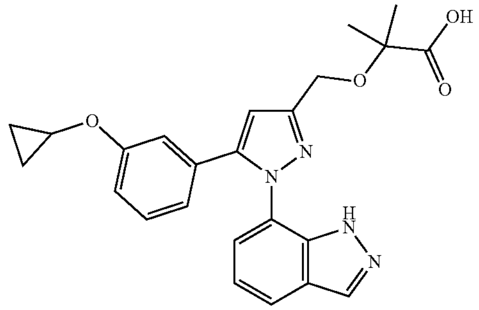 [SMILES: CC(C)(OCc1cc(-c2cccc(OC3CC3)c2)n(-c2cccc3cn[nH]c23)n1)C(=O)O]

(i) 2-([5-(3-Cyclopropoxyphenyl)-1-(1-[[2-(trimethylsilyl)ethoxy]methyl]-1H-indazol-7-yl)-1H-pyrazol-3-yl]methoxy)-2-methylpropanoic acid A solution of Int. H-76 (100 mg, 0.17 mmol, 1.00 equiv) and LiOH (20 mg, 0.84 mmol, 4.00 equiv) in THF/$H_2O$ (4/1 mL) was stirred for 2 h at room temperature, then cooled to 0° C. The pH was adjusted to 1 with 1 M HCl. The resulting solution was extracted with 2×100 mL EtOAc, and the combined organic layers were washed with 100 mL of brine, dried over $Na_2SO_4$ and concentrated under vacuum, to afford 50 mg (51%) of the title compound as a white solid. LC-MS: (ES, m/z): 563.

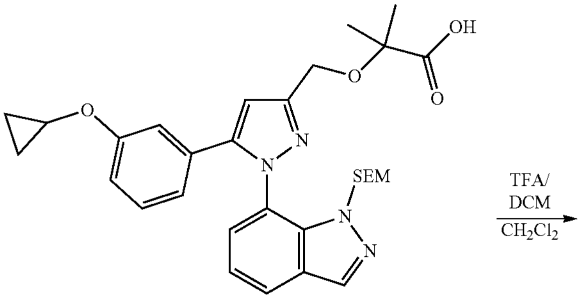

-continued

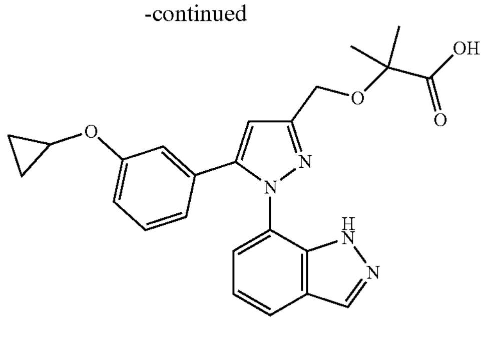

(ii) 2-([5-(3-Cyclopropoxyphenyl)-1-(1H-indazol-7-yl)-1H-pyrazol-3-yl]methoxy)-2-methylpropanoic acid A solution of the product from the previous step (50 mg, 0.09 mmol, 1.00 equiv) and TFA (3 mL) in $CH_2Cl_2$ (10 mL) was stirred for 5 h at room temperature, then concentrated under vacuum. The crude product (50 mg) was purified by Prep-HPLC with the following conditions (2#-AnalyseHPLC-SHIMADZU(HPLC-10)): Column, Xselect CSH OBD Column 30*150 mm 5 um, n; mobile phase, Water (0.1% FA) and ACN (43.0% ACN up to 55.0% in 7 min); Detector, UV 254/220 nm, to afford 15 mg (39%) of the title compound as a white solid. LC-MS: (ES, m/z): 433. $^1$H NMR (300 MHz, DMSO-$d_6$) δ 13.09 (s, 1H), 8.18 (s, 1H), 7.81 (dd, J=7.0, 2.0 Hz, 1H), 7.20 (t, J=7.9 Hz, 1H), 7.14-7.02 (m, 2H), 6.95-6.85 (m, 2H), 6.85-6.80 (m, 1H), 6.71 (s, 1H), 4.55 (s, 2H), 3.45 (tt, J=6.3, 3.0 Hz, 1H), 1.44 (s, 6H), 0.58-0.43 (m, 2H), 0.43-0.26 (m, 2H).

Example 153: 2-([5-(3-Cyclopropoxyphenyl)-1-(1H-indazol-4-yl)-1H-pyrazol-3-yl]methoxy)-2-methylpropanoic acid

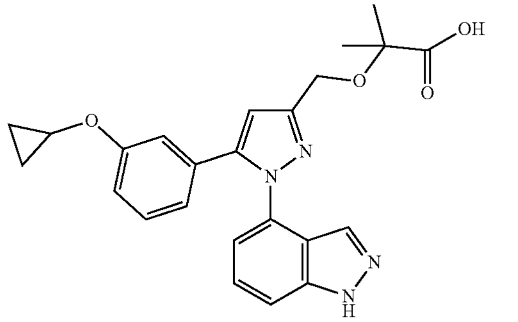 [SMILES: CC(C)(OCc1cc(-c2cccc(OC3CC3)c2)n(-c2cccc3[nH]ncc23)n1)C(=O)O]

(i) 2-([5-(3-cyclopropoxyphenyl)-1-(1-[[2-(trimethylsilyl)ethoxy]methyl]-1H-indazol-4-yl)-1H-pyrazol-3-yl]methoxy)-2-methylpropanoic acid A solution of Int. H-77 (160 mg, 0.28 mmol, 1.00 equiv) and LiOH (70 mg, 2.92 mmol, 10.54 equiv) in THF/MeOH/$H_2O$ (5/1/1 mL) was stirred for 3 h at room temperature. The pH value was adjusted to 5 with 1 M HCl. The resulting solution was extracted with 3×20 mL EtOAc. The combined organic layers were concentrated under reduced pressure and dried, to afford 140 mg (90%) of the title compound as light yellow oil. LC-MS: (ES, m/z): 563.2.

(ii) 2-([5-(3-Cyclopropoxyphenyl)-1-(1H-indazol-4-yl)-1H-pyrazol-3-yl]methoxy)-2-methylpropanoic acid A solution of the product from the previous step (140 mg, 0.25 mmol, 1.00 equiv) and HCl/dioxane (5 mL) was stirred for 3 h at room temperature, then concentrated under vacuum. The crude product (100 mg) was purified by Prep-HPLC with the following conditions (2#-AnalyseHPLC-SHIMADZU(HPLC-10)): Column, Xselect CSH F-Phenyl OBD Column 19*150 mm 5 um, n; mobile phase, Water (0.1% FA) and ACN (35.0% ACN up to 45.0% in 7 min); Detector, uv 254/220 nm, to afford 18.9 mg (18%) of the title compound as a white solid. LC-MS: (ES, m/z): 433.05. $^1$H NMR (300 MHz, DMSO) δ 13.29 (s, 1H), 7.69 (d, J=1.0 Hz, 1H), 7.57 (d, J=8.4 Hz, 1H), 7.35 (dd, J=8.4, 7.3 Hz, 1H), 7.21 (t, J=7.9, 7.9 Hz, 1H), 6.91 (dtd, J=8.3, 5.8, 4.8, 3.0 Hz, 3H), 6.81 (m, 1H), 6.70 (s, 1H), 4.53 (s, 2H), 3.52 (tt, J=6.2, 6.2, 3.0, 3.0 Hz, 1H), 1.44 (s, 6H), 0.46 (m, 2H), 0.36 (m, 2H).

Example 154: 2-([5-(3-cyclopropoxyphenyl)-1-(3-methyl-1H-indazol-4-yl)-1H-pyrazol-3-yl]methoxy)-2-methylpropanoic acid

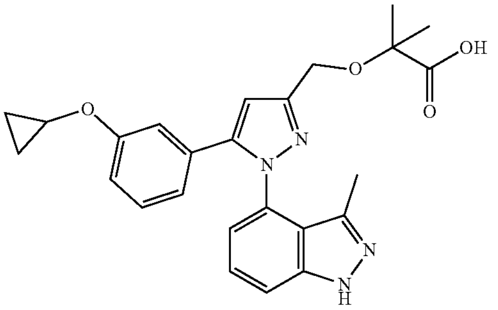 [SMILES: Cc1n[nH]c2cccc(-n3nc(COC(C)(C)C(=O)O)cc3-c3cccc(OC4CC4)c3)c12]

(i) 2-([5-(3-cyclopropoxyphenyl)-1-(3-methyl-1-[[2-(trimethylsilyl)ethoxy]methyl]-1H-indazol-4-yl)-1H-pyrazol-3-yl]methoxy)-2-methylpropanoic acid A solution of Int. H-78 (100 mg, 0.17 mmol, 1.00 equiv) and LiOH (40 mg, 1.67 mmol, 10.00 equiv) in THF/MeOH/$H_2O$ (5/1/1 mL) was stirred for 3 h at room temperature. The pH value of the solution was adjusted to 5 with 1 M HCl. The resulting solution was extracted with 3×15 mL of EtOAc. The combined organic layers were dried over $Na_2SO_4$ and concentrated under vacuum, to afford 80 mg (82%) of the title compound as light yellow oil. LC-MS: (ES, m/z): 577.3.

(ii) 2-([5-(3-cyclopropoxyphenyl)-1-(3-methyl-1H-indazol-4-yl)-1H-pyrazol-3-yl]methoxy)-2-methylpropanoic acid A solution of the product from the previous step (80 mg, 0.14 mmol, 1.00 equiv) in HCl/dioxane (5 mL) was stirred 3 h at room temperature, then concentrated under vacuum. The crude product was purified by Prep-HPLC with the following conditions (2#-AnalyseHPLC-SHIMADZU(HPLC-10)): Column, Xselect CSH OBD Column 30*150 mm 5 um, n; mobile phase, Water (0.1% FA) and ACN (40.0% ACN up to 50.0% in 7 min); Detector, UV 254/220 nm, to afford 8.2 mg (13%) of the title compound as a white solid. LC-MS: (ES, m/z): 447.15. $^1$H NMR (300 MHz, MeOD) δ 7.62 (dd, J=8.5, 0.8 Hz, 1H), 7.42 (dd, J=8.5, 7.2 Hz, 1H), 7.17 (t, J=7.9, 7.9 Hz, 1H), 6.99 (m, 2H), 6.80 (m, 3H), 4.65 (s, 2H), 3.25 (dt, J=5.7, 2.6, 2.6 Hz, 1H), 2.07 (s, 3H), 1.54 (s, 6H), 0.41 (m, 4H).

The following substituted pyrazole carboxylic acids were obtained from LiOH hydrolysis of the corresponding methyl esters:

TABLE 25

Examples 155-276.

| Ex. | Ester | Structure | IUPAC Name<br>Purification Analytical data |
|---|---|---|---|
| 155 | H-134 | 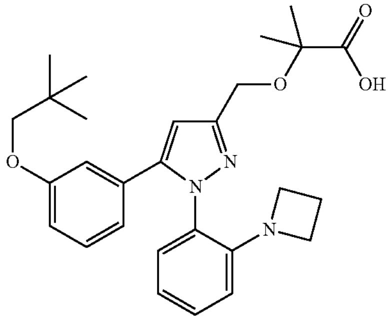 [SMILES: CC(C)(C)COc1cccc(-c2cc(COC(C)(C)C(=O)O)nn2-c2ccccc2N2CCC2)c1] | 2-([1-[2-(Azetidin-1-yl)phenyl]-5-[3-(2,2-dimethylpropoxy)phenyl]-1H-pyrazol-3-yl]methoxy)-2-methylpropanoic acid<br>XSelect: 63% ACN up to 83% in 7 min<br>LC-MS: (ES, m/z): 478.25.<br>$^1$H NMR (300 MHz, MeOD) δ 7.30 (ddd, J = 8.6, 7.4, 1.6 Hz, 1H), 7.20 (t, J = 7.9, 7.9 Hz, 1H), 7.03 (m, 2H), 6.87 (t, J = 2.0, 2.0 Hz, 1H), 6.82 (ddd, J = 8.2, 2.5, 1.0 Hz, 1H), 6.75 (td, J = 7.6, 7.5, 1.3 Hz, 1H), 6.70 (s, 1H), 6.55 (dd, J = 8.2, 1.3 Hz, 1H), 4.59 (s, 2H), 3.57 (d, J = 21.2 Hz, 4H), 2.13 (p, J = 7.3, 7.3, 7.3, 7.3 Hz, 2H), 1.53 (s, 6H), 0.98 (s, 9H). |
| 156 | H-38 | 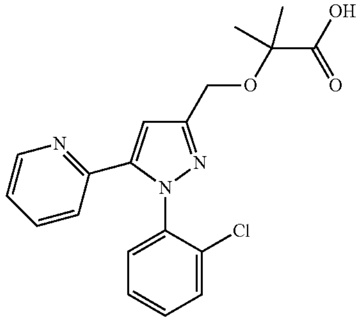 [SMILES: CC(C)(OCc1cc(-c2ccccn2)n(-c2ccccc2Cl)n1)C(=O)O] | 2-([1-(2-Chlorophenyl)-5-(pyridin-2-yl)-1H-pyrazol-3-yl]methoxy)-2-methylpropanoic acid<br>Xselect: 10% ACN up to 67% in 7 min<br>LC-MS: (ES, m/z): 371.95.<br>H-NMR: $^1$H NMR (300 MHz, DMSO) δ 12.68 (s, 1H), 8.31 (ddd, J = 4.9, 1.8, 0.9 Hz, 1H), 7.77 (td, J = 7.8, 7.7, 1.8 Hz, 1H), 7.51 (m, 5H), 7.24 (ddd, J = 7.6, 4.8, 1.1 Hz, 1H), 6.96 (s, 1H), 4.49 (s, 2H), 1.43 (s, 6H). |
| 157 | H-40 | 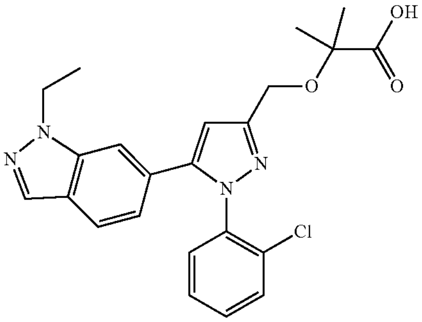 | 2-([1-(2-chlorophenyl)-5-(1-ethyl-1H-indazol-6-yl)-1H-pyrazol-3-yl]methoxy)-2-methylpropanoic acid<br>XBridge: 30% ACN up to 57% in 7 min<br>LC-MS: (ES, m/z): 381.<br>$^1$H-NMR: (DMSO, ppm): 8.02 (d, J = 1.1 Hz, 1H), 7.89-7.75 (m, 1H), 7.73-7.47 (m, 5H), 7.34 (d, J = 1.4 Hz, 1H), 6.95 (dt, J = 8.4, 1.4 Hz, 1H), 4.44-4.22 (m, 2H), 3.88 (d, J = 1.4 Hz, 3H), 1.24 (td, J = 7.1, 1.4 Hz, 3H). |
| 158 | H-27 | 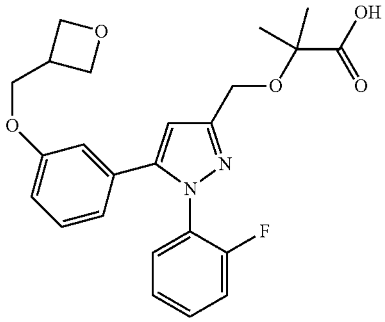 [SMILES: CC(C)(OCc1cc(-c2cccc(OCC3COC3)c2)n(-c2ccccc2F)n1)C(=O)O] | 2-([1-(2-Fluorophenyl)-5-[3-(oxetan-3-ylmethoxy)phenyl]-1H-pyrazol-3-yl]-methoxy)-2-methylpropanoic acid<br>XBridge: 25% ACN up to 60% in 7 min<br>LC-MS0: (ES, m/z): 441.<br>$^1$H NMR: (DMSO) δ: 12.71 (s, 1H), 7.63-7.47 (m, 2H), 7.40-7.29 (m, 2H), 7.22 (t, J = 8.0 Hz, 1H), 6.91 (ddd, J = 8.4, 2.6, 1.0 Hz, 1H), 6.85-6.68 (m, 3H), 4.67 (dd, J = 7.9, 6.0 Hz, 2H), 4.49 (s, 2H), 4.35 (t, J = 6.0 Hz, 2H), 4.09 (d, J = 6.8 Hz, 2H), 3.34-3.23 (m, 1H), 1.43 (s, 6H). |

TABLE 25-continued

| Examples 155-276. | | | |
|---|---|---|---|
| Ex. | Ester | Structure | IUPAC Name Purification Analytical data |
| 159 | H-28 | 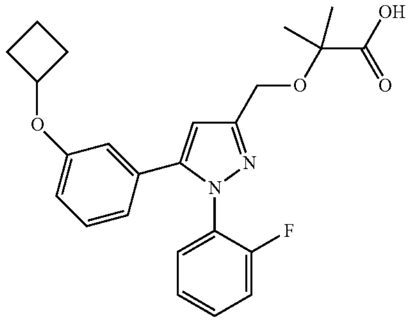 [SMILES: CC(C)(OCc1cc(-c2cccc(OC3CCC3)c2)n(-c2ccccc2F)n1)C(=O)O] | 2-([5-(3-Cyclobutoxyphenyl)-1-(2-fluorophenyl)-1H-pyrazol-3-yl]-methoxy)-2-methylpropanoic acid XBridge: 47% ACN up to 67% in 7 min LC-MS: (ES, m/z): 425. $^{1}$H NMR: (400 MHz, DMSO-d6) δ 7.65-7.48 (m, 2H), 7.41-7.29 (m, 2H), 7.23 (t, J = 8.0 Hz, 1H), 6.93-6.74 (m, 2H), 6.67 (s, 1H), 6.57 (dd, J = 2.5, 1.5 Hz, 1H), 4.48 (s, 2H), 4.43 (q, J = 7.1 Hz, 1H), 2.23 (dddd, J = 9.2, 7.8, 6.5, 2.6 Hz, 2H), 1.91 (qdd, J = 9.8, 7.7, 2.7 Hz, 2H), 1.78-1.66 (m, 1H), 1.64-1.50 (m, 1H), 1.43 (s, 6H). |
| 160 | H-29 | 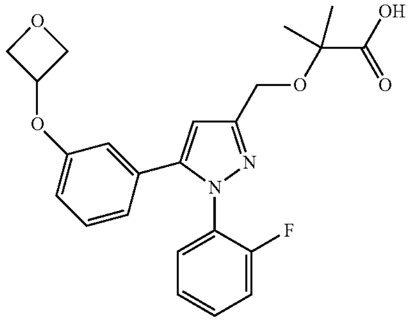 | 2-([1-(2-Fluorophenyl)-5-[3-(oxetan-3-yloxy)phenyl]-1H-pyrazol-3-yl]-methoxy)-2-methylpropanoic acid XBridge: 28% ACN up to 54% in 7 min LC-MS: (ES, m/z): 427. $^{1}$H NMR: (300 MHz, DMSO) δ 7.58 (td, J = 8.0, 7.8, 1.9 Hz, 1H), 7.51 (m, 1H), 7.36 (m, 2H), 7.27 (m, 1H), 6.88 (dt, J = 7.7, 1.2, 1.2 Hz, 1H), 6.77 (ddd, J = 8.3, 2.6, 0.9 Hz, 1H), 6.68 (s, 1H), 6.49 (dd, J = 2.6, 1.5 Hz, 1H), 5.09 (m, 1H), 4.73 (m, 2H), 4.48 (s, 2H), 4.37 (m, 2H), 1.42 (s, 6H). |
| 161 | H-5 | 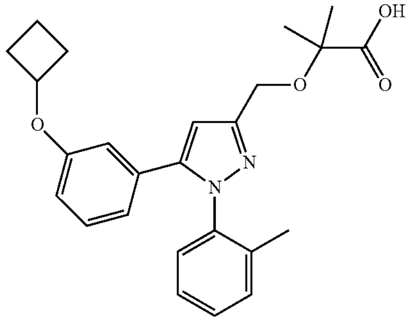 [SMILES: Cc1ccccc1-n1nc(COC(C)(C)C(=O)O)cc1-c1cccc(OC2CCC2)c1] | 2-([5-(3-Cyclobutoxyphenyl)-1-(2-methylphenyl)-1H-pyrazol-3-yl]-methoxy)-2-methylpropanoic acid XBridge: 48% ACN up to 69% in 7 min LC-MS: (ES, m/z): 421. $^{1}$H NMR: (400 MHz, DMSO-$d_6$) δ 12.70 (s, 1H), 7.45-7.25 (m, 4H), 7.20 (t, J = 8.0 Hz, 1H), 6.90-6.81 (m, 1H), 6.75 (dd, J = 8.2, 2.4 Hz, 1H), 6.66 (s, 1H), 6.55-6.45 (m, 1H), 4.48 (s, 2H), 4.34 (p, J = 7.2 Hz, 1H), 2.22 (dddt, J = 11.6, 8.7, 5.9, 2.4 Hz, 2H), 1.92 (ddd, J = 9.8, 7.6, 2.7 Hz, 2H), 1.88 (s, 3H), 1.71 (dd, J = 11.7, 8.5 Hz, 1H), 1.57 (tt, J = 10.1, 8.1 Hz, 1H), 1.43 (s, 6H). |
| 162 | H-30 | 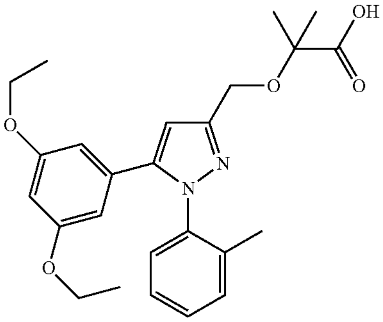 [SMILES: CCOc1cc(OCC)cc(-c2cc(COC(C)(C)C(=O)O)nn2-c2ccccc2C)c1] | 2-([5-(3,5-Diethoxyphenyl)-1-(2-methylphenyl)-1H-pyrazol-3-yl]methoxy)-2-methylpropanoic acid XSelect: 48% ACN up to 75% in 7 min LC-MS: (ES, m/z): 439.15. $^{1}$H NMR (300 MHz, DMSO) δ 12.70 (s, 1H), 7.32 (m, 4H), 6.68 (s, 1H), 6.35 (t, J = 2.2, 2.2 Hz, 1H), 6.28 (d, J = 2.2 Hz, 2H), 4.48 (s, 2H), 3.81 (q, J = 6.9, 6.9, 6.9 Hz, 4H), 1.87 (s, 3H), 1.42 (s, 6H), 1.19 (t, J = 6.9, 6.9 Hz, 6H). |

TABLE 25-continued

| Examples 155-276. | | | |
|---|---|---|---|
| Ex. | Ester | Structure | IUPAC Name<br>Purification Analytical data |
| 163 | H-82 | 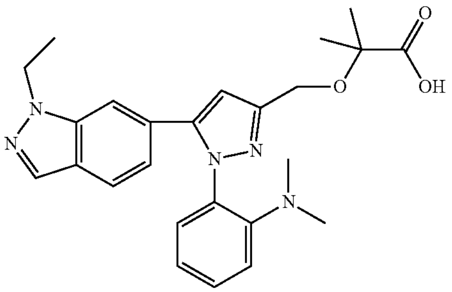 [SMILES: CCn1ncc2ccc(-c3cc(COC(C)(C)C(=O)O)nn3-c3ccccc3N(C)C)cc21] | 2-([1-[2-(dimethylamino)phenyl]-5-(1-ethyl-1H-indazol-6-yl)-1H-pyrazol-3-yl]methoxy)-2-methylpropanoic acid<br>XSelect: 35% ACN up to 65% in 7 min<br>LC-MS (ES, m/z): 448.20.<br>$^1$H NMR (300 MHz, DMSO) δ 8.16 (s, 0.12H), 7.97 (d, J = 0.9 Hz, 1H), 7.60 (dd, J = 8.4, 0.8 Hz, 1H), 7.32 (m, 3H), 6.98 (m, 2H), 6.85 (dd, J = 8.2, 1.3 Hz, 1H), 6.73 (s, 1H), 4.52 (s, 2H), 4.25 (q, J = 7.1, 7.1, 7.1 Hz, 2H), 2.13 (s, 6H), 1.43 (s, 6H), 1.20 (t, J = 7.2, 7.2 Hz, 3H). |
| 164 | H-31 | 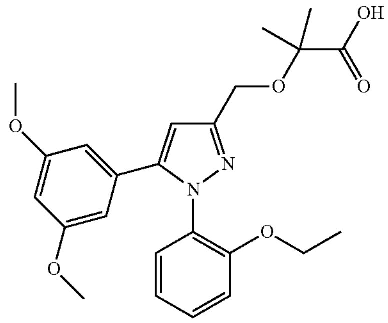 [SMILES: CCOc1ccccc1-n1nc(COC(C)(C)C(=O)O)cc1-c1cc(OC)cc(OC)c1] | 2-([5-(3,5-Dimethoxyphenyl)-1-(2-ethoxyphenyl)-1H-pyrazol-3-yl]-methoxy)-2-methylpropanoic acid<br>XBridge: 35% ACN up to 65% in 7 min<br>LC-MS: (ES, m/z): 441.<br>$^1$H NMR: (300 MHz, MeOH-$d_4$) δ 7.44 (td, J = 7.6, 1.5 Hz, 2H), 7.15-6.99 (m, 2H), 6.68 (s, 1H), 6.44-6.35 (m, 3H), 4.61 (s, 2H), 3.82 (d, J = 18.7 Hz, 2H), 3.62 (s, 6H), 1.55 (s, 6H), 1.06 (t, J = 7.0 Hz, 3H). |
| 165 | H-6 | 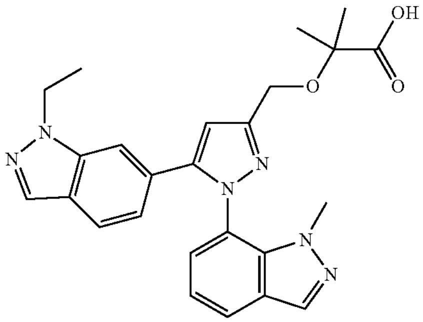 [SMILES: CCn1ncc2ccc(-c3cc(COC(C)(C)C(=O)O)nn3-c3cccc4cnn(C)c34)cc21] | 2-([5-(1-Ethyl-1H-indazol-6-yl)-1-(1-methyl-1H-indazol-7-yl)-1H-pyrazol-3-yl]methoxy)-2-methylpropanoic acid<br>XSelect: 30% ACN up to 53% in 7 min<br>LC-MS: (ES, m/z): 459.<br>$^1$H NMR (300 MHz, DMSO-$d_6$) δ 12.75 (s, 1H), 8.16 (s, 1H), 7.96 (d, J = 0.9 Hz, 1H), 7.89 (dd, J = 8.2, 1.0 Hz, 1H), 7.63-7.51 (m, 2H), 7.45 (dd, J = 7.3, 1.0 Hz, 1H), 7.17 (dd, J = 8.1, 7.3 Hz, 1H), 6.94 (dd, J = 8.4, 1.4 Hz, 1H), 6.89 (s, 1H), 4.56 (s, 2H), 4.25 (q, J = 7.1 Hz, 2H), 3.47 (s, 3H), 1.45 (s, 6H), 1.16 (t, J = 7.1 Hz, 3H). |
| 166 | H-7 | 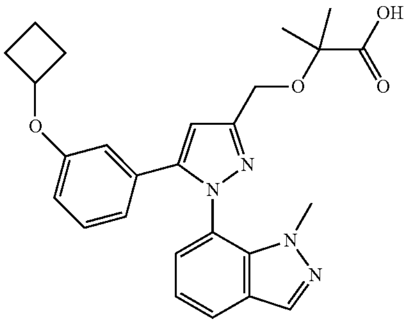 [SMILES: Cn1ncc2cccc(-n3nc(COC(C)(C)C(=O)O)cc3-c3cccc(OC4CCC4)c3)c21] | 2-([5-(3-Cyclobutoxyphenyl)-1-(1-methyl-1H-indazol-7-yl)-1H-pyrazol-3-yl]methoxy)-2-methylpropanoic acid<br>XSelect: 53% ACN up to 78% in 7 min<br>LC-MS: (ES, m/z): 461. $^1$H NMR: (300 MHz, DMSO-$d_6$) δ 12.71 (s, 1H), 8.22 (s, 1H), 7.94 (dd, J = 8.1, 1.0 Hz, 1H), 7.39 (dd, J = 7.3, 1.0 Hz, 1H), 7.27-7.13 (m, 2H), 6.90 (dt, J = 7.8, 1.2 Hz, 1H), 6.80 (s, 1H), 6.72 (ddd, J = 8.3, 2.6, 1.0 Hz, 1H), 6.50-6.42 (m, 1H), 4.54 (s, 2H), 4.14 (p, J = 7.0 Hz, 1H), 3.45 (s, 3H), 2.01 (d, J = 9.2 Hz, 2H), 1.89-1.74 (m, 2H), 1.74-1.59 (m, 1H), 1.57-1.47 (m, 1H), 1.44 (s, 6H). |

TABLE 25-continued

Examples 155-276.

| Ex. | Ester | Structure | IUPAC Name<br>Purification Analytical data |
|---|---|---|---|
| 167 | H-8 | 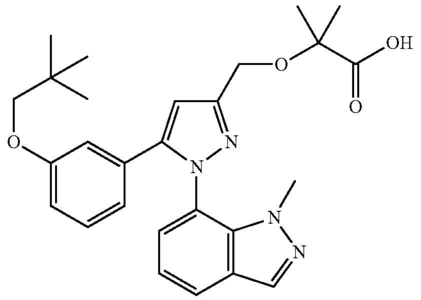 [SMILES: Cn1ncc2cccc(-n3nc(COC(C)(C)C(=O)O)cc3-c3cccc(OCC(C)(C)C)c3)c21] | 2-([5-[3-(2,2-dimethylpropoxy)phenyl]-1-(1-methyl-1H-indazol-7-yl)-1H-pyrazol-3-yl]methoxy)-2-methyl-propanoic acid<br>XSelect: 50% ACN up to 80% in 7 min<br>LC-MS: (ES, m/z): 477.20.<br>$^1$H NMR: (300 MHz, DMSO) δ 8.18 (s, 1H), 7.91 (dd, J = 8.1, 1.0 Hz, 1H), 7.39 (dd, J = 7.3, 1.0 Hz, 1H), 7.16 (m, 2H), 6.80 (m, 3H), 6.63 (dd, J = 2.5, 1.5 Hz, 1H), 4.54 (s, 2H), 3.43 (s, 3H), 3.17 (s, 2H), 1.44 (s, 6H), 0.87 (s, 9H). |
| 168 | H-9 | 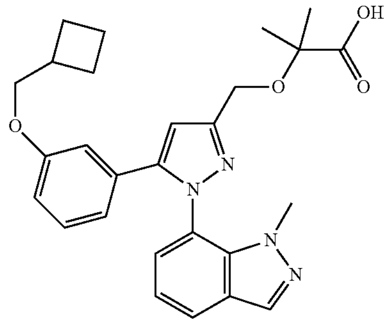 [SMILES: Cn1ncc2cccc(-n3nc(COC(C)(C)C(=O)O)cc3-c3cccc(OCC4CCC4)c3)c21] | 2-([5-[3-(cyclobutylmethoxy)phenyl]-1-(1-methyl-1H-indazol-7-yl)-1H-pyrazol-3-yl]methoxy)-2-methylpropanoic acid<br>XSelect: 45% ACN up to 80% in 8 min<br>LC-MS: (ES, m/z): 475.<br>$^1$H NMR: (300 MHz, DMSO-$d_6$) δ 12.73 (s, 1H), 8.20 (s, 1H), 7.93 (dd, J = 8.1, 1.0 Hz, 1H), 7.40 (dd, J = 7.3, 1.0 Hz, 1H), 7.30-7.10 (m, 2H), 6.94-6.76 (m, 3H), 6.67 (dd, J = 2.5, 1.6 Hz, 1H), 4.54 (s, 2H), 3.57 (d, J = 6.8 Hz, 2H), 3.44 (s, 3H), 2.46 (d, J = 7.4 Hz, 1H), 2.05-1.76 (m, 4H), 1.74-1.55 (m, 2H), 1.44 (s, 6H). |
| 169 | H-32 | 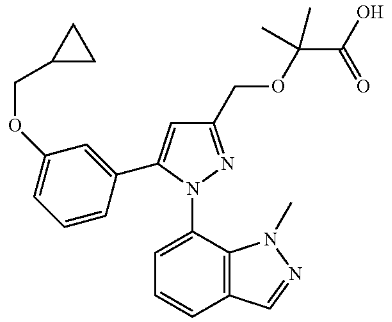 [SMILES: Cn1ncc2cccc(-n3nc(COC(C)(C)C(=O)O)cc3-c3cccc(OCC4CC4)c3)c21] | 2-([5-[3-(Cyclopropylmethoxy)phenyl]-1-(1-methyl-1H-indazol-7-yl)-1H-pyrazol-3-yl]methoxy)-2-methylpropanoic acid<br>XSelect: 40% ACN up to 70% in 7 min<br>LC-MS: (ES, m/z): 461.<br>$^1$H NMR: (300 MHz, DMSO-$d_6$) δ 12.71 (s, 1H), 8.19 (s, 1H), 7.91 (dd, J = 8.1, 1.0 Hz, 1H), 7.40 (dd, J = 7.3, 1.0 Hz, 1H), 7.28-7.04 (m, 2H), 6.80 (d, J = 8.0 Hz, 3H), 6.72-6.58 (m, 1H), 4.54 (s, 2H), 3.48 (d, J = 7.0 Hz, 2H), 3.44 (s, 3H), 1.44 (s, 6H), 1.00 (dddd, J = 15.0, 10.1, 5.1, 2.3 Hz, 1H), 0.55-0.43 (m, 2H), 0.25-0.11 (m, 2H). |
| 170 | H-10 | 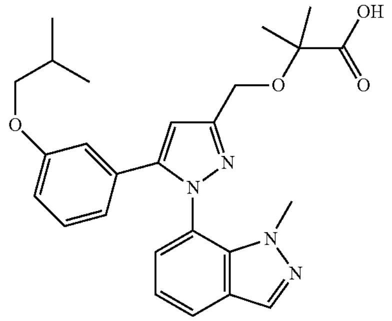 [SMILES: CC(C)COc1cccc(-c2cc(COC(C)(C)C(=O)O)nn2-c2cccc3cnn(C)c23)c1] | 2-methyl-2-([1-(1-methyl-1H-indazol-7-yl)-5-[3-(2-methylpropoxy)phenyl]-1H-pyrazol-3-yl]methoxy[propanoic acid<br>XSelect: 50% ACN up to 80% in 7 min<br>LC-MS: (ES, m/z): 463.<br>$^1$H NMR: (300 MHz, DMSO-$d_6$) δ 12.73 (s, 1H), 8.18 (s, 1H), 7.91 (dd, J = 8.1, 1.0 Hz, 1H), 7.39 (dd, J = 7.3, 1.0 Hz, 1H), 7.26-7.05 (m, 2H), 6.94-6.73 (m, 3H), 6.63 (dd, J = 2.5, 1.6 Hz, 1H), 4.53 (s, 2H), 3.43 (s, 3H), 3.34 (d, J = 6.7 Hz, 2H), 1.79 (hept, J = 6.7 Hz, 1H), 1.43 (s, 6H), 0.84 (d, J = 6.7 Hz, 6H). |

TABLE 25-continued

| Examples 155-276. | | | |
|---|---|---|---|
| Ex. | Ester | Structure | IUPAC Name<br>Purification Analytical data |
| 171 | H-34 | 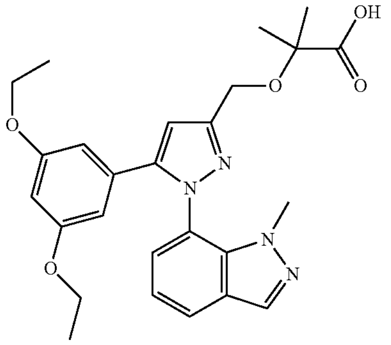 [SMILES: CCOc1cc(OCC)cc(-c2cc(COC(C)(C)C(=O)O)nn2-c2cccc3cnn(C)c23)c1] | 2-([5-(3,5-Diethoxyphenyl)-1-(1-methyl-1H-indazol-7-yl)-1H-pyrazol-3-yl]-methoxy)-2-methylpropanoic acid<br>XSelect: 45% ACN up to 81% in 7 min<br>LC-MS: (ES, m/z): 479.15.<br>$^{1}$H NMR: (300 MHz, DMSO) δ 12.70 (m, 1H), 8.18 (s, 1H), 7.91 (d, J = 8.1 Hz, 1H), 7.44 (d, J = 7.2 Hz, 1H), 7.20 (t, J = 7.7, 7.7 Hz, 1H), 6.81 (s, 1H), 6.31 (s, 3H), 4.53 (s, 2H), 3.73 (q, J = 7.0, 6.9, 6.9 Hz, 4H), 3.41 (s, 3H), 1.44 (s, 6H), 1.13 (t, J = 6.9, 6.9 Hz, 6H). |
| 172 | H-11 | 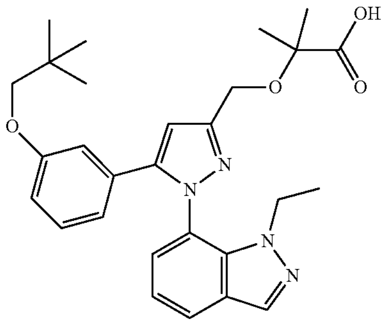 [SMILES: CCn1ncc2cccc(-n3nc(COC(C)(C)C(=O)O)cc3-c3cccc(OCC(C)(C)C)c3)c21] | 2-([5-[3-(2,2-Dimethylpropoxy)phenyl]-1-(1-ethyl-1H-indazol-7-yl)-1H-pyrazol-3-yl]methoxy)-2-methylpropanoic acid<br>XSelect: 50% ACN up to 85% in 7 min<br>LC-MS: (ES, m/z): 491.<br>$^{1}$H NMR: (300 MHz, DMSO-$d_6$) δ 12.67 (s, 1H), 8.24 (s, 1H), 7.92 (dd, J = 8.1, 1.1 Hz, 1H), 7.32 (dd, J = 7.3, 1.1 Hz, 1H), 7.24-6.98 (m, 2H), 6.85 (s, 1H), 6.79 (dddd, J = 7.2, 6.4, 2.5, 1.0 Hz, 2H), 6.65-6.55 (m, 1H), 4.53 (s, 2H), 3.71 (d, J = 36.9 Hz, 2H), 3.15 (s, 2H), 1.43 (s, 6H), 1.09 (t, J = 7.1 Hz, 3H), 0.86 (s, 9H). |
| 173 | H-37 | 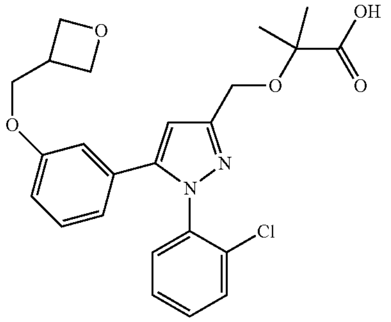 | 2-([1-(2-Chlorophenyl)-5-[3-(oxetan-3-ylmethoxy)phenyl]-1H-pyrazol-3-yl]-methoxy)-2-methylpropanoic acid<br>XBridge: 25% ACN up to 60% in 7 min<br>LC-MS: (ES, m/z): 457.0.<br>$^{1}$H-NMR: $\delta_H$ (300 MHz, DMSO-$d_6$) 12.70 (s, 1H), 7.64-7.45 (m, 4H), 7.20 (t, J = 8.0 Hz, 1H), 6.88 (ddd, J = 8.4, 2.5, 1.0 Hz, 1H), 6.82-6.69 (m, 3H), 4.67 (dd, J = 7.9, 6.0 Hz, 2H), 4.49 (s, 2H), 4.35 (t, J = 6.0 Hz, 2H), 4.06 (d, J = 6.8 Hz, 2H), 3.34-3.22 (m, 1H), 1.43 (s, 6H). |
| 174 | H-39 | 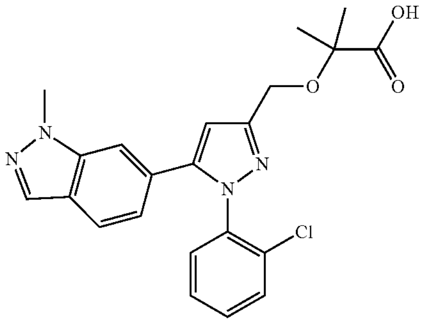 [SMILES: Cn1ncc2ccc(-c3cc(COC(C)(C)C(=O)O)nn3-c3ccccc3Cl)cc21] | 2-([1-(2-Chlorophenyl)-5-(1-methyl-1H-indazol-6-yl)-1H-pyrazol-3-yl]methoxy)-2-methylpropanoic acid<br>XBridge: 25% ACN up to 58% in 7 min<br>LC-MS: (ES, m/z): 425.<br>$^{1}$H NMR: (400 MHz, DMSO-$d_6$) δ 12.75 (s, 1H), 8.01 (d, J = 1.0 Hz, 1H), 7.66-7.60 (m, 2H), 7.58 (ddd, J = 4.0, 3.0, 1.9 Hz, 2H), 7.54-7.46 (m, 2H), 6.85 (dd, J = 8.4, 1.4 Hz, 1H), 6.79 (s, 1H), 4.52 (s, 2H), 3.95 (s, 3H), 1.45 (s, 6H). |

TABLE 25-continued

| Ex. | Ester | Structure | IUPAC Name<br>Purification Analytical data |
|---|---|---|---|
| | | Examples 155-276. | |
| 175 | H-41 | 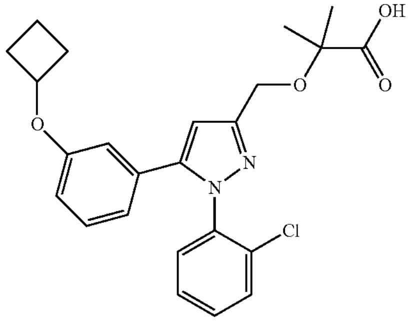 [SMILES: CC(C)(OCc1cc(-c2cccc(OC3CCC3)c2)n(-c2ccccc2Cl)n1)C(=O)O] | 2-([1-(2-Chlorophenyl)-5-(3-cyclo-butoxyphenyl)-1H-pyrazol-3-yl]-methoxy)-2-methylpropanoic acid<br>XBridge: 47% ACN up to 67% in 7 min<br>LC-MS: (ES, m/z): 441.<br>$^1$H-NMR: $^1$H NMR (400 MHz, DMSO-$d_6$) δ 12.71 (s, 1H), 7.60 (ddd, J = 12.7, 7.5, 2.0 Hz, 2H), 7.56-7.46 (m, 2H), 7.21 (t, J = 8.0 Hz, 1H), 6.84 (dt, J = 7.7, 1.2 Hz, 1H), 6.77 (ddd, J = 8.3, 2.5, 1.0 Hz, 1H), 6.68 (s, 1H), 6.53 (t, J = 2.0 Hz, 1H), 4.48 (s, 2H), 4.38 (p, J = 7.2 Hz, 1H), 2.31-2.18 (m, 2H), 1.91 (qdd, J = 9.6, 7.5, 2.8 Hz, 2H), 1.73 (qt, J = 10.1, 2.7 Hz, 1H), 1.65-1.50 (m, 1H), 1.43 (s, 6H). |
| 176 | H-42 | 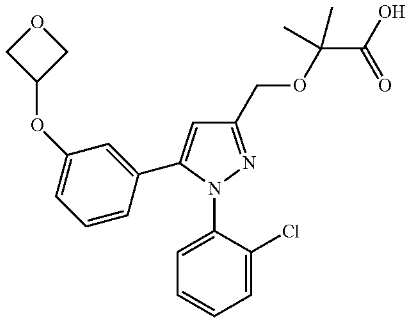 | 2-([1-(2-Chlorophenyl)-5-[3-(oxetan-3-yloxy)phenyl]-1H-pyrazol-3-yl]-methoxy)-2-methylpropanoic acid<br>XBridge: 25% ACN up to 60% in 7 min<br>LC-MS: (ES, m/z): 443.<br>$^1$H NMR: (300 MHz, DMSO) δ 12.72 (s, 1H), 7.60 (ddd, J = 6.2, 4.2, 2.7 Hz, 2H), 7.51 (ddd, J = 6.3, 3.5, 2.2 Hz, 2H), 7.24 (t, J = 8.0, 8.0 Hz, 1H), 6.87 (dt, J = 7.8, 1.1, 1.1 Hz, 1H), 6.74 (ddd, J = 8.2, 2.6, 0.9 Hz, 1H), 6.68 (s, 1H), 6.45 (dd, J = 2.6, 1.5 Hz, 1H), 5.06 (ddd, J = 6.0, 4.9, 1.1 Hz, 1H), 4.77 (m, 2H), 4.48 (s, 2H), 4.39 (m, 2H), 1.42 (s, 6H). |
| 177 | H-43 | 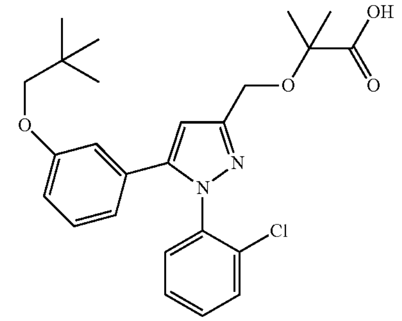 [SMILES: CC(C)(C)COc1cccc(-c2cc(COC(C)(C)C(=O)O)nn2-c2ccccc2Cl)c1] | 2-([1-(2-chlorophenyl)-5-[3-(2,2-dimethylpropoxy)phenyl]-1H-pyrazol-3-yl]methoxy)-2-methylpropanoic acid<br>XSelect: 0.1% DEA/57.0% ACN up to 85% ACN in 7 min<br>LC-MS: (ES, m/z): 457.05.<br>1H NMR (300 MHz, DMSO) δ 12.70 (s, 1H), 7.58 (m, 2H), 7.50 (m, 2H), 7.17 (t, J = 8.0, 8.0 Hz, 1H), 6.83 (ddd, J = 8.4, 2.5, 1.0 Hz, 1H), 6.75 (dt, J = 7.7, 1.2, 1.2 Hz, 1H), 6.70 (d, J = 3.1 Hz, 2H), 4.48 (s, 2H), 3.40 (s, 2H), 1.42 (s, 6H), 0.92 (s, 9H). |
| 178 | H-44 | 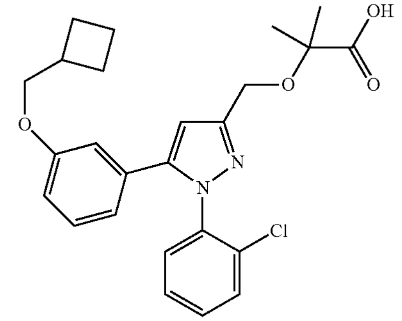 [SMILES: CC(C)(OCc1cc(-c2cccc(OCC3CCC3)c2)n(-c2ccccc2Cl)n1)C(=O)O] | 2-([1-(2-Chlorophenyl)-5-[3-(Cyclobutylmethoxy)phenyl]-1H-pyrazol-3-yl]methoxy)-2-methylpropanoic acid<br>XSelect: 55% up to 85% in 7 min<br>LC-MS: (ES, m/z): 455.09.<br>$^1$H NMR: (300 MHz, DMSO) δ 12.72 (s, 1H), 7.58 (ddd, J = 6.5, 4.9, 2.5 Hz, 2H), 7.49 (m, 2H), 7.17 (t, J = 8.0, 8.0 Hz, 1H), 6.82 (ddd, J = 8.3, 2.5, 0.9 Hz, 1H), 6.77 (m, 1H), 6.70 (d, J = 2.9 Hz, 2H), 4.49 (s, 2H), 3.74 (d, J = 6.8 Hz, 2H), 2.55 (m, 1H), 1.99 (m, 2H), 1.85 (m, 2H), 1.73 (m, 2H), 1.43 (s, 6H). |

TABLE 25-continued

| Ex. | Ester | Structure | IUPAC Name Purification Analytical data |
|---|---|---|---|
| | | Examples 155-276. | |
| 179 | H-45 | 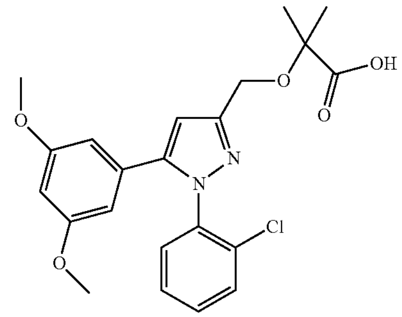 [SMILES: COc1cc(OC)cc(-c2cc(COC(C)(C)C(=O)O)nn2-c2ccccc2Cl)c1] | 2-([1-(2-Chlorophenyl)-5-(3,5-dimethoxyphenyl)-1H-pyrazol-3-yl]-methoxy)-2-methylpropanoic acid XBridge: 38% ACN up to 57% in 7 min LC-MS: (ES, m/z): 431. $^1$H NMR: (300 MHz, MeOH-$d_4$) δ 7.61-7.42 (m, 4H), 6.73 (s, 1H), 6.38 (dd, J = 9.8, 2.2 Hz, 3H), 4.61 (s, 2H), 3.63 (s, 6H), 1.53 (s, 6H). |
| 180 | H-12 | 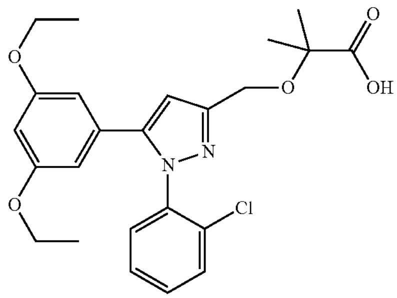 [SMILES: CCOc1cc(OCC)cc(-c2cc(COC(C)(C)C(=O)O)nn2-c2ccccc2Cl)c1] | 2-([1-(2-Chlorophenyl)-5-(3,5-diethoxy-phenyl)-1H-pyrazol-3-yl]methoxy)-2-methylpropanoic acid XBridge: 42% ACN up to 68% in 7 min LC-MS: (ES, m/z): 459.05. $^1$H NMR: (300 MHz, DMSO) δ 12.74 (s, 1H), 6 7.51 (m, 4H), 6.70 (s, 1H), 6.38 (t, J = 2.3, 2.3 Hz, 1H), 6.30 (d, J = 2.2 Hz, 2H), 4.48 (s, 2H), 3.84 (q, J = 7.0, 7.0, 7.0 Hz, 4H), 1.42 (s, 6H), 1.22 (t, J = 7.0, 7.0 Hz, 6H). |
| 181 | H-13 | 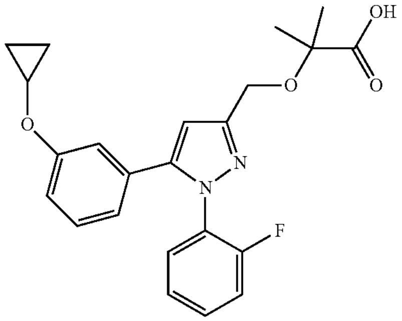 | 2-([5-(3-cyclopropoxyphenyl)-1-(2-fluorophenyl)-1H-pyrazol-3-yl]methoxy)-2-methylpropanoate SunFire: 69% ACN up to 71% in 8 min LC-MS: (ES, m/z): 411.3. $^1$H-NMR: $\delta_H$ (400 MHz, DMSO-$d_6$) 12.73 (1H, s), 7.54 (2H, m), 7.35 (2H, m), 7.26 (1H, t, J = 7.9, 7.9 Hz), 6.95 (1H, ddd, J = 8.3, 2.5, 1.0 Hz), 6.88 (2H, m), 6.68 (1H, s), 4.48 (2H, s), 3.62 (1H, tt, J = 6.0, 6.0, 3.0, 3.0 Hz), 1.43 (6H, s), 0.62 (2H, m), 0.50 (2H, m). |
| 182 | H-46 | 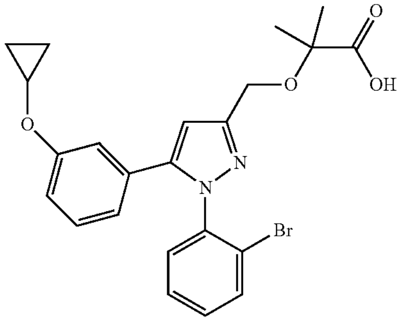 [SMILES: CC(C)(OCc1cc(-c2cccc(OC3CC3)c2)n(-c2ccccc2Br)n1)C(=O)O] | 2-([1-(2-Bromophenyl)-5-(3-cyclo-propoxyphenyl)-1H-pyrazol-3-yl]-methoxy)-2-methylpropanoic acid XBridge: 38% ACN up to 70% in 7 min LC-MS: (ES, m/z): 471. $^1$H NMR: (DMSO) δ: 12.71 (s, 1H), 7.81-7.71 (m, 1H), 7.59-7.37 (m, 3H), 7.23 (t, J = 8.0 Hz, 1H), 6.96-6.78 (m, 3H), 6.67 (s, 1H), 4.47 (s, 2H), 3.55 (tt, J = 6.0, 2.9 Hz, 1H), 1.42 (s, 6H), 0.71-0.43 (m, 4H). |

TABLE 25-continued

Examples 155-276.

| Ex. | Ester | Structure | IUPAC Name<br>Purification Analytical data |
|---|---|---|---|
| 183 | H-149 | 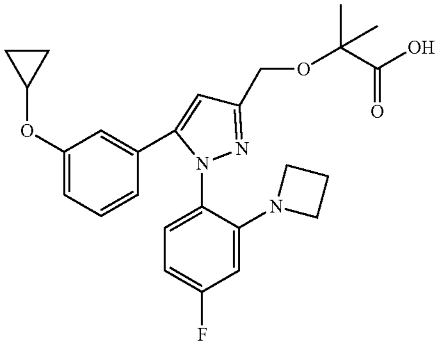 [SMILES: CC(C)(OCc1cc(-c2cccc(OC3CC3)c2)n(-c2ccc(F)cc2N2CCC2)n1)C(=O)O] | 2-([1-[2-(Azetidin-1-yl)-4-fluorophenyl]-5-(3-cyclopropoxyphenyl)-1H-pyrazol-3-yl]methoxy)-2-methylpropanoic acid<br>XBridge: 10% ACN up to 52% in 7 min<br>LC-MS: (ES, m/z): 466.20.<br>$^{1}$H NMR (300 MHz, DMSO) δ 7.26 (t, J = 8.2, 8.2 Hz, 1H), 7.00 (m, 3H), 6.92 (ddd, J = 8.2, 2.4, 1.1 Hz, 1H), 6.63 (s, 1H), 6.45 (td, J = 8.4, 8.4, 2.8 Hz, 1H), 6.29 (dd, J = 11.3, 2.8 Hz, 1H), 4.46 (s, 2H), 3.62 (tt, J = 6.1, 6.1, 3.0, 3.0 Hz, 1H), 3.49 (m, 4H), 2.07 (p, J = 7.2, 7.2, 7.2, 7.2 Hz, 2H), 1.39 (s, 6H), 0.69 (m, 2H), 0.56 (m, 2H). |
| 184 | H-48 | 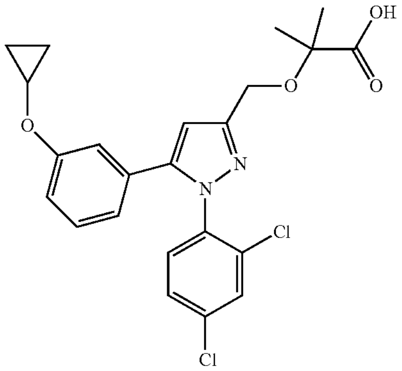 [SMILES: CC(C)(OCc1cc(-c2cccc(OC3CC3)c2)n(-c2ccc(Cl)cc2Cl)n1)C(=O)O] | 2-([5-(3-Cyclopropoxyphenyl)-1-(2,4-dichlorophenyl)-1H-pyrazol-3-yl]methoxy)-2-methylpropanoic acid<br>XSelect: 45% ACN up to 77% in 7 min<br>LC-MS: (ES, m/z): 461.00.<br>$^{1}$H NMR (300 MHz, DMSO) δ 12.72 (s, 1H), 7.81 (d, J = 2.2 Hz, 1H), 7.60 (m, 2H), 7.25 (t, J = 7.9, 7.9 Hz, 1H), 6.89 (m, 3H), 6.68 (s, 1H), 4.48 (s, 2H), 3.63 (tt, J = 6.1, 6.1, 3.0, 3.0 Hz, 1H), 1.42 (s, 6H), 0.66 (m, 2H), 0.51 (m, 2H). |
| 185 | H-49 | 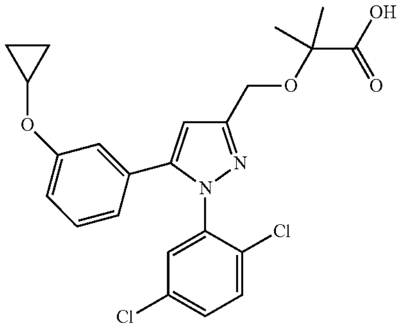 [SMILES: CC(C)(OCc1cc(-c2cccc(OC3CC3)c2)n(-c2cc(Cl)ccc2Cl)n1)C(=O)O] | 2-([5-(3-Cyclopropoxyphenyl)-1-(2,5-dichlorophenyl)-1H-pyrazol-3-yl]-methoxy)-2-methylpropanoic acid<br>XSelect: 48% ACN up to 74% in 7 min<br>LC-MS: (ES, m/z): 461.05.<br>$^{1}$H NMR (300 MHz, DMSO) δ 12.72 (s, 1H), 7.83 (m, 1H), 7.60 (d, J = 1.5 Hz, 2H), 7.25 (t, J = 7.9, 7.9 Hz, 1H), 6.91 (m, 3H), 6.69 (s, 1H), 4.50 (s, 2H), 3.61 (dt, J = 6.0, 3.1, 3.1 Hz, 1H), 1.43 (s, 6H), 0.65 (dd, J = 6.2, 2.0 Hz, 2H), 0.50 (tt, J = 6.2, 6.2, 3.4, 3.4 Hz, 2H). |
| 186 | H-50 | 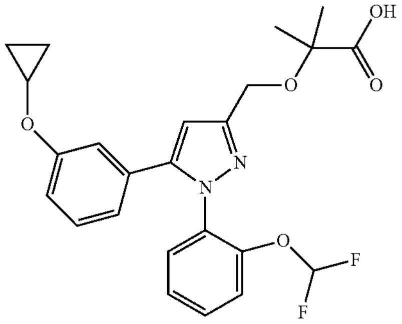 [SMILES: CC(C)(OCc1cc(-c2cccc(OC3CC3)c2)n(-c2ccccc2OC(F)F)n1)C(=O)O] | 2-([5-(3-Cyclopropoxyphenyl)-1-[2-(difluoromethoxy)phenyl]-1H-pyrazol-3-yl]methoxy)-2-methylpropanoic acid<br>XBridge: 40% ACN up to 65% in 7 min<br>LC-MS: (ES, m/z): 459.<br>$^{1}$H NMR: (300 MHz, DMSO-$d_6$) δ 12.72 (s, 1H), 7.59-7.47 (m, 2H), 7.42-7.13 (m, 3H), 6.95-6.79 (m, 3H), 6.66 (d, J = 10.0 Hz, 1H), 4.47 (s, 2H), 3.57 (tt, J = 6.1, 2.9 Hz, 1H), 1.42 (s, 6H), 0.67-0.42 (m, 4H). |

TABLE 25-continued

| Ex. | Ester | Structure | IUPAC Name<br>Purification Analytical data |
|---|---|---|---|
| | | Examples 155-276. | |
| 187 | H-51 | 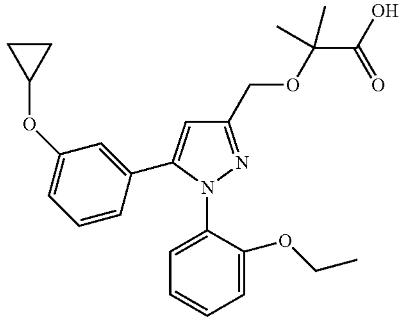 [SMILES: CCOc1ccccc1-n1nc(COC(C)(C)C(=O)O)cc1-c1cccc(OC2CC2)c1] | 2-([5-(3-cyclopropoxyphenyl)-1-(2-ethoxyphenyl)-1H-pyrazol-3-yl]-methoxy)-2-methylpropanoic acid<br>XBridge: 40% ACN up to 67% in 7 min<br>LC-MS: (ES, m/z): 437.<br>$^{1}$H NMR: (300 MHz, MeOH-$d_4$) δ 7.50-7.37 (m, 2H), 7.26-7.15 (m, 1H), 7.13-6.99 (m, 2H), 6.97-6.87 (m, 3H), 6.67 (s, 1H), 4.62 (s, 2H), 3.75 (s, 2H), 3.51 (tt, J = 6.1, 3.0 Hz, 1H), 1.55 (s, 6H), 1.02 (t, J = 7.0 Hz, 3H), 0.64 (d, J = 6.0 Hz, 2H), 0.57-0.47 (m, 2H). |
| 188 | H-52 | 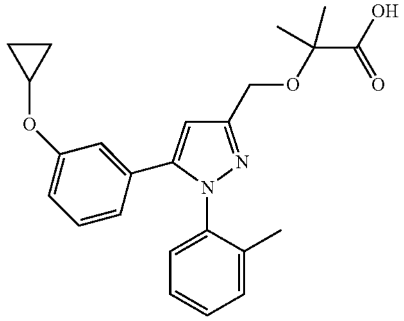 [SMILES: Cc1ccccc1-n1nc(COC(C)(C)C(=O)O)cc1-c1cccc(OC2CC2)c1] | 2-([5-(3-Cyclopropoxyphenyl)-1-(2-methylphenyl)-1H-pyrazol-3-yl]-methoxy)-2-methylpropanoic acid<br>XBridge: 40% ACN up to 67% in 7 min<br>LC-MS: (ES, m/z): 407.<br>$^{1}$H NMR: (300 MHz, MeOH-$d_4$) δ 7.44-7.27 (m, 4H), 7.20 (t, J = 8.0 Hz, 1H), 6.92 (tt, J = 8.5, 1.1 Hz, 2H), 6.84 (t, J = 2.1 Hz, 1H), 6.73 (s, 1H), 4.61 (s, 2H), 3.46 (tt, J = 6.1, 3.0 Hz, 1H), 1.96 (s, 3H), 1.54 (s, 6H), 0.63 (pd, J = 6.0, 3.8 Hz, 2H), 0.57-0.48 (m, 2H). |
| 189 | H-53 | 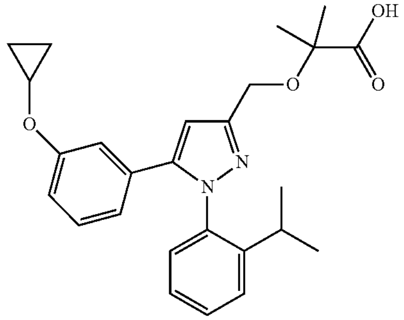 [SMILES: CC(C)c1ccccc1-n1nc(COC(C)(C)C(=O)O)cc1-c1cccc(OC2CC2)c1] | 2-([5-(3-cyclopropoxyphenyl)-1-[2-(propan-2-yl)phenyl]-1H-pyrazol-3-yl]-methoxy)-2-methylpropanoic acid<br>XSelect: 50% ACN up to 76% in 7 min<br>LC-MS: (ES, m/z): 435.<br>$^{1}$H-NMR: (DMSO, ppm): δ: 12.65 (s, 1H), 7.46 (dd, J = 3.7, 1.3 Hz, 2H), 7.36-7.16 (m, 3H), 6.94-6.76 (m, 3H), 6.68 (s, 1H), 4.49 (s, 2H), 3.53 (tt, J = 6.1, 2.9 Hz, 1H), 1.43 (s, 6H), 1.00 (s, 3H), 0.84 (s, 3H), 0.67-0.51 (m, 2H), 0.47 (tq, J = 5.5, 3.2 Hz, 2H). |
| 190 | H-54 | 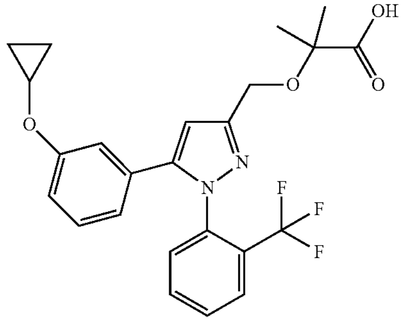 [SMILES: CC(C)(OCc1cc(-c2cccc(OC3CC3)c2)n(-c2ccccc2C(F)(F)F)n1)C(=O)O] | 2-([5-(3-Cyclopropoxyphenyl)-1-[2-(trifluoromethyl)phenyl]-1H-pyrazol-3-yl]methoxy)-2-methylpropanoic acid<br>XBridge: 40% ACN up to 63% in 7 min<br>LC-MS: (ES, m/z): 461.<br>$^{1}$H NMR (300 MHz, MeOH-$d_4$) δ 7.94-7.83 (m, 1H), 7.79-7.64 (m, 2H), 7.48-7.37 (m, 1H), 7.20 (t, J = 8.0 Hz, 1H), 6.91 (dddd, J = 6.4, 4.0, 2.7, 1.2 Hz, 2H), 6.83 (t, J = 2.0 Hz, 1H), 6.73 (s, 1H), 4.61 (s, 2H), 3.49 (tt, J = 6.1, 3.0 Hz, 1H), 1.53 (s, 6H), 0.71-0.58 (m, 2H), 0.53 (ddd, J = 6.2, 4.3, 2.8 Hz, 2H). |

TABLE 25-continued

Examples 155-276.

| Ex. | Ester | Structure | IUPAC Name<br>Purification Analytical data |
|---|---|---|---|
| 191 | H-55 | 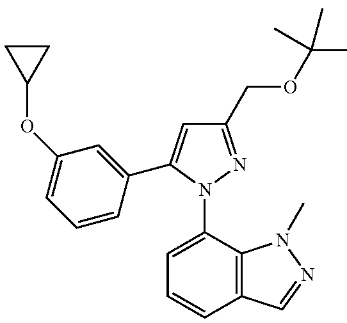 | 2-([5-(3-Cyclopropoxyphenyl)-1-(1-methyl-1H-indazol-7-yl)-1H-pyrazol-3-yl]methoxy)-2-methylpropanoic acid<br>XBridge: 38% ACN up to 62% in 7 min<br>LC-MS: (ES, m/z): 447.<br>$^{1}$H-NMR: (DMSO, ppm): δ: 12.74 (s, 1H), 8.20 (s, 1H), 7.92 (dd, J = 8.1, 1.0 Hz, 1H), 7.38 (dd, J = 7.3, 1.0 Hz, 1H), 7.27-7.13 (m, 2H), 6.99-6.76 (m, 4H), 4.54 (s, 2H), 3.49 (s, 3H), 3.43-3.34 (m, 1H), 1.44 (s, 6H), 0.52-0.36 (m, 4H). |
| 192 | H-14 | 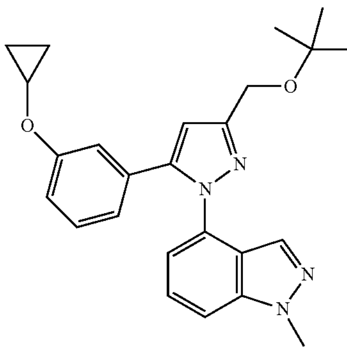 | 2-([5-(3-Cyclopropoxyphenyl)-1-(1-methyl-1H-indazol-4-yl)-1H-pyrazol-3-yl]methoxy)-2-methylpropanoic acid<br>XSelect: 35% ACN up to 68% in 7 min<br>LC-MS: (ES, m/z): 446.<br>$^{1}$H NMR: (300 MHz, DMSO-$d_6$) δ 7.80-7.59 (m, 2H), 7.41 (dd, J = 8.6, 7.3 Hz, 1H), 7.21 (t, J = 7.9 Hz, 1H), 7.07-6.80 (m, 4H), 6.71 (s, 1H), 4.54 (s, 2H), 4.07 (s, 3H), 3.56 (tt, J = 6.1, 2.9 Hz, 1H), 1.45 (s, 6H), 0.54-0.45 (m, 2H), 0.43-0.33 (m, 2H). |
| 193 | H-15 | 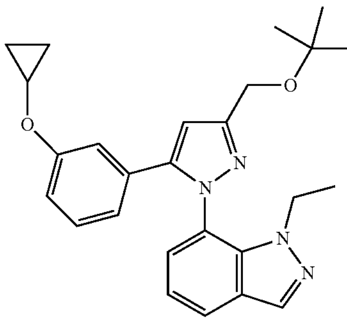 | 2-([5-(3-Cyclopropoxyphenyl)-1-(1-ethyl-1H-indazol-7-yl)-1H-pyrazol-3-yl]methoxy)-2-methylpropanoic acid<br>XSelect: 61% ACN up to 66% in 7 min<br>LC-MS: (ES, m/z): 461.<br>$^{1}$H NMR (300 MHz, DMSO-$d_6$) δ 12.71 (s, 1H), 8.25 (s, 1H), 7.92 (dd, J = 8.1, 1.1 Hz, 1H), 7.31 (dd, J = 7.3, 1.1 Hz, 1H), 7.25-7.09 (m, 2H), 6.94 (dt, J = 7.7, 1.2 Hz, 1H), 6.91-6.81 (m, 2H), 6.78 (dd, J = 2.5, 1.6 Hz, 1H), 4.55 (s, 2H), 3.77 (d, J = 28.7 Hz, 2H), 3.41-3.25 (m, J = 3.3 Hz, 1H), 1.44 (s, 6H), 1.12 (t, J = 7.1 Hz, 3H), 0.57-0.29 (m, 4H). |
| 194 | H-56 | 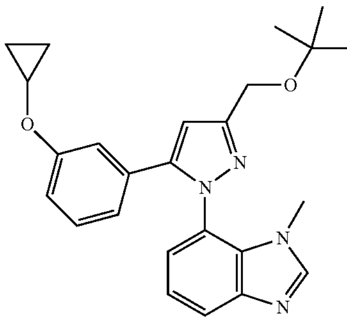 | 2-([5-(3-Cyclopropoxyphenyl)-1-(1-methyl-1H-1,3-benzodiazol-7-yl)-1H-pyrazol-3-yl]methoxy)-2-methylpropanoic acid<br>XSelect: 36% ACN up to 55% in 7 min<br>LC-MS: (ES, m/z): 447.10.<br>$^{1}$H NMR (300 MHz, DMSO) δ 12.72 (s, 1H), 8.18 (s, 1H), 7.78 (dd, J = 7.6, 1.5 Hz, 1H), 7.22 (m, 3H), 6.89 (m, 2H), 6.79 (t, J = 2.1, 2.1 Hz, 1H), 6.77 (s, 1H), 4.52 (s, 2H), 3.41 (dq, J = 6.1, 3.1, 3.0, 3.0 Hz, 1H), 3.29 (s, 3H), 1.43 (s, 6H), 0.47 (d, J = 6.1 Hz, 2H), 0.39 (m, 2H). |

TABLE 25-continued

Examples 155-276.

| Ex. | Ester | Structure | IUPAC Name Purification Analytical data |
| --- | --- | --- | --- |
| 195 | H-16 | 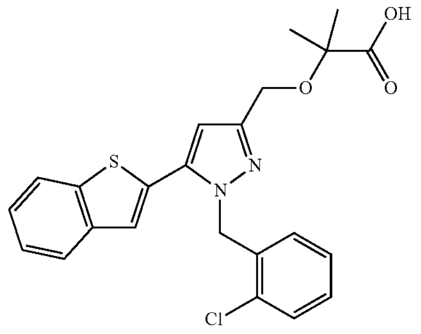 [SMILES: CC(C)(OCc1cc(-c2cc3ccccc3s2)n(Cc2ccccc2Cl)n1)C(=O)O] | 2-([5-(1-Benzothiophen-2-yl)-1-[(2-chlorophenyl)methyl]-1H-pyrazol-3-yl]methoxy)-2-methylpropanoic acid XSelect: 50% ACN up to 80% in 7 min LC-MS: (ES, m/z): 441. $^{1}$H NMR (400 MHz, DMSO-$d_6$) δ 12.68 (s, 1H), 8.02-7.95 (m, 1H), 7.90-7.81 (m, 1H), 7.57 (d, J = 0.8 Hz, 1H), 7.52-7.45 (m, 1H), 7.44-7.36 (m, 2H), 7.31 (pd, J = 7.4, 1.8 Hz, 2H), 6.77-6.70 (m, 1H), 6.68 (s, 1H), 5.62 (s, 2H), 4.45 (s, 2H), 1.42 (s, 6H). |
| 196 | H-57 | 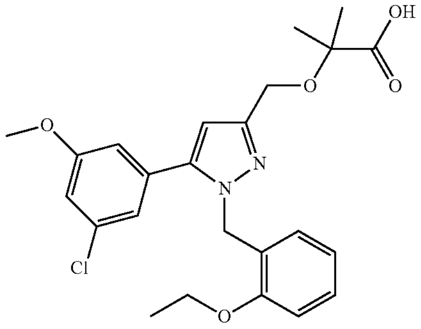 [SMILES: CCOc1ccccc1Cn1nc(COC(C)(C)C(=O)O)cc1-c1cc(Cl)cc(OC)c1] | 2-([5-(3-Chloro-5-methoxyphenyl)-1-[(2-ethoxyphenyl)methyl]-1H-pyrazol-3-yl]methoxy)-2-methylpropanoic acid XSelect: 50% ACN up to 76% in 7 min LC-MS: (ES, m/z): 459. $^{1}$H-NMR-PH-VET-168-0: (DMSO): δ: 12.62 (s, 1H), 7.24 (ddd, J = 8.5, 7.4, 1.8 Hz, 1H), 7.11-6.81 (m, 5H), 6.76 (dd, J = 7.6, 1.7 Hz, 1H), 6.48 (s, 1H), 5.27 (s, 2H), 4.41 (s, 2H), 3.99 (q, J = 6.9 Hz, 2H), 3.32 (s, 1H), 1.40 (s, 6H), 1.22 (t, J = 6.9 Hz, 3H). |
| 197 | H-17 | 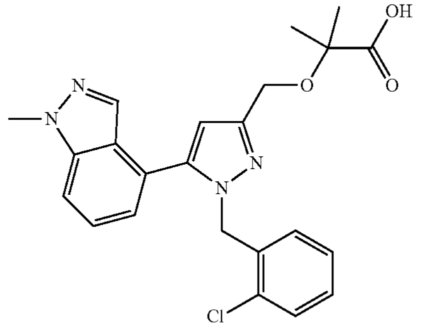 [SMILES: Cn1ncc2c(-c3cc(COC(C)(C)C(=O)O)nn3Cc3ccccc3Cl)cccc21] | 2-([1-[(2-Chlorophenyl)methyl]-5-(1-methyl-1H-indazol-4-yl)-1H-pyrazol-3-yl]methoxy)-2-methylpropanoic acid XSelect: 45% ACN up to 71% in 7 min LC-MS: (ES, m/z): 438. $^{1}$H NMR: (300 MHz, DMSO-$d_6$) δ 12.66 (s, 1H), 7.93 (d, J = 1.0 Hz, 1H), 7.70 (dt, J = 8.5, 0.9 Hz, 1H), 7.44 (dd, J = 8.5, 7.1 Hz, 1H), 7.39-7.30 (m, 1H), 7.30-7.20 (m, 2H), 7.09 (dd, J = 7.1, 0.8 Hz, 1H), 6.88-6.69 (m, 1H), 6.57 (s, 1H), 5.38 (s, 2H), 4.47 (s, 2H), 4.07 (s, 3H), 1.41 (s, 6H). |
| 198 | H-18 | 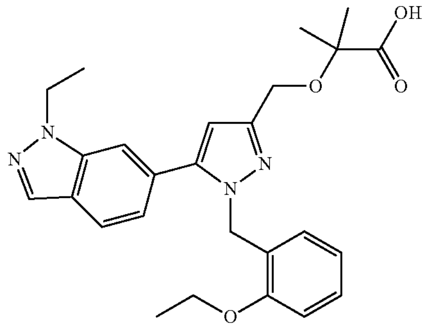 [SMILES: CCOc1ccccc1Cn1nc(COC(C)(C)C(=O)O)cc1-c1ccc2cnn(CC)c2c1] | 2-([1-[(2-Ethoxyphenyl)methyl]-5-(1-ethyl-1H-indazol-6-yl)-1H-pyrazol-3-yl]methoxy)-2-methylpropanoic acid XSelect: 45% ACN up to 65% in 7 min LC-MS: (ES, m/z): 463. $^{1}$H NMR: (300 MHz, DMSO-$d_6$) δ 12.70 (s, 1H), 8.09 (d, J = 0.9 Hz, 1H), 7.79 (dd, J = 8.3, 0.8 Hz, 1H), 7.68 (q, J = 1.1 Hz, 1H), 7.30-7.11 (m, 2H), 6.95 (dd, J = 8.3, 1.1 Hz, 1H), 6.86 (td, J = 7.5, 1.1 Hz, 1H), 6.72 (dd, J = 7.6, 1.7 Hz, 1H), 6.51 (s, 1H), 5.33 (s, 2H), 4.53-4.32 (m, 4H), 3.93 (q, J = 6.9 Hz, 2H), 1.42 (s, 6H), 1.33 (t, J = 7.2 Hz, 3H), 1.13 (t, J = 6.9 Hz, 3H). |

TABLE 25-continued

| Ex. | Ester | Structure | IUPAC Name Purification Analytical data |
|---|---|---|---|
| | | Examples 155-276. | |
| 199 | H-19 | 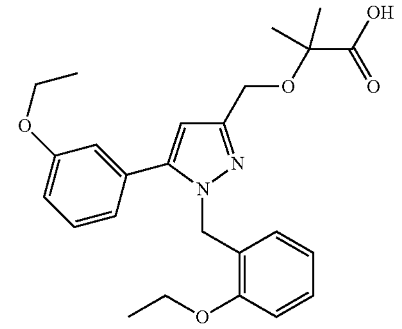 [SMILES: CCOc1cccc(-c2cc(COC(C)(C)C(=O)O)nn2Cc2ccccc2OCC)c1] | 2-([5-(3-Ethoxyphenyl)-1-[(2-ethoxy-phenyl)methyl]-1H-pyrazol-3-yl]-methoxy)-2-methylpropanoic acid XSelect: 45% ACN up to 80% in 7 min LC-MS: (ES, m/z): 439. $^1$H NMR: (300 MHz, DMSO-$d_6$) δ 12.68 (s, 1H), 7.33 (t, J = 7.9 Hz, 1H), 7.23 (ddd, J = 8.5, 7.5, 1.7 Hz, 1H), 7.03-6.91 (m, 3H), 6.91-6.82 (m, 2H), 6.69 (dd, J = 7.6, 1.7 Hz, 1H), 6.42 (s, 1H), 5.26 (s, 2H), 4.42 (s, 2H), 3.96 (dq, J = 20.8, 6.9 Hz, 4H), 1.40 (s, 6H), 1.25 (dt, J = 12.7, 6.9 Hz, 6H). |
| 200 | H-58 | 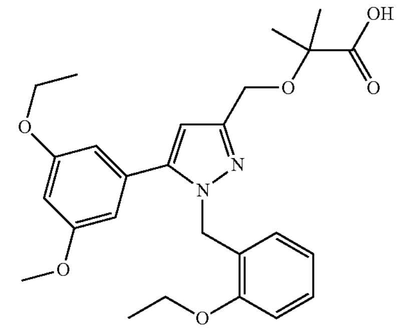 [SMILES: CCOc1cc(OC)cc(-c2cc(COC(C)(C)C(=O)O)nn2Cc2ccccc2OCC)c1] | 2-([5-(3-Ethoxy-5-methoxyphenyl)-1-[(2-ethoxyphenyl)methyl]-1H-pyrazol-3-yl]methoxy)-2-methylpropanoic acid XSelect: 52% ACN up to 71% in 7 min LC-MS: (ES, m/z): 469. $^1$H-NMR: (DMSO, ppm): δ: 12.63 (s, 1H), 7.24 (ddd, J = 8.6, 7.4, 1.7 Hz, 1H), 6.98 (dd, J = 8.3, 1.0 Hz, 1H), 6.87 (td, J = 7.5, 1.0 Hz, 1H), 6.67 (dd, J = 7.5, 1.6 Hz, 1H), 6.54-6.40 (m, 4H), 5.27 (s, 2H), 4.41 (s, 2H), 3.96 (dq, J = 28.8, 7.0 Hz, 4H), 3.67 (s, 3H), 1.40 (s, 6H), 1.25 (td, J = 6.9, 4.8 Hz, 6H). |
| 201 | H-59 | 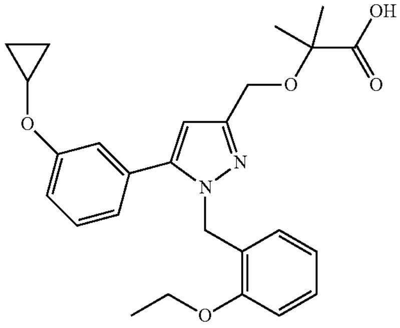 [SMILES: CCOc1ccccc1Cn1nc(COC(C)(C)C(=O)O)cc1-c1cccc(OC2CC2)c1] | 2-([5-(3-Cyclopropoxyphenyl)-1-[(2-ethoxyphenyl)methyl)-1H-pyrazol-3-yl]-methoxy)-2-methylpropanoic acid XBridge: 42% ACN up to 75% in 7 min LC-MS: (ES, m/z): 451. $^1$H NMR (300 MHz, DMSO-$d_6$) δ 12.68 (s, 1H), 7.35 (ddd, J = 8.2, 7.0, 1.1 Hz, 1H), 7.29-7.17 (m, 1H), 7.01 (tdd, J = 13.0, 8.6, 1.4 Hz, 4H), 6.87 (td, J = 7.5, 1.1 Hz, 1H), 6.68 (dd, J = 7.6, 1.7 Hz, 1H), 6.43 (s, 1H), 5.27 (s, 2H), 4.42 (s, 2H), 4.00 (q, J = 6.9 Hz, 2H), 3.69 (tt, J = 6.3, 3.1 Hz, 1H), 1.40 (s, 6H), 1.23 (t, J = 6.9 Hz, 3H), 0.71-0.51 (m, 4H). |
| 202 | H-150 | 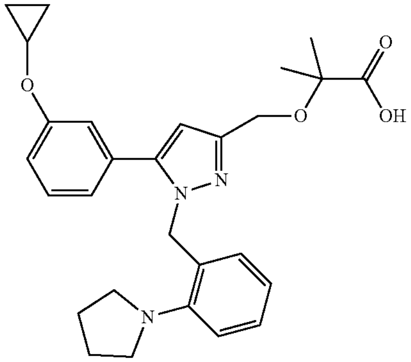 [SMILES: CC(C)(OCc1cc(-c2cccc(OC3CC3)c2)n(Cc2ccccc2N2CCCC2)n1)C(=O)O] | 2-([5-(3-Cyclopropoxyphenyl)-1-[[2-(pyrrolidin-1-yl)phenyl]methyl]-1H-pyrazol-3-yl]methoxy)-2-methylpropanoic acid XBridge: 28% ACN up to 58% in 7 min LC-MS: (ES, m/z): 476.15. $^1$H NMR: (400 MHz, DMSO) δ 7.31 (t, J = 7.9, 7.9 Hz, 1H), 7.15 (m, 1H), 7.00 (m, 2H), 6.94 (m, 2H), 6.85 (t, J = 7.6, 7.6 Hz, 1H), 6.60 (dd, J = 7.6, 1.8 Hz, 1H), 6.46 (s, 1H), 5.31 (s, 2H), 4.45 (s, 2H), 3.64 (m, 1H), 3.03 (m, 4H), 1.84 (m, 4H), 1.39 (s, 6H), 0.60 (dq, J = 5.3, 3.2, 2.4, 2.4 Hz, 2H), 0.55 (dq, J = 7.8, 3.6, 3.6, 3.4 Hz, 2H). |

TABLE 25-continued

Examples 155-276.

| Ex. | Ester | Structure | IUPAC Name<br>Purification Analytical data |
|---|---|---|---|
| 203 | H-60 | 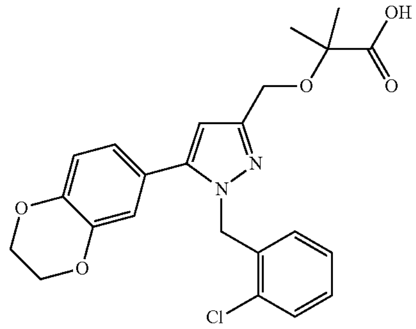 [SMILES: CC(C)(OCc1cc(-c2ccc3c(c2)OCCO3)n(Cc2ccccc2Cl)n1)C(=O)O] | 2-([1-[(2-Chlorophenyl)methyl]-5-(2,3-dihydro-1,4-benzodioxin-6-yl)-1H-pyrazol-3-yl]methoxy)-2-methylpropanoic acid<br>XBridge: 45% ACN up to 58% in 7 min<br>LC-MS: (ES, m/z): 443.<br>$^{1}$H NMR: (300 MHz, MeOD) δ 7.39 (m, 1H), 7.25 (tt, J = 7.4, 7.4, 5.6, 5.6 Hz, 2H), 6.85 (m, 1H), 6.77 (d, J = 7.8 Hz, 2H), 6.68 (m, 1H), 6.46 (s, 1H), 5.40 (s, 2H), 4.56 (s, 2H), 4.24 (q, J = 1.1, 1.0, 1.0 Hz, 4H), 1.51 (s, 6H). |
| 204 | H-61 | 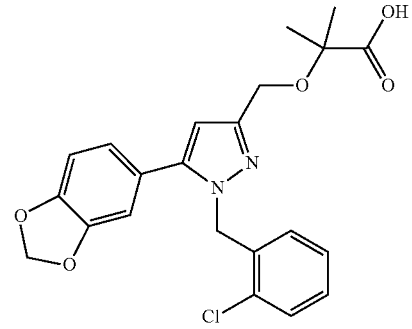 [SMILES: CC(C)(OCc1cc(-c2ccc3c(c2)OCO3)n(Cc2ccccc2Cl)n1)C(=O)O] | [[5-(2H-1,3-Benzodioxol-5-yl)-1-[(2-chlorophenyl)methyl]-1H-pyrazol-3-yl]methoxy)-2-methylpropanoic acid<br>XBridge: 45% ACN up to 60% in 7 min<br>LC-MS: (ES, m/z): 429.<br>$^{1}$H NMR: (DMSO) δ: 12.67 (s, 1H), 7.49-7.38 (m, 1H), 7.36-7.21 (m, 2H), 7.00-6.91 (m, 2H), 6.83 (dd, J = 7.9, 1.8 Hz, 1H), 6.76-6.66 (m, 1H), 6.37 (s, 1H), 6.05 (s, 2H), 5.35 (s, 2H), 4.39 (s, 2H), 1.38 (s, 6H) |
| 205 | H-62 | 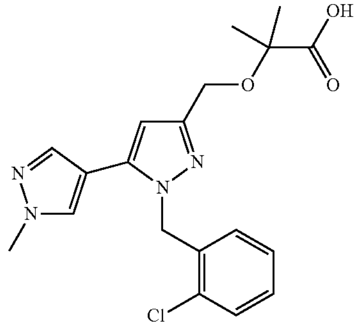 [SMILES: Cn1cc(-c2cc(COC(C)(C)C(=O)O)nn2Cc2ccccc2Cl)cn1] | 2-([1-[(2-Chlorophenyl)methyl]-5-(1-methyl-1H-pyrazol-4-yl)-1H-pyrazol-3-yl]methoxy)-2-methylpropanoic acid<br>XBridge: 25% ACN up to 52% in 7 min<br>$^{1}$H NMR (DMSO) δ: 7.93 (s, 1H), 7.55-7.46 (m, 2H), 7.29 (dtd, J = 21.6, 7.5, 1.6 Hz, 2H), 6.59 (dd, J = 7.6, 1.7 Hz, 1H), 6.43 (s, 1H), 5.43 (s, 2H), 4.38 (s, 2H), 3.83 (s, 3H), 1.39 (s, 6H) |
| 206 | H-21 | 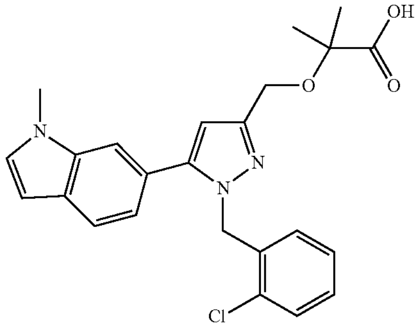 [SMILES: Cn1ccc2ccc(-c3cc(COC(C)(C)C(=O)O)nn3Cc3ccccc3Cl)cc21] | 2-([1-[(2-Chlorophenyl)methyl]-5-(1-methyl-1H-indol-6-yl)-1H-pyrazol-3-yl]-methoxy)-2-methylpropanoic acid<br>XSelect: 45% ACN up to 80% in 7 min<br>LC-MS: (ES, m/z): 437.<br>$^{1}$H NMR: (300 MHz, DMSO-$d_6$) δ 12.68 (s, 1H), 7.57 (dd, J = 8.2, 0.7 Hz, 1H), 7.48-7.36 (m, 3H), 7.34-7.26 (m, 2H), 7.01 (dd, J = 8.2, 1.5 Hz, 1H), 6.83-6.75 (m, 1H), 6.51-6.42 (m, 2H), 5.42 (s, 2H), 4.43 (s, 2H), 3.72 (s, 3H), 1.41 (s, 6H). |

TABLE 25-continued

| Examples 155-276. | | | |
|---|---|---|---|
| Ex. | Ester | Structure | IUPAC Name<br>Purification Analytical data |
| 207 | H-22 | 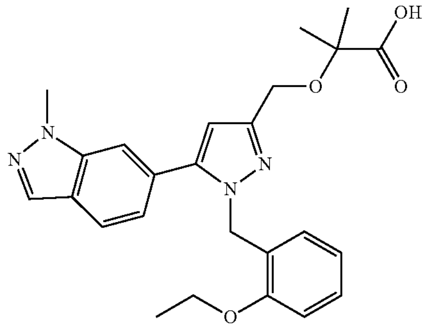 [SMILES: CCOc1ccccc1Cn1nc(COC(C)(C)C(=O)O)cc1-c1ccc2cnn(C)c2c1] | 2-([1-[(2-Ethoxyphenyl)methyl]-5-(1-methyl-1H-indazol-6-yl)-1H-pyrazol-3-yl]methoxy)-2-methylpropanoic acid<br>XSelect: 37% ACN up to 65% in 7 min<br>LC-MS: (ES, m/z): 449.<br>$^1$H NMR: (300 MHz, DMSO-$d_6$) δ 12.68 (s, 1H), 8.07 (d, J = 1.0 Hz, 1H), 7.78 (d, J = 8.3 Hz, 1H), 7.67 (d, J = 1.3 Hz, 1H), 7.29-7.10 (m, 2H), 7.01-6.81 (m, 2H), 6.74 (dd, J = 7.6, 1.7 Hz, 1H), 6.48 (s, 1H), 5.31 (s, 2H), 4.43 (s, 2H), 4.00 (s, 3H), 3.91 (q, J = 6.9 Hz, 2H), 1.40 (s, 6H), 1.11 (t, J = 6.9 Hz, 3H). |
| 208 | H-63 | 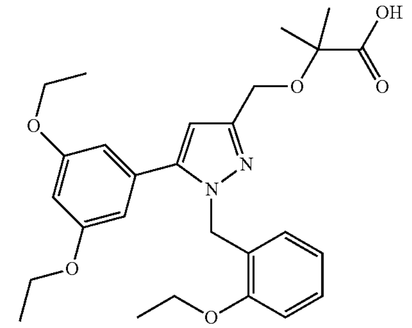 [SMILES: CCOc1cc(OCC)cc(-c2cc(COC(C)(C)C(=O)O)nn2Cc2ccccc2OCC)c1] | 2-([5-(3,5-Diethoxyphenyl)-1-[(2-ethoxyphenyl)methyl]-1H-pyrazol-3-yl]methoxy)-2-methylpropanoic acid<br>XBridge: 45% ACN up to 80% in 7 min<br>LC-MS: (ES, m/z): 483.15.<br>$^1$H NMR (300 MHz, DMSO) δ 7.22 (m, 1H), 6.97 (m, 1H), 6.86 (td, J = 7.4, 7.4, 1.1 Hz, 1H), 6.66 (dd, J = 7.6, 1.7 Hz, 1H), 6.45 (m, 3H), 6.42 (s, 1H), 5.26 (s, 2H), 4.40 (s, 2H), 4.00 (q, J = 7.0, 6.9, 6.9 Hz, 2H), 3.90 (q, J = 7.0, 7.0, 7.0 Hz, 4H), 1.39 (s, 6H), 1.24 (td, J = 7.0, 7.0, 2.6 Hz, 9H). |
| 209 | H-66 | 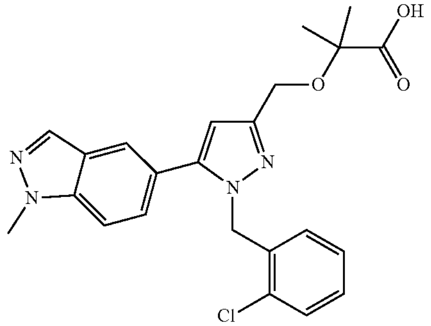 [SMILES: Cn1ncc2cc(-c3cc(COC(C)(C)C(=O)O)nn3Cc3ccccc3Cl)ccc21] | 2-([1-[(2-Chlorophenyl)methyl]-5-(1-methyl-1H-indazol-5-yl)-1H-pyrazol-3-yl]methoxy)-2-methylpropanoic acid<br>XSelect: 35% ACN up to 65% in 7 min<br>LC-MS: (ES, m/z): 439.<br>$^1$H NMR: (300 MHz, DMSO-$d_6$) δ 12.71 (s, 1H), 8.07 (d, J = 0.9 Hz, 1H), 7.79 (d, J = 1.4 Hz, 1H), 7.70 (dt, J = 8.8, 1.0 Hz, 1H), 7.49-7.36 (m, 2H), 7.32-7.22 (m, 2H), 6.76 (dd, J = 5.7, 3.7 Hz, 1H), 6.44 (s, 1H), 5.39 (s, 2H), 4.42 (s, 2H), 4.05 (s, 3H), 1.39 (s, 6H). |
| 210 | H-67 | 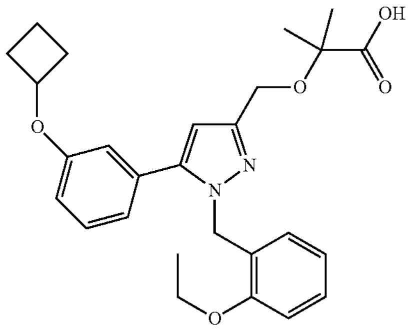 [SMILES: CCOc1ccccc1Cn1nc(COC(C)(C)C(=O)O)cc1-c1cccc(OC2CCC2)c1] | 2-([5-(3-cyclobutoxyphenyl)-1-[(2-ethoxyphenyl)methyl]-1H-pyrazol-3-yl]methoxy)-2-methylpropanoic acid<br>XBridge: 50% ACN up to 80% in 7 min<br>LC-MS: (ES, m/z): 465.<br>$^1$H NMR: (300 MHz, DMSO-$d_6$) δ 12.68 (s, 1H), 7.38-7.20 (m, 2H), 7.05-6.94 (m, 2H), 6.92-6.82 (m, 2H), 6.75-6.62 (m, 2H), 6.42 (s, 1H), 5.26 (s, 2H), 4.50 (q, J = 7.1 Hz, 1H), 4.42 (s, 2H), 4.02 (q, J = 6.9 Hz, 2H), 2.30-2.15 (m, 2H), 2.03-1.86 (m, 2H), 1.79-1.65 (m, 1H), 1.63-1.47 (m, 1H), 1.40 (s, 6H), 1.24 (t, J = 6.9 Hz, 3H). |

TABLE 25-continued

| Examples 155-276. | | | |
|---|---|---|---|
| Ex. | Ester | Structure | IUPAC Name<br>Purification Analytical data |
| 211 | H-71 | 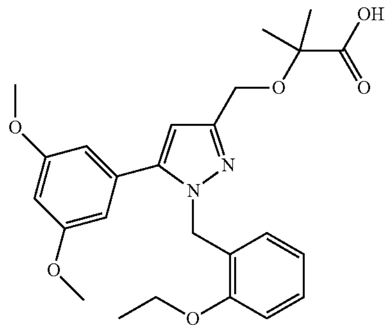 [SMILES: CCOc1ccccc1Cn1nc(COC(C)(C)C(=O)O)cc1-c1cc(OC)cc(OC)c1] | 2-([5-(3,5-Dimethoxyphenyl)-1-[(2-ethoxyphenyl)methyl]-1H-pyrazol-3-yl]-methoxy)-2-methylpropanoic acid<br>XBridge: 40% ACN up to 68% in 7 min<br>LC-MS: (ES, m/z): 455.<br>$^1$H NMR: (300 MHz, MeOH-$d_4$) δ 7.24 (td, J = 7.8, 7.4, 1.7 Hz, 1H), 6.99-6.81 (m, 2H), 6.69 (dd, J = 7.6, 1.6 Hz, 1H), 6.54-6.41 (m, 4H), 5.33 (s, 2H), 4.57 (s, 2H), 4.04 (q, J = 7.0 Hz, 2H), 3.64 (s, 6H), 1.52 (s, 6H), 1.34 (t, J = 7.0 Hz, 3H). |
| 212 | H-23 | 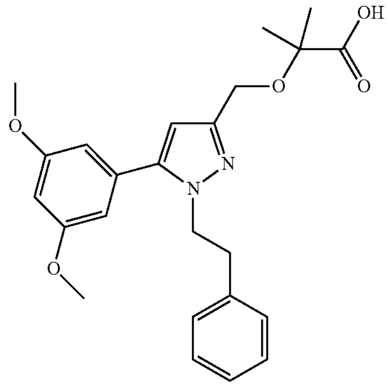 [SMILES: COc1cc(OC)cc(-c2cc(COC(C)(C)C(=O)O)nn2CCc2ccccc2)c1] | 2-([5-(3,5-Dimethoxyphenyl)-1-(2-phenylethyl)-1H-pyrazol-3-yl]methoxy)-2-methylpropanoic acid<br>XSelect: 40% ACN up to 66% in 7 min<br>LC-MS: (ES, m/z): 425.<br>$^1$H NMR: (300 MHz, DMSO-$d_6$) δ 12.67 (s, 1H), 7.32-7.11 (m, 3H), 7.06-6.92 (m, 2H), 6.53 (t, J = 2.3 Hz, 1H), 6.37 (d, J = 2.3 Hz, 2H), 6.26 (s, 1H), 4.43 (s, 2H), 4.34-4.20 (m, 2H), 3.74 (s, 6H), 3.13-2.99 (m, 2H), 1.41 (s, 6H). |
| 213 | H-74 | 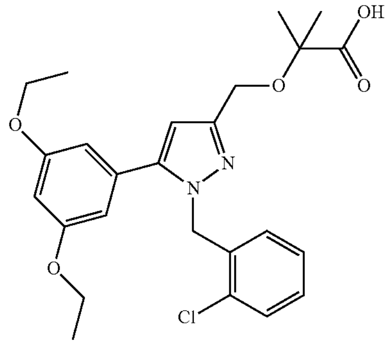 [SMILES: CCOc1cc(OCC)cc(-c2cc(COC(C)(C)C(=O)O)nn2Cc2ccccc2Cl)c1] | 2-([1-[(2-Chlorophenyl)methyl]-5-(3,5-diethoxyphenyl)-1H-pyrazol-3-yl]-methoxy)-2-methylpropanoic acid<br>XSelect: 53% ACN up to 76% in 7 min<br>LC-MS: (ES, m/z): 473.10.<br>$^1$H NMR: (300 MHz, DMSO) δ 12.63 (s, 1H), 7.45 (m, 1H), 7.30 (m, 2H), 6.72 (m, 1H), 6.45 (m, 4H), 5.38 (s, 2H), 4.41 (s, 2H), 3.91 (q, J = 7.0, 7.0, 7.0 Hz, 4H), 1.39 (s, 6H), 1.24 (t, J = 6.9, 6.9 Hz, 6H). |
| 214 | H-111 | 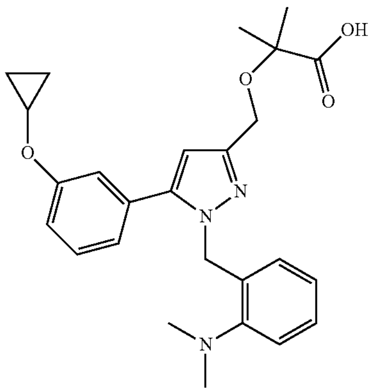 [SMILES: CN(C)c1ccccc1Cn1nc(COC(C)(C)C(=O)O)cc1-c1cccc(OC2CC2)c1] | 2-([5-(3-Cyclopropoxyphenyl)-1-[[2-(dimethylamino)phenyl]methyl]-1H-pyrazol-3-yl]methoxy)-2-methylpropanoic acid<br>XSelect: 67% ACN up to 68% in 7 min<br>LC-MS: (ES, m/z): 450.<br>$^1$H-NMR: (CDCl3, ppm): $^1$H NMR (300 MHz, MeOD) δ 7.25 (m, 2H), 7.17 (dd, J = 8.1, 1.4 Hz, 1H), 7.00 (m, 2H), 6.90 (m, 2H), 6.74 (dd, J = 7.6, 1.5 Hz, 1H), 6.51 (s, 1H), 5.43 (s, 2H), 4.59 (s, 2H), 3.55 (m, 1H), 2.60 (s, 6H), 1.53 (s, 6H), 0.59 (m, 4H). |

TABLE 25-continued

| Ex. | Ester | Structure | IUPAC Name<br>Purification Analytical data |
|---|---|---|---|
| | | Examples 155-276. | |
| 215 | H-99 | 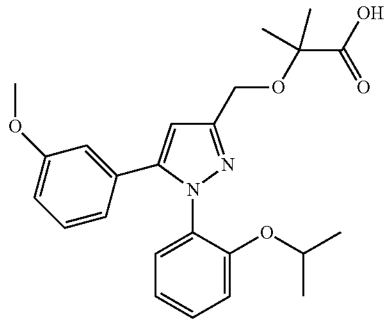 [SMILES: COc1cccc(-c2cc(COC(C)(C)C(=O)O)nn2-c2ccccc2OC(C)C)c1] | 2-([5-(3-Methoxyphenyl)-1-[2-(propan-2-yloxy)phenyl]-1H-pyrazol-3-yl]-methoxy)-2-methylpropanoic acid XBridge: 38% ACN up to 61% in 7 min LC-MS: (ES, m/z): 425. $^1$H NMR (300 MHz, DMSO) δ 7.46 (m, 1H), 7.38 (t, J = 7.9, 7.9 Hz, 1H), 7.18 (t, J = 7.9, 7.9 Hz, 1H), 7.03 (m, 2H), 6.81 (m, 2H), 6.68 (m, 1H), 6.58 (s, 1H), 4.45 (s, 2H), 4.34 (m, 1H), 3.57 (s, 3H), 1.41 (s, 6H), 0.96 (s, 3H), 0.59 (s, 3H). |
| 216 | H-96 | 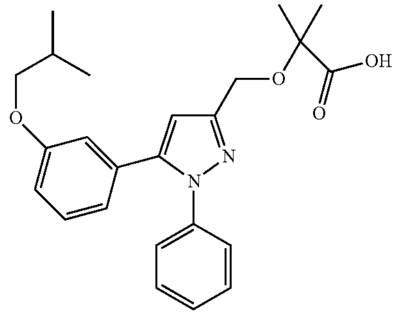 [SMILES: CC(C)COc1cccc(-c2cc(COC(C)(C)C(=O)O)nn2-c2ccccc2)c1] | 2-Methyl-2-([5-[3-(2-methylpropoxy)-phenyl]-1-phenyl-1H-pyrazol-3-yl]-methoxy)propanoic acid SunFire: 69% ACN up to to 71% ACN in 8 min LC-MS: (ES, m/z): 409. H-NMR: (MeOD, ppm): δ: 7.48-7.32 (m, 3H), 7.35-7.14 (m, 3H), 6.91-6.78 (m, 2H), 6.73-6.63 (m, 2H), 4.61 (s, 2H), 3.54 (d, J = 6.5 Hz, 2H), 1.92 (hept, J = 6.7 Hz, 1H), 1.53 (s, 6H), 0.95 (d, J = 6.7 Hz, 6H). |
| 217 | H-122 | 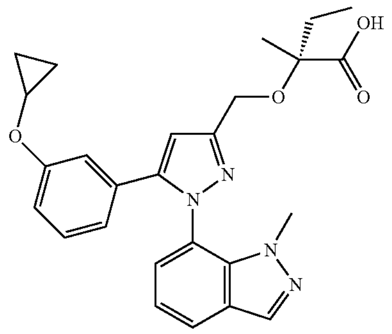 [SMILES: CC[C@@](C)(OCc1cc(-c2cccc(OC3CC3)c2)n(-c2cccc3cnn(C)c23)n1)C(=O)O] | (2R)-2-([5-(3-cyclopropoxyphenyl)-1-(1-methyl-1H-indazol-7-yl)-1H-pyrazol-3-yl]methoxy)-2-methylbutanoic acid XSelect 43% ACN up to 65% in 7 min LC-MS: (ES, m/z): 461. $^1$H NMR: (300 MHz, DMSO-$d_6$)[1] δ: 12.67 (s, 2H), 8.18 (s, 1H), 7.91 (d, J = 8.0 Hz, 2H), 7.37 (d, J = 7.3 Hz, 2H), 7.28-7.12 (m, 4H), 7.03-6.75 (m, 8H), 4.53 (s, 4H), 3.45 (s, 7H), 2.49 (s, 1H), 1.76 (dh, J = 14.3, 7.2 Hz, 4H), 1.40 (s, 5H), 0.88 (t, J = 7.4 Hz, 6H), 0.50-0.35 (m, 8H). |
| 218 | H-123 | 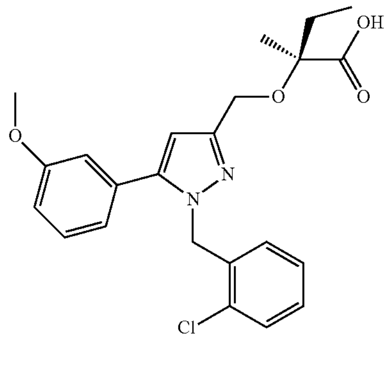 [SMILES: CC[C@](C)(OCc1cc(-c2cccc(OC)c2)n(Cc2ccccc2Cl)n1)C(=O)O] | (2S)-2-([1-[(2-chlorophenyl)methyl]-5-(3-methoxyphenyl)-1H-pyrazol-3-yl]methoxy)-2-methylbutanoic acid XSelect: 67% ACN up to 68% in 7 min) LC-MS: (ES, m/z): 429. $^1$H NMR (DMSO) δ: 12.64 (s, 1H), 7.50-7.22 (m, 4H), 7.02-6.84 (m, 3H), 6.78-6.69 (m, 1H), 6.45 (s, 1H), 5.38 (s, 2H), 4.41 (d, J = 1.9 Hz, 2H), 3.69 (s, 3H), 1.84-1.60 (m, J = 7.1 Hz, 2H), 1.36 (s, 3H), 0.85 (t, J = 7.4 Hz, 3H). |

TABLE 25-continued

Examples 155-276.

| Ex. | Ester | Structure | IUPAC Name<br>Purification Analytical data |
|---|---|---|---|
| 219 | H-124 | 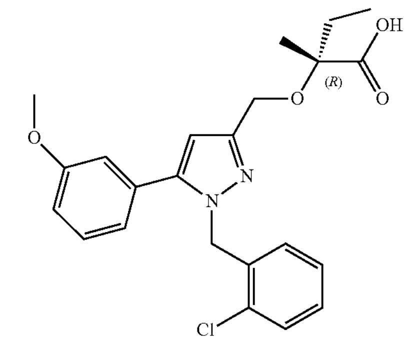 | (2R)-2-([1-[(2-chlorophenyl)methyl]-5-(3-methoxyphenyl)-1H-pyrazol-3-yl]-methoxy)-2-methylbutanoic acid<br>XBridge: 40% ACN up to 75% in 7 min<br>LC-MS: (ES, m/z): 429.<br>$^1$H NMR: (400 MHz, DMSO-$d_6$) δ 2.61 (s, 1H), 7.49-7.22 (m, 4H), 7.02-6.84 (m, 3H), 6.78-6.69 (m, 1H), 6.46 (s, 1H), 5.38 (s, 2H), 4.41 (d, J = 2.2 Hz, 2H), 3.69 (s, 3H), 1.84-1.61 (m, J = 7.6 Hz, 2H), 1.36 (s, 3H), 0.85 (t, J = 7.4 Hz, 3H) |
| 220 | H-130 | 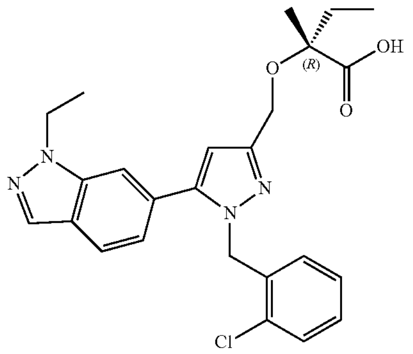 | (2R)-2-([1-[(2-chlorophenyl)methyl]-5-(1-ethyl-1H-indazol-6-yl)-1H-pyrazol-3-yl]methoxy)-2-methylbutanoic acid<br>XSelect: 48% ACN up to 67% in 7 min<br>LC-MS: (ES, m/z): 467.<br>$^1$H NMR: (300 MHz, DMSO-$d_6$)[1] δ: 12.63 (s, 1H), 8.08 (s, 1H), 7.79 (d, J = 8.4 Hz, 1H), 7.68 (s, 1H), 7.46-7.37 (m, 1H), 7.29 (q, J = 4.8 Hz, 2H), 7.13 (d, J = 8.4 Hz, 1H), 6.84-6.74 (m, 1H), 6.53 (s, 1H), 5.46 (s, 2H), 4.52-4.32 (m, 4H), 1.75 (hept, J = 7.0 Hz, 2H), 1.41-1.26 (m, 6H), 0.86 (t, J = 7.4 Hz, 3H). |
| 221 | H-142 | 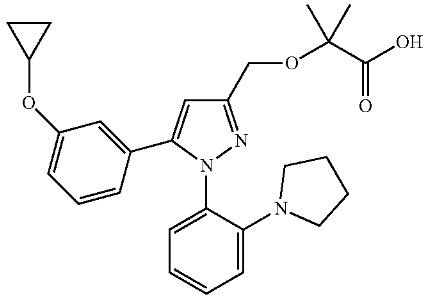 [SMILES: CC(C)(OCc1cc(-c2cccc(OC3CC3)c2)n(-c2ccccc2N2CCCC2)n1)C(=O)O] | 2-([5-(3-Cyclopropoxyphenyl)-1-[2-(pyrrolidin-1-yl)phenyl]-1H-pyrazol-3-yl]methoxy)-2-methylpropanoic acid<br>XBridge: 45% ACN up to 77% in 7 min<br>LC-MS: (ES, m/z): 462.1.<br>1H NMR: (300 MHz, DMSO) δ 7.22 (m, 2H), 7.03 (dd, J = 7.7, 1.7 Hz, 1H), 6.93 (m, 2H), 6.86 (ddd, J = 8.3, 2.5, 1.0 Hz, 1H), 6.74 (dd, J = 8.5, 1.3 Hz, 1H), 6.67 (td, J = 7.5, 7.5, 1.2 Hz, 1H), 6.63 (s, 1H), 4.47 (s, 2H), 3.51 (tt, J = 6.1, 6.1, 3.0, 3.0 Hz, 1H), 2.75 (qq, J = 8.5, 8.5, 8.5, 5.0, 5.0, 4.6 Hz, 4H), 1.64 (m, 4H), 1.41 (s, 6H), 0.62 (m, 2H), 0.50 (m, 2H). |
| 222 | H-129 | 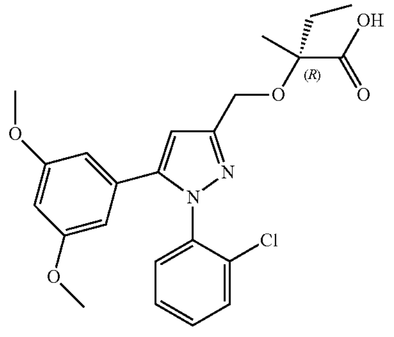 | (2R)-2-([1-(2-Chlorophenyl)-5-(3,5-dimethoxyphenyl)-1H-pyrazol-3-yl]-methoxy)-2-methylbutanoic acid<br>XSelect: 45% ACN up to 64% in 7 min<br>LC-MS: (ES, m/z): 445.<br>$^1$H NMR: (300 MHz, DMSO-$d_6$) δ 12.67 (s, 1H), 7.74-7.38 (m, 4H), 6.71 (s, 1H), 6.41 (t, J = 2.2 Hz, 1H), 6.32 (d, J = 2.2 Hz, 2H), 4.47 (d, J = 2.0 Hz, 2H), 3.60 (s, 6H), 1.77 (hept, J = 7.0 Hz, 2H), 1.39 (s, 3H), 0.88 (t, J = 7.4 Hz, 3H). |

TABLE 25-continued

| Examples 155-276. | | | |
|---|---|---|---|
| Ex. | Ester | Structure | IUPAC Name<br>Purification Analytical data |
| 223 | H-126 | 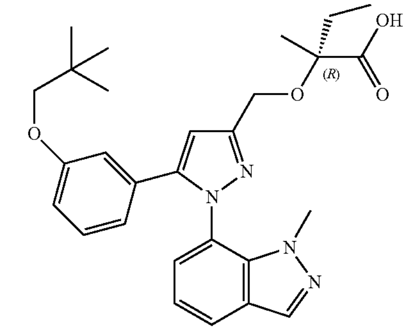 | (2R)-2-([5-[3-(2,2-Dimethyl-propoxy)phenyl]-1-(1-methyl-1H-indazol-7-yl)-1H-pyrazol-3-yl]methoxy)-2-methylbutanoic acid<br>XSelect: 55% ACN up to 81% in 7 min<br>LC-MS: (ES, m/z): 491.<br>$^1$H NMR: (300 MHz, DMSO-$d_6$) δ 12.70 (s, 1H), 8.20 (s, 1H), 7.92 (dd, J = 8.1, 1.0 Hz, 1H), 7.41 (dd, J = 7.3, 1.0 Hz, 1H), 7.29-7.04 (m, 2H), 6.92-6.75 (m, 3H), 6.63 (dd, J = 2.5, 1.6 Hz, 1H), 4.54 (s, 2H), 3.44 (s, 3H), 3.19 (s, 2H), 1.91-1.69 (m, 2H), 1.41 (s, 3H), 0.89 (d, J = 4.1 Hz, 12H). |
| 224 | H-107 | 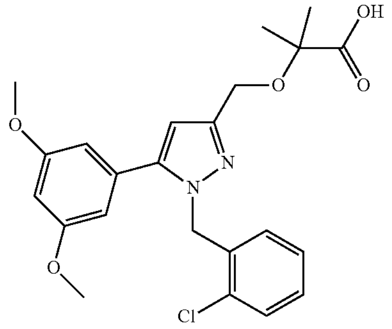 [SMILES: COc1cc(OC)cc(-c2cc(COC(C)(C)C(=O)O)nn2Cc2ccccc2Cl)c1] | 2-([1-[(2-Chlorophenyl)methyl]-5-(3,5-dimethoxyphenyl)-1H-pyrazol-3-yl]-methoxy)-2-methylpropanoic acid<br>XBridge: 45% ACN up to 65% in 7 min<br>LC-MS: (ES, m/z): 445.<br>$^1$H-NMR: (MeOD): δ: 7.46-7.36 (m, 1H), 7.35-7.21 (m, 2H), 6.80-6.71 (m, 1H), 6.58-6.39 (m, 4H), 5.43 (s, 2H), 4.58 (s, 2H), 3.66 (s, 6H), 1.52 (s, 6H). |
| 225 | H-112 | 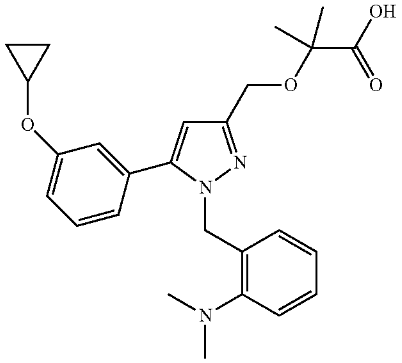 | 2-([5-(3-Cyclopropoxyphenyl)-1-[2-(dimethylamino)phenyl]-1H-pyrazol-3-yl]methoxy)-2-methylpropanoic acid<br>XSelect: 64% ACN up to 78% in 7 min<br>LC-MS: (ES, m/z): 436.<br>$^1$H-NMR: (MeOD, ppm): δ: 7.47-7.29 (m, 2H), 7.26-7.06 (m, 3H), 6.96-6.81 (m, 3H), 6.71 (s, 1H), 4.63 (s, 2H), 3.50 (tt, J = 6.2, 3.0 Hz, 1H), 2.44 (s, 6H), 1.54 (s, 6H), 0.70-0.47 (m, 4H). |
| 226 | H-108 | 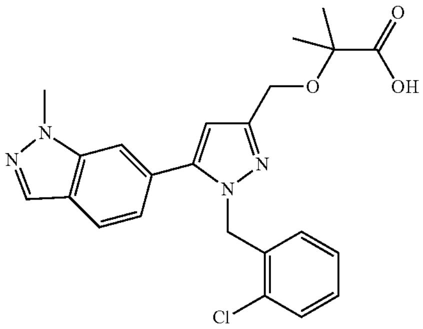 [SMILES: Cn1ncc2ccc(-c3cc(COC(C)(C)C(=O)O)nn3Cc3ccccc3Cl)cc21] | 2-([1-[(2-Chlorophenyl)methyl]-5-(1-methyl-1H-indazol-6-yl)-1H-pyrazol-3-yl]methoxy)-2-methylpropanoic acid<br>XBridge: 38% ACN up to 61% in 7 min<br>LC-MS: (ES, m/z): 439.<br>$^1$H NMR: (300 MHz, MeOH-$d_4$) δ 8.02 (d, J = 1.0 Hz, 1H), 7.77 (dd, J = 8.4, 0.9 Hz, 1H), 7.46 (q, J = 1.1 Hz, 1H), 7.43-7.32 (m, 1H), 7.32-7.20 (m, 2H), 7.13 (dd, J = 8.4, 1.4 Hz, 1H), 6.95-6.77 (m, 1H), 6.64 (s, 1H), 5.49 (s, 2H), 4.61 (s, 2H), 3.97 (s, 3H), 1.53 (s, 6H). |

TABLE 25-continued

| Ex. | Ester | Structure | IUPAC Name Purification Analytical data |
|---|---|---|---|
| Examples 155-276. | | | |
| 227 | H-109 | 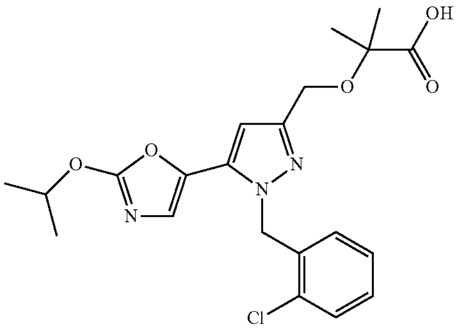 [SMILES: CC(C)Oc1ncc(-c2cc(COC(C)(C)C(=O)O)nn2Cc2ccccc2Cl)o1] | 2-([1-[(2-Chlorophenyl)methyl]-5-[2-(propan-2-yloxy)-1,3-oxazol-5-yl]-1H-pyrazol-3-yl]methoxy)-2-methylpropanoic acid XBridge: 35% ACN up to 50% in 7 min LC-MS: (ES, m/z): 434. $^1$H NMR (400 MHz, DMSO-$d_6$) δ 7.59 (s, 1H), 7.49 (dd, J = 7.7, 1.6 Hz, 1H), 7.31 (dtd, J = 16.7, 7.5, 1.7 Hz, 2H), 6.78 (dd, J = 7.5, 1.9 Hz, 1H), 6.54 (s, 1H), 5.50 (s, 2H), 4.37 (s, 2H), 4.11 (p, J = 6.7 Hz, 1H), 1.38 (s, 6H), 1.26 (d, J = 6.7 Hz, 6H). |
| 228 | H-133 | 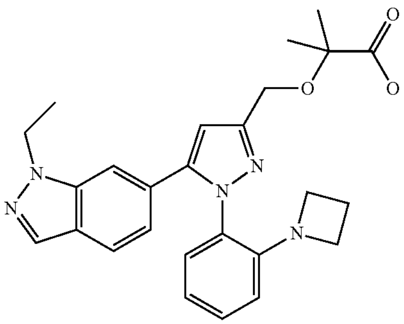 [SMILES: CCn1ncc2ccc(-c3cc(COC(C)(C)C(=O)O)nn3-c3ccccc3N3CCC3)cc21] | 2-([1-[2-(Azetidin-1-yl)phenyl]-5-(1-ethyl-1H-indazol-6-yl)-1H-pyrazol-3-yl]methoxy)-2-methylpropanoic acid XSelect: 38% ACN up to 64% in 7 min LC-MS: (ES, m/z): 460.15. $^1$H NMR (300 MHz, DMSO) δ 7.99 (d, J = 0.9 Hz, 1H), 7.65 (d, J = 8.5 Hz, 1H), 7.54 (d, J = 1.3 Hz, 1H), 7.27 (ddd, J = 8.5, 7.4, 1.6 Hz, 1H), 7.09 (ddd, J = 20.0, 8.1, 1.5 Hz, 2H), 6.71 (m, 2H), 6.49 (dd, J = 8.2, 1.3 Hz, 1H), 4.49 (s, 2H), 4.28 (q, J = 7.2, 7.2, 7.2 Hz, 2H), 3.47 (dt, J = 11.8, 7.3, 7.3 Hz, 4H), 2.05 (m, 2H), 1.43 (s, 6H), 1.23 (t, J = 7.1, 7.1 Hz, 3H). |
| 229 | H-135 | 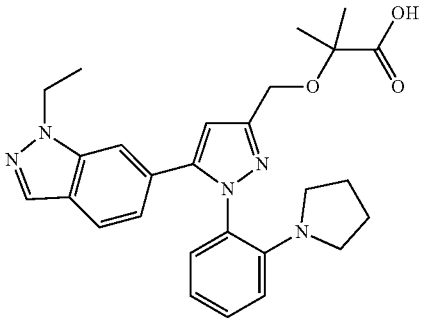 [SMILES: CCn1ncc2ccc(-c3cc(COC(C)(C)C(=O)O)nn3-c3ccccc3N3CCCC3)cc21] | 2-([5-(1-ethyl-1H-indazol-6-yl)-1-[2-(pyrrolidin-1-yl)phenyl]-1H-pyrazol-3-yl]methoxy)-2-methylpropanoic acid XSelect: 52% ACN up to 78% in 7 min LC-MS: (ES, m/z): 474. $^1$H NMR (300 MHz, DMSO) δ 12.66 (s, 1H), 7.98 (d, J = 1.0 Hz, 1H), 7.63 (d, J = 8.4 Hz, 1H), 7.43 (d, J = 1.4 Hz, 1H), 7.25 (ddd, J = 8.6, 7.2, 1.7 Hz, 1H), 7.07 (ddd, J = 8.4, 5.7, 1.5 Hz, 2H), 6.72 (m, 3H), 4.50 (s, 2H), 4.25 (q, J = 7.2, 7.2, 7.2 Hz, 2H), 2.77 (m, 4H), 1.70 (m, 2H), 1.60 (m, 2H), 1.43 (s, 6H), 1.22 (t, J = 7.2, 7.2 Hz, 3H). |
| 230 | H-136 | 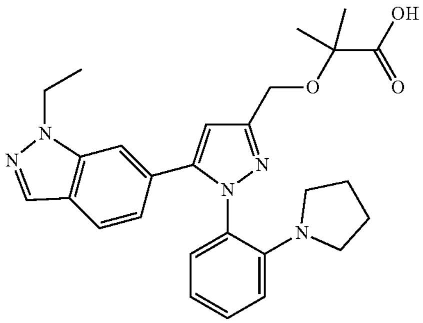 | 2-Methyl-2-([5-(1-methyl-1H-indazol-6-yl)-1-[2-(pyrrolidin-1-yl)phenyl]-1H-pyrazol-3-yl]methoxy]propanoic acid XBridge: 18% ACN up to 39% in 7 min LC-MS: (ES, m/z): 460. $^1$H NMR: (300 MHz, DMSO-$d_6$) δ 7.97 (d, J = 0.9 Hz, 1H), 7.60 (d, J = 8.5 Hz, 1H), 7.47 (s, 1H), 7.25 (ddd, J = 8.6, 7.2, 1.7 Hz, 1H), 7.14-6.94 (m, 2H), 6.82-6.57 (m, 3H), 4.50 (s, 2H), 3.88 (s, 3H), 2.77 (q, J = 6.0, 4.4 Hz, 4H), 1.84-1.48 (m, 4H), 1.40 (s, 6H). |

TABLE 25-continued

| Ex. | Ester | Structure | IUPAC Name<br>Purification Analytical data |
|---|---|---|---|
| | | Examples 155-276. | |
| 231 | H-137 | 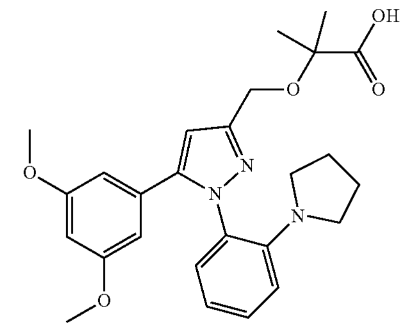 [SMILES: COc1cc(OC)cc(-c2cc(COC(C)(C)C(=O)O)nn2-c2ccccc2N2CCCC2)c1] | 2-([5-(3,5-Dimethoxyphenyl)-1-[2-(pyrrolidin-1-yl)phenyl]-1H-pyrazol-3-yl]methoxy)-2-methylpropanoic acid<br>XSelect: 42% ACN up to 75% in 7 min<br>LC-MS: ES, m/z): 466.<br>H NMR: (300 MHz, DMSO-$d_6$) δ 12.59 (s, 1H), 7.25 (ddd, J = 8.7, 7.2, 1.7 Hz, 1H), 7.00 (dd, J = 7.7, 1.7 Hz, 1H), 6.80-6.72 (m, 1H), 6.71-6.62 (m, 2H), 6.42 (d, J = 2.3 Hz, 2H), 6.37 (t, J = 2.2 Hz, 1H), 4.46 (s, 2H), 2.79 (t, J = 5.5 Hz, 4H), 1.79-1.55 (m, 4H), 1.41 (s, 6H). |
| 232 | H-143 | 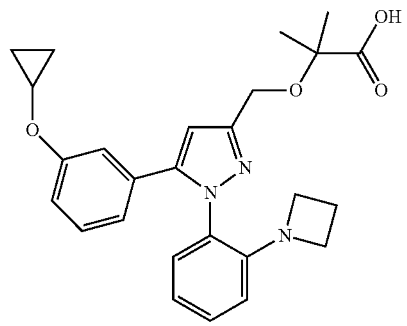 [SMILES: CC(C)(OCc1cc(-c2cccc(OC3CC3)c2)n(-c2ccccc2N2CCC2)n1)C(=O)O] | 2-([1-[2-(Azetidin-1-yl)phenyl]-5-(3-cyclopropoxyphenyl)-1H-pyrazol-3-yl]-methoxy)-2-methylpropanoic acid<br>XSelect: 57% ACN up to 67% in 7 min<br>LC-MS: (ES, m/z): 448.3.<br>$^1$H NMR: (300 MHz, MeOD) δ 7.29 (ddd, J = 8.2, 7.3, 1.6 Hz, 1H), 7.20 (m, 1H), 7.05 (dd, J = 7.3, 1.6 Hz, 3H), 6.89 (m, 1H), 6.74 (td, J = 7.6, 7.6, 1.3 Hz, 1H), 6.69 (s, 1H), 6.54 (dd, J = 8.2, 1.3 Hz, 1H), 4.59 (s, 2H), 3.49 (m, 5H), 2.13 (m, 2H), 1.53 (s, 6H), 0.66 (q, J = 5.7, 5.0, 5.0 Hz, 2H), 0.56 (tt, J = 6.0, 6.0, 3.1, 3.1 Hz, 2H). |
| 233 | H-144 | 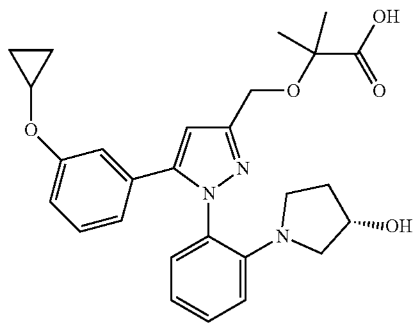 [SMILES: CC(C)(OCc1cc(-c2cccc(OC3CC3)c2)n(-c2ccccc2N2CC[C@H](O)C2)n1)C(=O)O] | 2-([5-(3-Cyclopropoxyphenyl)-1-[2-[(3S)-3-hydroxypyrrolidin-1-yl]phenyl]-1H-pyrazol-3-yl]methoxy)-2-methylpropanoic acid<br>XSelect: 36% ACN up to 64% in 7 min<br>LC-MS: (ES, m/z): 478.<br>$^1$H NMR (300 MHz, DMSO) δ 7.22 (m, 2H), 7.02 (m, 2H), 6.89 (m, 2H), 6.73 (m, 1H), 6.63 (dd, J = 16.0, 5.1 Hz, 2H), 4.47 (m, 2H), 4.10 (m, 1H), 3.52 (dp, J = 8.9, 3.1, 3.1, 3.0, 3.0 Hz, 1H), 3.08 (q, J = 8.8, 8.8, 8.6 Hz, 1H), 2.95 (dt, J = 9.1, 4.4, 4.4 Hz, 1H), 2.86 (dt, J = 10.0, 4.7, 4.7 Hz, 1H), 2.74 (dt, J = 9.2, 5.4, 5.4 Hz, 1H), 2.63 (ddd, J = 11.3, 5.4, 2.6 Hz, 1H), 1.78 (ddd, J = 12.9, 8.4, 4.8 Hz, 1H), 1.64 (m, 1H), 1.41 (d, J = 2.2 Hz, 6H), 0.62 (q, J = 7.7, 6.1, 6.1 Hz, 2H), 0.48 (dq, J = 8.5, 3.2, 3.2, 3.2 Hz, 2H). |
| 234 | H-145 | 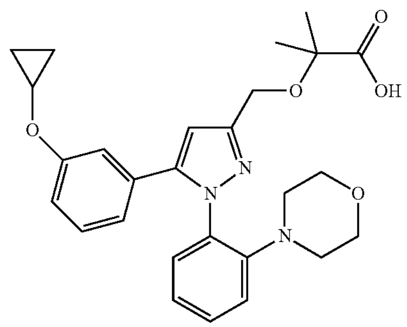 [SMILES: CC(C)(OCc1cc(-c2cccc(OC3CC3)c2)n(-c2ccccc2N2CCOCC2)n1)C(=O)O] | 2-([5-(3-Cyclopropoxyphenyl)-1-[2-(morpholin-4-yl)phenyl]-1H-pyrazol-3-yl]methoxy)-2-methylpropanoic acid<br>XBridge: 40% ACN up to 65% in 7 min<br>LC-MS: (ES, m/z): 478.1.<br>$^1$H NMR: (300 MHz, DMSO) δ 7.50 (dd, J = 7.8, 1.6 Hz, 1H), 7.39 (td, J = 7.7, 7.7, 1.7 Hz, 1H), 7.19 (dd, J = 8.4, 7.1 Hz, 2H), 6.93 (m, 2H), 6.83 (m, 2H), 6.69 (s, 1H), 4.48 (s, 2H), 3.49 (tt, J = 5.9, 5.9, 3.3, 3.3 Hz, 1H), 3.32 (dd, J = 9.8, 5.7 Hz, 2H), 3.11 (m, 2H), 2.39 (d, J = 12.6 Hz, 2H), 2.15 (m, 2H), 1.41 (s, 6H), 0.52 (m, 4H). |

TABLE 25-continued

| Ex. | Ester | Structure | IUPAC Name Purification Analytical data |
|---|---|---|---|
| | | | Examples 155-276. |
| 235 | H-146 | 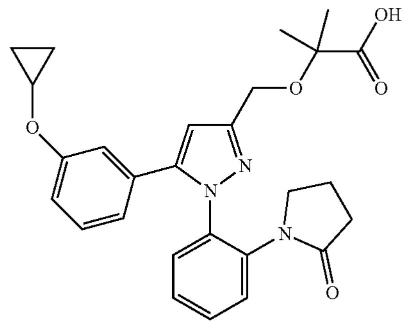 [SMILES: CC(C)(OCc1cc(-c2cccc(OC3CC3)c2)n(-c2ccccc2N2CCCC2=O)n1)C(=O)O] | 2-([5-(3-Cyclopropoxyphenyl)-1-[2-(2-oxopyrrolidin-1-yl)phenyl]-1H-pyrazol-3-yl]methoxy)-2-methylpropanoic acid XSelect: 33% ACN up to 58% in 7 min LC-MS: (ES, m/z): 476.10. $^1$H NMR (300 MHz, DMSO) δ 12.65 (s, 1H), 7.45 (m, 2H), 7.31 (m, 1H), 7.22 (t, J = 7.9, 7.9 Hz, 1H), 7.12 (m, 1H), 7.06 (m, 1H), 7.01 (dt, J = 7.6, 1.2, 1.2 Hz, 1H), 6.88 (ddd, J = 8.3, 2.5, 1.0 Hz, 1H), 6.57 (s, 1H), 4.45 (s, 2H), 3.56 (tt, J = 6.1, 6.1, 3.0, 3.0 Hz, 1H), 3.38 (t, J = 6 Hz, 2H), 2.11 (t, J = 7.9, 7.9 Hz, 2H), 1.92 (p, J = 7.4, 7.4, 7.2, 7.2 Hz, 2H), 1.41 (s, 6H), 0.54 (m, 2H), 0.44 (m, 2H). |
| 236 | H-147 | 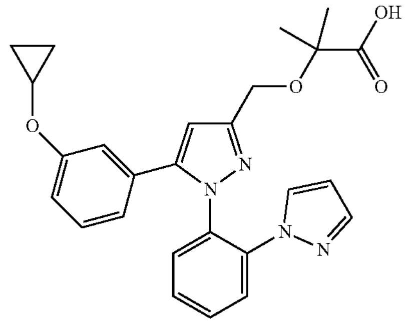 [SMILES: CC(C)(OCc1cc(-c2cccc(OC3CC3)c2)n(-c2ccccc2-n2cccn2)n1)C(=O)O] | 2-([5-(3-Cyclopropoxyphenyl)-1-[2-(1H-pyrazol-1-yl)phenyl]-1H-pyrazol-3-yl]-methoxy)-2-methylpropanoic acid XSelect: 38% ACN up to 65% in 7 min LC-MS: (ES, m/z): 459.15. 1H NMR (300 MHz, DMSO) δ 7.63 (m, 3H), 7.52 (m, 2H), 7.09 (t, J = 7.9, 7.9 Hz, 1H), 6.83 (m, 2H), 6.63 (dd, J = 2.5, 1.5 Hz, 1H), 6.56 (m, 2H), 6.28 (dd, J = 2.5, 1.8 Hz, 1H), 4.48 (s, 2H), 3.52 (dt, J = 6.0, 3.1, 3.1 Hz, 1H), 1.41 (s, 6H), 0.61 (m, 2H), 0.47 (m, 2H). |
| 237 | H-148 | 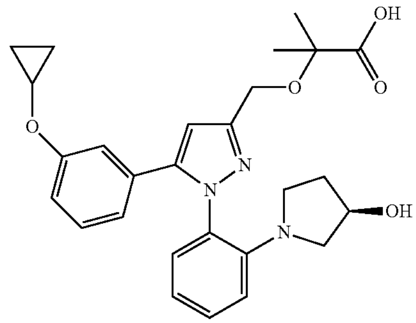 [SMILES: CC(C)(OCc1cc(-c2cccc(OC3CC3)c2)n(-c2ccccc2N2CC[C@@H](O)C2)n1)C(=O)O] | 2-([5-(3-Cyclopropoxyphenyl)-1-[2-[(3R)-3-hydroxypyrrolidin-1-yl]phenyl]-1H-pyrazol-3-yl]methoxy)-2-methylpropanoic acid XSelect: 37% ACN up to 64% in 7 min LC-MS: (ES, m/z): 478.15. $^1$H NMR (300 MHz, DMSO) δ 7.22 (m, 2H), 7.02 (m, 2H), 6.90 (m, 2H), 6.74 (m, 1H), 6.63 (m, 2H), 4.46 (m, 2H), 4.10 (p, J = 5.2, 5.2, 4.5, 4.5 Hz, 1H), 3.52 (m, 1H), 3.06 (p, J = 8.4, 8.4, 8.2, 8.2 Hz, 1H), 2.95 (td, J = 9.0, 8.5, 4.0 Hz, 1H), 2.86 (dt, J = 9.9, 4.7, 4.7 Hz, 1H), 2.74 (dt, J = 9.3, 5.4, 5.4 Hz, 1H), 2.63 (ddd, J = 10.6, 5.9, 2.5 Hz, 1H), 1.78 (ddd, J = 12.8, 8.3, 4.8 Hz, 1H), 1.64 (dd, J = 7.7, 4.1 Hz, 1H), 1.41 (d, J = 2.2 Hz, 6H), 0.61 (dd, J = 9.2, 4.6 Hz, 2H), 0.48 (dq, J = 10.3, 3.1, 2.7, 2.7 Hz, 2H). |
| 238 | H-151 | 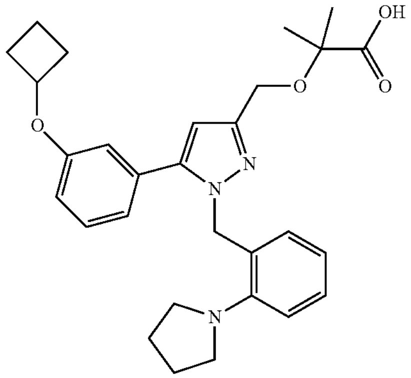 [SMILES: CC(C)(OCc1cc(-c2cccc(OC3CCC3)c2)n(Cc2ccccc2N2CCCC2)n1)C(=O)O] | 2-([5-(3-Cyclobutoxyphenyl)-1-[[2-(pyrrolidin-1-yl)phenyl]methyl]-1H-pyrazol-3-yl]methoxy)-2-methylpropanoic acid XSelect: 60% ACN up to 95% in 7 min LC-MS: (ES, m/z): 490. $^1$H NMR: (300 MHz, DMSO-$d_6$) δ 12.67 (s, 1H), 7.29 (t, J = 8.0 Hz, 1H),7.19 (ddd, J = 8.7, 7.2, 1.6 Hz, 1H), 7.06 (dd, J = 8.2, 1.2 Hz, 1H), 6.97-6.80 (m, 3H), 6.64-6.54 (m, 2H), 6.45 (s, 1H), 5.30 (s, 2H), 4.44 (s, 2H), 4.41 (d, J = 7.1 Hz, 1H), 3.19-2.87 (m, 4H), 2.26-2.07 (m, 2H), 1.99-1.88 (m, 2H), 1.88-1.80 (m, 4H), 1.71 (q, J = 10.1 Hz, 1H), 1.62-1.46 (m, 1H), 1.41 (s, 6H), 1.20 (s, 1H). |

TABLE 25-continued

| Examples 155-276. | | | |
|---|---|---|---|
| Ex. | Ester | Structure | IUPAC Name<br>Purification Analytical data |
| 239 | H-156 | 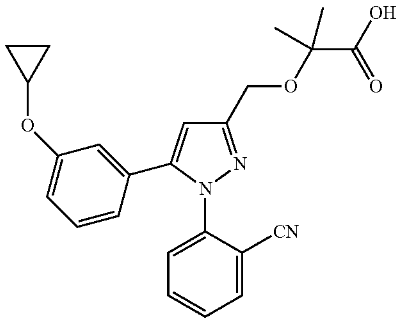 [SMILES: CC(C)(OCc1cc(-c2cccc(OC3CC3)c2)n(-c2ccccc2C#N)n1)C(=O)O] | 2-([1-(2-Cyanophenyl)-5-(3-cyclopropoxyphenyl)-1H-pyrazol-3-yl]methoxy)-2-methylpropanoic acid<br>XBridge: 35% ACN up to 64% in 7 min<br>LC-MS: (ES, m/z): 418.<br>$^1$H-NMR: (DMSO, ppm): $^1$H NMR (300 MHz, DMSO-$d_6$) δ 12.73 (s, 1H), 7.99 (dd, J = 7.7, 1.5 Hz, 1H), 7.83 (td, J = 7.8, 1.6 Hz, 1H), 7.73-7.52 (m, 2H), 7.27 (t, J = 7.9 Hz, 1H), 6.97 (ddd, J = 8.3, 2.5, 1.0 Hz, 1H), 6.91-6.79 (m, 2H), 6.75 (s, 1H), 4.52 (s, 2H), 3.64 (tt, J = 6.1, 3.0 Hz, 1H), 1.44 (s, 6H), 0.70-0.44 (m, 4H). |
| 240 | | 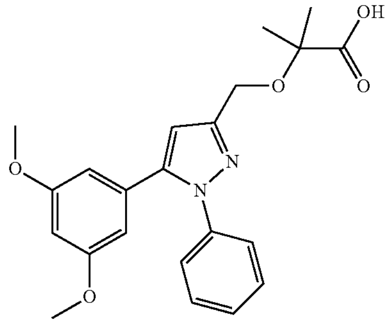 [SMILES: COc1cc(OC)cc(-c2cc(COC(C)(C)C(=O)O)nn2-c2ccccc2)c1] | 2-([5-(3,5-Dimethoxyphenyl)-1-phenyl-1H-pyrazol-3-yl]methoxy)-2-methylpropanoic acid<br>LC-MS (ES, m/z): 395.<br>$^1$H NMR ($CDCl_3$): δ 1.61 (s, 6H), 3.66 (s, 6H), 4.69 (s, 2H), 6.37 (d, J = 2.30, 2H), 6.41-6.44 (m, 1H), 6.55 (s, 1H), 7.30-7.40 (m, 5H). |
| 241 | | 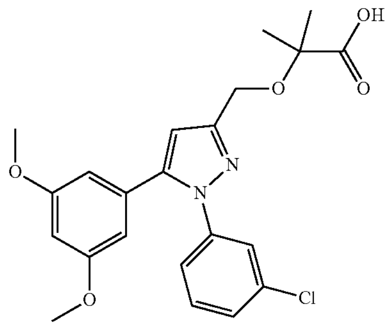 [SMILES: COc1cc(OC)cc(-c2cc(COC(C)(C)C(=O)O)nn2-c2cccc(Cl)c2)c1] | 2-([5-(3,5-Dimethoxyphenyl)-1-(3-chlorophenyl)-1H-pyrazol-3-yl]methoxy)-2-methylpropanoic acid<br>LC-MS (ES, m/z): 431.<br>$^1$H NMR ($CDCl_3$): δ 1.59 (s, 6H), 3.68 (s, 6H), 4.65 (s, 2H), 6.35 (d, J = 2.15 hZ, 2H), 6.40-6.46 (m, 1H), 6.53 (s, 1H), 7.08-7.14 (m, 1H), 7.19-7.31 (m, 2H), 7.39-7.44 (m, 1H). |
| 242 | | 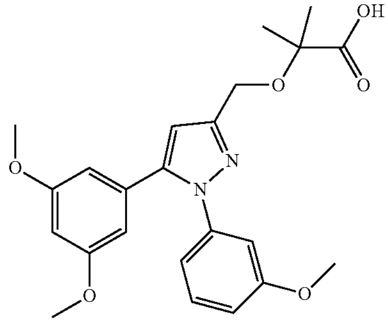 [SMILES: COc1cc(OC)cc(-c2cc(COC(C)(C)C(=O)O)nn2-c2cccc(OC)c2)c1] | 2-([5-(3,5-Dimethoxyphenyl)-1-(3-methoxyphenyl)-1H-pyrazol-3-yl]methoxy)-2-methylpropanoic acid<br>LC-MS (ES, m/z): 427.<br>$^1$H NMR ($CDCl_3$): δ 1.59 (s, 6H), 3.66 (s, 6H), 3.73 (s, 3H), 4.66 (s, 2H), 6.36 (d, J = 2.25 Hz, 2H), 6.41 (t, J = 2.21 Hz, 1H), 6.79-6.95 (m, 3H), 7.21 (t, J = 8.10 Hz, 1H). |

TABLE 25-continued

Examples 155-276.

| Ex. | Ester | Structure | IUPAC Name<br>Purification Analytical data |
|---|---|---|---|
| 243 | | 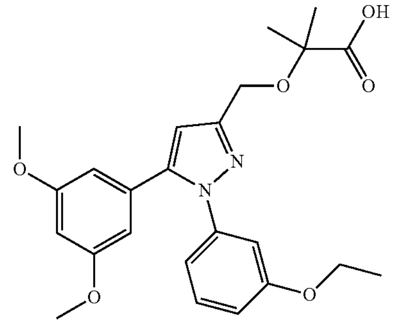 [SMILES: CCOc1cccc(-n2nc(COC(C)(C)C(=O)O)cc2-c2cc(OC)cc(OC)c2)c1] | 2-([5-(3,5-Dimethoxyphenyl)-1-(3-ethoxyphenyl)-1H-pyrazol-3-yl]-methoxy)-2-methylpropanoic acid<br>LC-MS (ES, m/z): 441.<br>$^1$H NMR ($CDCl_3$): δ 1.33 (t, J = 7.00 Hz, 3H), 1.54 (s, 6H), 3.63 (s, 6H), 3.92 (q, J = 7.00 Hz, 2H), 4.63 (s, 2H), 6.34-6.38 (m, 3H), 6.48 (s, 1H), 6.81-6.88 (m, 3H), 7.16 (t, J = 8.00 Hz, 1H). |
| 244 | | 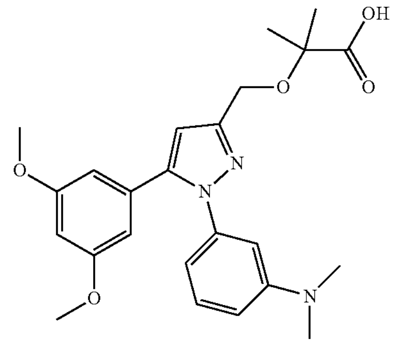 [SMILES: COc1cc(OC)cc(-c2cc(COC(C)(C)C(=O)O)nn2-c2cccc(N(C)C)c2)c1] | 2-([5-(3,5-Dimethoxyphenyl)-1-[3-(dimethylamino)phenyl]-1H-pyrazol-3-yl]methoxy)-2-methylpropanoic acid<br>LC-MS (ES, m/z): 441.<br>$^1$H NMR ($CDCl_3$): δ 1.51 (s, 6H), 2.85 (s, 6H), 3.62 (s, 6H), 4.58 (s, 2H), 6.38-6.41 (m, 3H), 6.54-6.6.57 (m, 1H), 6.61 (s, 1H), 7.74-6.76 (m, 1H), 7.20 (t, J = 8.11 Hz, 1H). |
| 245 | | 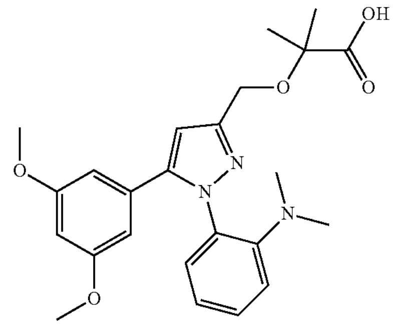 [SMILES: COc1cc(OC)cc(-c2cc(COC(C)(C)C(=O)O)nn2-c2ccccc2N(C)C)c1] | 2-([5-(3,5-Dimethoxyphenyl)-1-[2-(dimethylamino)phenyl]-1H-pyrazol-3-yl]methoxy)-2-methylpropanoic acid<br>LC-MS (ES, m/z): 440.<br>$^1$H NMR ($CDCl_3$): δ 1.52 (s, 6H), 2.23 (s, 6H), 3.57 (s, 6H), 4.60 (s, 2H), 6.31-6.36 (m, 3H), 6.67 (s, 1H), 6.91 (d, J = 8.00 Hz, 1H), 7.03-7.04 (m, 1H), 7.33-7.38 (m, 2H). |
| 246 | H-139 | 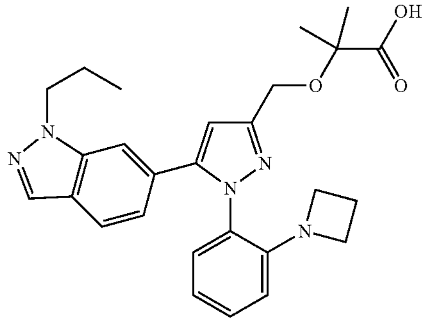 [SMILES: CCCn1ncc2ccc(-c3cc(COC(C)(C)C(=O)O)nn3-c3ccccc3N3CCC3)cc21] | 2-([1-[2-(Azetidin-1-yl)phenyl]-5-(1-propyl-1H-indazol-6-yl)-1H-pyrazol-3-yl]methoxy)-2-methylpropanoic acid<br>XSelect: 40% ACN up to 70% in 7 min<br>LC-MS: (ES, m/z): 474.10<br>$^1$H NMR (300 MHz, MeOD) δ 7.96 (d, J = 0.9 Hz, 1H), 7.71 (dd, J = 8.5, 0.8 Hz, 1H), 7.42 (s, 1H), 7.31 (m, 2H), 7.13 (d, J = 7.8 Hz, 1H), 6.80 (d, J = 13.8 Hz, 2H), 6.56 (d, J = 8.2 Hz, 1H), 4.63 (s, 2H), 4.17 (t, J = 7.0, 7.0 Hz, 2H), 3.57 (m, 4H), 2.14 (q, J = 7.2, 7.2, 7.2 Hz, 2H), 1.69 (q, J = 7.2, 7.2, 7.2 Hz, 2H), 1.54 (s, 6H), 0.79 (t, J = 7.4, 7.4 Hz, 3H). |

TABLE 25-continued

| Ex. | Ester | Structure | IUPAC Name<br>Purification Analytical data |
|---|---|---|---|
| Examples 155-276. | | | |
| 247 | H-70 | 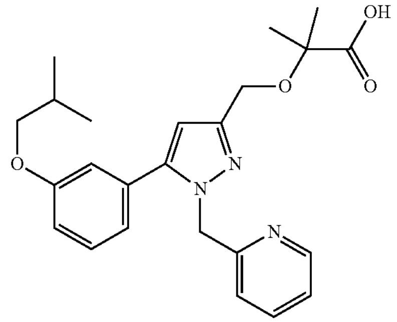 [SMILES: CC(C)COc1cccc(-c2cc(COC(C)(C)C(=O)O)nn2Cc2ccccn2)c1] | 2-Methyl-2-([5-[3-(2-methylpropoxy)-phenyl]-1-([pyridin-2-yl]methyl)-1H-pyrazol-3-yl]methoxy)propanoic acid<br>XSelect: 40% ACN up to 70% in 7 min<br>LC-MS: (ES, m/z): 424.<br>$^{1}$H NMR (300 MHz, Methanol-$d_4$) δ 8.70 (ddd, J = 5.5, 1.7, 0.8 Hz, 1H), 8.27 (td, J = 7.9, 1.7 Hz, 1H), 7.75 (ddd, J = 7.7, 5.5, 1.2 Hz, 1H), 7.51-7.31 (m, 2H), 7.15-6.88 (m, 3H), 6.57 (s, 1H), 5.65 (s, 2H), 4.58 (s, 2H), 3.71 (d, J = 6.5 Hz, 2H), 2.04 (dq, J = 13.2, 6.6 Hz, 1H), 1.52 (s, 6H), 1.03 (d, J = 6.7 Hz, 6H). |
| 248 | H-80 | 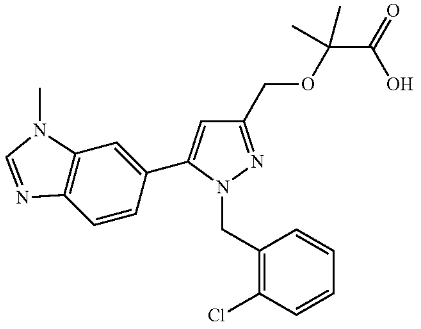 [SMILES: Cn1cnc2ccc(-c3cc(COC(C)(C)C(=O)O)nn3Cc3ccccc3Cl)cc21] | 2-([1-[(2-Chlorophenyl)methyl]-5-(1-methyl-1H-1,3-benzodiazol-6-yl)-1H-pyrazol-3-yl]methoxy)-2-methylpropanoic acid<br>XBridge: 20% ACN up to 34% in 7 min<br>LC-MS: (ES, m/z): 438.<br>$^{1}$H NMR (DMSO-$d_6$) δ: 8.23 (s, 1H), 7.65 (d, J = 8.4 Hz, 1H), 7.57 (s, 1H), 7.47-7.36 (m, 1H), 7.34-7.20 (m, 2H), 7.17 (d, J = 8.3 Hz, 1H), 6.83-6.73 (m, 1H), 6.47 (s, 1H), 5.42 (s, 2H), 4.46 (s, 2H), 3.78 (s, 3H), 1.36 (s, 6H). |
| 249 | H-33 | 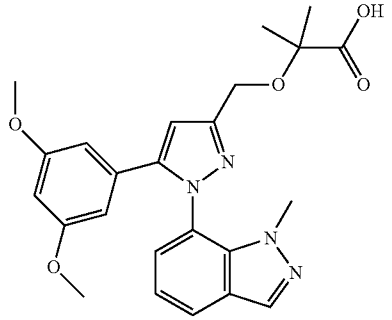 [SMILES: COc1cc(OC)cc(-c2cc(COC(C)(C)C(=O)O)nn2-c2cccc3cnn(C)c23)c1] | 2-([5-(3,5-Dimethoxyphenyl)-1-(1-methyl-1H-indazol-7-yl)-1H-pyrazol-3-yl]methoxy)-2-methylpropanoic acid<br>XSelect: 30% ACN up to 65% in 7 min<br>LC-MS: (ES, m/z): 451.<br>$^{1}$H NMR (300 MHz, DMSO-$d_6$) δ 8.19 (s, 1H), 7.92 (s, 1H), 7.44 (dd, J = 7.3, 1.0 Hz, 1H), 7.21 (s, 1H), 6.84 (s, 1H), 6.35 (dt, J = 10.9, 2.2 Hz, 3H), 4.53 (s, 2H), 3.52 (s, 6H), 3.41 (s, 3H), 1.44 (s, 6H). |
| 250 | H-140 | 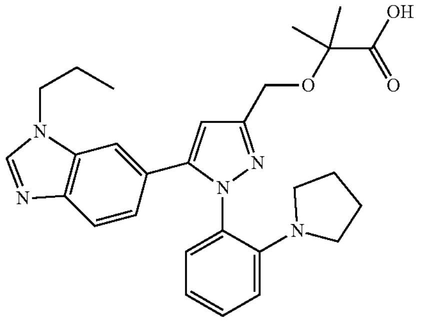 [SMILES: CCCn1cnc2ccc(-c3cc(COC(C)(C)C(=O)O)nn3-c3ccccc3N3CCCC3)cc21] | 2-Methyl-2-([5-(1-propyl-1H-indazol-6-yl)-1-[2-(pyrrolidin-1-yl)phenyl]-1H-pyrazol-3-yl]methoxy]propanoic acid<br>XBridge: 10% ACN up to 50% in 7 min<br>LC-MS: (ES, m/z): 488.2.<br>$^{1}$H NMR (300 MHz, DMSO-$d_6$) δ 7.98 (s, 1H), 7.64 (d, J = 8.4 Hz, 1H), 7.37 (s, 1H), 7.25 (m, 1H), 7.08 (t, J = 7.5, 7.5 Hz, 2H), 6.72 (m, 3H), 4.50 (s, 2H), 4.14 (t, J = 7.1, 7.1 Hz, 2H), 2.77 (q, J = 6.4, 6.4, 5.2 Hz, 4H), 1.63 (tt, J = 15.4, 15.4, 7.1, 7.1 Hz, 6H), 1.40 (s, 6H), 0.72 (t, J = 7.4, 7.4 Hz, 3H). |

TABLE 25-continued

Examples 155-276.

| Ex. | Ester | Structure | IUPAC Name<br>Purification Analytical data |
|---|---|---|---|
| 251 | H-138 | 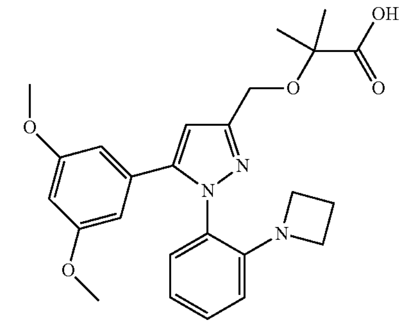 [SMILES: COc1cc(OC)cc(-c2cc(COC(C)(C)C(=O)O)nn2-c2ccccc2N2CCC2)c1] | 2-((1-(2-(Azetidin-1-yl)phenyl)-5-(3,5-dimethoxyphenyl)-1H-pyrazol-3-yl)methoxy)-2-methylpropanoic acid<br>XBridge: 25% ACN up to 37% in 7 min<br>LC-MS: (ES, m/z): 452.<br>$^1$H NMR (300 MHz, DMSO-$d_6$) δ 7.26 (t, J = 7.4 Hz, 1H), 6.95 (d, J = 7.5 Hz, 1H), 6.67 (q, J = 7.0, 6.0 Hz, 2H), 6.58-6.43 (m, 3H), 6.38 (t, J = 2.2 Hz, 1H), 4.47 (s, 2H), 3.59 (s, 6H), 3.45 (dq, J = 31.0, 7.3 Hz, 4H), 2.17-1.89 (m, 2H), 1.36 (s, 6H). |
| 252 | H-72 | 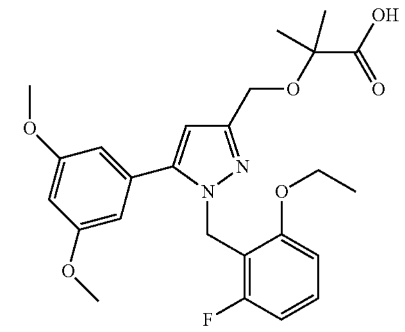 [SMILES: CCOc1cccc(F)c1Cn1nc(COC(C)(C)C(=O)O)cc1-c1cc(OC)cc(OC)c1] | 2-([5-(3,5-Dimethoxyphenyl)-1-[(2-ethoxy-6-fluorophenyl)methyl]-1H-pyrazol-3-yl]methoxy)-2-methylpropanoic acid<br>XSelect: 42% ACN up to 72% in 7 min<br>LC-MS: (ES, m/z): 473.<br>$^1$H NMR (300 MHz, DMSO-$d_6$) δ 7.27 (td, J = 8.4, 8.3, 6.9 Hz, 1H), 6.76 (dt, J = 8.8, 4.6, 4.6 Hz, 2H), 6.66 (d, J = 2.3 Hz, 2H), 6.57 (t, J = 2.2, 2.2 Hz, 1H), 6.25 (s, 1H), 5.26 (s, 2H), 4.27 (s, 2H), 3.88 (q, J = 7.0, 7.0, 7.0 Hz, 2H), 3.78 (s, 6H), 1.34 (s, 6H), 1.06 (t, J = 6.9, 6.9 Hz, 3H). |
| 253 | H-83 | 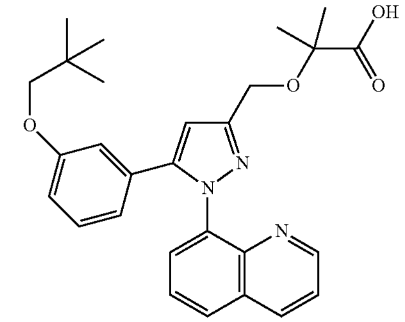 [SMILES: CC(C)(C)COc1cccc(-c2cc(COC(C)(C)C(=O)O)nn2-c2cccc3cccnc23)c1] | 2-([5-[3-(2,2-Dimethylpropoxy)phenyl]-1-(quinolin-8-yl)-1H-pyrazol-3-yl]methoxy)-2-methylpropanoic acid<br>XSelect: 50% ACN up to 80% in 7 min<br>LC-MS: (ES, m/z): [M + 1] = 474.<br>$^1$H-NMR: (DMSO, ppm): δ: 8.77 (dd, J = 4.2, 1.7 Hz, 1H), 8.46 (dd, J = 8.4, 1.7 Hz, 1H), 8.14 (dd, J = 8.2, 1.5 Hz, 1H), 7.83 (dd, J = 7.4, 1.5 Hz, 1H), 7.70 (dd, J = 8.2, 7.3 Hz, 1H), 7.55 (dd, J = 8.3, 4.2 Hz, 1H), 7.02 (t, J = 8.0 Hz, 1H), 6.79-6.60 (m, 3H), 6.53 (dd, J = 2.6, 1.5 Hz, 1H), 4.49 (s, 2H), 3.02 (s, 2H), 1.43 (s, 6H), 0.81 (s, 9H). |
| 254 | H-73 | 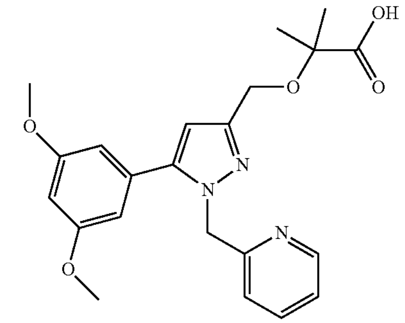 [SMILES: COc1cc(OC)cc(-c2cc(COC(C)(C)C(=O)O)nn2Cc2ccccn2)c1] | 2-([5-(3,5-Dimethoxyphenyl)-1-([pyridin-2-yl]methyl)-1H-pyrazol-3-yl]methoxy)-2-methylpropanoic acid<br>XSelect: 25% ACN up to 56% in 7 min<br>LC-MS: (ES, m/z): 412.05.<br>$^1$H NMR (300 MHz, DMSO) δ 12.62 (s, 1H), 8.52 (ddd, J = 4.8, 1.8, 0.9 Hz, 1H), 7.78 (td, J = 7.7, 7.7, 1.8 Hz, 1H), 7.30 (ddd, J = 7.6, 4.8, 1.2 Hz, 1H), 7.08 (dt, J = 7.8, 1.1, 1.1 Hz, 1H), 6.70 (d, J = 2.3 Hz, 2H), 6.52 (t, J = 2.3, 2.3 Hz, 1H), 6.42 (s, 1H), 5.37 (s, 2H), 4.38 (s, 2H), 3.70 (s, 6H), 1.38 (s, 6H). |

TABLE 25-continued

Examples 155-276.

| Ex. | Ester | Structure | IUPAC Name Purification Analytical data |
|---|---|---|---|
| 255 | H-35 | 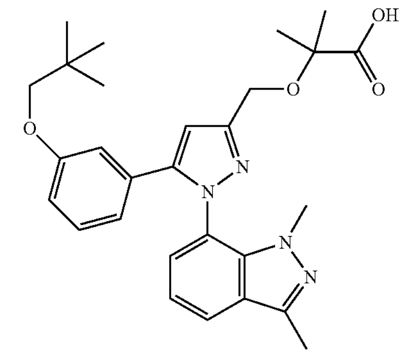 | 2-([1-(1,3-Dimethyl-1H-indazol-7-yl)-5-[3-(2,2-dimethylpropoxy)phenyl]-1H-pyrazol-3-yl]methoxy)-2-methylpropanoic acid<br>XSelect: 50% ACN up to 80% in 7 min<br>LC-MS: (ES, m/z): 405.35.<br>$^{1}$H NMR (300 MHz, DMSO) δ 12.60 (s, 1H), 7.83 (dd, J = 8.1, 1.0 Hz, 1H), 7.34 (dd, J = 7.3, 0.9 Hz, 1H), 7.12 (m, 2H), 6.78 (m, 3H), 6.60 (m, 1H), 4.52 (s, 2H), 3.33 (s, 3H), 3.14 (s, 2H), 2.46 (s, 3H), 1.42 (s, 6H), 0.85 (s, 9H). |
| 256 | H-69 | 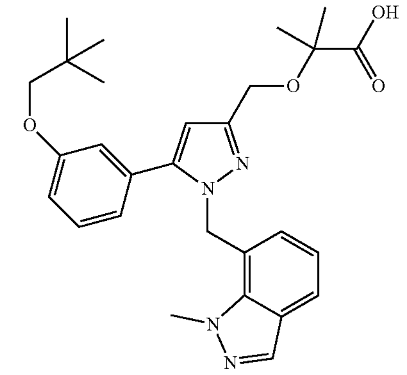 [SMILES: Cn1ncc2cccc(Cn3nc(COC(C)(C)C(=O)O)cc3-c3cccc(OCC(C)(C)C)c3)c21] | 2-([5-[3-(2,2-Dimethylpropoxy)phenyl]-1-[(1-methyl-1H-indazol-7-yl)methyl]-1H-pyrazol-3-yl]methoxy)-2-methylpropanoic acid<br>XSelect: 60% ACN up to 70% in 7 min<br>LC-MS: (ES, m/z): 491.25.<br>$^{1}$H NMR (400 MHz, DMSO) δ 8.03 (s, 1H), 7.66 (d, J = 8.0 Hz, 1H), 7.33 (t, J = 7.9, 7.9 Hz, 1H), 7.02 (m, 2H), 6.94 (dd, J = 8.3, 2.4 Hz, 1H), 6.88 (s, 1H), 6.56 (d, J = 7.2 Hz, 1H), 6.51 (s, 1H), 5.95 (s, 2H), 4.43 (s, 2H), 4.20 (s, 3H), 3.32 (s, 2H), 1.39 (s, 6H), 0.88 (s, 9H). |
| 257 | H-131 | 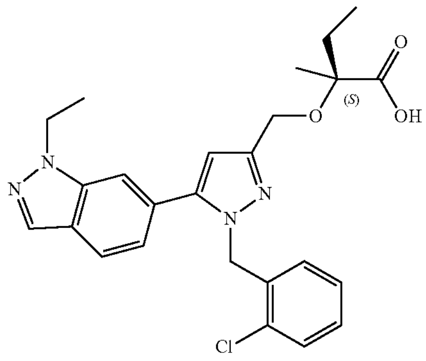 | (S)-2-((1-(2-chlorobenzyl)-5-(1-ethyl-1H-indazol-6-yl)-1H-pyrazol-3-yl)methoxy)-2-methylbutanoic acid<br>LC-MS: (ES, m/z): 467.10.<br>$^{1}$H NMR (300 MHz, DMSO-d6) δ 12.64 (s, 1H), 8.07 (d, J = 0.9 Hz, 1H), 7.78 (dd, J = 8.3, 0.8 Hz, 1H), 7.67 (d, J = 1.3 Hz, 1H), 7.49-7.34 (m, 1H), 7.36-7.18 (m, 2H), 7.11 (dd, J = 8.3, 1.3 Hz, 1H), 6.84-6.72 (m, 1H), 6.52 (s, 1H), 5.45 (s, 2H), 4.43 (d, J = 2.2 Hz, 2H), 4.37 (q, J = 7.2 Hz, 2H), 1.74 (hept, J = 7.0 Hz, 2H), 1.37 (s, 3H), 1.31 (t, J = 7.2 Hz, 3H), 0.85 (t, J = 7.4 Hz, 3H). |
| 258 | H-36 | 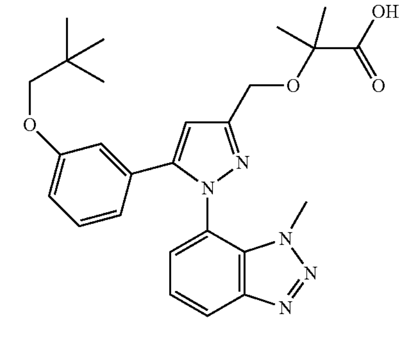 [SMILES: Cn1nnc2cccc(-n3nc(COC(C)(C)C(=O)O)cc3-c3cccc(OCC(C)(C)C)c3)c21] | 2-([5-[3-(2,2-Dimethylpropoxy)phenyl]-1-(1-methyl-1H-1,2,3-benzotriazol-7-yl)-1H-pyrazol-3-yl]methoxy)-2-methylpropanoic acid<br>XSelect: 50% ACN up to 70% in 7 min<br>LC-MS: (ES, m/z): 478.<br>$^{1}$H NMR (300 MHz, DMSO-d6) δ 12.80 (s, 1H), δ 8.17 (dd, J = 8.2, 1.1 Hz, 1H), 7.59-7.31 (m, 2H), 7.12 (t, J = 8.0 Hz, 1H), 6.89-6.77 (m, 2H), 6.76-6.62 (m, 2H), 4.54 (s, 2H), 3.81 (s, 3H), 3.29 (s, 2H), 1.42 (s, 6H), 0.87 (s, 9H). |

TABLE 25-continued

Examples 155-276.

| Ex. | Ester | Structure | IUPAC Name<br>Purification Analytical data |
|---|---|---|---|
| 259 | H-65 | 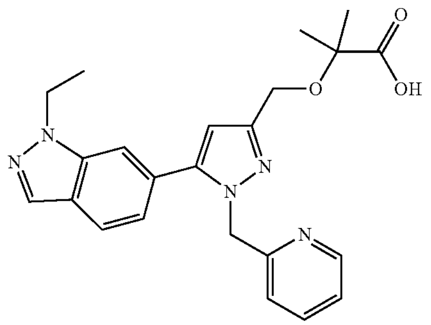 [SMILES: CCn1ncc2ccc(-c3cc(COC(C)(C)C(=O)O)nn3Cc3ccccn3)cc21] | 2-([5-(1-Ethyl-1H-indazol-6-yl)-1-([pyridin-2-yl]methyl)-1H-pyrazol-3-yl]methoxy)-2-methylpropanoic acid<br>SunFire: 36% ACN up to 50% in 7 min<br>LC-MS: (ES, m/z): 420.2.<br>$^1$H NMR (300 MHz, DMSO) δ 8.50 (dd, J = 4.9, 1.7 Hz, 1H), 8.07 (d, J = 0.9 Hz, 1H), 7.87 (t, J = 1.2 Hz, 1H), 7.78 (d, J = 8.4 Hz, 1H), 7.73 (dd, J = 7.7, 1.8 Hz, 1H), 7.27 (m, 2H), 7.07 (d, J = 7.8 Hz, 1H), 6.49 (s, 1H), 5.42 (s, 2H), 4.39 (m, 4H), 1.38 (s, 6H), 1.33 (t, J = 7.2 Hz, 3H). |
| 260 | H-141 | 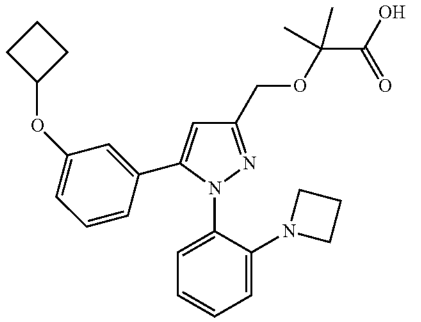 [SMILES: CC(C)(OCc1cc(-c2cccc(OC3CCC3)c2)n(-c2ccccc2N2CCC2)n1)C(=O)O] | 2-([1-[2-(Azetidin-1-yl)phenyl]-5-(3-cyclobutoxyphenyl)-1H-pyrazol-3-yl]methoxy)-2-methylpropanoic acid<br>XSelect: 55% ACN up to 70% in 7 min<br>LC-MS: (ES, m/z): 462.1.<br>$^1$H NMR (300 MHz, DMSO-d6) δ 7.27 (td, J = 7.8, 1.6 Hz, 1H), 7.19 (t, J = 7.9 Hz, 1H), 6.97 (td, J = 6.2, 3.2 Hz, 2H), 6.75-6.64 (m, 3H), 6.61 (s, 1H), 6.50 (dd, J = 8.3, 1.3 Hz, 1H), 4.43 (s, 2H), 4.29 (p, J = 7.1 Hz, 1H), 3.44 (dt, J = 14.4, 7.3 Hz, 4H), 2.31-2.13 (m, 2H), 2.03 (p, J = 7.3 Hz, 2H), 1.95-1.82 (m, 2H), 1.78-1.64 (m, 1H), 1.62-1.46 (m, 1H), 1.39 (s, 6H). |
| 261 | H-81 | 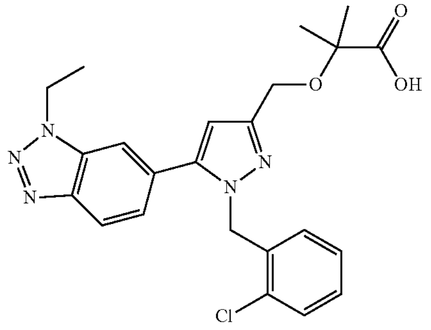 [SMILES: CCn1nnc2ccc(-c3cc(COC(C)(C)C(=O)O)nn3Cc3ccccc3Cl)cc21] | 2-([1-[(2-chlorophenyl)methyl]-5-(1-ethyl-1H-1,2,3-benzotriazol-6-yl)-1H-pyrazol-3-yl]methoxy)-2-methylpropanoic acid<br>XSelect: 40% ACN up to 62% in 7 min<br>LC-MS: (ES, m/z): 454.<br>$^1$H NMR (400 MHz, DMSO-d6) δ 12.70 (s, 1H), 8.08 (d, J = 8.6 Hz, 1H), 8.00 (t, J = 1.1 Hz, 1H), 7.50-7.37 (m, 2H), 7.31-7.23 (m, 2H), 6.86-6.79 (m, 1H), 6.58 (s, 1H), 5.48 (s, 2H), 4.73 (q, J = 7.2 Hz, 2H), 4.45 (s, 2H), 1.47 (t, J = 7.3 Hz, 3H), 1.41 (s, 6H). |
| 262 | H-128 | 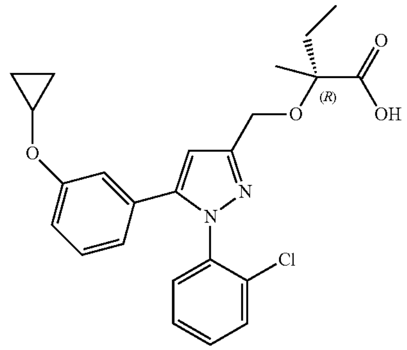 | (2R)-2-([1-(2-Chlorophenyl)-5-(3-cyclopropoxyphenyl)-1H-pyrazol-3-yl]methoxy)-2-methylbutanoic acid<br>XSelect: 57% ACN up to 61% in 7 min<br>LC-MS: (ES, m/z): 440.9.<br>$^1$H NMR (300 MHz, DMSO-d6) δ 12.65 (s, 1H), 7.69-7.38 (m, 4H), 7.22 (t, J = 8.0 Hz, 1H), 6.89 (ddt, J = 11.0, 7.6, 1.1 Hz, 2H), 6.80 (dd, J = 2.4, 1.6 Hz, 1H), 6.66 (s, 1H), 4.45 (d, J = 2.2 Hz, 2H), 3.55 (tt, J = 6.1, 2.9 Hz, 1H), 1.75 (hept, J = 7.0 Hz, 2H), 1.38 (s, 3H), 0.86 (t, J = 7.4 Hz, 3H), 0.71-0.57 (m, 2H), 0.52-0.41 (m, 2H). |

TABLE 25-continued

| Examples 155-276. | | | |
|---|---|---|---|
| Ex. | Ester | Structure | IUPAC Name<br>Purification Analytical data |
| 263 | H-127 | 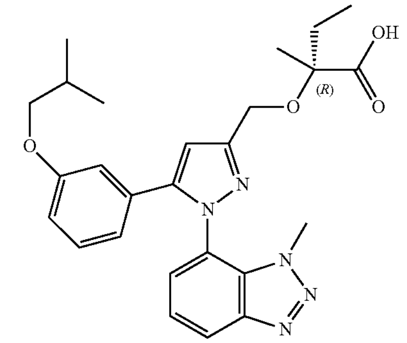 | (2R)-2-Methyl-2-([1-(1-methyl-1H-indazol-7-yl)-5-[3-(2-methylpropoxy)-phenyl]-1H-pyrazol-3-yl]methoxy]-butanoic acid<br>XSelect: 55% ACN up to 71% in 7 min<br>LC-MS: (ES, m/z): 477.1.<br>$^1$H NMR (300 MHz, DMSO-d6) δ 8.17 (s, 1H), 7.89 (d, J = 8.0 Hz, 1H), 7.38 (d, J = 7.2 Hz, 1H), 7.24-7.10 (m, 2H), 6.82-6.75 (m, 3H), 6.61 (t, J = 2.0 Hz, 1H), 4.51 (s, 2H), 3.41 (s, 3H), 3.32 (d, J = 6.7 Hz, 2H), 1.87-1.65 (m, 3H), 1.38 (s, 3H), 0.89-0.81 (m, 9H). |
| 264 | H-132 | 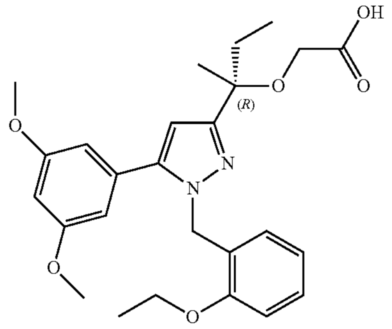 | (2R)-2-([5-(3,5-Dimethoxyphenyl)-1-[(2-ethoxyphenyl)methyl]-1H-pyrazol-3-yl]methoxy)-2-methylbutanoic acid<br>XSelect: 60% ACN up to 64% in 7 min<br>LC-MS: (ES, m/z): 469.0.<br>$^1$H NMR (300 MHz, DMSO-d6) δ 7.21 (ddd, J = 8.7, 7.5, 1.7 Hz, 1H), 6.95 (dd, J = 8.4, 1.0 Hz, 1H), 6.84 (td, J = 7.5, 1.0 Hz, 1H), 6.74 (s, 1H), 6.66 (dd, J = 7.5, 1.7 Hz, 1H), 6.54-6.38 (m, 4H), 5.24 (s, 2H), 4.38 (d, J = 2.4 Hz, 2H), 3.97 (q, J = 6.9 Hz, 2H), 3.65 (s, 7H), 1.85-1.59 (m, J = 7.4 Hz, 2H), 1.34 (s, 3H), 1.21 (t, J = 6.9 Hz, 4H), 0.83 (t, J = 7.4 Hz, 3H) |
| 265 | H-110 | 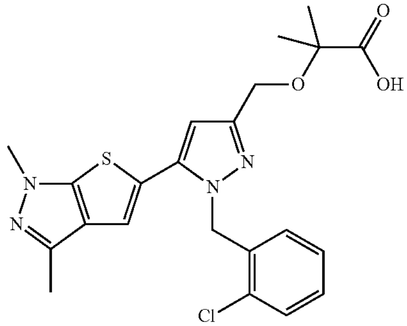 [SMILES: Cc1nn(C)c2sc(-c3cc(COC(C)(C)C(=O)O)nn3Cc3ccccc3Cl)cc12] | 2-([1-[(2-Chlorophenyl)methyl]-5-[1,3-dimethyl-1H-thieno[2,3-c]pyrazol-5-yl]-1H-pyrazol-3-yl]methoxy)-2-methylpropanoic acid<br>XSelect: 48% ACN up to 52% in 7 min<br>LC-MS: (ES, m/z): 459.<br>$^1$H NMR (300 MHz, DMSO-d6) δ 7.52-7.44 (m, 1H), 7.35-7.20 (m, 2H), 7.11 (s, 1H), 6.70 (dd, J = 6.9, 2.5 Hz, 1H), 6.48 (s, 1H), 5.50 (s, 2H), 4.38 (s, 2H), 3.81 (s, 3H), 2.29 (s, 3H), 1.37 (s, 6H). |
| 266 | H-153 | 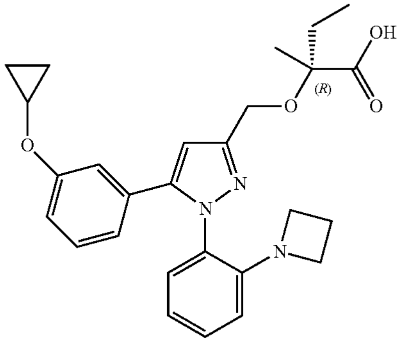 | (2R)-2-([1-[2-Azetidin-1-yl)phenyl]-5-(3-cyclopropoxyphenyl)-1H-pyrazol-3-yl]methoxy)-2-methylbutanoic acid<br>SunFire: 72% ACN up to 82% in 7 min<br>LC-MS: (ES, m/z): 462.3.<br>$^1$H NMR (300 MHz, DMSO-d6) δ 7.29-7.21 (m, 2H), 7.10-6.95 (m, 3H), 6.94-6.84 (m, 1H), 6.75-6.63 (m, 1H), 6.61 (s, 1H), 6.48 (d, J = 8.2 Hz, 1H), 4.43 (s, 2H), 3.56-3.50 (m, 5H), 2.02 (q, J = 7.3 Hz, 2H), 1.74 (p, J = 7.1 Hz, 2H), 1.37 (s, 3H), 0.85 (t, J = 7.4 Hz, 3H), 0.64 (d, J = 6.0 Hz, 2H), 0.51 (q, J = 4.4, 3.3 Hz, 2H). |

TABLE 25-continued

Examples 155-276.

| Ex. | Ester | Structure | IUPAC Name<br>Purification Analytical data |
| --- | --- | --- | --- |
| 267 | H-152 | 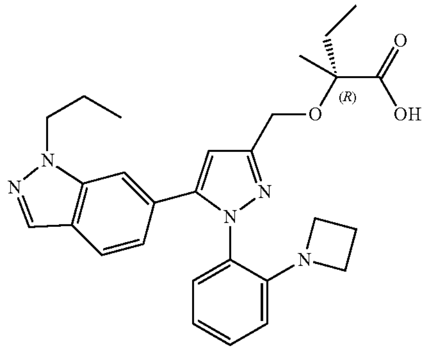 | (2R)-2-([1-[2-(azetidin-1-yl)phenyl]-5-(1-propyl-1H-indazol-6-yl)-1H-pyrazol-3-yl]methoxy)-2-methylbutanoic acid<br>XSelect: 57% ACN up to 61% in 7 min<br>LC-MS: (ES, m/z): 488.3.<br>$^1$H NMR (300 MHz, DMSO-d6) δ 7.98 (s, 1H), 7.66 (d, J = 8.4 Hz, 1H), 7.46 (s, 1H), 7.26 (t, J = 7.8 Hz, 1H), 7.15 (d, J = 8.5 Hz, 1H), 7.09-7.00 (m, 1H), 6.70 (d, J = 11.2 Hz, 2H), 6.48 (d, J = 8.2 Hz, 1H), 4.46 (s, 2H), 4.15 (t, J = 7.1 Hz, 2H), 3.53-3.44 (m, 4H), 2.04 (q, J = 7.4, 6.7 Hz, 2H), 1.74 (dq, J = 14.6, 7.3 Hz, 2H), 1.61 (h, J = 7.3 Hz, 2H), 1.38 (s, 3H), 0.86 (t, J = 7.4 Hz, 3H), 0.72 (t, J = 7.4 Hz, 3H). |
| 268 | H-154 | 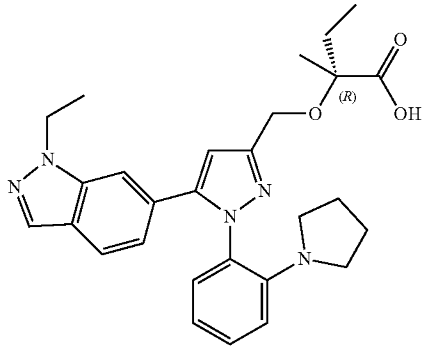 | (2R)-2-([5-(1-ethyl-1H-indazol-6-yl)-1-[2-(pyrrolidin-1-yl)phenyl]-1H-pyrazol-3-yl]methoxy)-2-methylbutanoic acid<br>XSelect: 50% ACN up to 72% in 7 min<br>LC-MS: (ES, m/z): 488.<br>$^1$H NMR (300 MHz, DMSO-d6) δ 12.71 (s, 1H), 6 7.96 (d, J = 0.9 Hz, 1H), 7.62 (d, J = 8.4 Hz, 1H), 7.46-7.40 (m, 1H), 7.24 (ddd, J = 8.5, 7.1, 1.6 Hz, 1H), 7.07 (td, J = 6.7, 6.3, 3.3 Hz, 2H), 6.87-6.59 (m, 3H), 4.48 (s, 2H), 4.23 (q, J = 7.2 Hz, 2H), 2.76 (d, J = 7.5 Hz, 4H), 1.74 (dh, J = 14.0, 7.2 Hz, 4H), 1.62-1.50 (m, 2H), 1.38 (s, 3H), 1.20 (t, J = 7.2 Hz, 3H), 0.86 (t, J = 7.4 Hz, 3H). |
| 269 | H-155 | 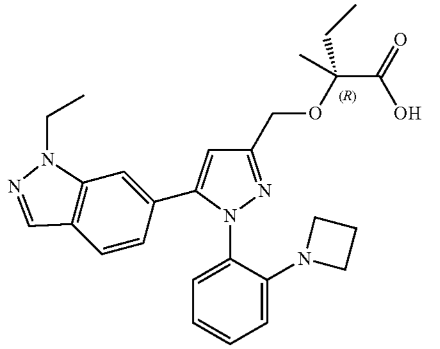 | (2R)-2-([1-[2-(Azetidin-1-yl)phenyl]-5-(1-ethyl-1H-indazol-6-yl)-1H-pyrazol-3-yl]methoxy)-2-methylbutanoic acid<br>XBridge: 44% ACN up to 54% in 7 min<br>LC-MS: (ES, m/z): 474.<br>$^1$H NMR (300 MHz, DMSO-d6) δ 7.96 (s, 1H), 7.63 (d, J = 8.4 Hz, 1H), 7.50 (s, 1H), 7.24 (t, J = 7.6 Hz, 1H), 7.08 (dd, J = 20.7, 8.1 Hz, 2H), 6.88-6.58 (m, 2H), 6.46 (d, J = 8.4 Hz, 1H), 4.48 (s, 2H), 4.25 (q, J = 7.2 Hz, 2H), 3.45 (dd, J = 22.1, 7.2 Hz, 4H), 2.18-1.88 (m, 2H), 1.71 (dd, J = 15.0, 7.4 Hz, 2H), 1.33 (s, 3H), 1.20 (t, J = 7.1 Hz, 3H), 0.84 (t, J = 7.3 Hz, 3H). |

The activity of the compounds in Examples 1-269 as MCT4 inhibitors is illustrated in the following assays. The other compounds listed above, which have not yet been made and/or tested, are predicted to have activity in these assays as well.

Biological Activity Assays

The following are assays that may be used to evaluate the biological efficacy of compounds of Formula (I) in a manner similar to that previously reported for MCT1 and MCT4 and are known to those with skill in the art. See, e.g., Murray, C. M. et al., "Monocarboxylate transporter MCT1 is a target for immunosuppression," *Nature chemical biology* 1, 371-376 (2005); and Ovens, M. J., et al., "AR-C155858 is a potent inhibitor of monocarboxylate transporters MCT1 and MCT2 that binds to an intracellular site involving transmembrane helices 7-10," *The Biochemical Journal* 425, 523-530, (2010).

Preparing BCECF-Loaded Cells

Cells (~7x10$^6$) are trypsinized (0.05% Trypsin-EDTA), pelleted (300 g, 5 min), and resuspended in 1 mL Tyrode's Solution, pH 7.4 (119 mM NaCl, 5 mM KCl, 25 mM HEPES, pH 7.4, 2 mM $CaCl_2$), 2 mM $MgCl_2$, 6 g/L glucose). 10 □L of a 30 mM DMSO stock of BCECF-AM ester (Life Technologies) is added and the cells are incubated at 37° C. for 5 min. The cells are pelleted (300 g, 5 min), washed once with 1 mL Tyrode's Solution, pH 7.4, re-pelleted (300 g, 5 min), and resuspended in 1 mL Tyrode's Solution, pH 7.4.

Assay 1: Lactate Transport in MCT4-Expressing MDA-MB-453 Breast Cancer Cells.

MCT4 may be stably expressed in MDA-MB-453 breast cancer cells that do not express native MCT1 or MCT4. MCT4 activity may be assessed by monitoring the intracellular pH change that accompanies lactate/proton symport, using the pH-sensitive fluorescent dye 2',7'-bis-(carboxyethyl)-5(6)-carboxyfluorescein (BCECF), in a manner similar to that previously reported for MCT1 and MCT4. The following is an exemplary procedure for assaying MCT4 activity of the compounds of Formula (I).

Assay 2: MCT4-Mediated Lactate Transport in NCI-H358 Lung Adenocarcinoma Cells.

NCI-H358 lung adenocarcinoma cells may be used to measure MCT4 activity in cells with high native levels of MCT4 and low levels of MCT1 and are known to those with skill in the art. Preparation of BCECF-loaded cells and lactate transport activity may be determined as described for Assay 1.

Assay 3: MCT4-Mediated Lactate Transport in MDA-MB-231 Breast Cancer Cells.

MDA-MB-231 breast cancer cells may be used to measure MCT4 activity in cells with high native levels of MCT4 and low levels of MCT1 and are known to those with skill in the art. MCT4 activity may be assessed by monitoring the intracellular pH change that accompanies lactate/proton symport, using the pH-sensitive fluorescent dye 2',7'-bis-(carboxyethyl)-5(6)-carboxyfluorescein (BCECF), in a manner similar to that previously reported for MCT1 and MCT4. The following is an exemplary procedure for assaying MCT4 activity of the compounds of Formula (I).

Assay 4: MCT1-Mediated Lactate Transport in BT20 Breast Cancer Cells.

MCT1 activity may be measured using BT-20 breast cancer cells that express high native levels of MCT1, but do not express MCT4 and are known to those with skill in the art. Preparation of BCECF loaded cells are as described for Assay 1. Lactate transport assay is as described for Assay 1, except 10 mM L-lactate (rather than 50 mM) is added.

Results of the assays above are given below in Tables 26 and 27, in which "ND" means no data. As can be seen, most compounds disclosed herein are selective for MCT4 over MCT1.

TABLE 26

MCT Activity.

| Example | MCT4 $IC_{50}$ (nM) MDA-MB-453 + MCT4 | MCT4 $IC_{50}$ (nM) NCI-H358 | MCT1 $IC_{50}$ (nM) BT20 |
|---|---|---|---|
| 1 | 340 | 140 | 50,000 |
| 2 | 450 | 240 | 29,000 |
| 3 | 72 | 60 | 25,000 |
| 4 | 68 | 54 | 33,000 |
| 5 | 160 | 63 | 1,800 |
| 6 | 2,400 | 4,600 | 6,600 |
| 7 | 720 | 460 | 70,000 |
| 8 | 69 | 81 | 46,000 |
| 9 | 320 | 340 | 39,000 |
| 10 | 21 | 33 | 8,800 |
| 11 | 45 | 25 | 29,000 |
| 12 | 38 | 49 | 58,000 |
| 13 | 20 | 22 | 17,000 |
| 14 | 26 | 44 | >100,000 |
| 15 | 900 | 440 | >33,000 |
| 16 | 1,000 | 640 | 73,000 |
| 17 | 440 | 860 | 1,200 |
| 18 | 5,300 | 4,200 | 45,000 |
| 19 | 110 | 160 | 57,000 |

TABLE 26-continued

MCT Activity.

| Example | MCT4 $IC_{50}$ (nM) MDA-MB-453 + MCT4 | MCT4 $IC_{50}$ (nM) NCI-H358 | MCT1 $IC_{50}$ (nM) BT20 |
|---|---|---|---|
| 20 | 17,000 | 22,000 | 7,900 |
| 21 | 35,000 | 48,000 | 300,000 |
| 22 | 14,000 | 39,000 | 150,000 |
| 23 | 1,500 | 2,100 | >300,000 |

TABLE 27

MCT Activity.

| Ex. | MCT4 $IC_{50}$ (nM) MDA-MB-231 | MCT1 $IC_{50}$ (nM) BT20 |
|---|---|---|
| 14 | 30 | >100,000 |
| 24 | 30 | >100,000 |
| 25 | 33 | 77,000 |
| 26 | 9.4 | 27,000 |
| 27 | 1 | 5,600 |
| 28 | 12 | 15,000 |
| 29 | 3.7 | 16,000 |
| 30 | 8.8 | 27,000 |
| 31 | 53 | 42,000 |
| 32 | 79 | 83,000 |
| 33 | 3.2 | 9,100 |
| 34 | 9.3 | >11,000 |
| 35 | 5.2 | 59,000 |
| 36 | 82 | 50,000 |
| 37 | 7.6 | 8,400 |
| 38 | 48 | 60,000 |
| 39 | 5.4 | 10,000 |
| 40 | 520 | >100,000 |
| 41 | 55 | 1,200 |
| 42 | 2.6 | 9,800 |
| 43 | 13 | >33,000 |
| 44 | 1.1 | 8,400 |
| 45 | 19 | 12,000 |
| 46 | 142 | 47,000 |
| 47 | 410 | >100,000 |
| 48 | 89 | 55,000 |
| 49 | 240 | 130,000 |
| 50 | 70 | 34,000 |
| 51 | 15 | 6,000 |
| 52 | 190 | 84,000 |
| 53 | 160 | >100,000 |
| 54 | 37 | 27,000 |
| 55 | 260 | >100,000 |
| 56 | 8,000 | >133,000 |
| 57 | 110 | >133,000 |
| 58 | 150 | 78,000 |
| 59 | 340 | 81,000 |
| 60 | 13 | 44,000 |
| 61 | 3.1 | 11,000 |
| 62 | 33 | 27,000 |
| 63 | 37 | 17,000 |
| 64 | 8.3 | 45,000 |
| 65 | 8 | 13,000 |
| 66 | 7.8 | 45,000 |
| 67 | 11 | 17,000 |
| 68 | 9.1 | 26,000 |
| 69 | 5,800 | >100,000 |
| 70 | 9,300 | >100,000 |
| 71 | 34,000 | 64,000 |
| 72 | 220 | 45,000 |
| 73 | 21 | >11,000 |
| 74 | 6,400 | >100,000 |
| 75 | 1,700 | >100,000 |
| 76 | 400 | 38,000 |
| 77 | 340 | 9,000 |
| 79 | 59 | 15,000 |
| 80 | 81 | 61,000 |
| 81 | 6,300 | 6,600 |

TABLE 27-continued

| MCT Activity. | | |
|---|---|---|
| Ex. | MCT4 $IC_{50}$ (nM) MDA-MB-231 | MCT1 $IC_{50}$ (nM) BT20 |
| 82 | 460 | 16,000 |
| 101 | 3.4 | 12,000 |
| 102 | 15 | 42,000 |
| 103 | 2.6 | 28,000 |
| 104 | 20 | 12,000 |
| 105 | 7.6 | 15,000 |
| 106 | 12 | 21,000 |
| 107 | 170 | 9,900 |
| 108 | 36 | 5,200 |
| 109 | 2.1 | >11,000 |
| 110 | 20 | 30,000 |
| 111 | 7.9 | 32,000 |
| 112 | 29 | 94,000 |
| 113 | 6.7 | 33,000 |
| 114 | 4.3 | 73,000 |
| 115 | 34,000 | >100,000 |
| 116 | 11,000 | 61,000 |
| 117 | 430 | >100,000 |
| 118 | 170 | 50,000 |
| 119 | 67 | 65,000 |
| 120 | 4 | 22,000 |
| 121 | 8 | 21,000 |
| 122 | 50 | 2,500 |
| 123 | 1,500 | 11,000 |
| 124 | 420 | 31,000 |
| 125 | 5,900 | 61,000 |
| 126 | 130 | 35,000 |
| 127 | 41 | 15,000 |
| 128 | 1.2 | >11,000 |
| 129 | 2.8 | 16,000 |
| 130 | 98 | 55 |
| 131 | 225 | 650 |
| 132 | 8.6 | 8,200 |
| 133 | 13 | >33,000 |
| 134 | 38 | 72,000 |
| 135 | 53 | 220 |
| 136 | 920 | >33,000 |
| 137 | 1,400 | >100,000 |
| 138 | 535 | >100,000 |
| 139 | 9,700 | >100,000 |
| 140 | 8.3 | 16,000 |
| 141 | 6.7 | 33,000 |
| 142 | 6.3 | 26,000 |
| 143 | 195 | 3,300 |
| 144 | 127 | 2,400 |
| 150 | 2.8 | 25,000 |
| 151 | 3.6 | 70,000 |
| 152 | 80 | >100,000 |
| 153 | 830 | 44,000 |
| 154 | 240 | >100,000 |
| 155 | 0.32 | >33,000 |
| 156 | 1400 | >100,000 |
| 157 | 26 | 86,000 |
| 158 | 580 | >100,000 |
| 159 | 11 | >100,000 |
| 160 | 270 | >100,000 |
| 161 | 3.3 | 22,000 |
| 162 | 6.4 | 34,000 |
| 163 | 4.4 | 73,000 |
| 164 | 43 | >100,000 |
| 165 | 85 | 99,000 |
| 166 | 5.9 | 53,000 |
| 167 | 0.59 | 36,000 |
| 168 | 1.7 | 61,000 |
| 169 | 12.2 | 68,000 |
| 170 | 2.0 | 32,000 |
| 171 | 12 | 32,000 |
| 172 | 0.59 | 33,000 |
| 173 | 230 | 66,000 |
| 174 | 101 | >100,000 |
| 175 | 5.1 | 28,000 |
| 176 | 180 | >100,000 |
| 177 | 1.4 | 35,000 |
| 178 | 2.5 | 27,000 |

TABLE 27-continued

| MCT Activity. | | |
|---|---|---|
| Ex. | MCT4 $IC_{50}$ (nM) MDA-MB-231 | MCT1 $IC_{50}$ (nM) BT20 |
| 179 | 13 | >100,000 |
| 180 | 2.9 | 28,000 |
| 181 | 20 | 25,000 |
| 182 | 5.9 | 12,000 |
| 183 | 1.3 | 86,000 |
| 184 | 22 | >33,000 |
| 185 | 9.3 | 17,000 |
| 186 | 21.5 | 90,000 |
| 187 | 43 | 63,000 |
| 188 | 7.5 | 15,000 |
| 189 | 18 | 22,000 |
| 190 | 7.8 | 31,000 |
| 191 | 17 | 16,000 |
| 192 | 190 | 47,000 |
| 193 | 18 | 38,000 |
| 194 | 3500 | >100,000 |
| 195 | 5.3 | 13,000 |
| 196 | 1.9 | 38,000 |
| 197 | 2000 | 76,000 |
| 198 | 3.5 | 26,000 |
| 199 | 9.6 | 34,000 |
| 200 | 1.9 | 17,000 |
| 201 | 7.2 | 15,000 |
| 202 | 6.2 | 23,000 |
| 203 | 185 | 93,000 |
| 204 | 40 | >100,000 |
| 205 | 890 | >100,000 |
| 206 | 16 | 45,000 |
| 207 | 15 | 3,200 |
| 208 | 7.5 | 17,000 |
| 209 | 31 | 95,000 |
| 210 | 2.4 | 7,300 |
| 211 | 2.4 | 20,000 |
| 212 | 195 | >100,000 |
| 213 | 12 | 12,000 |
| 214 | 6.0 | 94,000 |
| 215 | 360 | >100,000 |
| 216 | N.D. | N.D |
| 217 | 8.7 | 18,000 |
| 218 | 7.5 | 22,000 |
| 219 | 4.0 | 14,000 |
| 220 | 0.54 | 33,000 |
| 221 | 3.2 | 38,000 |
| 222 | 3.9 | 94,000 |
| 223 | 0.3 | 21,000 |
| 224 | 4.1 | 30,000 |
| 225 | N.D. | N.D. |
| 226 | 15 | 54,000 |
| 227 | 690 | 37,000 |
| 228 | 5.9 | 31,000 |
| 229 | 1.9 | 42,000 |
| 230 | 8.1 | 92,000 |
| 231 | 4.5 | 63,000 |
| 232 | 2.1 | 29,000 |
| 233 | 700 | >100,000 |
| 234 | 960 | 70,000 |
| 235 | >30,000 | >100,000 |
| 236 | 170 | >100,000 |
| 237 | 160 | >100,000 |
| 238 | 3.7 | 21,000 |
| 239 | 150 | >100,000 |
| 240 | 28 | 62,000 |
| 241 | 25 | 8,500 |
| 242 | 59 | 57,000 |
| 243 | 23 | 78,000 |
| 244 | 68 | 16,000 |
| 245 | 7.6 | 77,000 |
| 246 | 3.10 | 32,000 |
| 247 | 23.00 | >100,000 |
| 248 | 560.00 | >100,000 |
| 249 | 39.00 | >100,000 |
| 250 | 1.30 | 41,000 |
| 251 | 5.60 | 98,000 |
| 252 | 25.00 | 43,000 |

TABLE 27-continued

| MCT Activity. | | |
|---|---|---|
| Ex. | MCT4 $IC_{50}$ (nM) MDA-MB-231 | MCT1 $IC_{50}$ (nM) BT20 |
| 253 | 19.00 | 55,000 |
| 254 | 285.00 | >100,000 |
| 255 | 2.40 | 7,300 |
| 256 | 2.60 | 17,000 |
| 257 | 0.35 | 19,000 |
| 258 | 12.00 | 27,000 |
| 259 | 850.00 | >100,000 |
| 260 | 0.83 | 26,000 |
| 261 | 17.00 | 43,000 |
| 262 | 9.10 | 7,900 |
| 263 | 2.20 | 16,000 |
| 264 | 0.35 | 10,000 |
| 265 | 5.60 | 84,000 |
| 266 | 0.36 | 64,000 |
| 267 | 0.57 | 11,000 |
| 268 | 0.30 | 36,000 |
| 269 | 1.00 | 58,000 |

N.D. = not determined

Metabolic Stability Assays

The following are assays that may be used to evaluate the metabolic stability of compounds of Formula (I) in human, rat, or mouse microsomes. The assays follow a common procedure recited below.

1. Master solution: 200 □L of 200 mM Phosphate buffer, 106 □L of ultra-pure water, 40 □L of 50 mM $MgCl_2$, and 10 □L of 20 mg/mL liver microsomes (human, rat, or mouse).
2. Two separated experiments were performed as follows. a) With NADPH: 10 μL of 20 mg/mL liver microsomes and 40 μL of 10 mM NADPH were added to the incubations. The final concentrations of microsomes and NADPH were 0.5 mg/mL and 1 mM, respectively. b) Without NADPH: 10 μL of 20 mg/mL liver microsomes and 40 μL of ultra-pure $H_2O$ were added to the incubations. The final concentration of microsomes was 0.5 mg/mL.
3. The reaction was started with the addition of 4 μL of 200 μM control compound or test compound solutions. Verapamil was used as positive control in this study. The final concentration of test compound or control compound was 2 μM.
4. Aliquots of 50 μL were taken from the reaction solution at 0, 15, 30, 45 and 60 min. The reaction was stopped by the addition of 4 volumes of cold acetonitrile with IS (100 nM alprazolam, 200 nM labetalol and 2 μM ketoprofen). Samples were centrifuged at 3,220 g for 40 minutes. A 90 μL aliquot of the supernatant was mixed with 90 μL of ultra-pure $H_2O$ and then used for LC-MS/MS analysis.
5. Data analysis. All calculations were carried out using Microsoft Excel. Peak areas were determined from extracted ion chromatograms. The slope value, k, was determined by linear regression of the natural logarithm of the remaining percentage of the parent drug vs. incubation time curve. The in vitro half-life (in vitro ti/2) was determined from the slope value: in vitro ti/2=−(0.693)/k.

Results are given below in Table 28, wherein "ND" means no data.

TABLE 28

| Metabolic Stability. | | | | | | |
|---|---|---|---|---|---|---|
| Ex. | Human microsome $t_{1/2}$, min | Human microsome % 60 min | Mouse microsome $t_{1/2}$, min | Mouse microsome % 60 min | Rat microsome $t_{1/2}$, min | Rat microsome % 60 min |
| 14 | 245 | 82 | 1300 | 95 | ND | ND |
| 27 | 50 | 43 | 61 | 50 | ND | ND |
| 35 | 115 | 67 | 35 | 31 | ND | ND |
| 36 | 290 | 85 | 1200 | 99 | ND | ND |
| 38 | 76 | 56 | 79 | 61 | ND | ND |
| 39 | 380 | 89 | 370 | 88 | ND | ND |
| 54 | 78 | 59 | 760 | 95 | ND | ND |
| 57 | 190 | 80 | >2000 | 100 | ND | ND |
| 64 | 200 | 82 | 270 | 84 | ND | ND |
| 65 | 140 | 78 | 560 | 92 | ND | ND |
| 66 | 120 | 73 | 260 | 83 | ND | ND |
| 68 | 790 | 95 | 380 | 91 | ND | ND |
| 110 | 2377 | 99 | 223 | 86 | 549 | 94 |
| 120 | 198 | 81 | 410 | 101 | 51 | 44 |
| 121 | 198 | 82 | 186 | 81 | 86 | 61 |
| 132 | 116 | 70 | 98 | 64 | 112 | 70 |
| 133 | 1006 | 97 | 344 | 90 | 404 | 91 |
| 134 | 186 | 80 | 109 | 72 | 264 | 85 |
| 140 | 109 | 67 | 64 | 62 | 59 | 48 |
| 150 | 341 | 90 | ∞ | 103 | 1715 | 98 |
| 155 | 52 | 62 | 38 | 37 | 73 | 70 |
| 157 | 149 | 78 | 9639 | 102 | 748 | 97 |
| 161 | 194 | 82 | ∞ | 99 | 259 | 80 |
| 166 | 1265 | 94 | 194 | 82 | ∞ | 102 |
| 167 | 250 | 84 | 430 | 97 | 74 | 72 |
| 168 | 187 | 78 | 229 | 81 | 173 | 81 |
| 170 | 471 | 87 | ∞ | 99 | ∞ | 95 |
| 175 | 212 | 83 | 711 | 94 | 315 | 87 |
| 177 | 184 | 75 | 334 | 87 | 634 | 90 |
| 178 | 115 | 66 | 125 | 70 | 145 | 72 |
| 179 | 644 | 93 | ∞ | 98 | 318 | 85 |
| 180 | 276 | 88 | ∞ | 103 | 2293 | 98 |

TABLE 28-continued

| Metabolic Stability. | | | | | | |
|---|---|---|---|---|---|---|
| Ex. | Human microsome $t_{1/2}$, min | Human microsome % 60 min | Mouse microsome $t_{1/2}$, min | Mouse microsome % 60 min | Rat microsome $t_{1/2}$, min | Rat microsome % 60 min |
| 183 | 99 | 66 | 122 | 73 | 101 | 71 |
| 188 | ∞ | 101 | 1400 | 92 | 490 | 87 |
| 191 | 1405 | 98 | 1005 | 97 | 556 | 94 |
| 196 | 88 | 62 | 37 | 33 | 38 | 32 |
| 198 | 207 | 80 | 243 | 84 | 205 | 82 |
| 201 | 83 | 58 | 83 | 58 | 45 | 39 |
| 202 | 37 | 32 | 38 | 32 | 11 | 2 |
| 211 | 180 | 78 | 49 | 43 | 73 | 57 |
| 220 | ∞ | 105 | 1038 | 102 | 292 | 86 |
| 221 | 68 | 56 | 38 | 34 | 37 | 33 |
| 222 | ∞ | 110 | 1004 | 94 | 335 | 90 |
| 224 | 736 | 91 | 829 | 98 | 132 | 73 |
| 226 | 468 | 95 | 682 | 95 | 455 | 88 |
| 228 | 130 | 71 | 767 | 96 | 395 | 91 |
| 229 | 103 | 64 | 196 | 81 | 109 | 69 |
| 232 | 97 | 65 | 73 | 59 | 70 | 50 |
| 243 | 433 | 88 | 1301 | 97 | 302 | 88 |
| 246 | 95 | 65 | 168 | 81 | 109 | 69 |
| 251 | 181 | 77 | 93 | 63 | 181 | 83 |
| 257 | 1297 | 96 | ∞ | 102 | ∞ | 103 |

Pharmacokinetic Assays in Mouse and Rat

The following are assays that may be used to evaluate the pharmacokinetic properties of Formula (I) in mouse or rat. The assays follow a common procedure recited below.

1. Formulations: For IV, DMSO/PEG400/30% HP-□-CD (10:20:70). For PO (oral gavage), DMSO/PEG400 (10:90). Formulations freshly prepared on the day of dosing or prior to dosing. Storage at room temperature.
2. Test Species: For Mouse: Male CD1 strain, approximately 6-8 weeks in age, approximately 20-30 g. For Rat: Male Sprague-Dawley strain, approximately 6-8 weeks in age, approximately 200-300 g.
3. Dose Level: For IV, 3 mg/kg. For PO, 10 mg/kg.
4. Number of animals: 3 per assay.
5. PK time points: For IV (plasma): 5 min, 15 min, 1, 2, 4, 6, 8, 24 h post dose. For PO (plasma): 15 min, 30 min, 1, 2, 4, 6, 8, 24 h post dose.
6. Blood Sample Collection and Processing. Blood was collected (~0.2 mL per time point) from jugular vein. Blood of each sample was transferred into plastic micro centrifuge tubes containing anticoagulant of EDTA-$K_2$. Blood samples were centrifuged at 2,000 g for 5 minutes at 4° C. to obtain plasma.
7. Samples Analysis: Plasma samples were analyzed using LC/MS/MS method, and pharmacokinetic parameters (half-life: $t_{1/2}$; oral bioavailability: F; volume of distribution: Vss).

Results are given below in Table 29, where "ND" means no data.

TABLE 29

| Pharmacoknetic Properties in Rodents. | | | | | | |
|---|---|---|---|---|---|---|
| Ex. | Mouse $t_{1/2}$ (h) | Mouse F (%) | Mouse Vss (L/kg) | Rat $t_{1/2}$ (h) | Rat F (%) | Rat Vss (L/kg) |
| 14 | 5.4 | 100 | 0.79 | 3.8 | 64 | 1.3 |
| 110 | 26.7 | 100 | 0.81 | 4.7 | 84 | 0.34 |
| 150 | 4.9 | 89 | 9.9 | 3.6 | 43 | 1.2 |
| 161 | ND | ND | ND | 5.7 | 61 | 0.32 |
| 167 | 1.7 | 24 | 2.6 | 2.2 | 72 | 1.2 |

TABLE 29-continued

| Pharmacoknetic Properties in Rodents. | | | | | | |
|---|---|---|---|---|---|---|
| Ex. | Mouse $t_{1/2}$ (h) | Mouse F (%) | Mouse Vss (L/kg) | Rat $t_{1/2}$ (h) | Rat F (%) | Rat Vss (L/kg) |
| 170 | 2.6 | 100 | 2.0 | 2.4 | 18 | 1.1 |
| 175 | ND | ND | ND | 4.2 | 48 | 0.40 |
| 179 | ND | ND | ND | 2.2 | 76 | 0.30 |
| 180 | ND | ND | ND | 4.4 | 49 | 0.39 |
| 191 | ND | ND | ND | 6.3 | 97 | 1.0 |
| 211 | 1.9 | 57 | 1.5 | 3.6 | 55 | 3.6 |
| 220 | 6.9 | 100 | 1.7 | 2.8 | 29 | 0.68 |
| 224 | ND | ND | ND | 2.6 | 53 | 1.3 |
| 228 | 4.4 | 100 | 2.0 | 3.1 | 94 | 1.3 |
| 229 | 4.2 | 100 | 1.9 | 2.7 | 100 | 1.0 |
| 232 | 3.1 | 56 | 0.21 | 2.6 | 52 | 0.15 |
| 246 | ND | ND | ND | 4.7 | 52 | 1.7 |
| 251 | ND | ND | ND | 3.0 | 98 | 0.38 |
| 257 | 3.6 | 76 | 2.8 | 2.7 | 76 | 1.6 |
| 260 | 5.2 | 86 | 0.22 | 3.7 | 85 | 0.20 |
| 264 | 2.7 | 94 | 1.1 | 4.6 | 100 | 2.5 |
| 266 | 3.8 | 100 | 0.36 | 2.7 | 100 | 0.23 |
| 267 | 3.3 | 64 | 3.9 | 2.6 | 54 | 7.7 |
| 268 | 2.7 | 77 | 0.77 | 2.2 | 57 | 0.76 |
| 269 | 3.3 | 100 | 1.3 | ND | ND | ND |

Adjuvant-Induced Arthritis Model in Rat

The following assays are used to evaluate anti-inflammatory properties of Formula (I) in rat. The assays follow a common procedure recited below.

1. Formulation: 0.5% Methylcellulose in saline. Formulation freshly prepared on day of dosing.
2. Test Species: SD rat, approximately 6-8 weeks in age, approximately 200 g.
3: Arthritis Induction Procedure: Complete Freund's Adjuvant (CFA; 50 □L/rat, *M. Tuberculosis* at 4 mg/mL) was administered via left paw sub-plantar injection.
4: Dosing: PO (oral gavage), 3 days post CFA injection.
5: Body Weight. Body weights of all animals were recorded during the course of study, at Day 1 and Day 3.

6: Difference of Weight Bearing Test (DWB). Distribution of body weight of rats between CFA-injected and contra-lateral paws were measured by weight balance changing instrument. Animals were tested to register the weight load exerted by the hind paws by means of a force plate inserted in the floor. The mean weight bearing (in g) between CFA injected paw and contra-lateral paw were determined over 10 seconds. Measurements were taken three times, including baseline prior to dose, 1 hour, and 4 hours post dosing on Day 3.

7: Mechanical Allodynia Test (MA). Mechanical allodynia of the left hind paw will be measured during course of study by determining withdrawal thresholds to Von Frey filament. The filament was applied perpendicularly to the plantar surface of the paw with increasing force. The threshold for paw withdrawal was calculated by taking the average of 2-3 repeated stimuli (in g) which induced a reflex paw withdrawal. Measurements were taken three times, including baseline prior to dose, 1 hour, and 4 hours post dosing on Day 3.

8: Minimal Efficacious Dose was determined by comparison of Formula (I) compounds to positive control Dexamethasone.

TABLE 31

Efficacy in Rat Adjuvant-Induced Arthritis Model

| Ex. | Difference in Weight Bearing, Minimal Efficacious Dose (mg/kg) | Mechanical Allodynia (Von Frey), Minimal Efficacious Dose (mg/kg) |
|---|---|---|
| 14 | 30 | 30 |
| 110 | 10 | 10 |
| 150 | 10 | 10 |
| 161 | ≤10 | ≤10 |
| 170 | 3 | 3 |
| 175 | >10 | >10 |
| 179 | ≤10 | ≤10 |
| 180 | >10 | >10 |
| 191 | >10 | >10 |
| 220 | 3 | 3 |
| 224 | ≤10 | ≤10 |
| 229 | 3 | 3 |
| 232 | 1 | 1 |
| 260 | 1 | 1 |
| 264 | 1 | 1 |
| 266 | 3 | 3 |
| 267 | 3 | 3 |
| 268 | 1 | 1 |

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for treating idiopathic pulmonary fibrosis in a subject in need thereof, comprising administering to the subject a compound of structural Formula VIII:

(VIII)

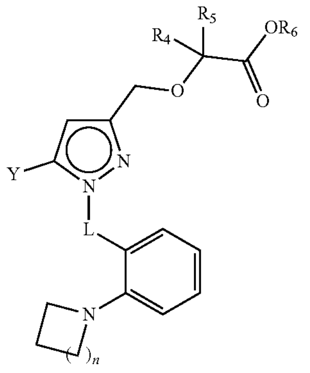

or a salt thereof, wherein:

L is chosen from a bond and methylene;

Y is chosen from

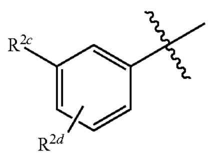

and

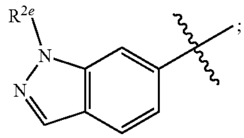

;

$R^{2c}$ is chosen from H, $C_1$-$C_4$alkoxy and $C_1$-$C_4$cycloalkoxy;

$R^{2d}$ is chosen from null and $C_1$-$C_4$alkoxy;

$R^{2e}$ is $C_1$-$C_4$alkyl;

n is 1 or 2;

$R^4$ and $R^5$ are independently chosen from $C_1$-$C_3$alkyl; and $R^6$ is chosen from H and $C_1$-$C_4$alkyl.

2. The method as recited in claim 1, wherein n is 1.

3. The method as recited in claim 1, wherein L is a bond.

4. The method as recited in claim 1, wherein Y is

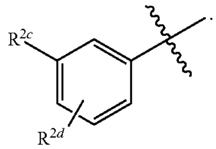

.

5. A method for treating idiopathic pulmonary fibrosis in a subject in need thereof, comprising administering to the subject a compound of structural Formula XI:

(XI)

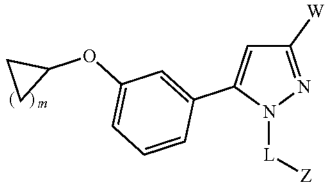

or a salt thereof, wherein:

W is chosen from

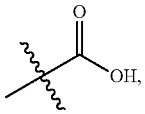
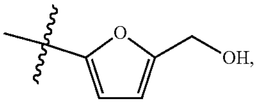
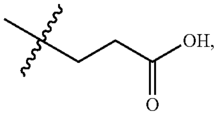
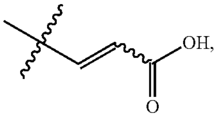
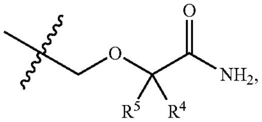
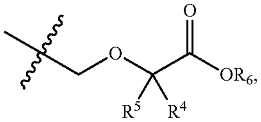
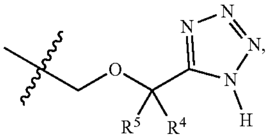
and
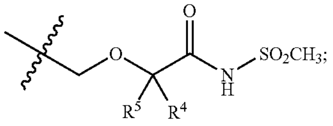

m is 1, 2, or 3;

L is chosen from a bond and methylene;

Z is chosen from

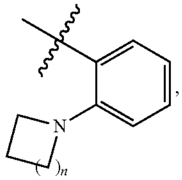
,
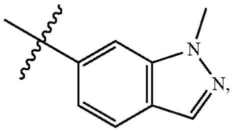
and

-continued

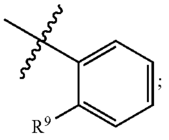
;

n is 1 or 2;

$R^4$ and $R^5$ are independently chosen from $C_1$-$C_3$alkyl;

$R^6$ is chosen from H and $C_1$-$C_4$alkyl; and $R^9$ is chosen from halo, amino, and $C_1$-$C_4$alkoxy.

6. The method as recited in claim 5, wherein W is

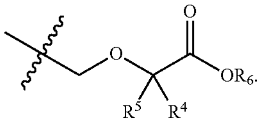

7. The method as recited in claim 5, wherein L is a bond.

8. The method as recited in claim 5, wherein n is 1.

9. A method for treating idiopathic pulmonary fibrosis in a subject in need thereof, comprising administering to the subject a compound of structural formula:

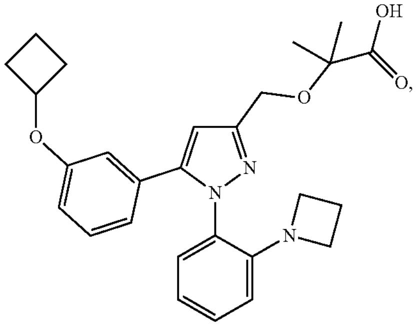 [SMILES: CC(C)(OCc1cc(-c2cccc(OC3CCC3)c2)n(-c2ccccc2N2CCC2)n1)C(=O)O]

or a salt thereof.

* * * * *